US008592367B2

(12) United States Patent
Kondorosi-Kuzsel et al.

(10) Patent No.: US 8,592,367 B2
(45) Date of Patent: Nov. 26, 2013

(54) NODULE SPECIFIC MEDICAGO PEPTIDES HAVING ANTIMICROBIAL ACTIVITY AND PHARMACEUTICAL COMPOSITIONS CONTAINING THE SAME

(75) Inventors: Eva Kondorosi-Kuzsel, Bures sur Yvette (FR); Peter Mergaert, Orsay (FR); Willem Van de Velde, Ghent (BE); Gergely Maroti, Szeged (HU); Attila Farkas, Szeged (HU); Attila Kereszt, Papa (HU)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/378,067

(22) PCT Filed: Jun. 15, 2010

(86) PCT No.: PCT/EP2010/058417
§ 371 (c)(1),
(2), (4) Date: Feb. 22, 2012

(87) PCT Pub. No.: WO2010/146067
PCT Pub. Date: Dec. 23, 2010

(65) Prior Publication Data
US 2012/0157374 A1    Jun. 21, 2012

(30) Foreign Application Priority Data

Jun. 15, 2009  (EP) .................................... 09305547

(51) Int. Cl.
*A01N 37/18*  (2006.01)
*A61K 38/04*  (2006.01)
*A61K 38/00*  (2006.01)
*A61P 31/10*  (2006.01)

(52) U.S. Cl.
USPC .......................................... 514/2.8; 514/3.3

(58) Field of Classification Search
None
See application file for complete search history.

(56) References Cited

FOREIGN PATENT DOCUMENTS

WO    WO 97/29765    *  8/1997 ............. A61K 38/00

OTHER PUBLICATIONS

Mergaert et al.,Plant Physiology, American Society of Plant Biologists US, 2003, vol. 132, No. 1, pp. 161-173.*
Mergaert et al.,p. 42 of supplemental material of above document.*
Mergaert et al., Plant Physiology, May 2003, vol. 132, pp. 161-173.*
Mergaert et al., Plant Physiology, May 2003, vol. 132, pp. 161-173. (supplemental material).*
Weinberg et al., Crit Rev Oral Biol Med, 1998, 9 (4), 399-414.*
Alunni Benoit et al: "Genomic organization and evolutionary insights on GRP and NCR genes, two large nodule-specific gene families in Medicago truncatula", Molecular Plant Microbe Interactions, vol. 20, No. 9, Jan. 1, 2007, pp. 1138-1148, XP009124365.
Mergaert P et al: "A novel family in Medicago truncatula consisting of more than 300 nodule-specific genes coding for small , secreted polypeptides with conserved cysteine motifs" Plant Physiology, American Society of Plant Biologists US, vol. 132, No. 1, May 1, 2003, pp. 161-173, XP002550829.
International Search Report, dated Sep. 22, 2010, in PCT/EP2010/058417.

\* cited by examiner

*Primary Examiner* — Cecilia J Tsang
*Assistant Examiner* — Kaipeen Yang
(74) *Attorney, Agent, or Firm* — Young & Thompson

(57) ABSTRACT

The present invention relates to the use of at least one peptide originated from *Medicago truncatula* nodules, including the SEQ IDs NO: 1-463 or at least one peptide having a sequence derived from the SEQ IDs NO: 1-463 by deletion of about 9 to about 44 contiguous amino acids, from the N-terminal part of the peptide, in particular peptides having the SEQ IDS NO: 464 to 925, for the preparation of a drug intended for the treatment of human, animal or plant diseases induced by microorganisms, wherein the peptides have a broad-spectrum and fast antibiotic activity, in particular killing of the bacteria within 1 to 3 hours.

12 Claims, 44 Drawing Sheets

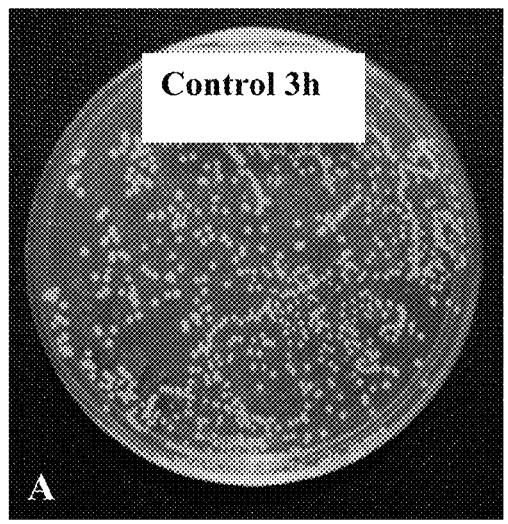
FIGURE 1A
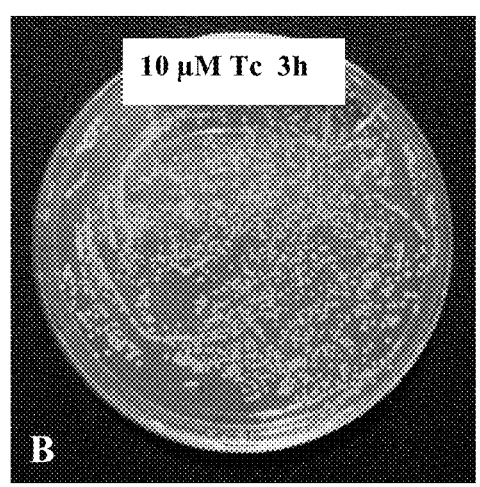 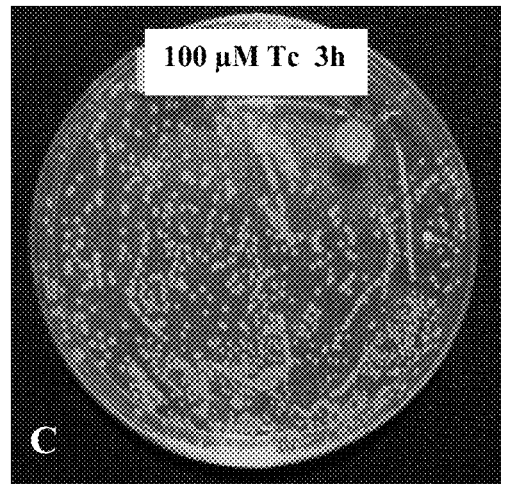
FIGURE 1B                    FIGURE 1C

A

B

SEQUENCE LISTING

<160> NUMBER OF SEQ ID NOS: 925

<210> SEQ ID NO 1
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 1

Met Ala Gln Phe Leu Leu Phe Val Tyr Ser Leu Ile Ile Phe Leu Ser
1               5                   10                  15

Leu Phe Phe Gly Glu Ala Ala Phe Glu Arg Thr Glu Thr Arg Met Leu
            20                  25                  30

Thr Ile Pro Cys Thr Ser Asp Ala Asn Cys Pro Lys Val Ile Ser Pro

```
                        35                  40                  45

Cys His Thr Lys Cys Phe Asp Gly Phe Cys Trp Tyr Ile Glu Gly
    50                  55                  60

Ser Tyr Glu Gly Pro
65

<210> SEQ ID NO 2
<211> LENGTH: 54
<212> TYPE: PRT
<213> ORGANISM: Artificial sequence
<220> FEATURE:
<223> OTHER INFORMATION: Peptide derived from Medicago truncatula

<400> SEQUENCE: 2

Cys Phe Gly Glu Ala Ala Phe Glu Thr Thr Glu Pro Met Leu Thr Thr
1               5                   10                  15

Tyr Leu Ile Leu Cys Val Ser Glu Ala Asp Cys Pro Lys Val Val Lys
                20                  25                  30

Pro Asn Tyr Thr Met Cys Ala Gly Gly Ile Cys Trp Gln Ser Val Gln
            35                  40                  45

Gly Ser Asn Gln Gly Pro
    50

<210> SEQ ID NO 3
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 3

Thr Gln Phe Leu Leu Phe Ile Tyr Ser Leu Ile Ile Phe Leu Ser Leu
1               5                   10                  15

Phe Leu Gly Glu Ala Ala Leu Glu Arg Thr Arg Thr Thr Met Leu Thr
                20                  25                  30

Ser Tyr Asn Ile Gly Cys Lys Ser Asp Ala Asp Cys Pro Lys Ala Ile
            35                  40                  45

Glu Pro His Tyr Thr Arg Cys Val Asp Gly His Cys Trp Leu Tyr Phe
    50                  55                  60

Gly Glu Gly Pro Lys Leu His Asn
65                  70

<210> SEQ ID NO 4
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 4

Met Ala Gln Phe Leu Leu Phe Ile Tyr Ser Leu Ile Ile Phe Leu Ser
1               5                   10                  15

Leu Phe Leu Gly Glu Ala Trp Phe Lys Arg Thr Glu Thr Gly Glu Ile
                20                  25                  30

Ile Trp Val Val Arg Cys Val Thr Asp Thr Asp Cys Pro Lys Met Gly
            35                  40                  45

Glu Pro Gln Tyr Phe Lys Cys Leu Asn Gly Val Cys Leu Glu His Ile
    50                  55                  60

Arg Glu Leu Pro
65
```

```
<210> SEQ ID NO 5
<211> LENGTH: 53
<212> TYPE: PRT
<213> ORGANISM: Artificial sequence
<220> FEATURE:
<223> OTHER INFORMATION: Peptide derived from Medicago truncatula

<400> SEQUENCE: 5

Gly Glu Ala Ala Leu Glu Arg Thr Glu Thr Thr Met His Asn Val Gln
1               5                   10                  15

Pro Ser His Phe Ile Pro Cys Phe Thr Ala Ala Asp Cys Pro Met Ile
            20                  25                  30

Asp Glu Pro His Tyr Ile Glu Cys Val Thr Gly Phe Cys Trp Ala Leu
        35                  40                  45

Met Arg Asn Leu His
    50

<210> SEQ ID NO 6
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 6

Met Ala Gln Val Ile Met Phe Val Gly Ala Leu Ile Ile Phe Leu Ser
1               5                   10                  15

Leu Phe Leu Val Glu Thr Lys Lys Thr Asp Ile Pro Cys Asp Ser Arg
            20                  25                  30

Asn Asp Cys Pro Gln Gln Ile Leu Pro Arg Tyr Val Leu Cys Val Asn
        35                  40                  45

Gly Leu Cys Arg Ile Tyr Phe Pro
    50                  55

<210> SEQ ID NO 7
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 7

Met Ala Gln Phe Leu Leu Phe Ile Tyr Ser Leu Ile Ile Phe Leu Ser
1               5                   10                  15

Leu Phe Phe Gly Glu Ala Ala Tyr Glu Arg Thr Glu Pro Ile Met His
            20                  25                  30

Asn Gly Glu Pro Ile Asn Leu Ile Pro Cys Val Thr Val Ala Asp Cys
        35                  40                  45

Pro Arg Met Asp Glu Pro Leu His Met Thr Cys Leu Val Gly Ala Cys
    50                  55                  60

Trp Pro Cys Ile Arg Ser Leu Tyr
65                  70

<210> SEQ ID NO 8
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 8

Met Ala Gln Phe Leu Leu Phe Ile Tyr Ser Leu Ile Ile Phe Leu Ser
```

```
                1               5                   10                  15
Pro Phe Leu Gly Glu Ala Val Phe Lys Arg Thr Glu Thr Gly Glu Ile
                    20                  25                  30

Ile Trp Thr Leu Pro Cys Ala Thr Asp Thr Asp Cys Pro Lys Met Gly
            35                  40                  45

Glu Pro Met Tyr Phe Lys Cys Leu Asn Gly Phe Cys Leu Glu His Ile
        50                  55                  60

Arg Glu Leu His Asp
65

<210> SEQ ID NO 9
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 9

Met Ala Gln Ile Leu Lys Leu Val Tyr Ala Phe Thr Ile Phe Leu Phe
1               5                   10                  15

Ile Phe Leu Val Val Thr Asn Gly Gln Glu Cys Lys Asp Asp Gly Asp
                    20                  25                  30

Cys Pro Thr Asn Met Cys Leu Pro Ser Leu Val Ser Lys Cys Ile Asn
            35                  40                  45

Phe Ile Cys Glu Cys Thr His Ser Met Ser Thr Asp
        50                  55                  60

<210> SEQ ID NO 10
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 10

Met Ala Gln Ile Ile Met Phe Phe Tyr Ala Leu Ile Ile Phe Leu Ser
1               5                   10                  15

Pro Phe Leu Val Asp Arg Arg Ser Phe Pro Ser Ser Phe Val Ser Pro
                    20                  25                  30

Lys Ser Tyr Thr Ser Glu Ile Pro Cys Lys Ala Thr Arg Asp Cys Pro
            35                  40                  45

Tyr Glu Leu Tyr Tyr Glu Thr Lys Cys Val Asp Ser Leu Cys Thr Tyr
        50                  55                  60

Trp
65

<210> SEQ ID NO 11
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 11

Met Ala Gln Ile Ile Pro Phe Leu Gly Ala Leu Ile Ile Phe Leu Ser
1               5                   10                  15

Leu Phe Leu Val Glu Ser Lys Gln Thr Asn Ile Pro Cys Lys Ser Ala
                    20                  25                  30

Glu Asp Cys Pro Lys Pro Ile Tyr Pro Arg Tyr Val Leu Cys Ser Tyr
            35                  40                  45
```

```
Gly Phe Cys Arg Ile Phe Phe Pro
    50                  55

<210> SEQ ID NO 12
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 12

Met Ala Gln Phe Leu Met Phe Ile Tyr Val Leu Ile Ile Phe Leu Tyr
1               5                   10                  15

Leu Phe Tyr Val Glu Ala Ala Met Phe Glu Leu Thr Lys Ser Thr Ile
            20                  25                  30

Arg Cys Val Thr Asp Ala Asp Cys Pro Asn Val Lys Pro Leu Lys
        35                  40                  45

Pro Lys Cys Val Asp Gly Phe Cys Glu Tyr Thr
    50                  55

<210> SEQ ID NO 13
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 13

Met Ala Gln Phe Leu Leu Phe Val Tyr Phe Ile Ile Ile Ile Val Ser
1               5                   10                  15

Leu Phe Leu Val Glu Ala Arg Glu Pro Thr Lys Ile Pro Cys Val Ser
            20                  25                  30

Asp Ser Asp Cys His Lys Val Lys Lys Pro Leu Leu Leu Thr Cys Ile
        35                  40                  45

Asp Gly Ile Cys Gln Tyr Thr Leu Glu Ala Thr Pro Phe Asp
    50                  55                  60

<210> SEQ ID NO 14
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 14

Met Ala His Ile Leu Met Phe Val Tyr Ala Leu Ile Ile Phe Leu Ser
1               5                   10                  15

Pro Phe Leu Ile Gly Arg Lys Gly Gly Pro Pro Gly Gly Arg Thr Tyr
            20                  25                  30

Ile Pro Cys Ile Ser Asp Asp Asp Cys Ile Val Ala Gln Pro Pro Tyr
        35                  40                  45

Val Leu Leu Cys Val Asn Asn Phe Cys Thr Tyr Phe Lys Asp Asp Asp
    50                  55                  60

Leu Pro Gln Arg
65

<210> SEQ ID NO 15
<211> LENGTH: 94
<212> TYPE: PRT
<213> ORGANISM: Artificial sequence
<220> FEATURE:
<223> OTHER INFORMATION: Peptide derived from Medicago truncatula
```

-continued

```
<400> SEQUENCE: 15

Met Val Gln Tyr Leu Met Phe Leu Tyr Ala Phe Ile Ile Phe Leu Ser
1               5                   10                  15

Leu Phe Val Val Gln Lys Ala Gln Ile Tyr Ile Thr Phe Phe Thr Ile
                20                  25                  30

Phe Ser Ile Phe Val Phe Tyr Thr Thr Phe Tyr His Leu Thr Leu Thr
            35                  40                  45

Thr Phe Phe Ser Phe His Asn Ala Gly Tyr Leu Pro Cys Ser Ser Asp
        50                  55                  60

Asp Asp Cys Pro Lys Glu Met Lys Pro Val Val Lys Cys Ile His
65                  70                  75                  80

Asn Phe Cys Glu His Phe Met Val Gly Glu Tyr Gly Pro
                85                  90

<210> SEQ ID NO 16
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 16

Phe Phe Asp His Leu Phe Phe Phe Cys Gly Leu Ala Glu Thr Lys Arg
1               5                   10                  15

Thr Asn Ile Pro Cys Phe Ser Asp Asp Cys Pro Lys Thr Cys Pro
                20                  25                  30

Pro Leu Val Phe Glu Val Arg
            35

<210> SEQ ID NO 17
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 17

Met Thr Gln Phe Leu Phe Phe Ile Phe Val Leu Met Ile Phe Leu Ser
1               5                   10                  15

Pro Phe Leu Val Glu Met Glu Lys Thr His Val Arg Cys Ile Thr Ala
                20                  25                  30

Asp Asp Cys Pro Lys Val Glu Arg Pro Leu Lys Met Lys Cys Ile Gly
            35                  40                  45

Asn Tyr Cys His Tyr Phe Leu Asn Asn Phe
        50                  55

<210> SEQ ID NO 18
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 18

Met Ala Lys Ile Ala Asn Phe Val Tyr Ser Met Ile Ile Phe Leu Ser
1               5                   10                  15

Leu Phe Leu Val Ala Thr Lys Ala Glu Trp Tyr Tyr Pro Cys Asn Thr
                20                  25                  30

Asp Ser Asp Cys Pro Gln Asn Met Cys Pro Pro Asp Met Glu Pro Arg
            35                  40                  45
```

```
Cys Trp Thr Gly Tyr Cys Ser Ser Cys Tyr Ile Arg Trp Gly Lys
    50                  55                  60

<210> SEQ ID NO 19
<211> LENGTH: 102
<212> TYPE: PRT
<213> ORGANISM: Artificial sequence
<220> FEATURE:
<223> OTHER INFORMATION: Peptide derived from Medicago truncatula

<400> SEQUENCE: 19

Met Lys Phe Ile Tyr Ile Met Ile Leu Ile Leu Ser Leu Phe Leu Val
1               5                   10                  15

Gln Phe Leu Thr Cys Lys Gly Leu Thr Val Pro Cys Glu Asn Pro Thr
            20                  25                  30

Thr Cys Pro Glu Asp Phe Cys Thr Pro Pro Met Ile Thr Arg Cys Ile
        35                  40                  45

Asn Phe Ile Cys Leu Cys Asp Gly Pro Glu Tyr Ala Glu Pro Glu Tyr
    50                  55                  60

Asp Gly Pro Val Glu Glu Tyr Asp His Lys Gly Asp Phe Leu Ser Val
65                  70                  75                  80

Lys Pro Lys Val Ile Asn Glu Asn Met Met Met Arg Glu Arg His Met
                85                  90                  95

Ile Lys Glu Ile Glu Val
            100

<210> SEQ ID NO 20
<211> LENGTH: 75
<212> TYPE: PRT
<213> ORGANISM: Artificial sequence
<220> FEATURE:
<223> OTHER INFORMATION: Peptide derived from Medicago truncatula

<400> SEQUENCE: 20

Met Gln Arg Leu Asp Asn Met Ala Lys Asn Val Lys Phe Ile Tyr Val
1               5                   10                  15

Ile Ile Leu Leu Leu Phe Ile Phe Leu Val Ile Ile Val Cys Asp Ser
            20                  25                  30

Ala Phe Val Pro Asn Ser Gly Pro Cys Thr Thr Asp Lys Asp Cys Lys
        35                  40                  45

Gln Val Lys Gly Tyr Ile Ala Arg Cys Arg Lys Gly Tyr Cys Met Gln
    50                  55                  60

Ser Val Lys Arg Thr Trp Ser Ser Tyr Ser Arg
65                  70                  75

<210> SEQ ID NO 21
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 21

Met Ala Ala Thr Arg Lys Phe Ile Tyr Val Leu Ser His Phe Leu Phe
1               5                   10                  15

Leu Phe Leu Val Thr Lys Ile Thr Asp Ala Arg Val Cys Lys Ser Asp
            20                  25                  30

Lys Asp Cys Lys Asp Ile Ile Ile Tyr Arg Tyr Ile Leu Lys Cys Arg
        35                  40                  45

Asn Gly Glu Cys Val Lys Ile Lys Ile
    50                  55
```

-continued

```
<210> SEQ ID NO 22
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 22

Met Val Lys Ile Leu Lys Phe Ile Tyr Val Met Ile Ile Phe Leu Ser
1               5                   10                  15

Leu Phe Leu Val Ala Thr Asn Val Asn Ala Ile Asn Lys Cys Ser Gln
            20                  25                  30

Asp Ser His Cys Pro Lys Asp Met Cys Lys Lys Pro Ser Lys Pro Arg
        35                  40                  45

Cys Val Val Ser Pro Lys Leu Pro Leu Ser Ser Lys Ser Gly Val Cys
    50                  55                  60

Thr Cys Val
65

<210> SEQ ID NO 23
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 23

Met Ala Lys Ile Val Lys Phe Ile Tyr Val Met Ile Ile Leu Ile Phe
1               5                   10                  15

Leu Phe Leu Val Ser Thr Asn Ile Asp Ala Ile Arg Asn Lys Cys Phe
            20                  25                  30

Arg Pro Ser Asp Cys Pro Pro Ser Met Tyr Cys Asp Ala Gly Phe Gln
        35                  40                  45

Ile Gly Cys Val Arg Lys Ile Cys Thr Cys Leu Arg Ile Leu Ala Pro
    50                  55                  60

Ile Asp Phe Val Pro Thr
65                  70

<210> SEQ ID NO 24
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 24

Met Gln Lys Glu Lys Asn Met Ala Lys Thr Phe Glu Phe Val Tyr Ala
1               5                   10                  15

Met Ile Ile Phe Ile Leu Leu Phe Leu Val Glu Asn Asn Phe Ala Ala
            20                  25                  30

Tyr Ile Ile Glu Cys Gln Thr Asp Asp Cys Pro Lys Ser Gln Leu
        35                  40                  45

Glu Met Phe Ala Trp Lys Cys Val Lys Asn Gly Cys His Leu Phe Gly
    50                  55                  60

Met Tyr Glu Asp Asp Asp Pro
65                  70

<210> SEQ ID NO 25
<211> LENGTH: 71
<212> TYPE: PRT
```

<213> ORGANISM: Artificial sequence
<220> FEATURE:
<223> OTHER INFORMATION: Peptide derived from Medicago truncatula

<400> SEQUENCE: 25

```
Met Val Lys Thr Leu Lys Leu Val Asn Tyr Met Ile Phe Phe Leu Ser
1               5                   10                  15

Ile Phe Leu Val Val Lys Asn Val Asp Gly Asp Asp Val Val Phe Gln
            20                  25                  30

Tyr Val Phe Asp Gly Cys Arg Ile Asp Ala Asp Cys Pro Ile Ser Gly
        35                  40                  45

Leu Gln Leu Leu Lys Trp Met Cys Ile Asn Asn Glu Cys Glu Phe Asn
    50                  55                  60

His Val Arg Pro Arg Tyr Val
65                  70
```

<210> SEQ ID NO 26
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 26

```
Met Ala Lys Thr Leu Asn Phe Val Cys Ala Met Ile Leu Phe Ile Ser
1               5                   10                  15

Leu Phe Leu Val Ser Lys Asn Val Ala Leu Tyr Ile Ile Glu Cys Lys
            20                  25                  30

Thr Asp Ala Asp Cys Pro Ile Ser Lys Leu Asn Met Tyr Asn Trp Arg
        35                  40                  45

Cys Ile Lys Ser Ser Cys His Leu Tyr Lys Val Ile Gln Phe Met Val
    50                  55                  60
```

<210> SEQ ID NO 27
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 27

```
Met Val Glu Ile Val Lys Phe Val Tyr Ile Ile Asn Ile Phe Ile Phe
1               5                   10                  15

Leu Phe Leu Val Ala Thr Asn Val Glu Ala Lys Phe Thr Arg Cys Phe
            20                  25                  30

Arg Asp Ser Asp Cys Pro Lys Thr Leu Cys His Ser Pro Gly Lys Ala
        35                  40                  45

Lys Cys Met His His Ser Ile Cys Lys Cys Ile Phe Phe Gly Tyr Asn
    50                  55                  60

Ile
65
```

<210> SEQ ID NO 28
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 28

```
Met Thr Lys Ile Leu Met Leu Phe Tyr Ala Met Ile Val Phe His Ser
1               5                   10                  15
```

Ile Phe Leu Val Ala Ser Tyr Thr Asp Glu Cys Ser Thr Asp Ala Asp
                    20                  25                  30

Cys Glu Tyr Ile Leu Cys Leu Phe Pro Ile Ile Lys Arg Cys Ile His
                35                  40                  45

Asn His Cys Lys Cys Val Pro Met Gly Ser Ile Glu Pro Met Ser Thr
            50                  55                  60

Ile Pro Asn Gly Val His Lys Phe His Ile Ile Asn Asn
65                  70                  75

<210> SEQ ID NO 29
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 29

Met Val Lys Thr Phe Lys Phe Ile Tyr Ser Ile Ile Phe Leu Ser
1               5                   10                  15

Pro Phe Leu Val Val Met Asn Val Asp Gly Glu Leu Ile Lys Cys Thr
                20                  25                  30

Met Asp Ala Asp Cys Pro Thr Ser Leu Asn Arg Lys Trp Leu Cys Ile
                35                  40                  45

Asn Asn Ile Cys Arg Lys Met Cys Val Thr Asn Val
            50                  55                  60

<210> SEQ ID NO 30
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 30

Met Ala Glu Ser Pro Lys Phe Val Tyr Val Leu Ile Leu Phe Ile Ser
1               5                   10                  15

Ile Phe Asn Val Ile Ile Val Cys Asp Phe Ala Phe Leu Pro Thr Ser
                20                  25                  30

Arg Asn Cys Ile Thr Asn Lys Asp Cys Arg Gln Val Arg Asn Tyr Ile
                35                  40                  45

Ala Arg Cys Arg Lys Gly Gln Cys Leu Gln Ser Pro Val Arg
            50                  55                  60

<210> SEQ ID NO 31
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 31

Met Ala Lys Thr Thr Lys Leu Ile Tyr Val Met Ile Leu Phe Leu Ser
1               5                   10                  15

Leu Phe Leu Val Ala Lys Asn Val Thr Ala Gln Ile Arg Cys Asn Asp
                20                  25                  30

Ala Phe Glu Cys Arg Arg Ser Ala Ile Cys Asn Phe Pro Asn Lys Trp
                35                  40                  45

Lys Cys Asn Asp His Lys Cys Glu Cys Val
            50                  55

```
<210> SEQ ID NO 32
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 32

Glu Thr Pro Lys Leu Val Tyr Val Leu Ile Leu Phe Leu Ser Ile Ile
1               5                   10                  15

Phe Ser Ile Ile Val Ser Asn Ser Phe Pro Asp Lys Ile Phe Ile Gly
            20                  25                  30

Asp Cys Lys Thr Asp Lys Asp Cys Lys Pro Lys Arg Gly Val Asn Phe
        35                  40                  45

Arg Cys Arg Lys Gly Lys Cys Tyr Pro Arg
    50                  55

<210> SEQ ID NO 33
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 33

Met Gln Arg Thr Lys Asn Met Ala Glu Thr Leu Lys Phe Val Tyr Val
1               5                   10                  15

Leu Ile Leu Phe Ile Ser Leu Phe Leu Val Leu Ile Val Cys Asp Ser
            20                  25                  30

Ala Phe Val Ala Asn Thr Glu Thr Cys Ile Thr Asp Lys Asp Cys Pro
        35                  40                  45

Asn Gly Arg Asn Tyr Ile Gly Arg Cys Arg Lys Gly His Cys Gln Gln
    50                  55                  60

Arg Leu Val Arg
65

<210> SEQ ID NO 34
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 34

Met Ser Lys Ile Leu Lys Phe Val Tyr Val Pro Ile Leu Tyr Phe Ser
1               5                   10                  15

Ile Leu Leu Val Leu Thr Ile His Asp Gln Val Tyr Phe Asn Asn Asn
            20                  25                  30

Ser Pro Pro Cys Val Thr Asp Lys Asp Cys Pro Arg Pro Gln Phe Arg
        35                  40                  45

Lys Ser Asn Val Arg Cys Arg Asn Gly His Cys Val Asn Leu Gly Asn
    50                  55                  60

<210> SEQ ID NO 35
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 35

Met Val Lys Thr Pro Lys Leu Val Tyr Val Leu Ile Leu Phe Leu Ser
1               5                   10                  15
```

```
Ile Phe Leu Ser Met Ile Val Ser Asn Ser Ser Phe Leu Gly Thr Phe
            20                  25                  30

Ile Ser Ser Cys Lys Arg Asp Lys Asp Cys Pro Lys Leu Tyr Gly Ala
        35                  40                  45

Asn Phe Arg Cys Arg Lys Gly Thr Cys Val Pro Pro Ile
    50                  55                  60
```

<210> SEQ ID NO 36
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 36

```
Met Ala Lys Ile Leu Lys Phe Val Tyr Val Pro Ile Leu Tyr Phe Ser
1               5                   10                  15

Ile Leu Leu Val Leu Thr Ile Tyr Asp Gln Ala Tyr Phe Asn Asp Pro
            20                  25                  30

Arg Pro Cys Val Ser Asp Lys Asp Cys Pro Arg Pro Lys Phe Gln Lys
        35                  40                  45

Ser Asn Val Arg Cys Arg Lys Gly Tyr Cys Val Asn Leu Asp Gly
    50                  55                  60
```

<210> SEQ ID NO 37
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 37

```
Met Ala Lys Ile Leu Lys Phe Val Tyr Val Pro Ile Leu Tyr Leu Ser
1               5                   10                  15

Ile Leu Leu Val Leu Thr Ile Tyr Asp Gln Val Tyr Phe Asn Asn Ser
            20                  25                  30

Pro Pro Cys Val Thr Asp Lys Asp Cys Pro Arg Pro Gln Phe Arg Lys
        35                  40                  45

Ser Asn Val Arg Cys Arg Asn Gly Tyr Cys Val Asn Leu Gly Asn
    50                  55                  60
```

<210> SEQ ID NO 38
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 38

```
Met Ala Lys Ile Met Lys Tyr Val Asn Val Pro Ile Leu Phe Leu Ser
1               5                   10                  15

Ile Leu Leu Val Leu Met Ser Tyr Gly Ser Asn Tyr Ser Pro Thr Pro
            20                  25                  30

Phe Pro Cys Leu Thr Asp Lys Asp Cys Thr Arg Arg Lys Gly Phe Ser
        35                  40                  45

Val Thr Cys Arg Lys Gly Phe Cys Val Glu Phe Lys His Phe
    50                  55                  60
```

<210> SEQ ID NO 39
<211> LENGTH: 63
<212> TYPE: PRT

```
<213> ORGANISM: Artificial sequence
<220> FEATURE:
<223> OTHER INFORMATION: Peptide derived from Medicago truncatula

<400> SEQUENCE: 39

Met Ala Lys Thr Ile Lys Cys Leu Asn Val Leu Ile Leu Phe Leu Tyr
1               5                   10                  15

Met Phe Leu Val Leu Thr Leu Leu Asp Phe Gly Ser Ser Thr Thr Pro
                20                  25                  30

Thr Pro Cys Arg Thr Asp Gln Asp Cys Pro Arg Lys Lys Lys Phe Ser
        35                  40                  45

Val Thr Cys Arg Lys Gly Phe Cys Ala Glu Ile Arg His Val Tyr
    50                  55                  60

<210> SEQ ID NO 40
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 40

Gly Glu Thr Leu Lys Ser Val Tyr Leu Leu Ile Leu Phe Ile Ser Leu
1               5                   10                  15

Phe Leu Val Ile Ile Val Ser His Ser Val Thr Ser Pro Trp Val Leu
                20                  25                  30

Lys Gln His Cys Val Thr Asp Lys Asp Cys Pro Gln Met Gly Lys Ile
        35                  40                  45

Lys Ile Arg Cys Arg Asn Gly Glu Cys Val Gln Gly Phe
    50                  55                  60

<210> SEQ ID NO 41
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 41

Met Gln Ile Gly Lys Asn Met Val Glu Thr Gln Lys Leu Val Tyr Val
1               5                   10                  15

Ile Leu Leu Phe Leu Ser Ile Phe Leu Phe Thr Asn Ser Pro Leu Ser
                20                  25                  30

Gln Ile Ile Phe Ser Glu Cys Lys Thr Asp Lys Asp Cys Pro Lys Tyr
        35                  40                  45

Gln Arg Ala Asn Ile Arg Cys Arg Lys Gly Gln Cys Val Arg Ile
    50                  55                  60

<210> SEQ ID NO 42
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 42

Met Val Glu Thr Pro Lys Phe Val Tyr Asn Leu Ile Leu Leu Ile Tyr
1               5                   10                  15

Ile Phe Leu Phe Ile Ile Ile Cys Asp Ser Thr Tyr Leu Pro Thr Thr
                20                  25                  30

Arg Ile Cys Ile Thr Asp Lys Asp Cys Pro Ser Val Lys Asn Tyr Ile
        35                  40                  45
```

```
Gly Arg Cys Arg Lys Gly Tyr Cys Gln Ala Ser Lys Leu Arg
        50                  55                  60
```

<210> SEQ ID NO 43
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 43

```
Met Val Gln Thr Pro Lys Leu Val Tyr Val Ile Val Leu Leu Leu Ser
1               5                   10                  15

Ile Phe Leu Gly Met Thr Ile Cys Asn Ser Ser Phe Ser His Phe Phe
            20                  25                  30

Glu Gly Ala Cys Lys Ser Asp Lys Asp Cys Pro Lys Leu His Arg Ser
        35                  40                  45

Asn Val Arg Cys Arg Lys Gly Gln Cys Val Gln Ile
    50                  55                  60
```

<210> SEQ ID NO 44
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 44

```
Met Thr Glu Thr Leu Lys Phe Val Tyr Ile Leu Ile Leu Phe Ile Phe
1               5                   10                  15

Ile Phe Leu Val Leu Met Val Cys Asp Ser Ala Phe Ile Gln Leu Ser
            20                  25                  30

Lys Pro Cys Ile Ser Asp Lys Glu Cys Ser Ile Val Lys Asn Tyr Arg
        35                  40                  45

Ala Arg Cys Arg Lys Gly Tyr Cys Val Arg Arg Ile Arg
    50                  55                  60
```

<210> SEQ ID NO 45
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 45

```
Met Ala Asp Thr Leu Lys Phe Val His Val Leu Ile Leu Leu Ile Ser
1               5                   10                  15

Ile Phe Leu Val Ile Ile Val Ser Ser Phe Ile Phe Leu Pro Cys Ile
            20                  25                  30

Thr Asp Lys Asp Cys Gln Thr Leu Lys Lys Asn Lys Gly Lys Gly Arg
        35                  40                  45

Cys Arg Lys Gly Phe Cys Val Asp Gly Leu Ile Gly
    50                  55                  60
```

<210> SEQ ID NO 46
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 46

-continued

```
Ile Leu Phe Leu Ser Ile Phe Leu Cys Ile Ile Val Ser Asn Ser Ser
1               5                   10                  15

Phe Ser Lys Thr Phe Asp Arg Ala Cys Lys Thr Asp Lys Asp Cys Pro
            20                  25                  30

Lys Leu Arg Gly Val Asn Val Arg Cys Arg Lys Asp Gln Cys Val Thr
        35                  40                  45

Val

<210> SEQ ID NO 47
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 47

Met Thr Glu Thr Leu Lys Phe Val Tyr Val Leu Ile Leu Phe Ile Ser
1               5                   10                  15

Ile Phe Leu Val Ile Ile Val Cys Glu Ser Ser Phe Phe Pro Ser Ser
            20                  25                  30

Pro Val Cys Lys Thr Asp Lys Asp Cys Pro Gln Leu Arg Gly Tyr Thr
        35                  40                  45

Ala Arg Cys Arg Lys Thr Gln Cys Leu Leu Ile Pro Arg Gly
    50                  55                  60

<210> SEQ ID NO 48
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 48

Leu Val Ile Ile Val Cys Asp Ser Ile His Phe His Val Ser Arg Pro
1               5                   10                  15

Cys Met Thr Asp Asp Asp Cys Ala Pro Glu Lys Tyr Tyr Asn Ile Arg
            20                  25                  30

Cys Arg Lys Gly Phe Cys Val Gln Ile Arg Lys Tyr
        35                  40

<210> SEQ ID NO 49
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 49

Leu Val Ile Ile Leu Cys Asp Ser Ala Tyr Phe Pro Asn Ser Arg Pro
1               5                   10                  15

Cys Lys Thr Asp Lys Asn Cys Ala Gln Val Lys Asn Tyr Ile Ser Lys
            20                  25                  30

Cys Leu Lys Gly Leu Cys Val Gln Glu Glu
        35                  40

<210> SEQ ID NO 50
<211> LENGTH: 54
<212> TYPE: PRT
<213> ORGANISM: Artificial sequence
<220> FEATURE:
<223> OTHER INFORMATION: Peptide derived from Medicago truncatula

<400> SEQUENCE: 50
```

```
Val Tyr Ile Leu Ile Leu Phe Ile Cys Ile Phe Leu Val Met Ile Val
1               5                   10                  15

Cys Asp Ser Ala Tyr Leu Pro Leu Ser Arg Ser Cys Ile Thr Asp Lys
                20                  25                  30

Asp Cys Ser Arg Val Lys Asn Tyr Asn Ala Arg Cys Arg Lys Gly Tyr
            35                  40                  45

Cys Gln Tyr Leu Gln Tyr
        50
```

<210> SEQ ID NO 51
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 51

```
Met Ala Glu Ile Ile Lys Phe Ile Cys Leu Thr Ile Leu Phe Leu Ser
1               5                   10                  15

Leu Phe Leu Val Ala Ala Glu Glu Asp Ile Gly Gly His Leu Glu Cys
                20                  25                  30

Val Glu Asp Glu Asp Cys Met Glu Glu Ser Cys Pro Ile Phe Ser Val
            35                  40                  45

His Lys Cys Lys Asn Ser Gly Cys Glu Cys Asp Glu Met Phe Arg
        50                  55                  60
```

<210> SEQ ID NO 52
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 52

```
Met Ala Glu Thr Leu Lys Phe Val Tyr Val Met Ile Leu Phe Leu Ser
1               5                   10                  15

Ile Phe Leu Val Ile Thr Ile Ser Asn Ser Pro Tyr Ile Ile Asn
                20                  25                  30

Ile Leu Cys Lys Thr Asp Lys Asp Cys Pro Lys Val Gln Gly Ala Asn
            35                  40                  45

Ile Arg Cys Arg Ser Gly Lys Cys Val Gln Val
        50                  55
```

<210> SEQ ID NO 53
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 53

```
Met Thr His Ile Ser Lys Phe Val Phe Ala Leu Ile Ile Phe Leu Ser
1               5                   10                  15

Ile Tyr Val Gly Val Asn Asp Cys Lys Arg Ile Pro Cys Lys Asp Asn
                20                  25                  30

Asn Asp Cys Asn Asn Asn Trp Gln Leu Leu Ala Cys Arg Phe Glu Arg
            35                  40                  45

Glu Val Pro Arg Cys Ile Asn Ser Ile Cys Lys Cys Met Pro Met
        50                  55                  60
```

```
<210> SEQ ID NO 54
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 54

Met Thr Tyr Ile Ser Lys Val Val Tyr Ala Leu Ile Ile Phe Leu Ser
1               5                   10                  15

Ile Tyr Val Gly Val Asn Asp Cys Met Leu Val Thr Cys Glu Asp His
            20                  25                  30

Phe Asp Cys Arg Gln Asn Val Gln Gln Val Gly Cys Ser Phe Arg Glu
        35                  40                  45

Ile Pro Gln Cys Ile Asn Ser Ile Cys Lys Cys Met Lys Gly
    50                  55                  60

<210> SEQ ID NO 55
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 55

Met Thr His Ile Phe Lys Phe Val Tyr Ala Leu Ile Ile Phe Leu Ser
1               5                   10                  15

Ile Tyr Val Ala Val Asn Asp Cys Ile Arg Ile His Cys Lys Asp Asp
            20                  25                  30

Phe Asp Cys Ile Glu Asn Arg Leu Gln Val Gly Cys Arg Leu Gln Arg
        35                  40                  45

Glu Lys Pro Arg Cys Val Asn Leu Val Cys Arg Cys Leu Arg Arg
    50                  55                  60

<210> SEQ ID NO 56
<211> LENGTH: 86
<212> TYPE: PRT
<213> ORGANISM: Artificial sequence
<220> FEATURE:
<223> OTHER INFORMATION: Peptide derived from Medicago truncatula

<400> SEQUENCE: 56

Met Lys Ser Gln Asn His Ala Lys Phe Ile Ser Phe Tyr Lys Asn Asp
1               5                   10                  15

Leu Phe Lys Ile Phe Gln Asn Asn Asp Ser His Phe Lys Val Phe Phe
            20                  25                  30

Ala Leu Ile Ile Phe Leu Tyr Thr Tyr Leu His Val Thr Asn Gly Val
        35                  40                  45

Phe Val Ser Cys Asn Ser His Ile His Cys Arg Val Asn Asn His Lys
    50                  55                  60

Ile Gly Cys Asn Ile Pro Glu Gln Tyr Leu Leu Cys Val Asn Leu Phe
65                  70                  75                  80

Cys Leu Trp Leu Asp Tyr
            85

<210> SEQ ID NO 57
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 57
```

```
Met Asn His Ile Ser Lys Phe Val Tyr Ala Leu Ile Ile Phe Leu Ser
1               5                   10                  15

Val Tyr Leu Val Val Leu Asp Gly Arg Pro Val Ser Cys Lys Asp His
                20                  25                  30

Tyr Asp Cys Arg Arg Lys Val Lys Ile Val Gly Cys Ile Phe Pro Gln
            35                  40                  45

Glu Lys Pro Met Cys Ile Asn Ser Met Cys Thr Cys Ile Arg Glu Ile
50                      55                  60

Val Pro
65

<210> SEQ ID NO 58
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 58

Met Ala Gln Ile Ser Lys Phe Val Tyr Ala Leu Ile Ile Phe Phe Ser
1               5                   10                  15

Leu Ile Leu Ala Val Thr Asn Ala Gly Leu Phe Arg Cys Lys Val Asp
                20                  25                  30

Ile Asp Cys Pro Gln Ile Leu Cys Phe Asp Glu Gln Ile Ala Lys Cys
            35                  40                  45

Ile Ala Arg Met Cys Glu Cys Asp Tyr Glu
50                      55

<210> SEQ ID NO 59
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 59

Met Asp Leu Val His Met Phe Val Tyr Ala Phe Ile Ile Phe Leu Ser
1               5                   10                  15

Ile Pro Leu Pro Pro Ala Arg Ser Asp Phe Pro Cys Lys Thr Lys Asp
                20                  25                  30

Asp Cys Ala Gln Gln Ile Asp Tyr Ile Ala Glu Cys Ile Ile Gly Phe
            35                  40                  45

Cys Arg Tyr Phe Thr Pro Phe Glu His Pro Phe
50                      55

<210> SEQ ID NO 60
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 60

Met Thr Gln Ile Ser Ile Ser Phe Tyr Ala Leu Ile Ile Phe Phe Ser
1               5                   10                  15

Leu Phe Leu Val Val Thr Asn Gly Arg Asn Lys Thr Cys Asn Tyr Ser
                20                  25                  30

Ser Glu Cys Leu Phe His Asn Cys Pro Leu Gly Trp Val Met Lys Cys
            35                  40                  45

Phe Thr Tyr Phe Cys Ala Cys Ser Arg Leu
```

-continued

```
<210> SEQ ID NO 61
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 61

Met His Thr Arg Lys Asn Met Asp Leu Val His Met Phe Val Tyr Ala
1               5                   10                  15

Phe Thr Ile Phe Leu Ser Ile Pro Leu Pro Pro Val Arg Ser Asp Phe
            20                  25                  30

Pro Cys Lys Thr Lys Val Asp Cys Pro Gln His Lys Lys Tyr Ile Ala
        35                  40                  45

Glu Cys Ile Phe Gly Phe Cys Arg His Phe Lys Pro Leu Glu His Pro
    50                  55                  60

Phe
65

<210> SEQ ID NO 62
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 62

Met Gln Arg Arg Lys Asn Met Ala Gln Ile Leu Leu Phe Ala Tyr Val
1               5                   10                  15

Phe Ile Ile Ser Ile Ser Leu Phe Leu Val Val Thr Asn Gly Val Lys
            20                  25                  30

Ile Pro Cys Val Lys Asp Thr Asp Cys Pro Thr Leu Pro Cys Pro Leu
        35                  40                  45

Tyr Ser Lys Cys Val Asp Gly Phe Cys Lys Met Leu Ser Ile
    50                  55                  60

<210> SEQ ID NO 63
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 63

Leu His Met Leu Ile Tyr Ala Phe Ile Ile Phe Leu Ser Ile Pro Leu
1               5                   10                  15

Pro Pro Thr Arg Lys Thr Ile Pro Cys Lys Thr Lys Val Asp Cys Pro
            20                  25                  30

Gln Gln Ile Tyr Tyr Val Val Glu Cys Leu Asp Gly Phe Cys Asp Tyr
        35                  40                  45

Trp Arg Asp
    50

<210> SEQ ID NO 64
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 64
```

```
Met Gln Thr Met Arg Asn Met Asn Leu Val Tyr Met Phe Val Tyr Ala
1               5                   10                  15

Phe Ile Ile Phe Leu Ser Ile His Phe Pro Pro Arg Ile Lys Cys Asn
                20                  25                  30

Thr Glu Ala Asp Cys Pro Gln Arg Phe Asp Asn Ile Val Glu Cys Leu
            35                  40                  45

Phe Gly Ile Cys His Phe Tyr Ile Lys
        50                  55
```

<210> SEQ ID NO 65
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 65

```
Met Ala Arg Val Ile Ser Leu Phe Tyr Ala Leu Ile Ile Phe Leu Phe
1               5                   10                  15

Leu Phe Leu Val Ala Thr Asn Gly Asp Leu Ser Pro Cys Leu Arg Ser
                20                  25                  30

Gly Asp Cys Ser Lys Asp Glu Cys Pro Ser His Leu Val Pro Lys Cys
            35                  40                  45

Ile Gly Leu Thr Cys Tyr Cys Ile
        50                  55
```

<210> SEQ ID NO 66
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 66

```
Phe Leu Trp Ile Ile Ile Pro Ser Ile Leu Leu Ile Val Ser Asp Arg
1               5                   10                  15

Ile Pro Cys Ile Asp Asp Met Asp Cys Pro Asp Met Phe Pro Ser Leu
                20                  25                  30

Asn Thr Gln Cys Ile Asp Asn Phe Cys Asp Val Val Leu Gly Tyr Asn
            35                  40                  45
```

<210> SEQ ID NO 67
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 67

```
Ser Gln Ile Leu Met Phe Val Ser Val Leu Ile Ile Phe Leu Ser Leu
1               5                   10                  15

Phe Leu Ala Asp Thr Lys Gln Thr Asn Ile Pro Cys Glu Asn Lys Arg
                20                  25                  30

Asp Cys Pro Gln Pro Leu Tyr Pro Lys Phe Val Thr Cys Phe Glu Gly
            35                  40                  45

Leu Cys Arg Met His Tyr Pro Leu Lys Lys Ile
        50                  55
```

<210> SEQ ID NO 68
<211> LENGTH: 60
<212> TYPE: PRT

```
<213> ORGANISM: Artificial sequence
<220> FEATURE:
<223> OTHER INFORMATION: Peptide derived from Medicago truncatula

<400> SEQUENCE: 68

Met Ala Gln Ile Leu Met Phe Val Tyr Phe Leu Ile Ile Phe Leu Ser
1               5                   10                  15

Leu Phe Leu Val Glu Ser Ile Lys Ile Phe Thr Glu His Arg Cys Arg
                20                  25                  30

Thr Asp Ala Asp Cys Pro Ala Arg Glu Leu Pro Glu Tyr Leu Lys Cys
            35                  40                  45

Gln Gly Gly Met Cys Arg Leu Leu Ile Lys Lys Asp
        50                  55                  60

<210> SEQ ID NO 69
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 69

Met Ala Gln Leu Ile Ile Phe Val Tyr Ala Leu Ile Ile Phe Leu Tyr
1               5                   10                  15

Leu Leu Phe Val Glu Ala Gln Ile Thr Lys Leu Pro Cys Val Thr Val
                20                  25                  30

Asp Asp Cys Pro Lys Val Glu Lys Pro Ile Pro Met Val Ala Lys Cys
            35                  40                  45

Phe Gly Lys Ser Phe Ser Arg His Cys His Tyr Phe Tyr Phe
        50                  55                  60

<210> SEQ ID NO 70
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 70

Met Phe Val Tyr Val Leu Ile Ile Phe Leu Ser Leu Phe Leu Ile Glu
1               5                   10                  15

Ala Ser Ile Lys Thr Lys Ile Ala Cys Val Thr Asp Asn Asp Cys Pro
                20                  25                  30

Arg Ala Ile Lys Pro Val Val Met Trp Cys Ile Asn Asn Tyr Cys His
            35                  40                  45

Tyr Tyr Leu Tyr Gly Tyr Gln
        50                  55

<210> SEQ ID NO 71
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 71

Met Ala Gln Asn Lys Tyr Leu Phe Cys Ala Phe Ile Ile Phe Leu Ser
1               5                   10                  15

Leu Phe Phe Val Leu Thr Lys Ser Ser Ile Pro Cys Lys Thr Arg Thr
                20                  25                  30

Gln Cys Pro Glu Lys Met Cys Arg Leu Pro Lys Phe Val Trp Cys Ile
            35                  40                  45
```

```
Asp Gly Ser Cys Val Cys Ala
    50                  55

<210> SEQ ID NO 72
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 72

Met Thr Leu Leu Leu Lys Phe Leu Tyr Ala Leu Ile Ile Phe Ile Ser
1               5                   10                  15

Leu Leu Phe Val Val Thr Asn Gly Ala Gln Phe Leu Cys Ser Asp Asp
            20                  25                  30

Ser Asp Cys Pro Arg Asp Leu Cys Val Arg Asn Ser Leu Thr Leu Arg
        35                  40                  45

Cys Val Asn Tyr Ile Cys Gln Cys Arg
    50                  55

<210> SEQ ID NO 73
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 73

Met Gln Arg Lys Thr Asn Met Thr Gln Phe Ile Phe Phe Ile Tyr Val
1               5                   10                  15

Leu Met Ile Phe Leu Ser Leu Phe Leu Val Glu Ser Glu Lys Leu Asp
            20                  25                  30

Ile Arg Cys Ala Thr Val Asp Asp Cys Pro Lys Val Thr Lys Pro Val
        35                  40                  45

Val Met Met Cys Thr Gly Lys Phe Cys His Tyr Phe Phe Val Arg Lys
    50                  55                  60

Gln Ile Leu
65

<210> SEQ ID NO 74
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 74

Met Ala Arg Ile Ser Leu Phe Val Tyr Ala Leu Ile Ile Phe Phe Ser
1               5                   10                  15

Leu Phe Phe Val Leu Thr Asn Gly Glu Leu Glu Ile Arg Cys Val Ser
            20                  25                  30

Asp Ala Asp Cys Pro Leu Phe Pro Leu Pro His Asn Arg Cys Ile
        35                  40                  45

Asp Asp Val Cys His Leu Phe Thr Ser
    50                  55

<210> SEQ ID NO 75
<211> LENGTH: 57
<212> TYPE: PRT
<213> ORGANISM: Artificial sequence
<220> FEATURE:
<223> OTHER INFORMATION: Peptide derived from Medicago truncatula
```

```
<400> SEQUENCE: 75

Met Ala Gln Ile Leu Lys Phe Val Asp Ala Leu Ile Leu Phe Leu Ser
1               5                   10                  15

Leu Phe Phe Ile Leu Ile Asn Gly Asp Arg Ile Pro Cys Ala Thr Asp
                20                  25                  30

Ala Asp Gly Pro Pro Lys Ile Leu Pro Ile Ile His Lys Cys Ile Asn
            35                  40                  45

Asn Phe Cys Lys Leu Lys Leu Tyr Asn
    50                  55

<210> SEQ ID NO 76
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 76

Met Asn Gln Ile Pro Met Phe Gly Tyr Thr Leu Ile Ile Phe Phe Ser
1               5                   10                  15

Leu Phe Pro Val Ile Thr Asn Gly Asp Arg Ile Pro Cys Val Thr Asn
                20                  25                  30

Gly Asp Cys Pro Val Met Arg Leu Pro Leu Tyr Met Arg Cys Ile Thr
            35                  40                  45

Tyr Ser Cys Glu Leu Phe Phe Asp Gly Pro Asn Leu Cys Ala Val Glu
    50                  55                  60

Arg Ile
65

<210> SEQ ID NO 77
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 77

Met Ala His Phe Leu Met Phe Val Tyr Ala Leu Ile Thr Cys Leu Ser
1               5                   10                  15

Leu Phe Leu Val Glu Met Gly His Leu Ser Ile His Cys Val Ser Val
                20                  25                  30

Asp Asp Cys Pro Lys Val Glu Lys Pro Ile Thr Met Lys Cys Ile Asn
            35                  40                  45

Asn Tyr Cys Lys Tyr Phe Val Asp His Lys Leu
    50                  55

<210> SEQ ID NO 78
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 78

Met Val His Ile Leu Met Phe Val Tyr Ala Leu Ile Phe Ser Asn Phe
1               5                   10                  15

Ile Phe Leu Val Glu Ala Asn Met Val Val Leu Gly Cys Val Ser Asp
                20                  25                  30

Asp Asp Cys Pro Lys Val Pro Leu Pro Arg Phe Leu Lys Cys Ile Ala
            35                  40                  45
```

```
Asn Leu Cys Cys Leu Val Arg Lys Lys Asp Leu
    50                  55

<210> SEQ ID NO 79
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 79

Met Val Lys Thr Leu Lys Phe Val Tyr Tyr Met Ile Leu Phe Leu Ser
1               5                   10                  15

Leu Phe Leu Phe Ile Lys Asn Val Asp Gly Ala Phe Val Lys Cys Glu
            20                  25                  30

Thr Asp Asp Asp Cys Pro Lys Tyr Asn Gly Phe Arg Lys Tyr Glu Cys
        35                  40                  45

Val Asn Asn Trp Cys Arg Leu Thr Gly Leu His
    50                  55

<210> SEQ ID NO 80
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 80

Met Ser Lys Thr Ile Met Phe Leu Tyr Ala Met Thr Leu Phe Leu Phe
1               5                   10                  15

Leu Leu His Ile Glu Lys Ser Ser Gly Val Leu Ile Asp Cys Lys Thr
            20                  25                  30

Val Lys Asp Cys Pro Thr Ser Tyr Thr Lys Ile Tyr Arg Cys Glu Asp
        35                  40                  45

Asn Lys Cys Arg Phe Ser Phe Val Ile Gly Leu
    50                  55

<210> SEQ ID NO 81
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 81

Met Thr Glu Thr Leu Lys Phe Val Val Thr Lys Lys Lys Thr Leu Lys
1               5                   10                  15

Phe Val Tyr Ala Met Ile Leu Phe Leu Ser Phe Leu Ile Ala Ser
            20                  25                  30

Glu Val Gly Ala His Phe Gly Cys Glu Thr Asp Ala Asp Cys Pro Arg
        35                  40                  45

Ser Thr Asp Lys Asn Phe Phe Leu Arg Cys Ile Asn Lys Lys Cys Glu
    50                  55                  60

Trp Ala Ala Lys Arg His
65                  70

<210> SEQ ID NO 82
<211> LENGTH: 59
<212> TYPE: PRT
<213> ORGANISM: Artificial sequence
<220> FEATURE:
<223> OTHER INFORMATION: Peptide derived from Medicago truncatula
```

<400> SEQUENCE: 82

Met Thr Lys Ile Phe Lys Phe Ile His Ala Met Ile Leu Phe Leu Ser
1               5                   10                  15

Leu Phe Leu Val Ala Glu Ser Tyr Phe Ala Asp Ile Leu Cys Lys Val
                20                  25                  30

His Glu Asp Cys Pro Gln Lys Ser Thr His Lys Tyr Tyr Cys Ile Asp
            35                  40                  45

Asp Glu Cys Phe Leu Tyr Tyr Trp Glu Ala Pro
        50                  55

<210> SEQ ID NO 83
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 83

Met Ala Glu Ile Ile Lys Phe Val Tyr Thr Met Ile Leu Leu Leu Ser
1               5                   10                  15

Leu Phe Leu Val Thr Thr Lys Val Gly Ala Tyr Ile Ala Cys Gln Ser
                20                  25                  30

Glu Ile Asp Cys Pro Pro Asn Tyr Ser Phe Leu Phe Ala Ile Arg Cys
            35                  40                  45

Ile Lys Gln Lys Cys Val Thr Val Gly Arg Tyr Leu
        50                  55                  60

<210> SEQ ID NO 84
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 84

Met Thr Lys Thr Leu Lys Phe Ile Cys Ile Met Ile Leu Phe Leu Ser
1               5                   10                  15

Leu Phe Leu Val Ala Glu Ser Phe Ala Thr Gly Met Pro Cys Lys Thr
                20                  25                  30

Asp Lys Glu Cys Pro Asn Thr Ser Thr His Lys Tyr Lys Cys Ile Asn
            35                  40                  45

Asp Asp Cys Phe Cys Phe Tyr Ile Tyr Trp Pro Leu Gly Asn Ser Leu
        50                  55                  60

Val
65

<210> SEQ ID NO 85
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 85

Met Gln Met Glu Lys Asn Met Thr Lys Thr Leu Lys Phe Ile Tyr Val
1               5                   10                  15

Met Ile Leu Phe Leu Ser Leu Phe Leu Val Ala Glu Ser Phe Phe Val
                20                  25                  30

Asp Ile Met Cys Lys Val His Glu Asp Cys Pro Gln Lys Ser Thr His
            35                  40                  45

```
Lys Tyr Tyr Cys Val Asp Asp Lys Cys Phe Leu Tyr Tyr Trp Glu Gly
    50                  55                  60

Lys Pro
65

<210> SEQ ID NO 86
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 86

Met Ala Asn Thr His Lys Leu Val Ser Met Ile Leu Phe Ile Phe Leu
1               5                   10                  15

Phe Leu Val Ala Asn Asn Val Glu Gly Tyr Val Asn Cys Glu Thr Asp
                20                  25                  30

Ala Asp Cys Pro Pro Ser Thr Arg Val Lys Arg Phe Lys Cys Val Lys
            35                  40                  45

Gly Glu Cys Arg Trp Thr Arg Met Ser Tyr Ala
        50                  55

<210> SEQ ID NO 87
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 87

Met Ala His Lys Leu Val Tyr Thr Ile Ile Leu Phe Ile Phe Leu Phe
1               5                   10                  15

Leu Val Ala Asn Asn Val Glu Gly Asp Ile Val Cys Ile Thr Asp Asn
                20                  25                  30

Asp Cys Pro Pro Asn Thr Leu Val Gln Gly Tyr Arg Cys Ile Asp Gly
            35                  40                  45

Lys Cys Glu Ser Val Phe Leu Ser Tyr Arg
        50                  55

<210> SEQ ID NO 88
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 88

Met Ala Lys Thr Leu Asn Phe Met Phe Ala Leu Ile Leu Phe Ile Ser
1               5                   10                  15

Leu Phe Leu Val Ser Lys Asn Val Ala Ile Asp Ile Phe Val Cys Gln
                20                  25                  30

Thr Asp Ala Asp Cys Pro Lys Ser Glu Leu Ser Met Tyr Thr Trp Lys
            35                  40                  45

Cys Ile Asp Asn Glu Cys Asn Leu Phe Lys Val Met Gln Gln Met Val
        50                  55                  60

<210> SEQ ID NO 89
<211> LENGTH: 72
<212> TYPE: PRT
<213> ORGANISM: Artificial sequence
<220> FEATURE:
<223> OTHER INFORMATION: Peptide derived from Medicago truncatula
```

```
<400> SEQUENCE: 89

Met Ala Lys Thr Cys Lys Leu Val Phe Ala Leu Ile Leu Phe Val Ser
1               5                   10                  15

Leu Tyr Leu Val Ser Met Ser Ala Glu Leu Gly Gly Pro Cys Arg Ser
            20                  25                  30

Asp Glu Glu Cys Pro Gln Leu Ser Leu Arg Phe Phe Ala Ile Lys Cys
            35                  40                  45

Arg Glu Asn Val Cys Ile Tyr Val Asp Leu Asp Pro Tyr Lys Pro Arg
        50                  55                  60

Ala Glu Lys Asn Gln Phe Leu His
65                  70

<210> SEQ ID NO 90
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 90

Met Lys Arg Gly Lys Asn Met Ser Lys Ile Leu Lys Phe Ile Tyr Ala
1               5                   10                  15

Thr Leu Val Leu Tyr Leu Phe Leu Val Val Thr Lys Ala Ser Asp Asp
            20                  25                  30

Glu Cys Lys Ile Asp Gly Asp Cys Pro Ile Ser Trp Gln Lys Phe His
            35                  40                  45

Thr Tyr Lys Cys Ile Asn Gln Lys Cys Lys Trp Val Leu Arg Phe His
        50                  55                  60

Glu Tyr
65

<210> SEQ ID NO 91
<211> LENGTH: 81
<212> TYPE: PRT
<213> ORGANISM: Artificial sequence
<220> FEATURE:
<223> OTHER INFORMATION: Peptide derived from Medicago truncatula

<400> SEQUENCE: 91

Met Ala Lys Thr Leu Lys Phe Phe Tyr Thr Ile Ile Leu Phe Leu Ser
1               5                   10                  15

Leu Phe Leu Val Leu Gln Arg Lys Leu Thr Gly Cys Glu Val Asp Gly
            20                  25                  30

Asp Cys Pro Lys Val Phe Lys Leu Lys Val Met Ile Leu Phe Ile Lys
            35                  40                  45

Cys Ile Asn Asn Lys Cys Val Arg Gly Leu Leu Ser Gln Thr Gly Thr
        50                  55                  60

Gln Cys Pro Asp Phe Phe Leu Lys Arg Thr Leu Pro Arg Phe Tyr
65                  70                  75                  80

Phe

<210> SEQ ID NO 92
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 92
```

```
Met Ile Lys Ile Leu Thr Phe Leu Tyr Ala Leu Val Leu Phe Leu Ser
1               5                   10                  15

Leu Phe Ile Phe Ser Ile Ala Ala Gln Asn Leu Met Lys Cys Asn Thr
            20                  25                  30

Asp Asp Glu Cys Pro Lys Phe Asp Lys Pro Leu Ser Phe Lys
        35                  40                  45

Cys Ile Asn Asp Gly Cys Arg Met Val Ile Asn Asp Lys Tyr Lys His
    50                  55                  60

Lys Thr Val Gln Lys Leu Leu
65                  70

<210> SEQ ID NO 93
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 93

Met Ala Lys Ile Val Lys Tyr Val Tyr Val Ile Ile Ile Phe Leu Ser
1               5                   10                  15

Leu Phe Leu Val Ala Thr Lys Ile Glu Gly Tyr Tyr Tyr Lys Cys Phe
            20                  25                  30

Lys Asp Ser Asp Cys Val Lys Leu Leu Cys Arg Ile Pro Leu Arg Pro
        35                  40                  45

Lys Cys Met Tyr Arg His Ile Cys Lys Cys Lys Val Val Leu Thr Gln
    50                  55                  60

Asn Asn Tyr Val Leu Thr
65                  70

<210> SEQ ID NO 94
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 94

Met Ser Asn Thr Leu Met Phe Val Ile Thr Phe Ile Val Leu Val Thr
1               5                   10                  15

Leu Phe Leu Gly Pro Lys Asn Val Tyr Ala Phe Gln Pro Cys Val Thr
            20                  25                  30

Thr Ala Asp Cys Met Lys Thr Leu Lys Thr Asp Glu Asn Ile Trp Tyr
        35                  40                  45

Glu Cys Ile Asn Asp Phe Cys Ile Pro Phe Pro Ile Pro Lys Gly Arg
    50                  55                  60

Lys
65

<210> SEQ ID NO 95
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 95

Met Ala Glu Ile Leu Lys Phe Ile Tyr Asn Ala Ile Leu Phe Val Ser
1               5                   10                  15

Leu Tyr Phe Ile Val Ile Tyr Gly Glu Leu Val Cys Asp Thr Asp Asp
            20                  25                  30
```

```
Asp Cys Leu Lys Phe Phe Pro Asp Asn Pro Tyr Pro Met Glu Cys Ile
            35                  40                  45

Asn Ser Ile Cys Leu Ser Leu Thr Asp
    50                  55
```

<210> SEQ ID NO 96
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 96

```
Met Ala Arg Thr Leu Lys Phe Val Tyr Ala Val Ile Leu Phe Leu Ser
1               5                   10                  15

Leu Phe Leu Val Ala Lys Gly Asp Asp Val Lys Ile Lys Cys Val Val
                20                  25                  30

Ala Ala Asn Cys Pro Asp Leu Met Tyr Pro Leu Val Tyr Lys Cys Leu
            35                  40                  45

Asn Gly Ile Cys Val Gln Phe Thr Leu Thr Phe Pro Phe Val
    50                  55                  60
```

<210> SEQ ID NO 97
<211> LENGTH: 50
<212> TYPE: PRT
<213> ORGANISM: Artificial sequence
<220> FEATURE:
<223> OTHER INFORMATION: Peptide derived from Medicago truncatula

<400> SEQUENCE: 97

```
Met Ser Gln Ile Phe Met Phe Ala Tyr Val Leu Ile Ile Phe Leu Ser
1               5                   10                  15

Leu Phe His Val Glu Thr Asn Ile His Lys Ile Gly Cys Lys Thr Ser
                20                  25                  30

Glu Asp Cys Pro Tyr Leu Gly Lys Cys Ile Glu Asp Phe Cys Gln Phe
            35                  40                  45

Lys Lys
    50
```

<210> SEQ ID NO 98
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 98

```
Met Ala Lys Ile Val Tyr Phe Val Tyr Ser Met Ile Ile Phe Leu Ser
1               5                   10                  15

Leu Phe Leu Val Thr Thr Lys Ala Ala Glu Arg Ile Tyr Arg Cys Leu
                20                  25                  30

Asp His Ser His Cys Pro Thr Phe Met Cys Ser Pro Gly Leu Lys Pro
            35                  40                  45

Lys Cys Met Asn Pro Lys Val Cys Lys Cys Val Pro Val Gln Ser Arg
    50                  55                  60

Lys Tyr Tyr Ala Leu Thr
65                  70
```

<210> SEQ ID NO 99
<211> LENGTH: 65
<212> TYPE: PRT

<213> ORGANISM: Artificial sequence
<220> FEATURE:
<223> OTHER INFORMATION: Peptide derived from Medicago truncatula

<400> SEQUENCE: 99

Met Ala Gln Lys Phe Met Phe Phe Tyr Ala Leu Ile Ile Phe Leu Ser
1               5                   10                  15

Ser Phe Tyr Val Ile Ile Asn Thr Ile Asp Pro Pro His His Ile Thr
            20                  25                  30

Asn His Glu Ile Pro Cys Lys Tyr Asn His Asp Cys Pro Thr Ile Leu
        35                  40                  45

Asp Tyr Ile Ser Ile Cys Pro Tyr His Tyr Cys Glu Phe Trp Arg Thr
    50                  55                  60

Tyr
65

<210> SEQ ID NO 100
<211> LENGTH: 74
<212> TYPE: PRT
<213> ORGANISM: Artificial sequence
<220> FEATURE:
<223> OTHER INFORMATION: Peptide derived from Medicago truncatula

<400> SEQUENCE: 100

Met Ile Glu Thr Leu Lys Phe Val Tyr Ala Met Ile Leu Phe Leu Ser
1               5                   10                  15

Leu Phe Leu Ile Thr Ser Glu Val Gly Gly Leu Tyr Ile Gly Cys Glu
            20                  25                  30

Thr Asp Arg Asp Tyr Pro Pro Leu Ala Asn Lys Thr Phe Tyr Leu Lys
        35                  40                  45

Cys Ile Asp Lys Lys Cys Glu Trp Thr Val Thr Asp Ser Leu Ser Thr
    50                  55                  60

Arg Ser Gly Arg Met Gln Lys Leu Ser Ile
65                  70

<210> SEQ ID NO 101
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 101

Met Val Arg Thr Leu Lys Phe Val Tyr Val Ile Ile Leu Ile Leu Ser
1               5                   10                  15

Leu Phe Leu Val Ala Lys Gly Gly Lys Lys Ile Tyr Cys Glu Asn
            20                  25                  30

Ala Ala Ser Cys Pro Arg Leu Met Tyr Pro Leu Val Tyr Lys Cys Leu
        35                  40                  45

Asp Asn Lys Cys Val Lys Phe Met Met Lys Ser Arg Phe Val
    50                  55                  60

<210> SEQ ID NO 102
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 102

Met Ala Glu Ile Val Lys Tyr Val Tyr Val Ile Ile Phe Pro Ser
1               5                   10                  15

```
Leu Ile Leu Phe Ala Thr Asn Ile Glu Ala Ile Ile Arg Cys Phe His
            20                  25                  30

Asp Ala Asp Cys Val His Lys Ile Cys His Pro Pro Gln Ile Arg Lys
            35                  40                  45

Cys Val Ser Lys Ile Cys Lys Cys Arg Leu Met Ile Thr Gln Lys Asp
 50                  55                  60

Tyr Val Leu Thr
 65

<210> SEQ ID NO 103
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 103

Met Ala Lys Ile Val Asn Phe Val Tyr Ser Met Ile Ile Phe Val Ser
 1               5                  10                  15

Leu Phe Leu Val Ala Thr Lys Gly Gly Ser Lys Pro Phe Leu Thr Arg
            20                  25                  30

Pro Tyr Pro Cys Asn Thr Gly Ser Asp Cys Pro Gln Asn Met Cys Pro
            35                  40                  45

Pro Gly Tyr Lys Pro Gly Cys Glu Asp Gly Tyr Cys Asn His Cys Tyr
 50                  55                  60

Lys Arg Trp
 65

<210> SEQ ID NO 104
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 104

Glu Asp Phe Leu Tyr Ser Met Ile Ile Phe Leu Ser Leu Phe Leu Val
 1               5                  10                  15

Ala Thr Lys Ser Glu Pro Gly Gly His Arg Cys Ser Thr Asp Ser Phe
            20                  25                  30

Cys Pro Pro Asn Met Cys Pro Pro Gly Met Thr Pro Lys Cys Val Arg
            35                  40                  45

Phe Arg Cys Lys Cys Val Pro Ile Gly Trp Lys Asn Leu Ser His Val
 50                  55                  60

Leu Ala
 65

<210> SEQ ID NO 105
<211> LENGTH: 81
<212> TYPE: PRT
<213> ORGANISM: Artificial sequence
<220> FEATURE:
<223> OTHER INFORMATION: Peptide derived from Medicago truncatula

<400> SEQUENCE: 105

Met Ala Glu Ile Leu Lys Phe Val Tyr Ile Val Leu Phe Ile Ser
 1               5                  10                  15

Ile Leu Leu Val Val Glu Thr Glu Gln Tyr Cys Val Asp Asp Ala Asp
            20                  25                  30

Cys Gln Lys Leu Tyr Pro Phe His Arg Gln Leu Ser Leu Lys Cys Ile
```

```
                         35                  40                  45

Arg Ala Phe Cys Val Lys Leu Val Gly Gln Ala Asn Asp Asp Leu Phe
 50                  55                  60

Pro Ser Thr Val His Ala Ala Asp Ala Thr Gly Leu Gly Ile Asp Ala
 65                  70                  75                  80

Lys

<210> SEQ ID NO 106
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 106

Met Ala Lys Ile Val Asn Phe Ile Tyr Ser Met Ile Phe Leu Ser
 1               5                  10                  15

Leu Phe Leu Val Glu Thr Asn Ala Gln Cys Ile Tyr Pro Ala Cys Phe
                 20                  25                  30

Lys Asp His Met Cys Arg Gln Leu Lys Cys Ser Pro Gly Arg Thr Pro
             35                  40                  45

Lys Cys Val Asn Tyr Gln Cys Arg Cys Ser Pro Gln Ala Leu Gly Ser
         50                  55                  60

Tyr His Leu Leu Thr
 65

<210> SEQ ID NO 107
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 107

Met Ala Lys Thr Leu Lys Phe Val Tyr Ala Met Ile Ile Phe Leu Ser
 1               5                  10                  15

Leu Phe Leu Met Ala Thr Asn Ile Asp Ser Ala Leu Ile Glu Cys Gln
                 20                  25                  30

Ile Asp Asp Asp Cys Pro Pro Ile Lys Phe Ala Lys Tyr Leu Cys Ile
             35                  40                  45

Asn Tyr Lys Cys Arg Lys Ile Cys Leu Gly Glu
         50                  55

<210> SEQ ID NO 108
<211> LENGTH: 75
<212> TYPE: PRT
<213> ORGANISM: Artificial sequence
<220> FEATURE:
<223> OTHER INFORMATION: Peptide derived from Medicago truncatula

<400> SEQUENCE: 108

Met Ala Gly Thr Leu Asn Phe Val Tyr Ala Met Ile Leu Phe Leu Ser
 1               5                  10                  15

Leu Phe Leu Val Ala Arg Gly Glu Glu Ile Ile Ile Lys Cys Gln
                 20                  25                  30

Thr Ala Lys Asp Cys Pro Asp Ile Tyr Asn Leu Phe Pro Leu Val Tyr
             35                  40                  45

Lys Cys Ile Asp Asn Ile Cys Val Asp Val Lys Leu Glu Pro Pro Tyr
         50                  55                  60

Asp Met Ser Ile Thr Pro Asn Ser Val His Lys
```

-continued 65                    70                    75

<210> SEQ ID NO 109
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 109

Met Val Glu Lys Met Val Gly Ile Leu Lys Phe Val Cys Pro Phe Leu
1               5                   10                  15

Phe Leu Tyr Phe Leu Leu Leu Ser Met Leu Val Ile Ser Gly Lys His
            20                  25                  30

Asp Tyr His Met Phe Phe Gln Arg Ile Pro Cys Pro Lys Asp Lys Ile
        35                  40                  45

Leu Asp Cys Asn Leu Leu Glu Cys Trp Cys Lys
    50                  55

<210> SEQ ID NO 110
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 110

Met Thr Lys Thr Leu Ile Phe Ile Tyr Ala Leu Phe Ile Val Val Ser
1               5                   10                  15

Leu Phe Leu Val Val Thr Ser Glu Thr Arg Ile Pro Cys Val Ser Arg
            20                  25                  30

Asn Asp Cys Pro Lys Arg Pro Tyr Pro Leu Phe Met Lys Cys Ile Asp
        35                  40                  45

Asn Phe Cys Glu Ile Trp Lys Ile Gly Lys Glu
    50                  55

<210> SEQ ID NO 111
<211> LENGTH: 100
<212> TYPE: PRT
<213> ORGANISM: Artificial sequence
<220> FEATURE:
<223> OTHER INFORMATION: Peptide derived from Medicago truncatula

<400> SEQUENCE: 111

Met Ala Gln Arg Phe Met Phe Ile Tyr Ala Leu Ile Ile Phe Leu Ser
1               5                   10                  15

Gln Phe Phe Val Val Ile Asn Thr Ser Met Ser Ile Tyr Ile Thr Phe
            20                  25                  30

Lys Lys Phe Ile Ile Asp Phe Ile His Asn Val Tyr His Pro Ser Ile
        35                  40                  45

Thr Ser Asn Phe Ser Leu Phe Asn Asn Ala Gly Asp Ile Pro Asn Asn
    50                  55                  60

Ser Asn Arg Asn Ser Pro Lys Glu Asp Val Phe Cys Asn Ser Asn Asp
65                  70                  75                  80

Asp Cys Pro Thr Ile Leu Tyr Tyr Val Ser Lys Cys Val Tyr Asn Phe
                85                  90                  95

Cys Glu Tyr Trp
            100

<210> SEQ ID NO 112
<211> LENGTH: 61

```
<212> TYPE: PRT
<213> ORGANISM: Artificial sequence
<220> FEATURE:
<223> OTHER INFORMATION: Peptide derived from Medicago truncatula

<400> SEQUENCE: 112

Met Glu Asp Ile Val Lys Phe Val Tyr Val Ile Ile Phe Leu Ser
1               5                   10                  15

Ile Phe Ile Ile Ala Thr Asn Met Glu Ala Lys Thr Ile Cys Ile Gly
            20                  25                  30

Asp Ser Asp Cys Arg Asn Glu Arg Cys Met Pro Gly Ile Lys Pro Val
            35                  40                  45

Cys Ser Glu Gly Trp Cys Asp Cys Ile Gly Phe Ile Pro
50                  55                  60

<210> SEQ ID NO 113
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 113

Met Ala Lys Thr Leu Lys Val Met Tyr Thr Met Val Leu Phe Phe Ser
1               5                   10                  15

Leu Phe Leu Val Ala Lys Asn Val Asp Ala Tyr Val Trp Cys Glu Thr
            20                  25                  30

Val Glu Asp Cys Phe Lys Ser Gln Tyr Phe Ile Phe Asp Cys Ile Asn
            35                  40                  45

Asn Gln Cys Ile Asn Val Gly Lys Asn Pro Lys Glu Pro Arg Tyr Pro
50                  55                  60

Gly Ile Pro Arg Asp Gln
65                  70

<210> SEQ ID NO 114
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 114

Met Ile Lys Val Val Lys Phe Ile Tyr Val Met Ile Ile Leu Ser
1               5                   10                  15

Leu Phe Gln Leu Ser Ile Asn Ala Arg Glu Lys Val Asn Cys Leu Asp
            20                  25                  30

Asp Ala Asp Cys Leu Glu Val Ser Cys Leu Asn Gly Ser Asn Ala Glu
            35                  40                  45

Cys Val Gly Asn Ser Cys Val Cys Val Phe Val Phe Tyr Arg Glu Asn
50                  55                  60

Phe Asp Glu Gln Phe Arg Arg
65                  70

<210> SEQ ID NO 115
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 115

Met Asn Pro Asn Ile Arg Leu Phe Tyr Asp Leu Ile Ile Phe Leu Ser
```

```
                1               5                  10                 15
Leu Leu Leu Val Leu Thr Asp Gly Ser Val Pro Cys Leu Thr Ser Phe
                        20                  25                 30

Gly Cys Pro Arg Ser Thr Cys Tyr Pro Pro Ser Thr Pro Asn Cys Ile
                        35                  40                 45

Leu Arg Ile Cys Glu Cys Ile
            50                  55

<210> SEQ ID NO 116
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 116

Met Gly Glu Thr Leu Lys Phe Val Tyr Thr Met Ser Ile Phe Leu Ser
1               5                  10                 15

Leu Phe Leu Val Val Thr Ser Ile Val Gly Glu Glu Trp Asn Ser His
                        20                  25                 30

Ser Trp Asn Ser Glu Phe Tyr Leu Lys Lys Ser Cys Ser Ser Asp Phe
                        35                  40                 45

Asp Cys Pro Arg Thr Met Cys Ile Lys Leu Ser Leu Ala Arg Cys Phe
            50                  55                  60

Asn Asp Phe Cys His Cys Tyr
65                      70

<210> SEQ ID NO 117
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 117

Met Ala Arg Ile Leu Lys Asn Val Tyr Thr Ile Ile His Phe Leu Ile
1               5                  10                 15

Ile Asn Phe Leu Leu Leu Phe His Val Leu Asn Val Arg Arg Gln Thr
                        20                  25                 30

Glu Pro Pro Gly Pro Leu Ile Pro Cys Glu Phe Asp Tyr Asp Cys Pro
                        35                  40                 45

Leu Ile Asp Cys Ile Arg Thr Ser Asp Ser Arg Cys Ile Asn Gly Asn
            50                  55                  60

Cys His Cys Arg Glu
65

<210> SEQ ID NO 118
<211> LENGTH: 76
<212> TYPE: PRT
<213> ORGANISM: Artificial sequence
<220> FEATURE:
<223> OTHER INFORMATION: Peptide derived from Medicago truncatula

<400> SEQUENCE: 118

Met Gln Met Arg Lys Asn Met Ala Gln Ile Leu Phe Tyr Val Tyr Ala
1               5                  10                 15

Leu Leu Ile Leu Phe Ser Pro Phe Leu Val Ala Arg Ile Met Val Val
                        20                  25                 30

Asn Pro Asn Asn Pro Cys Val Thr Asp Ala Asp Cys Gln Arg Tyr Arg
                        35                  40                 45
```

```
His Lys Leu Ala Thr Arg Met Val Cys Asn Ile Gly Phe Cys Leu Met
    50                  55                  60

Asp Phe Thr His Asp Pro Tyr Ala Pro Ser Leu Pro
65                  70                  75

<210> SEQ ID NO 119
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 119

Met Gln Ile Gly Arg Lys Lys Met Gly Glu Thr Pro Lys Leu Val Tyr
1               5                   10                  15

Val Ile Ile Leu Phe Leu Ser Ile Phe Leu Cys Thr Asn Ser Ser Phe
            20                  25                  30

Ser Gln Met Ile Asn Phe Arg Gly Cys Lys Arg Asp Lys Asp Cys Pro
        35                  40                  45

Gln Phe Arg Gly Val Asn Ile Arg Cys Arg Ser Gly Phe Cys Thr Pro
    50                  55                  60

Ile Asp Ser
65

<210> SEQ ID NO 120
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 120

Met Ala Lys Phe Val Asn Phe Val Tyr Ser Met Ile Ile Phe Leu Ser
1               5                   10                  15

Leu Leu Val Val Ala Met Asn Ala Lys Arg Asn Tyr Gln Cys Asp Pro
            20                  25                  30

Cys Phe Gly His Pro Asp Asp Met Ile Asn Phe Cys Pro Pro Gly Thr
        35                  40                  45

Ala Pro Lys Cys Phe His Gly Leu Ile Lys Cys Val Pro Ile Met Arg
    50                  55                  60

Gly Thr Asn Arg Met Phe Ala
65                  70

<210> SEQ ID NO 121
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 121

Met Asp Ala Ile Leu Lys Phe Ile Tyr Ala Met Phe Leu Phe Leu Phe
1               5                   10                  15

Leu Phe Val Thr Thr Arg Asn Val Glu Ala Leu Phe Glu Cys Asn Arg
            20                  25                  30

Asp Phe Val Cys Gly Asn Asp Asp Glu Cys Val Tyr Pro Tyr Ala Val
        35                  40                  45

Gln Cys Ile His Arg Tyr Cys Lys Cys Leu Lys Ser Arg Asn
    50                  55                  60

<210> SEQ ID NO 122
```

```
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 122

Met Ala Val Ile Leu Lys Phe Val Tyr Ile Met Ile Phe Leu Phe
1               5                   10                  15

Leu Leu Tyr Val Val Asn Gly Thr Arg Cys Asn Arg Asp Glu Asp Cys
                20                  25                  30

Pro Phe Ile Cys Thr Gly Pro Gln Ile Pro Lys Cys Val Ser His Ile
            35                  40                  45

Cys Phe Cys Leu Ser Ser Gly Lys Glu Ala Tyr
        50                  55

<210> SEQ ID NO 123
<211> LENGTH: 76
<212> TYPE: PRT
<213> ORGANISM: Artificial sequence
<220> FEATURE:
<223> OTHER INFORMATION: Peptide derived from Medicago truncatula

<400> SEQUENCE: 123

Met Gln Lys Ala Arg Asn Met Ala Lys Leu Val Lys Leu Val Tyr Val
1               5                   10                  15

Ile Ile Val Phe Tyr Thr Leu Phe Leu Val Ala Thr Glu Ile Val Ser
                20                  25                  30

Gly Ile Pro Cys Asn Asp Val Asp Cys Pro Gln Thr Leu Cys Glu
            35                  40                  45

Gln Leu Ile Ala Asp Phe Lys Tyr Met Ile Asp Phe Lys Ser Glu Cys
        50                  55                  60

Val Ser Arg Met Cys Ala Cys Thr Gly Ser Pro Val
65                  70                  75

<210> SEQ ID NO 124
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 124

Met Ala His Ile Leu Lys Phe Val Tyr Ala Thr Ile Leu Val Leu Phe
1               5                   10                  15

Leu Phe Phe Val Ala Thr Lys Val Asp Gly Ala Val His Lys Glu Cys
                20                  25                  30

Lys Thr Asp Val Asp Cys Arg Gln Ile Trp Phe Val Thr Lys Cys Ile
            35                  40                  45

Asn His Glu Cys Gln Pro Ile Leu
        50                  55

<210> SEQ ID NO 125
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 125

Met Ala Lys Leu Val Lys Phe Val Tyr Val Ile Ile Val Phe Tyr Thr
1               5                   10                  15
```

```
Leu Phe Leu Val Gly Thr Glu Ile Val Ser Gly His Ala Cys Thr Val
            20                  25                  30

Asn Ala Asp Cys Glu Gln Ser Met Cys Asp Pro Phe Cys Val Gly Gly
            35                  40                  45

Tyr His Phe Thr Pro Ile Cys Val Ile Gly Trp Cys Val Cys Val Gly
            50                  55                  60

Asn Arg Val Ala Pro Val Leu
65                  70
```

<210> SEQ ID NO 126
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 126

```
Met Ile Gln Ile Leu Ile Phe Val Tyr Ala Leu Ile Ile Phe Ile Ser
1               5                   10                  15

Leu Phe Leu Val Val Thr Ser Glu Thr His Ile Pro Cys Val His His
            20                  25                  30

Asp Asp Cys Pro Lys Arg Pro Tyr Pro Arg Phe Met Lys Cys Val Asp
            35                  40                  45

Asn Phe Cys Glu Thr Trp Ile Ile Gly Trp Glu
            50                  55
```

<210> SEQ ID NO 127
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 127

```
Met Leu Arg Arg Lys Asn Thr Val Gln Ile Leu Met Phe Val Ser Ala
1               5                   10                  15

Leu Leu Ile Tyr Ile Phe Leu Phe Leu Val Ile Thr Ser Ser Ala Asn
            20                  25                  30

Ile Pro Cys Asn Ser Asp Ser Asp Cys Pro Trp Lys Ile Tyr Tyr Thr
            35                  40                  45

Tyr Arg Cys Asn Asp Gly Phe Cys Val Tyr Lys Ser Ile Asp Pro Ser
            50                  55                  60

Thr Ile Pro Gln Tyr Met Thr Asp Leu Ile Phe Pro Arg
65                  70                  75
```

<210> SEQ ID NO 128
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 128

```
Met Ala Gln Thr Leu Met Leu Val Tyr Ala Leu Ile Ile Phe Thr Ser
1               5                   10                  15

Leu Phe Leu Val Val Ile Ser Arg Gln Thr Asp Ile Pro Cys Lys Ser
            20                  25                  30

Asp Asp Ala Cys Pro Arg Val Ser Ser His His Ile Glu Cys Val Lys
            35                  40                  45

Gly Phe Cys Thr Tyr Trp Lys Leu Asp
            50                  55
```

<210> SEQ ID NO 129
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 129

Met Gln Arg Lys Lys Asn Met Gly Gln Ile Leu Ile Phe Val Phe Ala
1               5                   10                  15

Leu Ile Asn Phe Leu Ser Pro Ile Leu Val Glu Met Thr Thr Thr Thr
            20                  25                  30

Ile Pro Cys Thr Ser Ile Asp Asp Cys Pro Lys Met Pro Leu Val Val
        35                  40                  45

Lys Cys Ile Asp Asn Phe Cys Asn Tyr Phe Glu Ile Lys
    50                  55                  60

<210> SEQ ID NO 130
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 130

Met Val Lys Thr Phe Asn Phe Val Cys Thr Met Val Leu Leu Phe Phe
1               5                   10                  15

Leu Phe Leu Thr Ala Lys Lys Val Tyr Ala Tyr His Leu Cys Lys Thr
            20                  25                  30

Arg Phe Asp Cys Pro Arg Thr Tyr Leu Leu Phe Phe Pro Arg Met Trp
        35                  40                  45

Lys Cys Ile Asn Arg Arg Cys Arg Tyr Val Tyr Phe Phe Glu
    50                  55                  60

<210> SEQ ID NO 131
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 131

Met Ala Gln Ile Phe Lys Phe Phe Tyr Val Met Thr Ile Phe Ile Tyr
1               5                   10                  15

Leu Phe Leu Val Ser Thr Thr Val Asp Ala Gly Met Arg Cys Asn His
            20                  25                  30

Val Ser Asp Cys Pro Lys Asp Thr Phe Cys Trp Leu Asp Ser His Met
        35                  40                  45

Gln Cys Ile Lys His Gln Cys Lys Cys Val Arg Ile Phe Glu Pro Ile
    50                  55                  60

Asp Pro Ala
65

<210> SEQ ID NO 132
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 132

```
Met Ala Ile Ser Tyr Lys Phe Val Tyr Ala Ile Ile Phe Phe Ile Phe
1               5                   10                  15

Leu Phe Leu Val Ala Asn Asn Val Glu Gly Tyr Ile Val Cys Ile Thr
                20                  25                  30

Asp Asn Asp Cys Pro Glu Asn Thr Glu Val Arg Gln Tyr Glu Cys Ile
            35                  40                  45

Glu Gly Arg Cys Arg Leu Ser Arg Val Leu Asn Pro
50                  55                  60
```

<210> SEQ ID NO 133
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 133

```
Met Ala Gln Ile Leu Ile Leu Phe Tyr Val Met Thr Ile Phe Ile Tyr
1               5                   10                  15

Leu Phe Leu Val Ser Thr Asn Val Asp Ala Gly Ile Arg Cys Arg Asn
                20                  25                  30

Val Tyr Asp Cys Pro Lys Ala Thr Tyr Cys Arg Ala Gly Ser His Arg
            35                  40                  45

Val Gln Cys Ile Lys His Gln Cys Lys Cys Val Arg Ile Phe Glu Ser
50                  55                  60

Ile Asp Pro Ala
65
```

<210> SEQ ID NO 134
<211> LENGTH: 80
<212> TYPE: PRT
<213> ORGANISM: Artificial sequence
<220> FEATURE:
<223> OTHER INFORMATION: Peptide derived from Medicago truncatula

<400> SEQUENCE: 134

```
Leu Ser Lys Thr Leu Lys Phe Phe Tyr Ala Met Ile Leu Phe Leu Ser
1               5                   10                  15

Leu Phe Leu Val Ala Lys Glu Ile Glu Gly Cys Glu Asp Asp Ser Asp
                20                  25                  30

Cys Pro Gln Ile Phe Asn Phe His Pro Phe Ile Cys Lys Cys Ile Asn
            35                  40                  45

Asn Glu Cys Glu Lys Val Ile Leu Gln Lys Gly Tyr Met Ser Met Lys
50                  55                  60

Pro Lys Ile Leu His Lys Arg Tyr Thr Arg Lys Asn Glu Phe Leu His
65                  70                  75                  80
```

<210> SEQ ID NO 135
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 135

```
Met Ala Glu Ile Val Lys Leu Ile Tyr Val Met Ile Ile Phe Phe Tyr
1               5                   10                  15

Val Phe Leu Val Ser Met Asn Val Asp Ala Ser Asp Glu Cys Val Lys
                20                  25                  30

Val Ser Asp Cys Ser Pro Thr Lys Tyr Cys Leu Pro Gly Arg Arg Met
            35                  40                  45
```

```
Ile Cys Ser Lys Gly Lys Cys Lys Cys Leu Arg Asn Met Phe Ile Pro
    50                  55                  60

Ile Pro Glu
65

<210> SEQ ID NO 136
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 136

Met Ala His Lys Phe Val Tyr Ala Ile Ile Leu Phe Ile Phe Leu Phe
1               5                   10                  15

Leu Val Ala Lys Asn Val Lys Gly Tyr Val Val Cys Arg Thr Val Asp
            20                  25                  30

Asp Cys Pro Pro Asp Thr Arg Asp Leu Arg Tyr Arg Cys Leu Asn Gly
        35                  40                  45

Lys Cys Lys Ser Tyr Arg Leu Ser Tyr Gly
    50                  55

<210> SEQ ID NO 137
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 137

Asp Lys Thr Leu Lys Phe Val Tyr Ile Met Ile Leu Phe Leu Ser Ile
1               5                   10                  15

Phe Tyr Ile Leu Ile Val Cys Asp Ser Asn Ala Phe Gly Met Thr Leu
            20                  25                  30

Arg Pro Cys Leu Thr Asp Lys Asp Cys Pro Arg Met Pro Pro His Asn
        35                  40                  45

Ile Lys Cys Arg Lys Gly His Cys Val Pro Ile Gly Lys Pro Phe Lys
    50                  55                  60

<210> SEQ ID NO 138
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 138

Met Ala Lys Phe Ser Met Phe Val Tyr Ala Leu Ile Asn Phe Leu Ser
1               5                   10                  15

Leu Phe Leu Val Glu Thr Ala Ile Thr Asn Ile Arg Cys Val Ser Asp
            20                  25                  30

Asp Asp Cys Pro Lys Val Ile Lys Pro Leu Val Met Lys Cys Ile Gly
        35                  40                  45

Asn Tyr Cys Tyr Phe Phe Met Ile Tyr Glu Gly Pro
    50                  55                  60

<210> SEQ ID NO 139
<211> LENGTH: 65
<212> TYPE: PRT
<213> ORGANISM: Artificial sequence
<220> FEATURE:
<223> OTHER INFORMATION: Peptide derived from Medicago truncatula
```

```
<400> SEQUENCE: 139

Met Ala Gln Ile Leu Phe Tyr Val Tyr Ala Leu Ile Ile Leu Phe Ser
1               5                   10                  15

Pro Phe Leu Ala Ala Leu Val Ile Ile Asp His His Lys Pro Cys Val
                20                  25                  30

Ser Asp Thr Asp Cys Ala Phe Tyr Leu Asp Ile Pro Pro Thr Val Lys
            35                  40                  45

Tyr Cys Ser Asp Gly Leu Cys Ala Trp Tyr Phe Pro Asp Asn Pro Leu
    50                  55                  60

Pro
65

<210> SEQ ID NO 140
<211> LENGTH: 145
<212> TYPE: PRT
<213> ORGANISM: Artificial sequence
<220> FEATURE:
<223> OTHER INFORMATION: Peptide derived from Medicago truncatula

<400> SEQUENCE: 140

Met Ser Gln Val Val Met Phe Val Tyr Thr Leu Ile Ile Phe Leu Phe
1               5                   10                  15

Pro Ser His Val Ile Thr Asn Lys Ile Ala Ile Tyr Cys Val Ser Asp
                20                  25                  30

Asp Asp Cys Leu Lys Thr Phe Thr Pro Leu Asp Leu Lys Cys Val Asp
            35                  40                  45

Asn Val Cys Glu Phe Asn Leu Arg Cys Lys Gly Lys Cys Gly Glu Arg
    50                  55                  60

Asp Glu Lys Phe Val Phe Leu Lys Ala Leu Lys Lys Met Asp Gln Lys
65                  70                  75                  80

Leu Val Leu Glu Glu Gln Gly Asn Ala Arg Glu Val Lys Ile Pro Lys
                85                  90                  95

Lys Leu Leu Phe Asp Arg Ile Gln Val Pro Thr Pro Ala Thr Lys Asp
            100                 105                 110

Gln Val Glu Glu Asp Asp Tyr Asp Asp Asp Glu Glu Glu Glu
        115                 120                 125

Glu Glu Asp Asp Val Asp Met Trp Phe His Leu Pro Asp Val Val Cys
    130                 135                 140

His
145

<210> SEQ ID NO 141
<211> LENGTH: 136
<212> TYPE: PRT
<213> ORGANISM: Artificial sequence
<220> FEATURE:
<223> OTHER INFORMATION: Peptide derived from Medicago truncatula

<400> SEQUENCE: 141

Met Phe Val Tyr Thr Leu Ile Ile Phe Leu Phe Pro Ser His Val Val
1               5                   10                  15

Thr Asn Lys Ile Ala Ile Tyr Cys Val Ser Asp Asp Cys Leu Lys
                20                  25                  30

Thr Phe Thr Pro Leu Asp Leu Lys Cys Val Asp Asn Val Cys Glu Phe
            35                  40                  45

Asn Leu Arg Cys Lys Gly Lys Cys Gly Glu Arg Asp Glu Lys Val Val
    50                  55                  60
```

Leu Val Lys Ala Leu Lys Lys Ile Asp Glu Lys Val Leu Glu Glu
65                  70                  75                  80

Gln Gly Asn Ala Arg Glu Val Lys Ile Thr Lys Lys Leu Leu Phe Asp
                85                  90                  95

Gly Ile Pro Thr Pro Ala Thr Lys Asp Gln Val Glu Glu Asp Asp
            100                 105                 110

Tyr Gly Asp Asp Glu Glu Glu Glu Asp Asp Val Asp Met Trp Phe
        115                 120                 125

Asn Leu Pro Asp Val Val Cys Arg
    130                 135

<210> SEQ ID NO 142
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 142

Met Ala Gln Ile Leu Met Phe Phe Tyr Ser Leu Ile Ile Phe Ile Ser
1               5                   10                  15

Leu Leu Thr Ser His Pro Cys Ile Ser Asp Asp Asp Cys Pro Glu Ala
            20                  25                  30

Leu Ser Pro Gln Phe Pro Lys Cys Ile His Asn Val Cys Val Tyr Phe
        35                  40                  45

Val Glu Glu
    50

<210> SEQ ID NO 143
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 143

Met Ala Glu Thr Leu Lys Phe Val Tyr Val Leu Ile Leu Phe Ile Ser
1               5                   10                  15

Ile Leu Phe Val Val Ile Val Cys Asp Ser Ser Tyr Ile Pro Ile Ser
            20                  25                  30

His Pro Cys Thr Thr Val Lys Asp Cys Pro Glu Val Lys Asn Tyr Lys
        35                  40                  45

Ser Arg Cys Leu Lys Gly Leu Cys Ile Ser Gly Arg Leu Arg
    50                  55                  60

<210> SEQ ID NO 144
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 144

Met Gln Arg Arg Lys Lys Ser Met Ala Lys Met Leu Phe Phe Phe
1               5                   10                  15

Ala Ile Ile Leu Leu Leu Ser Leu Phe Leu Val Ala Thr Glu Val Gly
            20                  25                  30

Gly Ala Tyr Ile Glu Cys Glu Val Asp Asp Cys Pro Lys Pro Met
        35                  40                  45

Lys Asn Ser His Pro Asp Thr Tyr Lys Cys Val Lys His Arg Cys
    50                  55                  60

```
Gln Trp Ala Trp Lys
 65

<210> SEQ ID NO 145
<211> LENGTH: 54
<212> TYPE: PRT
<213> ORGANISM: Artificial sequence
<220> FEATURE:
<223> OTHER INFORMATION: Peptide derived from Medicago truncatula

<400> SEQUENCE: 145

Met Phe Val Tyr Asp Leu Ile Leu Phe Ile Ser Leu Ile Leu Val Val
  1               5                  10                  15

Thr Gly Ile Asn Ala Glu Ala Asp Thr Ser Cys His Ser Phe Asp Asp
             20                  25                  30

Cys Pro Trp Val Ala His His Tyr Arg Glu Cys Ile Glu Gly Leu Cys
         35                  40                  45

Ala Tyr Arg Ile Leu Tyr
     50

<210> SEQ ID NO 146
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 146

Met Gln Ile Arg Lys Ile Met Ser Gly Val Leu Lys Phe Val Tyr Ala
  1               5                  10                  15

Ile Ile Leu Phe Leu Phe Leu Phe Leu Val Ala Arg Glu Val Gly Gly
             20                  25                  30

Leu Glu Thr Ile Glu Cys Glu Thr Asp Gly Asp Cys Pro Arg Ser Met
         35                  40                  45

Ile Lys Met Trp Asn Lys Asn Tyr Arg His Lys Cys Ile Asp Gly Lys
     50                  55                  60

Cys Glu Trp Ile Lys Lys Leu Pro
 65                  70

<210> SEQ ID NO 147
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 147

Met Gln Arg Val Lys Lys Met Ser Glu Thr Leu Lys Phe Val Tyr Val
  1               5                  10                  15

Leu Ile Leu Phe Ile Ser Ile Phe His Val Val Ile Val Cys Asp Ser
             20                  25                  30

Ile Tyr Phe Pro Val Ser Arg Pro Cys Ile Thr Asp Lys Asp Cys Pro
         35                  40                  45

Asn Met Lys His Tyr Lys Ala Lys Cys Arg Lys Gly Phe Cys Ile Ser
     50                  55                  60

Ser Arg Val Arg
 65

<210> SEQ ID NO 148
<211> LENGTH: 60
<212> TYPE: PRT
```

```
<213> ORGANISM: Artificial sequence
<220> FEATURE:
<223> OTHER INFORMATION: Peptide derived from Medicago truncatula

<400> SEQUENCE: 148

Met Ala Lys Thr Leu Asn Tyr Val Tyr Val Leu Ile Leu Phe Ile Ser
1               5                   10                  15

Ile Phe Leu Ser Ile Thr Val Tyr Gly Tyr Ile Pro Gly Ile Val Asn
            20                  25                  30

Lys Pro Cys Lys Thr Asp Lys Asp Cys Pro Lys Lys Pro His Asn
        35                  40                  45

Ile Arg Cys Arg Lys Gly Gln Cys Val Glu Ile Leu
    50                  55                  60

<210> SEQ ID NO 149
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 149

Met Ala Gln Ser Leu Ile Phe Val Tyr Ala Leu Ile Ile Phe Leu Phe
1               5                   10                  15

Leu Phe Arg Val Glu Ala Glu His Leu Lys Ile Arg Cys Val Thr Asp
            20                  25                  30

Asp Asp Cys Pro Lys Val Glu Lys Pro Leu Tyr Met Tyr Cys Gly Asn
        35                  40                  45

His Trp Cys Ala Tyr Lys Leu His Phe Val
    50                  55

<210> SEQ ID NO 150
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 150

Met Ala Gly Ile Pro Cys Tyr Phe Tyr Gly Ser Ile Ile Phe Leu Ser
1               5                   10                  15

Leu Phe Leu Leu Ala Ala Phe Phe Glu Lys Gly Tyr Met Ile Pro Cys
            20                  25                  30

Ala Thr Ser Asp Asp Cys Leu Lys Asn Met Cys Arg Pro Pro Leu Thr
        35                  40                  45

Pro Arg Cys Ile Glu His Asn Cys Lys Cys Lys
    50                  55

<210> SEQ ID NO 151
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 151

Phe Phe Gly Ser Ser Ile Pro Ser Ile Leu Leu Ile Val Ser Asp Arg
1               5                   10                  15

Ile Pro Cys Ile Asp Asp Met Asp Cys Pro Asp Met Phe Pro Ser Leu
            20                  25                  30

Asn Thr Gln Cys Ile Asp Asn Phe Cys Asp Val Val Leu Gly Tyr Asn
        35                  40                  45
```

<210> SEQ ID NO 152
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 152

```
Ala Glu Ile Phe Lys Phe Val Tyr Lys Trp Ile Leu Phe Val Ser Leu
1               5                   10                  15

Phe Leu Val Ile Val Ala Lys Glu Asp Asp Ile Glu Cys Val Thr Asp
            20                  25                  30

Ala Asp Cys Tyr Glu Lys Leu Pro Ala Leu Gln Arg Ala Val Met Lys
        35                  40                  45

Cys Ile Gln Gly Phe Cys Lys Ile His Ile
    50                  55
```

<210> SEQ ID NO 153
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 153

```
Met Ala Gln Leu Ser Tyr Ile Phe Tyr Ala Phe Ile Ile Phe Leu Cys
1               5                   10                  15

Val Phe Phe Val Pro Thr Lys Ser Asn Ser Ile Pro Cys Thr Thr His
            20                  25                  30

Ala Gln Cys Pro Gly Asp Met Cys Glu Leu Pro Gln Ile Val Trp Cys
        35                  40                  45

Val Val Gly Phe Cys Glu Cys Ala
    50                  55
```

<210> SEQ ID NO 154
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 154

```
Ala Trp Asn Leu Lys Phe Val Tyr Val Met Val Leu Phe Phe Ser Leu
1               5                   10                  15

Leu Ile Val Val Ile Asn Ile Asp Ala Tyr Arg Ser Cys Lys Thr Asp
            20                  25                  30

Asp Asp Cys Pro Asp Tyr Leu Cys Thr Ser Pro Lys Ile Gly Lys Cys
        35                  40                  45

Met Asp Asn Asp Cys Tyr Cys Ile
    50                  55
```

<210> SEQ ID NO 155
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 155

```
Met Val Glu Ala Leu Lys Leu Val Asn Val Leu Ile Leu Phe Leu Ser
1               5                   10                  15
```

```
Ile Phe Leu Ser Ile Ile Val Ser Thr Ser Ser Phe Pro Trp Lys Leu
            20                  25                  30

Tyr Pro Cys Val Thr Asp Lys Asp Cys Pro Arg Lys Asn Arg His Val
            35                  40                  45

Val Lys Cys Arg Lys Gly Tyr Cys Val Gly Val Gln Ile Ile
50                  55                  60

<210> SEQ ID NO 156
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 156

Met Gln Ser Val Glu Asn Met Ala Glu Val Ile Lys Phe Val Asn Val
1               5                   10                  15

Ile Ile Ile Phe Ile Ser Leu Phe Pro Phe Ala Met Thr Val Asp Ala
            20                  25                  30

Asn Met Val Ile Cys Thr Gln Asp Phe Asp Cys Gln Thr Lys Ile Cys
            35                  40                  45

Pro Phe Asp Leu Gln Pro Lys Cys Thr Ile Leu Phe Glu Phe Leu Leu
            50                  55                  60

Ser Leu Cys Gly Cys Val
65                  70

<210> SEQ ID NO 157
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 157

Met Ala Ala Ile Ile Lys Phe Ile Tyr Thr Met Phe Leu Phe Ile Phe
1               5                   10                  15

Leu Phe Val Val Pro Thr Lys Val Asp Ala Leu Ala Gly Cys Ile Thr
            20                  25                  30

Asp Ala Asp Cys Val Ile Lys Lys Cys Ser Ser Ser Cys Arg Ile Lys
            35                  40                  45

Cys Ile Asp Phe Arg Cys Leu Cys Pro Thr Gly Phe
            50                  55                  60

<210> SEQ ID NO 158
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 158

Met Ala Arg Ile Leu Ser Phe Phe Tyr Ala Leu Leu Ile Phe Val Ser
1               5                   10                  15

Leu Phe Leu Val Thr Thr Asn Gly Ser Leu Pro Asp Ala Pro Pro Cys
            20                  25                  30

Leu Phe Thr Pro Glu Cys Pro Pro Asp Met Cys Pro Thr Asp Leu Thr
            35                  40                  45

Leu Lys Cys Ile Asn Leu Ser Cys Gln Cys Thr Ile Glu Tyr Asp Ile
            50                  55                  60

Asp Pro Asp Val Val Pro Ser
65                  70
```

<210> SEQ ID NO 159
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 159

Met Ala Asn Ile Thr Lys Phe Val Tyr Ile Ala Leu Phe Leu Ser
1               5                   10                  15

Leu Phe Phe Ile Gly Met Asn Asp Ala Ala Ile Leu Glu Cys Arg Glu
                20                  25                  30

Asp Ser His Cys Val Thr Lys Ile Lys Cys Val Leu Pro Arg Lys Pro
            35                  40                  45

Glu Cys Arg Asn Asn Ala Cys Thr Cys Tyr Lys Gly Gly Phe Ser Phe
    50                  55                  60

His His
65

<210> SEQ ID NO 160
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 160

Met Ala Gln Ile Pro Arg Tyr Phe Tyr Ala Phe Ile Ile Phe Leu Tyr
1               5                   10                  15

Leu Phe His Val Ala Thr Thr Asn Arg Phe Leu Tyr Arg Ile Gly Cys
                20                  25                  30

Asp Thr Ser Asn Asp Cys Pro Ser Tyr Met Cys Pro Pro Pro Leu Ser
            35                  40                  45

Pro Arg Cys Thr Lys Phe Tyr Cys Lys Cys Ile
    50                  55

<210> SEQ ID NO 161
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 161

Met Ala Glu Ile Leu Lys Phe Val Tyr Ile Val Ile Leu Phe Ile Ser
1               5                   10                  15

Ile Leu Leu Val Val Glu Thr Glu Gln Cys Val Tyr Asp Ala Asp Cys
                20                  25                  30

Glu Lys Ile Tyr Pro Leu His Arg Gln His Leu Phe Lys Cys Ile Lys
            35                  40                  45

Ala Phe Cys Val Arg Ser Ser
    50                  55

<210> SEQ ID NO 162
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 162

-continued

```
Met Ala Arg Ile Leu Tyr Phe Phe Tyr Thr Leu Ile Phe Val Ser
1               5                   10                  15

Leu Phe Met Ile Ala Ile Asn Gly Ser Leu Pro Asp Ala Pro Pro Cys
            20                  25                  30

Leu Phe Thr Pro Glu Cys Pro Pro Asp Met Cys Pro Thr Asp Leu Thr
            35                  40                  45

Leu Lys Cys Ile Asn Leu Thr Cys Gln Cys Thr Ser Glu Tyr Asp Ile
        50                  55                  60

Asp
65

<210> SEQ ID NO 163
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 163

Met Ala Lys Ile Ile Lys Phe Val Tyr Val Met Ile Ile Ile Ile Ser
1               5                   10                  15

Phe Phe Leu Val Ala Thr Asn Ala Lys Asp Asp Cys Leu Val Asp Ala
            20                  25                  30

Asp Cys Val Thr Leu Val Cys Glu Phe Asp Glu Arg Pro Gln Cys Val
            35                  40                  45

Ile Asn Thr Cys Arg Cys Arg Pro Leu Arg Phe Ser Gly Phe Tyr Tyr
        50                  55                  60

Glu Gln Leu His
65

<210> SEQ ID NO 164
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 164

Met Gln Lys Arg Arg Asn Met Ala Ala Ile Leu Lys Phe Val Tyr Ile
1               5                   10                  15

Met Ile Ile Tyr Leu Phe Val Leu Leu Val Ala Val Lys Ala Phe Glu
            20                  25                  30

Glu Cys Lys Glu Asp Ala Asp Cys His Pro Val Cys Ser Val Pro Gly
            35                  40                  45

Cys Ser Asn Ile Cys Thr Leu Pro Asp Val Pro Thr Cys Ile Asp Asn
        50                  55                  60

Asn Cys Phe Cys Ile
65

<210> SEQ ID NO 165
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 165

Met Ala Arg Thr Leu Lys Phe Val Tyr Ser Met Ile Leu Phe Leu Ser
1               5                   10                  15

Leu Phe Leu Val Ala Asn Gly Leu Lys Ile Phe Cys Ile Asp Val Ala
            20                  25                  30
```

```
Asp Cys Pro Lys Asp Leu Tyr Pro Leu Leu Tyr Lys Cys Ile Tyr Asn
        35                  40                  45

Lys Cys Ile Val Phe Thr Arg Ile Pro Phe Pro Phe Asp Trp Ile
 50                  55                  60
```

<210> SEQ ID NO 166
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 166

```
Lys Ile Ile Asn Phe Val Tyr Asn Met Ile Ile Phe Phe Ser Leu Phe
 1               5                  10                  15

Leu Val Ala Thr Asn Ala Gly Gly Cys Asn Pro Cys Leu Val Thr Cys
                20                  25                  30

Pro Asp Asp Leu Leu Asn Arg Cys Pro Pro Gly Met Glu Pro Ile Cys
            35                  40                  45

Glu Tyr Gly Val Ile Lys Cys Tyr Pro Ile Gly Lys Glu Thr Asn Arg
 50                  55                  60

Val Leu Thr
 65
```

<210> SEQ ID NO 167
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 167

```
Met Ala Arg Ile Leu Cys Phe Phe Tyr Gly Leu Leu Ile Phe Val Ser
 1               5                  10                  15

Leu Phe Met Val Ala Thr Asn Gln Ser Ile Pro Asp Val Leu Pro Cys
                20                  25                  30

Leu Phe Ser Asn Glu Cys Pro Pro Asp Leu Cys Pro Thr Asp Leu Phe
            35                  40                  45

Ala Lys Cys Ile Asn Leu Thr Cys Gln Cys Thr Ala Glu Tyr Asp Leu
 50                  55                  60

Asp
 65
```

<210> SEQ ID NO 168
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 168

```
Met Ala Ser Ile Leu Lys Phe Val Tyr Ile Met Ile Ile Tyr Leu Ser
 1               5                  10                  15

Val Leu Leu Val Val Ile Glu Gly Tyr Pro Phe Gln Glu Cys Lys Val
                20                  25                  30

Asp Ala Asp Cys Pro Thr Val Cys Thr Leu Pro Gly Cys Pro Asp Ile
            35                  40                  45

Cys Ser Phe Pro Asp Val Pro Thr Cys Ile Asp Asn Asn Cys Phe Cys
 50                  55                  60

Thr
```

-continued

<210> SEQ ID NO 169
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 169

Met Gly Glu Met Phe Lys Phe Ile Tyr Thr Phe Ile Leu Phe Val His
1               5                   10                  15

Leu Phe Leu Val Val Ile Phe Glu Asp Ile Gly His Ile Lys Tyr Cys
            20                  25                  30

Gly Ile Val Asp Asp Cys Tyr Lys Ser Lys Lys Pro Leu Phe Lys Ile
        35                  40                  45

Trp Lys Cys Val Glu Asn Val Cys Val Leu Trp Tyr Lys
    50                  55                  60

<210> SEQ ID NO 170
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 170

Met Gln Ile Gly Ser Asn Met Ala Glu Thr Met Lys Leu Val Tyr Val
1               5                   10                  15

Ile Ile Leu Phe Leu Ser Ile Phe Leu Gly Ile Thr Leu Ser Asn Ser
            20                  25                  30

Ala Phe Ser His Phe Ile Pro Gly Cys Lys Thr Asp Lys Asp Cys Pro
        35                  40                  45

Lys Phe Tyr Gly Ser Asn Val Arg Cys Arg Lys Gly Lys Cys Val Gln
    50                  55                  60

Leu Gly
65

<210> SEQ ID NO 171
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 171

Met Gly Glu Ile Met Lys Phe Val Tyr Val Met Ile Ile Tyr Leu Phe
1               5                   10                  15

Met Phe Asn Val Ala Thr Gly Ser Glu Phe Ile Phe Thr Lys Lys Leu
            20                  25                  30

Thr Ser Cys Asp Ser Ser Lys Asp Cys Arg Ser Phe Leu Cys Tyr Ser
        35                  40                  45

Pro Lys Phe Pro Val Cys Lys Arg Gly Ile Cys Glu Cys Ile
    50                  55                  60

<210> SEQ ID NO 172
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 172

```
Met Ala Asn Val Thr Lys Phe Val Tyr Ile Ala Ile Tyr Phe Leu Ser
 1               5                  10                  15

Leu Phe Phe Ile Ala Lys Asn Asp Ala Thr Thr Phe Cys His Asp
             20                  25                  30

Asp Ser His Cys Val Thr Lys Ile Lys Cys Val Leu Pro Arg Thr Pro
             35                  40                  45

Gln Cys Arg Asn Glu Ala Cys Gly Cys Tyr His Ser Asn Lys Phe Arg
 50                  55                  60
```

<210> SEQ ID NO 173
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 173

```
Met Ala Tyr Ile Ser Arg Ile Phe Tyr Val Leu Ile Ile Phe Leu Ser
 1               5                  10                  15

Leu Phe Phe Val Val Ile Asn Gly Val Lys Ser Leu Leu Leu Ile Lys
             20                  25                  30

Val Arg Ser Phe Ile Pro Cys Gln Arg Ser Asp Asp Cys Pro Arg Asn
             35                  40                  45

Leu Cys Val Asp Gln Ile Ile Pro Thr Cys Val Trp Ala Lys Cys Lys
 50                  55                  60

Cys Lys Asn Tyr Asn Asp
65                  70
```

<210> SEQ ID NO 174
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 174

```
Met Ala Val Val Ile Lys Phe Val Asn Val Met Leu Ile Phe Ile Ser
 1               5                  10                  15

Leu Phe Pro Phe Ala Met Asn Val Asp Ala Asn Ile Ile Ser Cys Thr
             20                  25                  30

Gln Asp Phe Asp Cys Gln Thr Lys Ile Cys Pro Phe His Leu Lys Pro
             35                  40                  45

Lys Cys Ile Val Leu Glu Ile Leu Pro His Ser Leu Ser Gly Gly Ile
 50                  55                  60

Cys Gly Cys Asp
65
```

<210> SEQ ID NO 175
<211> LENGTH: 78
<212> TYPE: PRT
<213> ORGANISM: Artificial sequence
<220> FEATURE:
<223> OTHER INFORMATION: Peptide derived from Medicago truncatula

<400> SEQUENCE: 175

```
Met Ala Glu Ile Leu Lys Cys Phe Tyr Thr Met Asn Leu Phe Ile Phe
 1               5                  10                  15

Leu Ile Ile Leu Pro Ala Lys Ile Arg Gly Glu His Ile Gln Cys Val
             20                  25                  30

Ile Asp Asp Asp Cys Pro Lys Ser Leu Asn Lys Leu Leu Ile Ile Lys
```

35                  40                  45

Cys Ile Asn His Val Cys Gln Tyr Val Gly Asn Leu Pro Asp Phe Ala
     50                  55                  60

Ser Gln Ile Pro Lys Ser Thr Lys Met Pro Tyr Lys Gly Glu
 65                  70                  75

<210> SEQ ID NO 176
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 176

Met Ala His Ile Phe Asn Tyr Val Tyr Ala Leu Leu Val Phe Leu Ser
 1               5                  10                  15

Leu Phe Leu Met Val Thr Asn Gly Ile His Ile Gly Cys Asp Lys Asp
                20                  25                  30

Arg Asp Cys Pro Lys Gln Met Cys His Leu Asn Gln Thr Pro Lys Cys
             35                  40                  45

Leu Lys Asn Ile Cys Lys Cys Val
     50                  55

<210> SEQ ID NO 177
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 177

Met Phe Lys Ile Leu Leu Phe Thr Ser Ser Ile Ile Val Phe Leu Ser
 1               5                  10                  15

Leu Phe Phe Val Thr Tyr Glu Asp Phe Trp Asn Val Cys Ala Tyr Asn
                20                  25                  30

Ser Asp Cys Gln Ser Tyr Pro Cys Asp Leu Gly Glu Ser Arg Asn Cys
             35                  40                  45

Thr Leu Asn Arg Cys Ile Cys Val Tyr Asn Ile
     50                  55

<210> SEQ ID NO 178
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 178

Met Gly Glu Ile Leu Lys Phe Val Tyr Asn Val Ile Leu Phe Gly Ser
 1               5                  10                  15

Leu Tyr Leu Leu Val Ile Tyr Ala Glu Arg Glu Cys Asp Thr Asp Ala
                20                  25                  30

Asp Cys Gln Lys Lys Phe Pro Gly Ser Asn Gln His Leu Leu Trp Cys
             35                  40                  45

Asn Asn Gly Phe Cys Asp Cys Arg Thr His
     50                  55

<210> SEQ ID NO 179
<211> LENGTH: 61
<212> TYPE: PRT
<213> ORGANISM: Artificial sequence
<220> FEATURE:

<223> OTHER INFORMATION: Peptide derived from Medicago truncatula
<220> FEATURE:
<221> NAME/KEY: misc_feature
<222> LOCATION: (2)..(2)
<223> OTHER INFORMATION: Xaa can be any naturally occurring amino acid

<400> SEQUENCE: 179

Met Xaa Asn Leu Arg Ile Leu Ile Ile Leu Ile Ile Phe Ile Phe Ile
1               5                   10                  15

Phe Leu Val Leu Ile Val Cys Asp Ser Thr Phe Ile His Phe Ser Ile
            20                  25                  30

Pro Cys Ile Thr Asp Lys Asp Cys Ser Ile Leu Gln Asn Tyr Lys Ala
        35                  40                  45

Arg Cys Arg Lys Gly Tyr Cys Leu Arg Arg Lys Ile Arg
    50                  55                  60

<210> SEQ ID NO 180
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 180

Met Val Gln Ile Gly Cys Phe Phe Tyr Ala Leu Ile Ile Leu Leu Ser
1               5                   10                  15

Pro Phe Leu Val Ala Thr His Gln Ser Ile Asp Asp Val Ile Pro Cys
            20                  25                  30

Val Leu Asn Thr Asp Cys Pro Arg Asp Met Cys Pro Ile His Leu Phe
        35                  40                  45

Pro Lys Cys Ile Asn Leu Leu Cys Arg Cys Ser Tyr Trp Glu Asp Asn
    50                  55                  60

<210> SEQ ID NO 181
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 181

Met Tyr Arg Glu Lys Asn Met Ala Lys Thr Leu Lys Phe Val Tyr Val
1               5                   10                  15

Ile Val Leu Phe Leu Ser Leu Phe Leu Ala Ala Lys Asn Ile Asp Gly
            20                  25                  30

Arg Val Ser Tyr Asn Ser Phe Ile Ala Leu Pro Val Cys Gln Thr Ala
        35                  40                  45

Ala Asp Cys Pro Glu Gly Thr Arg Gly Arg Thr Tyr Lys Cys Ile Asn
    50                  55                  60

Asn Lys Cys Arg Tyr Pro Lys Leu Leu Lys Pro Ile Gln
65                  70                  75

<210> SEQ ID NO 182
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 182

Ala Phe Phe Ile Phe Leu Ser Ile Ala His Arg Pro Pro Ala Asn Thr
1               5                   10                  15

```
Ile Pro Cys Phe Gly Thr Lys Asp Lys Cys Pro Phe Asn Leu Tyr Tyr
            20                  25                  30

Lys Val Glu Cys Ile Asp Gly Phe Cys Tyr Tyr Pro Val
            35                  40                  45

<210> SEQ ID NO 183
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 183

Met Val Lys Thr Pro Lys Leu Val Tyr Val Leu Ile Leu Phe Leu Ser
1               5                   10                  15

Ile Cys Phe Ser Ile Thr Ile Ser Asn Ser Ser Phe Gly Arg Ile Val
            20                  25                  30

Tyr Trp Asn Cys Lys Thr Asp Lys Asp Cys Lys Gln His Arg Gly Phe
        35                  40                  45

Asn Phe Arg Cys Arg Ser Gly Asn Cys Ile Pro Ile Arg Arg
    50                  55                  60

<210> SEQ ID NO 184
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 184

Met Gln Ile Val Lys Asn Met Val Lys Thr Pro Lys Leu Val Tyr Val
1               5                   10                  15

Leu Ile Leu Phe Leu Ser Ile Phe Phe Ser Ile Thr Val Ser Asn Ser
            20                  25                  30

Phe Asn Ser Lys Ile Val Phe Thr Asp Cys Lys Thr Asp Lys Asp Cys
        35                  40                  45

Gln Asn His Arg Gly Phe Asn Phe Arg Cys Arg Lys Gly Asn Cys Val
    50                  55                  60

Ala Lys Ile Arg
65

<210> SEQ ID NO 185
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 185

Met Ala Lys Thr Leu Met Phe Ile Tyr Ile Val Ile Leu Leu Thr Cys
1               5                   10                  15

Val Leu Ala Val Ile Asp Ile Asn Ala Phe Ser Phe Pro Cys Lys Thr
            20                  25                  30

Asn Ser Asp Cys Pro Ser Tyr Leu Cys His Tyr Pro Lys Asn Pro Glu
        35                  40                  45

Cys Val Glu Arg Glu Cys Ile Cys Trp
    50                  55

<210> SEQ ID NO 186
<211> LENGTH: 44
<212> TYPE: PRT
<213> ORGANISM: Artificial sequence
```

```
<220> FEATURE:
<223> OTHER INFORMATION: Peptide derived from Medicago truncatula

<400> SEQUENCE: 186

Phe Ile Val Leu Leu Ser Gln Phe Leu Val Val Ile Asn Gly Ser Ile
1               5                   10                  15

Pro Cys Glu Thr Thr Ala Asp Cys Pro Val Ala Val Pro Pro Glu Tyr
            20                  25                  30

Tyr Lys Cys Met Tyr Lys Val Cys Val Leu Ile Arg
        35                  40

<210> SEQ ID NO 187
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 187

Met Ala His Ile Ile Met Phe Val Tyr Ala Leu Ile Tyr Ala Leu Ile
1               5                   10                  15

Ile Phe Ser Ser Leu Phe Val Arg Asp Gly Ile Pro Cys Leu Ser Asp
            20                  25                  30

Asp Glu Cys Pro Glu Met Ser His Tyr Ser Phe Lys Cys Asn Asn Lys
        35                  40                  45

Ile Cys Glu Tyr Asp Leu Gly Glu Met Ser Asp Asp Tyr Tyr Leu
    50                  55                  60

Glu Met Ser Arg Glu
65

<210> SEQ ID NO 188
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 188

Met Thr Glu Ile Leu Lys Phe Val Cys Ile Met Ile Phe Leu Ser
1               5                   10                  15

Ser Phe Ile Val Ser Gln Asn Ile Asp Ala Gly Gly Asn Arg Lys Cys
            20                  25                  30

Phe Arg Asp Ser Asp Cys Pro Lys Phe Met Cys Pro Ser Tyr Leu Ala
        35                  40                  45

Val Lys Cys Ile Gly Arg Leu Cys Arg Cys Gly Arg Pro Glu Leu Gln
    50                  55                  60

Val Glu Leu Asn Pro Lys
65              70

<210> SEQ ID NO 189
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 189

Met Thr Glu Ile Leu Lys Phe Val Cys Val Met Ile Ile Phe Ile Ser
1               5                   10                  15

Ser Phe Ile Val Ser Lys Ser Leu Asn Gly Gly Gly Lys Asp Lys Cys
            20                  25                  30
```

```
Phe Arg Asp Ser Asp Cys Pro Lys His Met Cys Pro Ser Ser Leu Val
        35                  40                  45

Ala Lys Cys Ile Asn Arg Leu Cys Arg Cys Arg Arg Pro Glu Leu Gln
 50                  55                  60

Val Gln Leu Asn Pro
 65

<210> SEQ ID NO 190
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 190

Val Asn Phe Ile Tyr Ser Met Ile Ile Phe Leu Phe Leu Phe Pro Val
 1               5                   10                  15

Ala Thr Lys Thr Gln Phe Leu Pro Asn Tyr Tyr Glu Phe Tyr His Cys
             20                  25                  30

Tyr Asn His Ser Asp Cys Gln Gly Ser Met Cys Pro Thr Gly Ser Lys
         35                  40                  45

Pro Lys Cys Val Asp Gln Val Cys Glu Cys Ile Leu Ile Arg Met
 50                  55                  60

<210> SEQ ID NO 191
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 191

Lys Lys Lys Ile Ile Ile Val Leu Cys Thr Leu Phe Tyr His Leu Ser
 1               5                   10                  15

Asn Asn Phe Gln Leu Phe Asp Asn Thr Asp Thr Ala Thr Cys Ile Thr
             20                  25                  30

Asp Ala Asp Cys Pro Tyr Asp Gly Lys Cys Ile Asp Gly Phe Cys Arg
         35                  40                  45

Phe Asn Val Lys Asn Asn Asn Gln Val
 50                  55

<210> SEQ ID NO 192
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 192

Met Ala Lys Ile Phe Asn Tyr Val Tyr Ala Leu Ile Met Phe Leu Ser
 1               5                   10                  15

Leu Phe Leu Met Gly Thr Ser Gly Met Lys Asn Gly Cys Lys His Thr
             20                  25                  30

Gly His Cys Pro Arg Lys Met Cys Gly Ala Lys Thr Thr Lys Cys Arg
         35                  40                  45

Asn Asn Lys Cys Gln Cys Val
 50                  55

<210> SEQ ID NO 193
<211> LENGTH: 64
<212> TYPE: PRT
<213> ORGANISM: Artificial sequence
```

<220> FEATURE:
<223> OTHER INFORMATION: Peptide derived from Medicago truncatula

<400> SEQUENCE: 193

Met Ala Arg Thr Leu Gln Phe Val Tyr Val Met Ile Leu Phe Phe Ser
1               5                   10                  15

Leu Phe Leu Val Ala Lys Gly Asp Asp Val Lys Ile Lys Cys Val Ser
            20                  25                  30

Ala Ile Asp Cys Met Asp Leu Phe Asn Leu Pro Ile Val Tyr Lys
        35                  40                  45

Cys Ile Asn Asn Ile Cys Val Tyr Glu Gln Ser Ser Gln Arg Leu Ile
    50                  55                  60

<210> SEQ ID NO 194
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 194

Met Asp Glu Ile Leu Lys Phe Val Phe Cys Met Ile Ile Phe Leu Ser
1               5                   10                  15

Leu Phe Leu Ile Ala Thr Lys Val Gly Gly Glu His Asn Glu Cys Glu
            20                  25                  30

Thr Asp Ala Asp Cys Pro Lys His Thr Thr Ile Phe Phe Val Met Lys
        35                  40                  45

Cys Ile Asp His Ile Cys Arg Cys Met Lys Thr Ser Ile
    50                  55                  60

<210> SEQ ID NO 195
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 195

Phe Lys Val Leu Asn Ile Val Tyr Ala Met Ile Ile Phe Leu Ser Ile
1               5                   10                  15

Ser Phe Ser Ile Thr Asn Ser Phe Lys Met Phe Cys Arg Tyr Asp Glu
            20                  25                  30

Asp Cys Pro Pro Arg Met Cys Arg Leu Pro Gln Val Pro Gln Cys Asn
        35                  40                  45

Glu Phe Ile Cys Asp Cys Gly Met Pro Val Tyr Lys Pro Tyr Gln Asn
    50                  55                  60

Lys Tyr Ile Lys Lys
65

<210> SEQ ID NO 196
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 196

Met Ala Glu Ile Gly Lys Tyr Ile Tyr Val Ile Ile Phe Phe Ile Ser
1               5                   10                  15

Leu Phe Phe Ile Thr Thr Ser Val Glu Gly Trp Arg Cys Lys Thr Lys
            20                  25                  30

```
Tyr Asp Cys Ile Lys Ile Arg Phe Cys Lys Phe Pro Thr Ile Ala Arg
            35                  40                  45

Cys Thr Lys Pro Asp Phe Leu Phe Leu Glu Tyr Asp Arg Gly Phe Cys
 50                  55                  60

Thr Cys Asp Asp
 65
```

<210> SEQ ID NO 197
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 197

```
Met Gln Arg Leu Glu Asn Thr Thr Glu Val Val Met Leu Ile Tyr Val
  1               5                  10                  15

Met Ile Ile Phe Leu Cys Leu Leu Val Thr Met Asn Val Asn Ala
            20                  25                  30

Val Ile Lys Cys Phe Gln Asp Ser Asp Cys Pro Lys Tyr Met Cys Met
            35                  40                  45

Phe Pro Leu Lys Pro Lys Cys Val Tyr Ile Leu Val Phe Pro Pro Pro
 50                  55                  60

Trp Thr Ala Gln Cys Ile Cys Asp
 65                  70
```

<210> SEQ ID NO 198
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 198

```
Met Ala Gln Ile Ser Lys Ser Phe Tyr Ala Leu Ile Ile Phe Leu Ser
  1               5                  10                  15

Leu Ile Leu Val Val Thr Gly Ile Lys Leu Ile Lys Cys Thr Val Ser
            20                  25                  30

Asp Asp Cys Pro Met Asn Phe Arg Cys Pro Pro Asn Thr Phe Val Arg
            35                  40                  45

Cys Ile Ser Asp Leu Cys Thr Cys Arg Ser Leu Leu Asp Glu Gln Ser
 50                  55                  60
```

<210> SEQ ID NO 199
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 199

```
Met Gln Ile Gly Lys Asn Met Val Glu Thr Leu Lys Leu Val Tyr Val
  1               5                  10                  15

Ile Ile Leu Phe Phe Ser Ile Phe Leu Cys Ile Ala Val Ser Asn Ser
            20                  25                  30

Ser Phe Ser Glu Ile Ile Asp Ser Ala Cys Lys Thr Asp Lys Asp Cys
            35                  40                  45

Pro Lys Leu His Lys Val Asn Val Arg Cys Arg Lys Gly Lys Cys Val
 50                  55                  60

Ala Ile
 65
```

<210> SEQ ID NO 200
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 200

Met Ala Lys Val Thr Lys Phe Gly Tyr Ile Ile Ile His Phe Leu Ser
1               5                   10                  15

Leu Phe Phe Leu Ala Met Asn Val Ala Gly Gly Arg Glu Cys His Ala
                20                  25                  30

Asn Ser His Cys Val Gly Lys Ile Thr Cys Val Leu Pro Gln Lys Pro
            35                  40                  45

Glu Cys Trp Asn Tyr Ala Cys Val Cys Tyr Asp Ser Asn Lys Tyr Arg
        50                  55                  60

<210> SEQ ID NO 201
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 201

Met Ala Lys Ile Ile Lys Phe Val Tyr Ile Met Ile Leu Cys Val Ser
1               5                   10                  15

Leu Leu Leu Ile Val Glu Ala Gly Gly Lys Glu Cys Val Thr Asp Val
                20                  25                  30

Asp Cys Glu Lys Ile Tyr Pro Gly Asn Lys Lys Pro Leu Ile Cys Ser
            35                  40                  45

Thr Gly Tyr Cys Tyr Ser Leu Tyr Glu Glu Pro Pro Arg Tyr His Lys
        50                  55                  60

<210> SEQ ID NO 202
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 202

Glu Arg Thr Leu Lys Leu Val Leu Leu Asp Ala Leu Glu Thr Gln Ile
1               5                   10                  15

Val Gln Lys Ala Cys Val Ile Leu Leu Pro Asn Arg Ser Val Cys Thr
                20                  25                  30

Asn Pro Tyr Val Asn Val Tyr Glu Ser Ser Pro Lys Gly Ile Met Cys
            35                  40                  45

Ile His Glu His Val Cys Leu Pro Tyr Leu Arg Ala Tyr Thr Asn Tyr
        50                  55                  60

Ile Pro Ser
65

<210> SEQ ID NO 203
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 203

```
Met Ala Glu Ile Ile Lys Phe Val Tyr Ile Leu Ile Leu Cys Val Ser
1               5                   10                  15

Leu Leu Leu Ile Gly Glu Ala Ser Gly Lys Glu Cys Val Thr Asp Ala
            20                  25                  30

Asp Cys Glu Asn Leu Tyr Tyr Gly Asn Lys Trp Pro Leu Ile Cys Ser
        35                  40                  45

Asn Ile Gly Tyr Cys Leu Ser Ser Tyr Glu Gly Pro Pro His Lys
    50                  55                  60
```

<210> SEQ ID NO 204
<211> LENGTH: 53
<212> TYPE: PRT
<213> ORGANISM: Artificial sequence
<220> FEATURE:
<223> OTHER INFORMATION: Peptide derived from Medicago truncatula

<400> SEQUENCE: 204

```
Lys Ile Met Lys Phe Val His Ala Met Ile Leu Phe Leu Phe Leu Phe
1               5                   10                  15

Ala Ile Asn Val Thr Ala Phe Arg Asp Pro Cys Asn Phe Asp Phe Asp
            20                  25                  30

Cys Arg Asn Ser Asn Cys Thr Ala Pro Tyr Val Ala Thr Cys Met Tyr
        35                  40                  45

Glu His Cys Tyr Cys
    50
```

<210> SEQ ID NO 205
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 205

```
Met Gly Gln Ile Glu Lys Phe Val Tyr Ser Leu Ile Ile Ile Leu Ser
1               5                   10                  15

Leu Ala Leu Val Val Thr Cys Asn Gly Ile Pro Ile Cys Gln Thr Tyr
            20                  25                  30

Met Asp Cys Pro Ser Asp Met Cys Thr Arg Pro Lys His Ala Tyr Cys
        35                  40                  45

Val Ser Tyr Lys Cys Tyr Cys Val
    50                  55
```

<210> SEQ ID NO 206
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 206

```
Met Ala Glu Ile Ile Lys Phe Val Tyr Ile Met Ile Leu Cys Val Ser
1               5                   10                  15

Leu Leu Leu Ile Ala Glu Ala Ser Gly Lys Cys Val Thr Asp Ala
            20                  25                  30

Asp Cys Glu Asn Leu Tyr Pro Gly Asn Lys Lys Pro Met Phe Cys Asn
        35                  40                  45

Asn Thr Gly Tyr Cys Met Ser Leu Tyr Lys Glu Pro Ser Arg Tyr Met
    50                  55                  60
```

<210> SEQ ID NO 207

```
<211> LENGTH: 53
<212> TYPE: PRT
<213> ORGANISM: Artificial sequence
<220> FEATURE:
<223> OTHER INFORMATION: Peptide derived from Medicago truncatula

<400> SEQUENCE: 207

Tyr Ala Met Ile Leu Phe Ile Ser Met Phe Leu Ala Ala Arg Asn Val
1               5                   10                  15

Asp Ala Tyr Leu Lys Cys Lys Thr Val His Asp Cys Pro Lys Ser Gln
            20                  25                  30

Val Val Tyr Lys Cys Val Gly Asn Tyr Cys Arg Ala Val Lys Ile Arg
        35                  40                  45

Arg Trp Asn Leu Ser
    50

<210> SEQ ID NO 208
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 208

Thr Arg Ala Lys Val His Lys Phe Ile Tyr Ile Met Ile Val Phe Leu
1               5                   10                  15

Ser Ile Phe His Val Val Asn Ser Tyr Val Val Met Cys Glu Lys Asp
            20                  25                  30

Ser Asp Cys Val Asp Ser Phe Cys Val Pro Pro Asn Val Pro Lys Cys
        35                  40                  45

Arg Val Val Cys Lys Cys Leu Pro Lys
    50                  55

<210> SEQ ID NO 209
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 209

Met Asn Thr Ile Leu Lys Phe Ile Phe Val Val Phe Leu Phe Leu Ser
1               5                   10                  15

Ile Phe Leu Ser Ala Gly Asn Ser Lys Ser Tyr Gly Pro Cys Thr Thr
            20                  25                  30

Leu Gln Asp Cys Glu Thr His Asn Trp Phe Glu Val Cys Ser Cys Ile
        35                  40                  45

Asp Phe Glu Cys Lys Cys Trp Ser Leu Leu
    50                  55

<210> SEQ ID NO 210
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 210

Met Thr Lys Ile Leu Lys Cys Val Tyr Ala Met Ile Leu Phe Leu Pro
1               5                   10                  15

Leu Phe Val Val Ala Met Glu Val Gly Arg Arg Ala Asn Val Glu Cys
            20                  25                  30
```

```
Glu Ser Asp Lys Asp Cys Gln Glu His Trp Ser Glu Phe Ile Ile
         35                  40                  45

Gln Cys Ile Asp Asn Ile Cys Val Pro Ser Glu Arg Pro Leu
 50                  55                  60

<210> SEQ ID NO 211
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 211

Asn Ala Ile Leu Phe Val Ser Leu Tyr Leu Leu Val Ile Tyr Gly Asp
 1               5                  10                  15

Arg Glu Cys Asp Thr Asp Thr Glu Cys Gln Lys Lys Phe Pro Gly Val
                 20                  25                  30

Asn Ala His His Leu Trp Cys Asp Asn Gly Asn Cys Val Ser Tyr Pro
             35                  40                  45

Lys

<210> SEQ ID NO 212
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 212

Met Asp Lys Thr Ile Lys Phe Thr Tyr Val Met Ile Ile Phe Val Tyr
 1               5                  10                  15

Leu Phe Leu Ile Ala Thr Asn Val Glu Ala Tyr Lys Asn Arg Cys Phe
                 20                  25                  30

Arg Asp Ser Asp Cys Pro Lys Glu Met Cys Asn His Pro Lys Ile Pro
             35                  40                  45

Lys Cys Val Asn Asn Ala Tyr Cys Lys Cys Val Val Ala Met Tyr Phe
         50                  55                  60

Pro Pro Lys
 65

<210> SEQ ID NO 213
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 213

Met Ala Glu Ile Ile Lys Phe Val Tyr Ile Met Ile Leu Phe Val Ser
 1               5                  10                  15

Leu Leu Leu Ile Val Glu Ala Gly Gly Asn Glu Cys Val Thr Asp Val
                 20                  25                  30

Asp Cys Glu Lys Leu Tyr Pro Gly Asn Lys Lys Pro Leu Ile Cys Asn
             35                  40                  45

Ile Gly Tyr Cys Leu Ser Leu Tyr Lys Glu Pro Pro Arg Tyr Met
         50                  55                  60

<210> SEQ ID NO 214
<211> LENGTH: 69
<212> TYPE: PRT
<213> ORGANISM: Artificial sequence
<220> FEATURE:
```

-continued

<223> OTHER INFORMATION: Peptide derived from Medicago truncatula

<400> SEQUENCE: 214

Met Ala Glu Ile Val Lys Phe Val Tyr Val Met Ile Ile Phe Ala Ser
1               5                   10                  15

Pro Phe Leu Phe Ser Met Asn Leu Asp Ser Glu Asn Ile Cys Asp Gly
            20                  25                  30

Asp Tyr Asp Cys Asn Pro Asn Glu Trp Trp Cys Pro Pro Asn Tyr Val
        35                  40                  45

Leu Lys Cys Ile Asn Tyr Gln Cys Ser Cys Ile Gly Phe Thr Pro Ala
    50                  55                  60

Ile Tyr Ala Leu Asp
65

<210> SEQ ID NO 215
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 215

Met Asp Ala Val Leu Lys Phe Val Tyr Thr Met Ile Leu Tyr Leu Phe
1               5                   10                  15

Leu Leu His Val Ile Ala Glu Asp Phe Pro Phe His Lys Cys Glu Lys
            20                  25                  30

Asp Glu Asp Cys Leu Glu Ile Cys Ala Asp Asp Gln Met Ala Met Cys
        35                  40                  45

Ile Leu Asn Val Cys Phe Cys Tyr
    50                  55

<210> SEQ ID NO 216
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 216

Met Thr Thr Ile Leu Lys Phe Ala Tyr Val Met Ile Ile Cys Leu Phe
1               5                   10                  15

Leu Leu Gln Val Ala Ala Gln Glu Val Leu Glu Lys Glu Ile Phe Pro
            20                  25                  30

Cys Gln Thr Asp Gly Glu Cys Asp His Met Cys Val Thr Pro Gly Ile
        35                  40                  45

Pro Lys Cys Val Ala Asn Met Cys Phe Cys Phe Asp Asn Leu
    50                  55                  60

<210> SEQ ID NO 217
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 217

Met Arg Lys Ser Met Ala Thr Ile Leu Lys Phe Val Tyr Val Ile Met
1               5                   10                  15

Leu Phe Ile Tyr Ser Leu Phe Val Ile Glu Ser Phe Gly His Arg Phe
            20                  25                  30

Leu Ile Tyr Asn Asn Cys Lys Asn Asp Thr Glu Cys Pro Asn Asp Cys

-continued

```
                35                  40                  45

Gly Pro His Glu Gln Ala Lys Cys Ile Leu Tyr Ala Cys Tyr Cys Val
 50                  55                  60

Glu
 65

<210> SEQ ID NO 218
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 218

Met Ala Lys Val Thr Lys Phe Val Tyr Ile Ala Ile His Ile Leu Ser
  1               5                  10                  15

Leu Phe Phe Ile Ala Met Asn Asp Ala Val Ile Phe Glu Cys Ser Glu
                 20                  25                  30

Asp Ser His Cys Val Thr Lys Ile Lys Cys Val Leu Pro Arg Lys Pro
             35                  40                  45

Glu Cys Arg Asn Thr Gln Cys Thr Cys Tyr Arg Gly Tyr Lys Gly Ser
 50                  55                  60

Phe Thr Leu His His
 65

<210> SEQ ID NO 219
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 219

Met Ala Gly Ile Leu Lys Phe Phe Tyr Ile Ala Ile Ile Tyr Val Ser
  1               5                  10                  15

Leu Tyr Leu Val Val Ile Glu Gly Lys Asp Gly Cys Lys Thr Asn Phe
                 20                  25                  30

Asp Cys Leu Ile Lys Tyr Pro Asp His Asn Glu Asp Ile Leu Gln Cys
             35                  40                  45

Ile Gly Gly His Cys Leu Cys Leu Thr Asn
 50                  55

<210> SEQ ID NO 220
<211> LENGTH: 54
<212> TYPE: PRT
<213> ORGANISM: Artificial sequence
<220> FEATURE:
<223> OTHER INFORMATION: Peptide derived from Medicago truncatula

<400> SEQUENCE: 220

Met Ala Glu Ile Leu Lys Ile Leu Tyr Val Phe Ile Ile Phe Leu Ser
  1               5                  10                  15

Leu Ile Leu Ala Val Ile Ser Gln His Pro Phe Thr Pro Cys Glu Thr
                 20                  25                  30

Asn Ala Asp Cys Lys Cys Arg Asn His Lys Arg Pro Asp Cys Leu Trp
             35                  40                  45

His Lys Cys Tyr Cys Tyr
     50

<210> SEQ ID NO 221
<211> LENGTH: 58
```

```
<212> TYPE: PRT
<213> ORGANISM: Artificial sequence
<220> FEATURE:
<223> OTHER INFORMATION: Peptide derived from Medicago truncatula

<400> SEQUENCE: 221

Met Ala Glu Ile Leu Lys Phe Val Tyr Asn Ala Thr Leu Phe Phe Ser
1               5                   10                  15

Leu Tyr Leu Val Val Tyr Asn Ser Lys Leu Trp Cys Asp Thr Asp Ala
            20                  25                  30

Asp Cys Gln Glu Lys Phe Pro Gly Pro Ser Lys Tyr Pro Ile Lys Cys
        35                  40                  45

Met Lys Gly Ile Cys Lys Cys Val Ile Asn
    50                  55

<210> SEQ ID NO 222
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 222

Met Pro Glu Met Ile Gln Phe Asp Tyr Leu Met Ile Leu Phe Ile Phe
1               5                   10                  15

Leu Ile Phe Val Val Thr Asn Ile Met Ala Trp Arg Pro Asp Cys Lys
            20                  25                  30

Glu Asn Asn Asp Cys Pro Thr Phe Tyr Cys Ala Thr Trp Ile Asn Thr
        35                  40                  45

Cys Ile Lys Phe Lys Cys Tyr Cys Ile Arg Pro Trp Gly
    50                  55                  60

<210> SEQ ID NO 223
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 223

Met Arg Ile Asn Arg Thr Pro Ala Ile Phe Lys Phe Val Tyr Thr Ile
1               5                   10                  15

Ile Ile Tyr Leu Phe Leu Leu Arg Val Val Ala Lys Asp Leu Pro Phe
            20                  25                  30

Asn Ile Cys Glu Lys Asp Glu Asp Cys Leu Glu Phe Cys Ala His Asp
        35                  40                  45

Lys Val Ala Lys Cys Met Leu Asn Ile Cys Phe Cys Phe
    50                  55                  60

<210> SEQ ID NO 224
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 224

Met Val Gly Thr Leu Lys Phe Leu Arg Val His Ile Ser Phe Leu Thr
1               5                   10                  15

Ile Leu Leu Met Ile Ile Ile Cys Ala Phe Tyr Phe Ile Pro Asp Ser
            20                  25                  30

Gly Pro Cys Val Thr Asn Lys Asp Cys Glu Gln Glu Ile Gly Tyr Ile
```

```
                   35                  40                  45
Val Lys Cys Asp Thr Asn Thr Gly Phe Cys Val Lys Ile Leu Gln Arg
 50                  55                  60

Ser
 65

<210> SEQ ID NO 225
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 225

Glu Ile Leu Lys Phe Ile Phe Val Ile Ile Leu Phe Leu Ser Ile
  1               5                  10                  15

Ser Leu Val Ser Ala Asp Phe Asp Leu His Asn Asp Ser Tyr Asp Tyr
                 20                  25                  30

Leu Tyr Glu Phe Gln Glu Cys Glu Val Asp Asn Asp Cys Pro Gln Asp
                 35                  40                  45

Pro Leu Pro Met Lys Cys Ile Asn Tyr Ile Cys Val Val His Asn Glu
 50                  55                  60

Glu Pro Ser Asp Asn Leu
 65                  70

<210> SEQ ID NO 226
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 226

Met Ala Ala Thr Phe Lys Leu Val Tyr Val Met Ile Leu Leu Ile Ser
  1               5                  10                  15

Leu Tyr His Val Ala Gly Asn Phe Glu Asp Ile Ser Ile Glu Cys Met
                 20                  25                  30

Phe Ser Ile Asp Cys Pro Gln Ile Lys Ser Asn Ile Phe Arg Phe Lys
                 35                  40                  45

Cys Ile Glu Asp Arg Cys Lys Ile Glu Phe Ile Tyr Gln Arg Lys Lys
 50                  55                  60

Tyr Glu Ile
 65

<210> SEQ ID NO 227
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 227

Met Thr Thr Phe Leu Lys Val Ala Tyr Ile Met Ile Ile Cys Val Phe
  1               5                  10                  15

Val Leu His Leu Ala Ala Gln Val Asp Ser Gln Lys Arg Trp His Gly
                 20                  25                  30

Cys Lys Glu Asp Arg Asp Cys Asp Asn Ile Cys Ser Val His Ala Val
                 35                  40                  45

Thr Lys Cys Ile Gly Asn Met Cys Arg Cys Leu Ala Asn Val Lys
 50                  55                  60
```

-continued

<210> SEQ ID NO 228
<211> LENGTH: 73
<212> TYPE: PRT
<213> ORGANISM: Artificial sequence
<220> FEATURE:
<223> OTHER INFORMATION: Peptide derived from Medicago truncatula

<400> SEQUENCE: 228

Met Thr Thr Ile Leu Lys Phe Ala Tyr Ile Met Ile Ile Cys Leu Phe
1               5                   10                  15

Leu Phe Leu Leu His Val Ala Ala Gln Lys Asp Leu Lys Val Phe Thr
            20                  25                  30

Cys Gln Arg Asp Glu Asp Cys Lys Val Ala Cys Ala Thr Tyr Gly Gly
        35                  40                  45

Asp Pro Trp Cys Phe Arg Asn Val Cys Phe Cys Lys His Tyr Asn Glu
    50                  55                  60

Gly Gly Thr Leu His Ala Glu Leu His
65                  70

<210> SEQ ID NO 229
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 229

Met Asp Lys Ile Leu Lys Phe Val His Ile Val Ile Leu Phe Val Phe
1               5                   10                  15

Leu Leu Leu Val Leu Val Ala Ala Glu Gln His Phe Val Thr Leu Tyr
            20                  25                  30

Lys Lys Lys Glu Lys Cys Ala Leu Asp Val Asp Cys Leu Glu Leu Phe
        35                  40                  45

Pro Asn Ser Tyr Lys Tyr Leu Met Lys Cys Val Gly Gly Asp Cys Ile
    50                  55                  60

Ser Leu Ser Lys Gly Phe Ser His Asp Glu Ile Lys Glu
65                  70                  75

<210> SEQ ID NO 230
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 230

Met Thr Lys Ile Val Lys Phe Ile Tyr Val Met Ile Ile Ile Leu Ser
1               5                   10                  15

Leu Phe Gln Leu Ser Lys Asn Ala Lys Val Asn Cys Leu Asp Asp Ala
            20                  25                  30

Asp Cys Leu Glu Val Leu Cys Val Phe Gly Ser Lys Ala Glu Cys Val
        35                  40                  45

Val Asn Ile Cys Ile Cys Val Pro Pro Arg Phe Gly Lys Phe Asp Glu
    50                  55                  60

His Phe Arg
65

<210> SEQ ID NO 231
<211> LENGTH: 64
<212> TYPE: PRT
<213> ORGANISM: Artificial sequence

```
<220> FEATURE:
<223> OTHER INFORMATION: Peptide derived from Medicago truncatula

<400> SEQUENCE: 231

His Glu Ala Gln Ile Ser Lys Ser Phe Tyr Ala Leu Ile Ile Phe Leu
1               5                   10                  15

Ser Leu Ile Leu Val Val Thr Ser Lys Asp Ile Thr Cys Thr Val Ala
            20                  25                  30

Gly Asp Cys Pro Asn Phe Phe Val Cys Pro Pro Asn Asn Phe Val Arg
        35                  40                  45

Cys Ile Arg Asn Leu Cys Lys Cys Arg Ser Leu Ser Tyr Lys Gln Pro
    50                  55                  60

<210> SEQ ID NO 232
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 232

Met Ala Lys Phe Val Ile Val Val Cys Ser Val Ile Ile Phe Leu Ser
1               5                   10                  15

Ser Phe Leu Val Ala Glu Asn Ser Gln Pro Cys Asn Leu Ser Val Thr
            20                  25                  30

Asp Thr Arg Asp Ile Cys Pro Pro Gly Thr Thr Leu Gln Phe Val Tyr
        35                  40                  45

Lys Val Cys Arg Cys Tyr Pro Met Lys Trp Arg Leu Asp His Val Leu
    50                  55                  60

Thr
65

<210> SEQ ID NO 233
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 233

Ile Phe Phe Leu Tyr Leu Phe Ile Phe Ala Thr Asn Ile Asn Ala Ile
1               5                   10                  15

Cys Glu Cys Glu Glu Asp Ile Asp Cys Pro Arg Thr Trp Cys Phe Gly
            20                  25                  30

Gln Phe Phe Val Lys Cys Ile Thr Asn Glu Cys Ile Cys Val His Glu
        35                  40                  45

Asp Arg Leu Leu Pro Arg Ile Pro Trp Asp Pro Trp Ile Pro Met Ile
    50                  55                  60

<210> SEQ ID NO 234
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 234

Met Gln Lys Arg Lys Ser Met Thr Glu Val Leu Lys Leu Val Tyr Ile
1               5                   10                  15

Met Ile Ile Phe Leu Tyr Ile Phe Leu Val Val Ala Asp Thr Asp Pro
            20                  25                  30
```

```
Phe Ala Phe Cys Ile Lys Asp Ser Asn Cys Gly Gln Asp Leu Cys Thr
            35                  40                  45

Ser Pro Asn Glu Val Pro Glu Cys Arg Leu Leu Lys Cys Gln Cys Ile
 50                  55                  60

Lys Ser
 65
```

<210> SEQ ID NO 235
<211> LENGTH: 83
<212> TYPE: PRT
<213> ORGANISM: Artificial sequence
<220> FEATURE:
<223> OTHER INFORMATION: Peptide derived from Medicago truncatula

<400> SEQUENCE: 235

```
Met Ala Glu Ile Val Lys Phe Val Tyr Leu Met Ile Ile Phe Leu Ser
 1               5                  10                  15

Thr Phe Leu Val Ser Thr Lys Ile Leu Glu Lys His Lys Cys Val Thr
            20                  25                  30

Asp Gly Val Glu Ile Leu Glu Lys Gly Lys Cys Phe Thr Asp Trp Glu
        35                  40                  45

Cys Val Arg Asn Ser Trp Leu Cys Pro Val Asp Leu Val Val Arg Cys
 50                  55                  60

Ile Lys Glu Thr Cys Lys Cys Ile Lys Ile Leu Glu Pro Ile Asn Val
 65                  70                  75                  80

Val Pro Thr
```

<210> SEQ ID NO 236
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 236

```
Met Val Glu Thr Leu Arg Leu Phe Tyr Ile Met Ile Leu Phe Val Ser
 1               5                  10                  15

Leu Tyr Leu Val Val Asp Gly Val Ser Lys Leu Ala Gln Ser Cys
            20                  25                  30

Ser Glu Asp Phe Glu Cys Tyr Ile Lys Asn Pro His Ala Pro Phe Gly
        35                  40                  45

Gln Leu Arg Cys Phe Glu Gly Tyr Cys Gln Arg Leu Asp Lys Pro Thr
 50                  55                  60
```

<210> SEQ ID NO 237
<211> LENGTH: 85
<212> TYPE: PRT
<213> ORGANISM: Artificial sequence
<220> FEATURE:
<223> OTHER INFORMATION: Peptide derived from Medicago truncatula

<400> SEQUENCE: 237

```
Met Ala Lys Leu Met Lys Leu Phe Tyr Val Met Ile His Phe Ile Ser
 1               5                  10                  15

Leu Leu Leu Ile Thr Arg Asn Val Arg Ala Tyr Asp Asp Cys Tyr Asn
            20                  25                  30

His Ala Glu Cys Thr Asn Lys Ile Lys Cys Val Pro Pro Arg Ile Ala
        35                  40                  45

Gln Cys Val Arg Phe Lys Cys Asp Cys Ile Arg Leu Asn Asn Gly Pro
 50                  55                  60
```

```
Lys Thr Pro Trp Ser Ala Arg Pro Lys Arg Val His Ile Ser Pro Thr
 65                  70                  75                  80

Arg Lys Asn Asp Phe
                 85

<210> SEQ ID NO 238
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 238

Met Gln Met Lys Lys Met Ala Thr Ile Leu Lys Phe Val Tyr Leu Ile
 1               5                  10                  15

Ile Leu Leu Ile Tyr Pro Leu Leu Val Val Thr Glu Glu Ser His Tyr
                20                  25                  30

Met Lys Phe Ser Ile Cys Lys Asp Asp Thr Asp Cys Pro Thr Leu Phe
            35                  40                  45

Cys Val Leu Pro Asn Val Pro Lys Cys Ile Gly Ser Lys Cys His Cys
        50                  55                  60

Lys Leu Met Val Asn
 65

<210> SEQ ID NO 239
<211> LENGTH: 74
<212> TYPE: PRT
<213> ORGANISM: Artificial sequence
<220> FEATURE:
<223> OTHER INFORMATION: Peptide derived from Medicago truncatula

<400> SEQUENCE: 239

Met Gln Lys Asp Lys Ser Met Val Gln Ile Val Lys Phe Val Tyr Val
 1               5                  10                  15

Met Ile Val Leu Ser Ser Phe Val Val Ala Ile Asn Ser Asp Gly
                20                  25                  30

Tyr Leu Glu Cys Thr Thr Asp Tyr Asp Cys Arg Glu Glu Trp Leu Cys
            35                  40                  45

Pro Pro Asp Met Glu Ala Lys Cys Phe Val Ser Phe Ala Leu Ala Arg
        50                  55                  60

Phe Leu Ser Lys Gly Lys Cys Leu Cys Val
 65                  70

<210> SEQ ID NO 240
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 240

Met Val Ala Val Thr Lys Leu Ile Asn Val Met Leu Ile Phe Leu Thr
 1               5                  10                  15

Leu Phe Leu Gly Ala Leu Ser Ile Phe Pro Glu His Asn Glu Cys Arg
                20                  25                  30

Thr Ser Phe Asp Cys Arg Lys Tyr Phe Cys Gln Leu Pro Leu Arg Pro
            35                  40                  45

Thr Cys Asn Tyr Val Glu Ile Phe Arg His Tyr Tyr Asp Thr Thr Cys
        50                  55                  60

Gly Cys Ala
 65
```

<210> SEQ ID NO 241
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 241

Met Thr Ala Ile Leu Lys Val Ala Tyr Ile Met Ile Ile Cys Leu
1               5                   10                  15

Phe Leu Leu His Asp Ala Ala Ser Asp Asp Tyr Leu Lys Tyr Ile Tyr
            20                  25                  30

Arg Cys Gln Asn Asp Gly Asp Cys Asp Gln Ile Cys Ala Thr His Gly
        35                  40                  45

Ile Ser Lys Cys Val Ala Thr Met Cys Phe Cys Asn Leu Asn Leu
    50                  55                  60

<210> SEQ ID NO 242
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 242

Met Val Glu Ile His Asn Phe Ile Tyr Ala Met Ile Leu Leu Val Phe
1               5                   10                  15

Met Phe Ile Val Val Asp Ser Trp Ser Trp Gly Leu Thr Thr Glu
            20                  25                  30

Cys Val Thr Glu Leu Asp Cys Tyr Lys Lys Tyr Arg Leu Pro Ala Glu
        35                  40                  45

Lys Lys Met Lys Cys Ile Arg Gly Ser Cys Tyr Arg Val Arg Glu
    50                  55                  60

<210> SEQ ID NO 243
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 243

Met Asp Lys Ile His Lys Phe Ile Tyr Ala Leu Ile Phe Phe Leu Ala
1               5                   10                  15

Leu Phe Leu Val Val Asn Ala Arg Asn Gly Cys Ile Val Asp Pro Arg
            20                  25                  30

Cys Pro Tyr Gln Gln Cys Arg Arg Pro Leu Tyr Cys Arg Arg Arg
        35                  40                  45

<210> SEQ ID NO 244
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 244

Met Arg Tyr Ser Leu Ser Val Ser Ile Leu Ala Ile Ile Leu Glu Phe
1               5                   10                  15

Ile Tyr Ile Val Val Leu Phe Ser Pro Cys Leu Leu Val Thr Asp
            20                  25                  30

-continued

```
Ala Tyr Asn Ile Thr Cys Asn Ser Ala Leu Asp Cys Ala Ser Asn Arg
         35                  40                  45

Cys Ile Leu Pro Gly Met Pro Ile Cys Val Thr Asn Lys Cys Leu Cys
 50                  55                  60

Val
 65
```

<210> SEQ ID NO 245
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 245

```
Met Ala Gly Ile Leu Lys Phe Phe Tyr Ile Val Ile Tyr Val Ser
 1               5                  10                  15

Leu Phe Leu Phe Val Val Glu Ser Glu Arg Glu Cys Val Thr Asp Ala
             20                  25                  30

Asp Cys Gln Lys Lys Leu Pro Phe Pro His Ala Asn His Phe Ile Cys
         35                  40                  45

Met Asn Gly Leu Cys Ala Leu Val Phe His Asp
 50                  55
```

<210> SEQ ID NO 246
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 246

```
Met Ala Gln Phe Leu Ile Phe Val Tyr Thr Leu Ile Ile Phe Ile Ser
 1               5                  10                  15

Leu Phe Leu Asn Ala Val Gln Arg Pro Cys Val Thr Val Ala Asp Cys
             20                  25                  30

Pro Pro Val Lys Lys Pro Leu Lys Met Trp Cys Ile Arg Gln Thr Cys
         35                  40                  45

Phe Tyr Gly Phe Gly Lys Arg Pro Asp Leu
 50                  55
```

<210> SEQ ID NO 247
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 247

```
Met Val Gly Ile Leu Lys Leu Val Tyr Ile Val Ile Tyr Val Ser
 1               5                  10                  15

Phe Phe Leu Val Val Cys Lys Gly Glu Thr Cys Val Thr Val Asp Asp
             20                  25                  30

Cys Gln Gly Lys His His Leu Pro Pro Gly Tyr His Phe Ile Cys Met
         35                  40                  45

Asn Ser Arg Cys Val Leu Ile Tyr Tyr Asn
 50                  55
```

<210> SEQ ID NO 248
<211> LENGTH: 55
<212> TYPE: PRT
<213> ORGANISM: Artificial sequence

```
<220> FEATURE:
<223> OTHER INFORMATION: Peptide derived from Medicago truncatula

<400> SEQUENCE: 248

Met Asn Ile Ile Phe Lys Cys Val Tyr His Met Ile Val Ile Leu Leu
1               5                   10                  15

Leu Leu Leu Val Ala Thr Glu Ala Gly Thr Gly Asn Ile Arg Gln Ser
            20                  25                  30

Cys Glu Phe Asp Val Asp Cys Glu Asn Lys Tyr Cys Pro Pro Ser His
        35                  40                  45

Asp Gly Lys Cys Val Trp Glu
    50                  55

<210> SEQ ID NO 249
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 249

Ile Lys Ile Ile Lys Phe Val Tyr Ala Met Thr Phe Leu Ile Phe Leu
1               5                   10                  15

Phe Leu Phe Ile Thr Asp Thr Ala Gly Glu Cys Ile Thr Phe Leu Asp
            20                  25                  30

Cys Leu His Leu Pro Cys Met Pro Thr Glu Thr Gln Leu Cys Val Asp
        35                  40                  45

Lys Lys Cys Ile Cys Met Gly Leu Thr Ile Lys Ser Lys Asn Asn Tyr
    50                  55                  60

Ile Thr
65

<210> SEQ ID NO 250
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 250

Met Ala Lys Ile Ile Thr Ile Ile Gln Ile Phe Thr Ile Ile Met Leu
1               5                   10                  15

Phe Ile Phe Val Ile Val Thr Asp Ala Ser Tyr Pro Cys Lys Ile His
            20                  25                  30

Arg Asp Cys Thr Thr Ile Thr Cys Ser Tyr Pro Leu Val Pro Arg Cys
        35                  40                  45

Leu Ile Gln Lys Cys Tyr Cys Gly Phe Asn
    50                  55

<210> SEQ ID NO 251
<211> LENGTH: 54
<212> TYPE: PRT
<213> ORGANISM: Artificial sequence
<220> FEATURE:
<223> OTHER INFORMATION: Peptide derived from Medicago truncatula

<400> SEQUENCE: 251

Leu Lys Leu Val Tyr Ile Ala Ile Ile Tyr Val Ser Phe Phe Leu Val
1               5                   10                  15

Val Cys Glu Gly Glu Lys Cys Val Thr Ala Asp Asp Cys Gln Gly Lys
            20                  25                  30
```

```
His His Met Pro Ala Gly Tyr His Phe Ile Cys Met Asn Ala Arg Cys
        35                  40                  45

Val Leu Val Tyr Tyr Asn
    50
```

<210> SEQ ID NO 252
<211> LENGTH: 81
<212> TYPE: PRT
<213> ORGANISM: Artificial sequence
<220> FEATURE:
<223> OTHER INFORMATION: Peptide derived from Medicago truncatula

<400> SEQUENCE: 252

```
Met Lys Leu Phe Tyr Val Leu Ile Tyr Phe Ile Ser Leu Phe Leu Val
1               5                   10                  15

Ile Asn Val Gln Ala Phe Phe Asp Cys Glu Asn His Asp Asp Cys Lys
            20                  25                  30

Asn Lys Ile Lys Tyr Val Leu Pro Arg Ile Ala Glu Cys Arg Asp Tyr
        35                  40                  45

Lys Cys Asn Cys Phe Pro Leu Asn Leu Ser Lys Thr Leu Trp Ser Ala
    50                  55                  60

Ser Thr Lys Arg Val His Lys Ser Leu Ala Gln Thr Asn Asp Phe Leu
65                  70                  75                  80

His
```

<210> SEQ ID NO 253
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 253

```
Met Thr Thr Ile Leu Lys Phe Pro Tyr Ile Met Val Ile Cys Leu Leu
1               5                   10                  15

Leu Leu His Val Ala Ala Tyr Glu Asp Phe Glu Lys Glu Ile Phe Asp
            20                  25                  30

Cys Lys Lys Asp Gly Asp Cys Asp His Met Cys Val Thr Pro Gly Ile
        35                  40                  45

Pro Lys Cys Thr Gly Asn Gln Arg Phe Ser Val Trp Val Phe Gly Gly
    50                  55                  60

Ser Phe Leu Gln His Trp Ser Cys His Ser Ser Arg Ser
65                  70                  75
```

<210> SEQ ID NO 254
<211> LENGTH: 74
<212> TYPE: PRT
<213> ORGANISM: Artificial sequence
<220> FEATURE:
<223> OTHER INFORMATION: Peptide derived from Medicago truncatula

<400> SEQUENCE: 254

```
Met Asp Gln Ile Ser Lys Ser Phe Tyr Ala Leu Met Ile Phe Leu Ser
1               5                   10                  15

Leu Ile Leu Val Val Thr Ser Asn Asp Ile Lys Cys Thr Val Ala Gly
            20                  25                  30

Asp Cys Pro Asp Phe Phe Arg Cys Pro Pro Asn Thr Phe Val Arg Cys
        35                  40                  45

Ile Ser Asn Ile Cys Ile Cys Arg Leu Val Tyr Leu Asn Thr Phe Leu
    50                  55                  60
```

```
Glu Val Ile Ile Asp Lys Val Phe Val Phe
65                  70

<210> SEQ ID NO 255
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 255

Met Asp Gln Ile Ser Lys Ser Phe Tyr Ala Leu Met Ile Phe Leu Ser
1               5                   10                  15

Leu Ile Leu Val Val Thr Ser Asn Asp Ile Lys Cys Thr Val Ala Gly
            20                  25                  30

Asp Cys Pro Asp Phe Phe Arg Cys Pro Pro Asn Thr Phe Val Arg Cys
        35                  40                  45

Ile Ser Asn Ile Cys Ile Cys Arg Ser Leu Ser His
    50                  55                  60

<210> SEQ ID NO 256
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 256

Met Ala Gln Ile Ser Lys Ser Phe Tyr Ala Leu Ile Ile Leu Leu Cys
1               5                   10                  15

Leu Ser Leu Ile Val Thr Gly Lys Asp Ile Thr Cys Asn Val Ala Gly
            20                  25                  30

Asp Cys Pro Glu Tyr Phe Arg Cys Pro Pro Asn Thr Phe Val Arg Cys
        35                  40                  45

Val Ser Asn Ile Cys Glu Cys Arg Gly Leu Ser His Gln Gln Pro
    50                  55                  60

<210> SEQ ID NO 257
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 257

Met Ala Gln Ile Leu Ile Ser Val His Ala Leu Ser Val Phe Ile Phe
1               5                   10                  15

Pro Phe Leu Val Val Ile Ile Arg Asp Lys Pro Ala Pro Ile Pro Cys
            20                  25                  30

Lys Phe His Ala Asp Cys Pro Ile Met Leu Ser Ile Val Val Glu Cys
        35                  40                  45

Ile Asn Asn Val Cys Glu Phe Ile Tyr Ile
    50                  55

<210> SEQ ID NO 258
<211> LENGTH: 131
<212> TYPE: PRT
<213> ORGANISM: Artificial sequence
<220> FEATURE:
<223> OTHER INFORMATION: Peptide derived from Medicago truncatula

<400> SEQUENCE: 258

Met Thr Thr Thr Leu Lys Phe Val Tyr Ala Ile Ile Leu Phe Ile Ser
```

```
                1               5                   10                  15
Leu Phe Leu His Ala Leu Asn Ala Ala Gly Lys Lys Phe Leu Cys Leu
                20                  25                  30

Ser Asn Phe Leu Ile Tyr Phe Val Ile Phe Phe Gly Ser His Thr
                35                  40                  45

Ile Phe His Leu Val Leu Leu Asn Ile Leu Phe Ser Phe Ser Ser Glu
 50                  55                  60

Asn Ile Glu Cys Glu Val Asp Ala Asp Cys Pro Lys Ser Gln Val Asn
 65                  70                  75                  80

Ser Phe Val Ile Lys Cys Ile Lys Asn Leu Cys Leu Tyr Thr Lys Ile
                85                  90                  95

His Ile Leu Tyr Asp Thr Ile Ser Lys Ser Glu Ser Thr Leu Pro Gln
                100                 105                 110

Lys Lys Lys Ser Leu Ile Val His Leu His Ile Ser Arg Lys Asn Glu
            115                 120                 125

Leu Leu His
    130

<210> SEQ ID NO 259
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 259

Met Asp Glu Val Phe Lys Phe Val Tyr Val Met Ile Ile Phe Pro Phe
 1               5                   10                  15

Leu Ile Leu Asp Val Ala Thr Asn Ala Glu Lys Ile Arg Arg Cys Phe
                20                  25                  30

Asn Asp Ala His Cys Pro Pro Asp Met Cys Thr Leu Gly Val Ile Pro
            35                  40                  45

Lys Cys Ser Arg Phe Thr Ile Cys Ile Cys
        50                  55

<210> SEQ ID NO 260
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 260

Met Ala Gly Ile Leu Lys Ile Phe Tyr Ile Ala Ile Ile Tyr Val Ser
 1               5                   10                  15

Leu Phe Leu Val Val Ile Glu Asp Glu Arg Glu Cys Val Thr Asp Ala
                20                  25                  30

Asp Cys Gln Lys Lys Tyr Pro Gly Pro Tyr Glu His Leu Leu Lys Cys
            35                  40                  45

Val Ser Gly Tyr Cys Val Gly Val Thr Gly Phe
        50                  55

<210> SEQ ID NO 261
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 261
```

```
Met Gln Arg Arg Lys Leu Asn Met Val Glu Ile Leu Lys Phe Ser His
1               5                   10                  15

Ala Leu Ile Ile Phe Leu Phe Leu Ser Ala Leu Val Thr Asn Ala Asn
            20                  25                  30

Ile Phe Phe Cys Ser Thr Asp Glu Asp Cys Thr Trp Asn Leu Cys Arg
        35                  40                  45

Gln Pro Trp Val Gln Lys Cys Arg Leu His Met Cys Ser Cys Glu Lys
    50                  55                  60

Asn
65

<210> SEQ ID NO 262
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 262

Met Val Asn Ile Leu Lys Phe Ile Tyr Val Ile Ile Phe Phe Ile Leu
1               5                   10                  15

Met Phe Phe Val Leu Ile Asp Val Asp Gly His Val Leu Val Glu Cys
            20                  25                  30

Ile Glu Asn Arg Asp Cys Glu Lys Gly Met Cys Lys Phe Pro Phe Ile
        35                  40                  45

Val Arg Cys Leu Met Asp Gln Cys Lys Cys Val Arg Ile His Asn Leu
    50                  55                  60

Ile
65

<210> SEQ ID NO 263
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 263

Leu Ile Leu Phe Ile Ser Leu Phe Leu Asp Val Val Lys Gly His Asp
1               5                   10                  15

Gln Arg Glu Cys Tyr Thr Asn Tyr Asp Cys Cys Val Lys Tyr Ser Cys
            20                  25                  30

Pro Tyr Lys His Met Val Lys Cys Val Gly Gly Tyr Cys Leu Gly Phe
        35                  40                  45

Arg Asn Asp Tyr Gly Lys Lys Asn Leu Tyr
    50                  55

<210> SEQ ID NO 264
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 264

Val Ser Leu Phe Leu Ala Val Val Lys Ser Tyr Asp Ser Lys Glu Cys
1               5                   10                  15

Tyr Ser Asp Ser Asp Trp His Lys Lys Tyr Ser Cys Pro Tyr Thr His
            20                  25                  30

Met Met Lys Cys Val Gly Gly Tyr Cys
        35                  40
```

<210> SEQ ID NO 265
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 265

Met Ala Ile Ile Lys Phe Ile Tyr Thr Met Phe Leu Phe Ile Leu Leu
1               5                   10                  15

Phe Val Val Pro Thr Lys Val Asp Gly Arg Ile Thr His Asp Pro Ser
                20                  25                  30

Thr Arg Ser Thr Val Ser Gly Gly Phe Gly Lys Cys Val Arg Asp Ala
            35                  40                  45

Asp Cys Val Asp Glu Val Cys Ser Pro Gly Cys Asn Lys Arg Cys Val
    50                  55                  60

Gly Phe Glu Cys Gln Cys Pro Leu
65                  70

<210> SEQ ID NO 266
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 266

Met Ala Leu Lys Phe Tyr Ser Leu Phe Tyr Ile Gln Leu Phe Ile Pro
1               5                   10                  15

Phe His Leu Leu Asn Phe Leu Ala Tyr Ile Thr Ala Val Tyr Gly Cys
                20                  25                  30

Asn Asp Asp Thr Asp Cys Pro Pro Ser Cys Thr Thr Arg Gly Cys Pro
            35                  40                  45

Asp Ser Cys Ala Tyr Pro His Val Leu Arg Cys Ile Gly Lys Asn Cys
    50                  55                  60

Val Cys Thr
65

<210> SEQ ID NO 267
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 267

Met Ala Glu Ile Phe Lys Phe Tyr Ala Leu Ile Ile Phe Ile Ser
1               5                   10                  15

Leu Ile Leu Ser Val Ala Asn Ala Asp Pro Met Tyr Cys Phe Asn Asp
                20                  25                  30

Asp Asp Cys Arg Glu Leu Lys Cys Ser His Pro Arg Val Arg Lys Cys
            35                  40                  45

Arg Met Phe Leu Cys Arg Cys Glu Glu Val Asp Lys Glu Asp Glu Lys
    50                  55                  60

<210> SEQ ID NO 268
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 268

Met Gly Asp Ile Ile Lys Val Val Phe Ala Met Ile Ile Tyr Leu Tyr
1               5                   10                  15

Met Leu Thr Ile Val Thr Asn Ala Val Thr Ile Cys Asp Ser Asp Gln
            20                  25                  30

Asp Cys Arg Arg Tyr Arg Cys Asp Pro Pro Glu Tyr Pro Arg Cys Leu
        35                  40                  45

Gly Ile Leu Cys Lys Cys Val Tyr Val Ser Gly
    50                  55

<210> SEQ ID NO 269
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 269

Met Ala Lys Leu Met Met Phe Phe Tyr Val Met Ile Tyr Phe Phe Val
1               5                   10                  15

Leu Val Ala Cys Gln Lys Arg Arg Arg Ser Thr Glu Cys Arg Asn Asp
            20                  25                  30

Ser Asp Cys Glu Lys Met Val Lys Cys Val Leu Pro Arg Ile Ala Arg
        35                  40                  45

Cys Ile Lys Tyr Arg Cys Gln Cys Arg Asn Phe Leu Glu Ser Phe Glu
    50                  55                  60

<210> SEQ ID NO 270
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 270

Met Val Glu Val Thr Lys Leu Val Asn Val Met Leu Ile Phe Leu Thr
1               5                   10                  15

Leu Phe Val Val Ala Leu Ser Asn Asp Thr Gly Tyr Thr Asp Cys Leu
            20                  25                  30

Gln His Ser Asp Cys Gln Ala Tyr Ala Cys Glu Leu Pro Phe Lys Pro
        35                  40                  45

Asp Cys Leu Met Val Glu Tyr Ala Pro Gln Phe Phe Arg Leu Ala Cys
    50                  55                  60

Gly Cys Val
65

<210> SEQ ID NO 271
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 271

Met Ala Glu Asn Tyr Lys Phe Val Tyr Val Val Ile Phe Phe Val Ser
1               5                   10                  15

Leu Phe Leu Asp Val Val Asp Gly Glu Lys Gly Thr Ile Val Asp Ile
            20                  25                  30

Glu Thr Thr Gly Gln Cys Ala Asp Asp Tyr Glu Cys Tyr Arg Leu Phe
        35                  40                  45

Ser Cys Pro Arg Glu Val Ala Phe Lys Cys Ile Asn Gly Trp Cys Lys
            50                  55                  60

Cys Ile Leu
65

<210> SEQ ID NO 272
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 272

Phe Asp Arg Arg Phe Ile Cys Phe Asp Asn Ser Asp Cys Pro Gln His
1               5                   10                  15

Leu Cys His Glu Leu Ile Ile Pro Arg Cys Lys Ile Gly Val Cys Val
            20                  25                  30

Cys Leu Pro
        35

<210> SEQ ID NO 273
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 273

Met Asn Asn Met Val Glu Thr Cys Lys Tyr Phe Tyr Val Val Ile Leu
1               5                   10                  15

Phe Leu Phe Ile Phe Ile Met Ala Thr Asp Gly Val Tyr Leu Cys Glu
            20                  25                  30

Asp Asp Glu Asp Cys His Ile Met Pro Cys Met Val Pro Glu Tyr Ala
        35                  40                  45

Lys Cys Ile Arg Met Ile Cys Gln Cys Cys
    50                  55

<210> SEQ ID NO 274
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 274

Met Gln Arg Arg Lys Asn Met Ala Asn Asn His Met Leu Ile Tyr Ala
1               5                   10                  15

Met Ile Ile Cys Leu Phe Pro Tyr Leu Val Val Thr Phe Lys Thr Ala
            20                  25                  30

Ile Thr Cys Asp Cys Asn Glu Asp Cys Leu Asn Phe Phe Thr Pro Leu
        35                  40                  45

Asp Asn Leu Lys Cys Ile Asp Asn Val Cys Glu Val Phe Met
    50                  55                  60

<210> SEQ ID NO 275
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 275

```
Met Thr Gly Ile His Lys Phe Phe His Met Val Ile His Phe Val Phe
1               5                   10                  15

Leu Phe Leu Val Val Tyr Gly Ser Gly Ile Ala Glu Lys Glu Cys Ile
                20                  25                  30

Thr Asp Asp Asp Cys Asn Arg Lys Tyr Pro Met His Ala Asn Arg Gly
            35                  40                  45

Leu Gln Cys Leu Asn Gly Glu Cys Lys Ser Ser Arg Ile Ile Lys Ser
        50                  55                  60

Arg
65

<210> SEQ ID NO 276
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 276

Met Thr Pro Ile Thr Lys Asn Ile Phe Asp Met Ile Ile Phe Ile Ser
1               5                   10                  15

Pro Leu Ile Val Thr Met Ser Met Arg Val Leu Cys Gly Arg Asp Gly
                20                  25                  30

Arg Cys Pro Lys Phe Met Cys Arg Thr Phe Leu
            35                  40

<210> SEQ ID NO 277
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 277

Phe Val Trp Leu Leu Ile Ile Phe Leu Ser Leu Phe Leu Phe Glu Ile
1               5                   10                  15

Thr Val Gly Gly Arg Tyr Thr Thr Pro Trp Cys Val Arg Asp Ile Asp
                20                  25                  30

Cys Pro Lys Glu Lys Cys Lys His Pro Phe Lys Pro Arg Cys Leu Thr
            35                  40                  45

His Ser Cys Val Cys Arg Leu Trp Gly Ser Gln Asp Val Ile
        50                  55                  60

<210> SEQ ID NO 278
<211> LENGTH: 54
<212> TYPE: PRT
<213> ORGANISM: Artificial sequence
<220> FEATURE:
<223> OTHER INFORMATION: Peptide derived from Medicago truncatula

<400> SEQUENCE: 278

Ile Lys Phe Met Tyr Val Ile Ile Val Leu Phe Val Phe Leu Ser
1               5                   10                  15

Val Arg Lys Asn Thr Asp Ala Lys Asn Ile Cys Ile Asp Asp Val His
                20                  25                  30

Cys Gln Lys Tyr Lys Cys Ser Pro Gly Leu Tyr Pro Thr Cys Ile Asn
            35                  40                  45

Gly Trp Cys Glu Cys Lys
        50

<210> SEQ ID NO 279
```

<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 279

Met Lys Phe Val Tyr Val Met Ile Leu Phe Leu Ser Leu Phe Ile Val
1               5                   10                  15

Ser Thr Asn Gly Tyr Glu Lys Ile Ser Cys Gln Asn Asp Phe Asp Cys
            20                  25                  30

Pro Glu Ser Met Cys Glu Phe Gly Met Ile Arg Arg Cys Ile Ser Tyr
        35                  40                  45

Lys Cys Gln Cys His Glu Ala Tyr
    50                  55

<210> SEQ ID NO 280
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 280

Met Asp Lys Val Tyr Lys Phe Val Tyr Val Met Ile Ile Phe Phe Ser
1               5                   10                  15

Gln Ile Ile Val Ala Thr Asn Ala Gln Lys Ile Arg Arg Cys Phe Asn
            20                  25                  30

Asp Ala His Cys Pro Pro Asp Met Cys Thr Pro Gly Val Ile Pro Lys
        35                  40                  45

Cys Lys Phe Thr Ile Cys Lys Cys
    50                  55

<210> SEQ ID NO 281
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 281

Met Gly Gln Ile Gln Lys Phe Ile Ser Ser Leu Ile Ile Ile Ile Ser
1               5                   10                  15

Leu Val Leu Val Val Thr Cys Asn Cys Ile Pro Met Ile His Pro Leu
            20                  25                  30

Leu Tyr Lys Lys Arg Val Val Pro Asn Cys Gln Thr Ile Val Asp Cys
        35                  40                  45

Pro Asp Asn Met Cys Thr His Pro Lys Glu Val Tyr Cys Ile Gly Tyr
    50                  55                  60

Arg Cys Tyr Cys Leu Lys
65                  70

<210> SEQ ID NO 282
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 282

Met Asp Glu Ile Leu Lys Phe Val Tyr Thr Leu Ile Ile Phe Phe Ser
1               5                   10                  15

-continued

Leu Phe Phe Ala Ala Asn Asn Val Asp Ala Asn Ile Met Asn Cys Gln
                20                  25                  30

Ser Thr Phe Asp Cys Pro Arg Asp Met Cys Ser His Ile Arg Asp Val
            35                  40                  45

Ile Cys Ile Phe Lys Lys Cys Lys Cys Ala Gly Gly Arg Tyr Met Pro
 50                  55                  60

Gln Val Pro
 65

<210> SEQ ID NO 283
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 283

Met Ala Gln Ile Leu Tyr Tyr Phe Phe Ala Phe Leu Ile Phe Val Ser
 1               5                  10                  15

Leu Phe Leu Val Val Thr Asn Gln Ser Ile Pro Asp Val Leu Pro Cys
                20                  25                  30

Leu Phe Ser Asn Glu Cys Pro Pro Asp Leu Cys Pro Ile Asp Leu Phe
            35                  40                  45

Pro Lys Cys Ile Asn Leu Ser Cys Gln Cys Ser Ala Glu Phe Tyr Asn
 50                  55                  60

Ile Asp
 65

<210> SEQ ID NO 284
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 284

Asp Met Ile Ile Phe Leu Ser Pro Leu Ile Val Thr Met Ser Met Lys
 1               5                  10                  15

Val Leu Cys Gly Arg Asp Gly Thr Cys Pro Arg Phe Met Cys Gly Pro
                20                  25                  30

Gly Ile Ile Pro Lys Cys Val Gly Arg Tyr Cys Glu Cys
            35                  40                  45

<210> SEQ ID NO 285
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 285

Met Val Lys Ile Ile Lys Phe Val Tyr Phe Met Thr Leu Phe Leu Ser
 1               5                  10                  15

Met Leu Leu Val Thr Thr Lys Glu Asp Gly Ser Val Glu Cys Ile Ala
                20                  25                  30

Asn Ile Asp Cys Pro Gln Ile Phe Met Leu Pro Phe Val Met Arg Cys
            35                  40                  45

Ile Asn Phe Arg Cys Gln Ile Val Asn Ser Glu Asp Thr
 50                  55                  60

<210> SEQ ID NO 286

<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 286

Met Ala Lys Ile Ile Lys Phe Val Tyr Val Leu Ala Ile Phe Phe Ser
1               5                   10                  15

Leu Phe Leu Val Ala Lys Asn Val Asn Gly Trp Thr Cys Val Glu Asp
            20                  25                  30

Ser Asp Cys Pro Ala Asn Ile Cys Gln Pro Pro Met Gln Arg Met Cys
        35                  40                  45

Phe Tyr Gly Glu Cys Ala Cys Val Arg Ser Lys Phe Cys Thr
    50                  55                  60

<210> SEQ ID NO 287
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 287

Met Thr Gly Val Leu Lys Phe Val Tyr Thr Met Val Phe Phe Leu Ser
1               5                   10                  15

Leu Phe Leu Ile Ala Ile Asp Ile Lys Val Ala Ala Phe Leu Arg Cys
            20                  25                  30

Asp Phe Asp Leu Asp Cys Pro Pro Lys Met Cys Tyr Ser His Leu Tyr
        35                  40                  45

Phe Val Pro Met Cys Val Asp Asn His Cys Asp Cys Thr Gln Trp Lys
    50                  55                  60

Asp Ile Ile Pro Thr Ile Pro
65                  70

<210> SEQ ID NO 288
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 288

Thr Thr Phe His Pro Ile Leu Val Ile Leu Phe Tyr Ser Leu Phe Pro
1               5                   10                  15

Phe Ile Pro Ala Pro Ile Arg Cys Asn Arg Val Ser Asp Cys Pro Lys
            20                  25                  30

Ile Arg Cys Asn Ile Gly Phe Val Leu Arg Cys Leu Tyr Asn Gln Cys
        35                  40                  45

Lys Cys Val Arg Ile Thr Gln Leu Val Asp Tyr Val Leu Lys
    50                  55                  60

<210> SEQ ID NO 289
<211> LENGTH: 85
<212> TYPE: PRT
<213> ORGANISM: Artificial sequence
<220> FEATURE:
<223> OTHER INFORMATION: Peptide derived from Medicago truncatula

<400> SEQUENCE: 289

Met Ala Ile Ile Lys Phe Ile Tyr Thr Met Phe Leu Phe Ile Phe Leu
1               5                   10                  15

```
Phe Val Ile Pro Thr Lys Val Asp Gly Arg Ile Thr His Glu Thr Leu
            20                  25                  30

Pro Leu Pro Val Ser Lys Pro Ile Pro Ile Leu Gly Gly Glu Cys Ile
            35                  40                  45

Ser Asp Ala Asp Cys Lys His Pro Glu Cys Asn Cys Arg Gly Val
 50                  55                  60

Cys Leu Asn Ser Arg Cys Ile Cys Met Ala Arg Ser Gly Trp Thr Tyr
 65                  70                  75                  80

Thr Ile Pro Gln Asn
                85

<210> SEQ ID NO 290
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 290

Ala Ile Ile Tyr Leu Ser Leu Phe Leu Phe Val Phe Glu Asp Lys Arg
 1               5                  10                  15

Glu Cys Asp Thr Asn Phe Asp Cys Gln Gln Lys Phe Ser Thr Gln Ala
            20                  25                  30

Glu Asp Leu Leu Trp Cys Ile Arg Gly Tyr Cys Met Ser Ile Pro Asn
            35                  40                  45

<210> SEQ ID NO 291
<211> LENGTH: 52
<212> TYPE: PRT
<213> ORGANISM: Artificial sequence
<220> FEATURE:
<223> OTHER INFORMATION: Peptide derived from Medicago truncatula

<400> SEQUENCE: 291

Met Ile Leu Cys Phe Ser Val Phe Leu Phe Ala Lys Asn Ile Asp Ala
 1               5                  10                  15

Leu His Cys Asn Asn Asp Asn Glu Cys Pro Pro Ser Thr Trp Lys Pro
            20                  25                  30

Phe Val Arg Cys Lys Met Asn Arg Cys Ile Tyr Ser Arg Val Gln Pro
            35                  40                  45

Pro Trp Ala Cys
 50

<210> SEQ ID NO 292
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 292

Phe Ser Phe Leu Phe Leu Val Val Ala Thr Leu Ile Glu Glu Cys Val
 1               5                  10                  15

Thr Asp Ala Asp Cys Tyr Lys Ile Tyr Pro Glu Ala Ser Phe Leu His
            20                  25                  30

Met Phe Cys Ile Asp Gly Val Cys Lys Thr Pro Ile Pro Leu
            35                  40                  45

<210> SEQ ID NO 293
<211> LENGTH: 67
<212> TYPE: PRT
<213> ORGANISM: Artificial sequence
```

```
<220> FEATURE:
<223> OTHER INFORMATION: Peptide derived from Medicago truncatula

<400> SEQUENCE: 293

Met Ala Glu Ile Leu Lys Phe Val Phe Gly Ile Ile Ile Phe Leu Pro
1               5                   10                  15

Ile Phe Leu Val Ala Met Asp Ile Val Asp Lys Ile Asp Glu Cys Glu
            20                  25                  30

Ser Asn Val Asp Cys Pro Lys Ser Tyr Ile Ile Asn Trp Asp Lys Asn
        35                  40                  45

Tyr Val His Lys Cys Ile Asn Asn Arg Cys Glu Trp Ile Lys Ile Ile
    50                  55                  60

Arg Arg Arg
65

<210> SEQ ID NO 294
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 294

Leu Tyr Leu Val Asp Leu Gly Cys Val Thr Asp Ala Asp Cys Lys Asp
1               5                   10                  15

Lys Phe Pro Gly Asn Lys Tyr Pro Ile Lys Cys Ile Asn Gly Ile Cys
            20                  25                  30

Lys Ser Val Pro Asn
        35

<210> SEQ ID NO 295
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 295

Met Thr Glu Ile Arg Lys Phe Phe Tyr Met Leu Ile His Val Phe Phe
1               5                   10                  15

Leu Phe Ile Val Arg Lys Tyr Gly Ser Glu Cys Ile Ser Asp Thr Asp
            20                  25                  30

Cys Asn Val Leu Tyr Pro Met Tyr Ile Asn Arg Arg Leu Arg Cys Ile
        35                  40                  45

Gln Gly Ile Cys His Thr Thr Thr Ala Arg Arg Arg
    50                  55                  60

<210> SEQ ID NO 296
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 296

Met Asp Glu Thr Leu Lys Phe Val Tyr Ile Leu Ile Leu Phe Val Ser
1               5                   10                  15

Leu Cys Leu Val Val Ala Asp Gly Val Lys Asn Ile Asn Arg Glu Cys
            20                  25                  30

Thr Gln Thr Ser Asp Cys Tyr Lys Lys Tyr Pro Phe Ile Pro Trp Gly
        35                  40                  45
```

-continued

```
Lys Val Arg Cys Val Lys Gly Arg Cys Arg Leu Asp Met
    50                  55                  60
```

<210> SEQ ID NO 297
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 297

```
Met Ala His Lys Leu Val Tyr Ala Ile Thr Leu Phe Ile Phe Leu Phe
1               5                   10                  15

Leu Ile Ala Asn Asn Ile Glu Asp Asp Ile Phe Cys Ile Thr Asp Asn
            20                  25                  30

Asp Cys Pro Pro Asn Thr Leu Val Gln Arg Tyr Arg Cys Ile Asn Gly
        35                  40                  45

Lys Cys Asn Leu Ser Phe Val Ser Tyr Gly
    50                  55
```

<210> SEQ ID NO 298
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 298

```
Ala Ile His Cys Asn Asp Val Asn Asp Cys Pro Pro Asp Ile Ser Asp
1               5                   10                  15

Pro Phe Val Arg Cys Glu Ser Asn Arg Cys Ile Tyr Ser Arg Leu Glu
            20                  25                  30

Pro Pro Phe Gly Cys
        35
```

<210> SEQ ID NO 299
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 299

```
Met Arg Lys Asn Met Thr Lys Ile Leu Met Ile Gly Tyr Ala Leu Met
1               5                   10                  15

Ile Phe Ile Phe Leu Ser Ile Ala Val Ser Ile Thr Gly Asn Leu Ala
            20                  25                  30

Arg Ala Ser Arg Lys Lys Pro Val Asp Val Ile Pro Cys Ile Tyr Asp
        35                  40                  45

His Asp Cys Pro Arg Lys Leu Tyr Phe Leu Glu Arg Cys Val Gly Arg
    50                  55                  60

Val Cys Lys Tyr Leu
65
```

<210> SEQ ID NO 300
<211> LENGTH: 85
<212> TYPE: PRT
<213> ORGANISM: Artificial sequence
<220> FEATURE:
<223> OTHER INFORMATION: Peptide derived from Medicago truncatula

<400> SEQUENCE: 300

```
Met Thr Ile Ile Ile Lys Phe Val Asn Val Leu Ile Ile Phe Leu Ser
```

```
                1               5                  10                 15
Leu Phe His Val Ala Lys Asn Asp Asp Asn Lys Leu Leu Leu Ser Phe
                               20                 25                 30

Ile Glu Glu Gly Phe Leu Cys Phe Lys Asp Ser Asp Cys Pro Tyr Asn
                35                 40                 45

Met Cys Pro Ser Pro Leu Lys Glu Met Cys Tyr Phe Ile Lys Cys Val
     50                 55                 60

Cys Gly Val Tyr Gly Pro Ile Arg Glu Arg Arg Leu Tyr Gln Ser His
 65                 70                 75                 80

Asn Pro Met Ile Gln
                85
```

<210> SEQ ID NO 301
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 301

```
Ile Ser Leu Phe Leu Val Val Tyr Cys Glu Lys Cys Ala Asn Asp
 1               5                  10                 15

Ile Asp Cys Tyr Lys Ile Phe Leu Gly Pro Pro Leu Ile Pro Met Lys
                20                 25                 30

Cys Ile Asp Gly Glu Cys Lys Arg Ile Thr
             35                 40
```

<210> SEQ ID NO 302
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 302

```
Met Ala Glu Ile Phe Lys Phe Val Tyr Ser Val Ile Leu Phe Val Ser
 1               5                  10                 15

Leu Tyr Leu Phe Val Ile Tyr Ala Glu Lys Glu Cys Asp Thr Asp Ala
                20                 25                 30

Asp Cys Arg Lys Lys Phe Ala Gly Ala Asn Gln His Leu Leu Trp Cys
             35                 40                 45

Asn Asn Gly Tyr Cys Glu Cys His Thr His
     50                 55
```

<210> SEQ ID NO 303
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 303

```
Met Thr Glu Thr Leu Lys Phe Phe Tyr Ala Met Ile Leu Phe Leu Ser
 1               5                  10                 15

Leu Phe Leu Ile Thr Thr Asn Val Gly Gly Ser Tyr Tyr Gly Cys Glu
                20                 25                 30

Thr Asp Ala Asp Cys Pro Arg Ser Met Asn Lys Asp Phe Tyr Leu Lys
             35                 40                 45

Cys Val Asp Lys Lys Cys Glu Trp Thr Ala Lys Ile
     50                 55                 60
```

-continued

<210> SEQ ID NO 304
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 304

Phe Arg Ala Ile His Glu Cys Arg Ala His Ser His Cys Val Ala Arg
1               5                   10                  15

Ile Asn Cys Val Leu Pro Arg Lys Pro Gln Cys Arg Asn Tyr Ala Cys
            20                  25                  30

Gly Cys Tyr Asp Ser Asn Lys Tyr Arg
        35                  40

<210> SEQ ID NO 305
<211> LENGTH: 73
<212> TYPE: PRT
<213> ORGANISM: Artificial sequence
<220> FEATURE:
<223> OTHER INFORMATION: Peptide derived from Medicago truncatula

<400> SEQUENCE: 305

Met Gln Arg Ser Arg Asn Met Thr Thr Ile Phe Lys Phe Ala Tyr Ile
1               5                   10                  15

Met Ile Ile Cys Val Phe Leu Leu Asn Ile Ala Ala Gln Glu Ile Glu
            20                  25                  30

Asn Gly Ile His Pro Cys Lys Lys Asn Glu Asp Cys Asn His Met Cys
        35                  40                  45

Val Met Pro Gly Leu Pro Trp Cys His Glu Asn Asn Leu Cys Phe Cys
    50                  55                  60

Tyr Glu Asn Ala Tyr Gly Asn Thr Arg
65                  70

<210> SEQ ID NO 306
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 306

Met Ile Lys Gln Phe Ser Val Cys Tyr Ile Gln Met Arg Arg Asn Met
1               5                   10                  15

Thr Thr Ile Leu Lys Phe Pro Tyr Ile Met Val Ile Cys Leu Leu Leu
            20                  25                  30

Leu His Val Ala Ala Tyr Glu Asp Phe Glu Lys Glu Ile Phe Asp Cys
        35                  40                  45

Lys Lys Asp Gly Asp Cys Asp His Met Cys Val Thr Pro Gly Ile Pro
    50                  55                  60

Lys Cys Thr Gly Tyr Val Cys Phe Cys Phe Glu Asn Leu
65                  70                  75

<210> SEQ ID NO 307
<211> LENGTH: 52
<212> TYPE: PRT
<213> ORGANISM: Artificial sequence
<220> FEATURE:
<223> OTHER INFORMATION: Peptide derived from Medicago truncatula

<400> SEQUENCE: 307

Gly Leu Phe Ser Phe Phe Ile Pro Thr Gly Trp Arg Cys Lys Lys Thr

-continued

```
                1               5                  10                 15
Asp Asp Cys Leu Lys Ile Glu Phe Cys Lys Phe Pro Lys Ile Ala Arg
                       20                  25                 30

Gly Thr Lys Pro Lys Phe Leu Phe Phe Glu Phe Gly Thr Gly Phe Cys
                       35                  40                 45

Thr Trp Asp Asp
            50
```

<210> SEQ ID NO 308
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 308

```
Met Ala Lys Val Tyr Met Phe Val Tyr Ala Leu Ile Ile Phe Val Ser
1               5                  10                 15

Pro Phe Leu Leu Ala Thr Phe Arg Thr Arg Leu Pro Cys Glu Lys Asp
                       20                  25                 30

Asp Asp Cys Pro Glu Ala Phe Leu Pro Pro Val Met Lys Cys Val Asn
                       35                  40                 45

Arg Phe Cys Gln Tyr Glu Ile Leu Glu
            50                  55
```

<210> SEQ ID NO 309
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 309

```
Met Gln Arg Arg Lys Lys Lys Ala Gln Val Val Met Phe Val His Asp
1               5                  10                 15

Leu Ile Ile Cys Ile Tyr Leu Phe Ile Val Ile Thr Thr Arg Lys Thr
                       20                  25                 30

Asp Ile Arg Cys Arg Phe Tyr Tyr Asp Cys Pro Arg Leu Glu Tyr His
                       35                  40                 45

Phe Cys Glu Cys Ile Glu Asp Phe Cys Ala Tyr Ile Arg Leu Asn
            50                  55                  60
```

<210> SEQ ID NO 310
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 310

```
Met Ala Asn Thr His Lys Leu Val Ser Met Ile Leu Phe Ile Phe Leu
1               5                  10                 15

Phe Leu Ala Ser Asn Asn Val Glu Gly Tyr Val Asn Cys Glu Thr Asp
                       20                  25                 30

Ala Asp Cys Pro Pro Ser Thr Arg Val Lys Arg Phe Lys Cys Val Lys
                       35                  40                 45

Gly Glu Cys Arg Trp Thr Arg Met Ser Tyr Ala
            50                  55
```

<210> SEQ ID NO 311
<211> LENGTH: 61

```
<212> TYPE: PRT
<213> ORGANISM: Artificial sequence
<220> FEATURE:
<223> OTHER INFORMATION: Peptide derived from Medicago truncatula

<400> SEQUENCE: 311

Met Ala Gly Ile Ile Lys Phe Val His Val Leu Ile Ile Phe Leu Ser
1               5                   10                  15

Leu Phe His Val Val Lys Asn Asp Asp Gly Ser Phe Cys Phe Lys Asp
                20                  25                  30

Ser Asp Cys Pro Asp Glu Met Cys Pro Ser Pro Leu Lys Glu Met Cys
            35                  40                  45

Tyr Phe Leu Gln Cys Lys Cys Gly Val Asp Thr Ile Ala
    50                  55                  60

<210> SEQ ID NO 312
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 312

Met Gln Arg Glu Lys Asn Met Ala Lys Ile Phe Glu Phe Val Tyr Ala
1               5                   10                  15

Met Ile Ile Phe Ile Leu Leu Phe Leu Val Glu Lys Asn Val Val Ala
                20                  25                  30

Tyr Leu Lys Phe Glu Cys Lys Thr Asp Asp Cys Gln Lys Ser Leu
            35                  40                  45

Leu Lys Thr Tyr Val Trp Lys Cys Val Lys Asn Glu Cys Tyr Phe Phe
    50                  55                  60

Ala Lys Lys
65

<210> SEQ ID NO 313
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 313

Met Asn His Ile Ser Lys Phe Val Tyr Ala Leu Ile Ile Phe Leu Ser
1               5                   10                  15

Ile Tyr Leu Val Val Leu Asp Gly Leu Pro Ile Ser Cys Lys Asp His
                20                  25                  30

Phe Glu Cys Arg Arg Lys Ile Asn Ile Leu Arg Cys Ile Tyr Arg Gln
            35                  40                  45

Glu Lys Pro Met Cys Ile Asn Ser Ile Cys Thr Cys Val Lys Leu Leu
    50                  55                  60

<210> SEQ ID NO 314
<211> LENGTH: 76
<212> TYPE: PRT
<213> ORGANISM: Artificial sequence
<220> FEATURE:
<223> OTHER INFORMATION: Peptide derived from Medicago truncatula

<400> SEQUENCE: 314

Met Gln Met Arg Lys Asn Met Ala Gln Ile Leu Phe Tyr Val Tyr Ala
1               5                   10                  15

Leu Leu Ile Leu Phe Thr Pro Phe Leu Val Ala Arg Ile Met Val Val
```

-continued

```
                    20                  25                  30

Asn Pro Asn Asn Pro Cys Val Thr Asp Ala Asp Cys Gln Arg Tyr Arg
            35                  40                  45

His Lys Leu Ala Thr Arg Met Ile Cys Asn Gln Gly Phe Cys Leu Met
        50                  55                  60

Asp Phe Thr His Asp Pro Tyr Ala Pro Ser Leu Pro
65                  70                  75

<210> SEQ ID NO 315
<211> LENGTH: 74
<212> TYPE: PRT
<213> ORGANISM: Artificial sequence
<220> FEATURE:
<223> OTHER INFORMATION: Peptide derived from Medicago truncatula

<400> SEQUENCE: 315

Met Gln Lys Arg Lys Asn Met Ala Gln Ile Ile Phe Tyr Val Tyr Ala
1               5                   10                  15

Leu Ile Ile Leu Phe Ser Pro Phe Leu Ala Ala Arg Leu Val Phe Val
                    20                  25                  30

Asn Pro Glu Lys Pro Cys Val Thr Asp Ala Asp Cys Asp Arg Tyr Arg
            35                  40                  45

His Glu Ser Ala Ile Tyr Ser Asp Met Phe Cys Lys Asp Gly Tyr Cys
        50                  55                  60

Phe Ile Asp Tyr His His Asp Pro Tyr Pro
65                  70

<210> SEQ ID NO 316
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 316

Met Thr Ala Ile Leu Lys Lys Phe Ile Asn Ala Val Phe Leu Phe Ile
1               5                   10                  15

Val Leu Phe Leu Ala Thr Thr Asn Val Glu Asp Phe Val Gly Gly Ser
                    20                  25                  30

Asn Asp Glu Cys Val Tyr Pro Asp Val Phe Gln Cys Ile Asn Asn Ile
            35                  40                  45

Cys Lys Cys Val Ser His His Arg Thr
        50                  55

<210> SEQ ID NO 317
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 317

Met Phe Glu Ile Phe Lys Phe Val Tyr Val Val Ile Phe Leu Ser
1               5                   10                  15

Leu Tyr Ile Leu Ser Ile Glu Val Gly Gly Ala Leu Ile Glu Cys Glu
                    20                  25                  30

Ile Asp Leu Asp Cys Pro Lys Ser Tyr Ile Lys Leu Trp Asp Arg Asn
            35                  40                  45

Tyr Ala His Arg Cys Val Asn Asn Ile Cys Glu Trp Val Lys Lys Pro
        50                  55                  60
```

Arg Ile Tyr
65

<210> SEQ ID NO 318
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 318

Met Phe Glu Ile Phe Lys Phe Val Tyr Val Val Ile Phe Leu Ser
1               5                   10                  15

Leu Tyr Ile Leu Ser Thr Leu Ile Glu Cys Glu Ile Asp Leu Asp Cys
                20                  25                  30

Pro Lys Ser Tyr Ile Lys Leu Trp Asp Lys Asn Tyr Ala His Arg Cys
                35                  40                  45

Val Asn Asn Ile Cys Glu Trp Val Lys Lys Pro Arg Ile Tyr
            50                  55                  60

<210> SEQ ID NO 319
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 319

Met Gln Ile Gly Arg Lys Lys Gly Glu Thr Pro Lys Leu Val Tyr
1               5                   10                  15

Val Ile Ile Leu Phe Leu Ser Ile Phe Leu Cys Thr Asn Ser Ser Phe
                20                  25                  30

Ser Gln Met Ile Asn Phe Ser Gly Cys Lys Arg Asp Lys Asp Cys Pro
            35                  40                  45

Gln Phe Arg Gly Val Asn Ile Arg Cys Arg Ser Gly Phe Cys Thr Pro
        50                  55                  60

Ile Asp Ser
65

<210> SEQ ID NO 320
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 320

Met Gln Ile Gly Lys Asn Met Val Glu Thr Pro Lys Leu Val Tyr Phe
1               5                   10                  15

Ile Ile Leu Phe Leu Ser Ile Phe Leu Cys Ile Thr Val Ser Asn Ser
                20                  25                  30

Ser Phe Ser Gln Ile Phe Asn Ser Ala Cys Lys Thr Asp Lys Asp Cys
            35                  40                  45

Pro Lys Phe Gly Arg Val Asn Val Arg Cys Arg Lys Gly Asn Cys Val
        50                  55                  60

Pro Ile
65

<210> SEQ ID NO 321
<211> LENGTH: 57
<212> TYPE: PRT
<213> ORGANISM: Artificial sequence

```
<220> FEATURE:
<223> OTHER INFORMATION: Peptide derived from Medicago truncatula

<400> SEQUENCE: 321

Met Thr Thr Ser Leu Lys Phe Val Tyr Val Ala Ile Leu Phe Leu Ser
1               5                  10                  15

Leu Leu Leu Val Val Met Gly Gly Ile Arg Lys Lys Glu Cys Arg Gln
            20                  25                  30

Asp Ser Asp Cys Pro Ser Tyr Phe Cys Glu Lys Leu Thr Ile Ala Lys
        35                  40                  45

Cys Ile His Ser Thr Cys Leu Cys Lys
    50                  55

<210> SEQ ID NO 322
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 322

Met Thr Thr Ser Leu Lys Phe Val Tyr Val Ala Ile Leu Phe Leu Ser
1               5                  10                  15

Leu Leu Leu Val Val Met Gly Gly Ile Arg Arg Phe Glu Cys Arg Gln
            20                  25                  30

Asp Ser Asp Cys Pro Ser Tyr Phe Cys Glu Lys Leu Thr Val Pro Lys
        35                  40                  45

Cys Phe Trp Ser Lys Cys Tyr Cys Lys
    50                  55

<210> SEQ ID NO 323
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 323

Met Ala Thr Ile Leu Met Tyr Val Tyr Ile Thr Ile Leu Phe Ile Ser
1               5                  10                  15

Ile Leu Thr Val Leu Thr Glu Gly Leu Tyr Glu Pro Leu Tyr Asn Phe
            20                  25                  30

Arg Arg Asp Pro Asp Cys Arg Arg Asn Ile Asp Cys Pro Ser Tyr Leu
        35                  40                  45

Cys Val Ala Pro Lys Val Pro Arg Cys Ile Met Phe Glu Cys His Cys
    50                  55                  60

Lys Asp Ile Pro Ser Asp His
65                  70

<210> SEQ ID NO 324
<211> LENGTH: 78
<212> TYPE: PRT
<213> ORGANISM: Artificial sequence
<220> FEATURE:
<223> OTHER INFORMATION: Peptide derived from Medicago truncatula

<400> SEQUENCE: 324

Met Gln Met Arg Gln Asn Met Ala Thr Ile Leu Asn Phe Val Phe Val
1               5                  10                  15

Ile Ile Leu Phe Ile Ser Leu Leu Leu Val Val Thr Lys Gly Tyr Arg
            20                  25                  30
```

```
Glu Pro Phe Ser Ser Phe Thr Glu Gly Pro Thr Cys Lys Glu Asp Ile
        35                  40                  45

Asp Cys Pro Ser Ile Ser Cys Val Asn Pro Gln Val Pro Lys Cys Ile
 50                  55                  60

Met Phe Glu Cys His Cys Lys Tyr Ile Pro Thr Thr Leu Lys
 65                  70                  75
```

<210> SEQ ID NO 325
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 325

```
Met Phe His Ala Gln Ala Glu Asn Met Ala Lys Val Ser Asn Phe Val
 1               5                  10                  15

Cys Ile Met Ile Leu Phe Leu Ala Leu Phe Phe Ile Thr Met Asn Asp
            20                  25                  30

Ala Ala Arg Phe Glu Cys Arg Glu Asp Ser His Cys Val Thr Arg Ile
        35                  40                  45

Lys Cys Val Leu Pro Arg Lys Pro Glu Cys Arg Asn Tyr Ala Cys Gly
 50                  55                  60

Cys Tyr Asp Ser Asn Lys Tyr Arg
 65                  70
```

<210> SEQ ID NO 326
<211> LENGTH: 78
<212> TYPE: PRT
<213> ORGANISM: Artificial sequence
<220> FEATURE:
<223> OTHER INFORMATION: Peptide derived from Medicago truncatula

<400> SEQUENCE: 326

```
Met Val Glu Ile Leu Lys Asn Phe Tyr Ala Met Asn Leu Phe Ile Phe
 1               5                  10                  15

Leu Ile Ile Leu Ala Val Lys Ile Arg Gly Ala His Phe Pro Cys Val
            20                  25                  30

Thr Asp Asp Asp Cys Pro Lys Pro Val Asn Lys Leu Arg Val Ile Lys
        35                  40                  45

Cys Ile Asp His Ile Cys Gln Tyr Ala Arg Asn Leu Pro Asp Phe Ala
 50                  55                  60

Ser Glu Ile Ser Glu Ser Thr Lys Met Pro Cys Lys Gly Glu
 65                  70                  75
```

<210> SEQ ID NO 327
<211> LENGTH: 100
<212> TYPE: PRT
<213> ORGANISM: Artificial sequence
<220> FEATURE:
<223> OTHER INFORMATION: Peptide derived from Medicago truncatula

<400> SEQUENCE: 327

```
Met Ala Glu Ile Leu Lys Asp Phe Tyr Ala Met Asn Leu Phe Ile Phe
 1               5                  10                  15

Leu Ile Ile Leu Pro Ala Lys Ile Arg Gly Glu Thr Leu Ser Leu Thr
            20                  25                  30

His Pro Lys Cys His His Ile Met Leu Pro Ser Leu Phe Ile Thr Glu
        35                  40                  45

Val Phe Gln Arg Val Thr Asp Asp Gly Cys Pro Lys Pro Val Asn His
 50                  55                  60
```

```
Leu Arg Val Val Lys Cys Ile Glu His Ile Cys Glu Tyr Gly Tyr Asn
 65                  70                  75                  80

Tyr Arg Pro Asp Phe Ala Ser Gln Ile Pro Glu Ser Thr Lys Met Pro
                 85                  90                  95

Arg Lys Arg Glu
            100

<210> SEQ ID NO 328
<211> LENGTH: 95
<212> TYPE: PRT
<213> ORGANISM: Artificial sequence
<220> FEATURE:
<223> OTHER INFORMATION: Peptide derived from Medicago truncatula

<400> SEQUENCE: 328

Met Ala Glu Ile Ile Lys Phe Val Tyr Ile Met Ile Leu Cys Val Ser
  1               5                  10                  15

Leu Leu Leu Ile Glu Val Ala Gly Glu Glu Cys Val Thr Asp Ala Asp
                 20                  25                  30

Cys Asp Lys Leu Tyr Pro Asp Ile Arg Lys Pro Leu Met Cys Ser Ile
             35                  40                  45

Gly Glu Cys Tyr Ser Leu Tyr Lys Gly Lys Phe Ser Leu Ser Ile Ile
 50                  55                  60

Ser Lys Thr Ser Phe Ser Leu Met Val Tyr Asn Val Thr Leu Val
 65                  70                  75                  80

Ile Cys Leu Arg Leu Ala Tyr Ile Ser Leu Leu Leu Lys Phe Leu
                 85                  90                  95

<210> SEQ ID NO 329
<211> LENGTH: 79
<212> TYPE: PRT
<213> ORGANISM: Artificial sequence
<220> FEATURE:
<223> OTHER INFORMATION: Peptide derived from Medicago truncatula

<400> SEQUENCE: 329

Met Ala Glu Ile Leu Lys Phe Val Tyr Ile Val Ile Leu Phe Val Ser
  1               5                  10                  15

Leu Leu Leu Ile Val Val Ala Ser Glu Arg Glu Cys Val Thr Asp Asp
                 20                  25                  30

Asp Cys Glu Lys Leu Tyr Pro Thr Asn Glu Tyr Arg Met Met Cys Asp
             35                  40                  45

Ser Gly Tyr Cys Met Asn Leu Leu Asn Gly Lys Ile Ile Tyr Leu Leu
 50                  55                  60

Cys Leu Lys Lys Lys Lys Phe Leu Ile Ile Ile Ser Val Leu Leu
 65                  70                  75

<210> SEQ ID NO 330
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 330

Met Leu Arg Leu Tyr Leu Val Ser Tyr Phe Leu Leu Lys Arg Thr Leu
  1               5                  10                  15

Leu Val Ser Tyr Phe Ser Tyr Phe Ser Thr Tyr Ile Ile Glu Cys Lys
                 20                  25                  30

Thr Asp Asn Asp Cys Pro Ile Ser Gln Leu Lys Ile Tyr Ala Trp Lys
```

```
Cys Val Lys Asn Gly Cys His Leu Phe Asp Val Ile Pro Met Met Tyr
 50                  55                  60

Glu
 65
```

<210> SEQ ID NO 331
<211> LENGTH: 96
<212> TYPE: PRT
<213> ORGANISM: Artificial sequence
<220> FEATURE:
<223> OTHER INFORMATION: Peptide derived from Medicago truncatula

<400> SEQUENCE: 331

```
Met Gln Ile Gly Lys Asn Met Val Glu Thr Pro Lys Leu Asp Tyr Val
 1               5                  10                  15

Ile Ile Phe Phe Phe Leu Tyr Phe Phe Arg Gln Met Ile Ile Leu
                 20                  25                  30

Arg Leu Asn Thr Thr Phe Arg Pro Leu Asn Phe Lys Met Leu Arg Phe
             35                  40                  45

Trp Gly Gln Asn Arg Asn Ile Met Lys His Arg Gly Gln Lys Val His
 50                  55                  60

Phe Ser Leu Ile Leu Ser Asp Cys Lys Thr Asn Lys Asp Cys Pro Lys
 65                  70                  75                  80

Leu Arg Arg Ala Asn Val Arg Cys Arg Lys Ser Tyr Cys Val Pro Ile
                 85                  90                  95
```

<210> SEQ ID NO 332
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 332

```
Met Ala Lys Ile Val Asn Phe Val Tyr Ser Met Ile Val Phe Leu Phe
 1               5                  10                  15

Leu Phe Leu Val Ala Thr Lys Ala Ala Arg Gly Tyr Leu Cys Val Thr
                 20                  25                  30

Asp Ser His Cys Pro Pro His Met Cys Pro Pro Gly Met Glu Pro Arg
             35                  40                  45

Cys Val Arg Arg Met Cys Lys Cys Leu Pro Ile Gly Trp Arg Lys Tyr
 50                  55                  60

Phe Val Pro
 65
```

<210> SEQ ID NO 333
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 333

```
Met Val Glu Thr Leu Arg Leu Phe Tyr Ile Met Ile Leu Phe Val Ser
 1               5                  10                  15

Leu Cys Leu Val Val Asp Gly Glu Ser Lys Leu Glu Gln Thr Cys
                 20                  25                  30

Ser Glu Asp Phe Glu Cys Tyr Ile Lys Asn Pro His Val Pro Phe Gly
             35                  40                  45
```

His Leu Arg Cys Phe Glu Gly Phe Cys Gln Gln Leu Asn Gly Pro Ala
            50                  55                  60

<210> SEQ ID NO 334
<211> LENGTH: 76
<212> TYPE: PRT
<213> ORGANISM: Artificial sequence
<220> FEATURE:
<223> OTHER INFORMATION: Peptide derived from Medicago truncatula

<400> SEQUENCE: 334

Met Tyr Lys Val Val Glu Ser Ile Phe Ile Arg Tyr Met His Arg Lys
1               5                   10                  15

Pro Asn Met Thr Lys Phe Phe Lys Phe Val Tyr Thr Met Phe Ile Leu
            20                  25                  30

Ile Ser Leu Phe Leu Val Val Thr Asn Ala Asn Ala His Asn Cys Thr
        35                  40                  45

Asp Ile Ser Asp Cys Ser Ser Asn His Cys Ser Tyr Glu Gly Val Ser
    50                  55                  60

Leu Cys Met Asn Gly Gln Cys Ile Cys Ile Tyr Glu
65                  70                  75

<210> SEQ ID NO 335
<211> LENGTH: 76
<212> TYPE: PRT
<213> ORGANISM: Artificial sequence
<220> FEATURE:
<223> OTHER INFORMATION: Peptide derived from Medicago truncatula

<400> SEQUENCE: 335

Met Ala Lys Ile Met Lys Phe Val Tyr Asn Met Ile Pro Phe Leu Ser
1               5                   10                  15

Ile Phe Ile Ile Thr Leu Gln Val Asn Val Val Cys Glu Ile Asp
            20                  25                  30

Ala Asp Cys Pro Gln Ile Cys Met Pro Pro Tyr Glu Val Arg Cys Val
        35                  40                  45

Asn His Arg Cys Gly Trp Val Asn Thr Asp Asp Ser Leu Phe Leu Thr
    50                  55                  60

Gln Glu Phe Thr Arg Ser Lys Gln Tyr Ile Ile Ser
65                  70                  75

<210> SEQ ID NO 336
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 336

Met Thr Lys Ile Val Val Phe Ile Tyr Val Val Ile Leu Leu Leu Thr
1               5                   10                  15

Ile Phe His Val Ser Ala Lys Lys Arg Tyr Ile Glu Cys Glu Thr
            20                  25                  30

His Glu Asp Cys Ser Gln Val Phe Met Pro Pro Phe Val Met Arg Cys
        35                  40                  45

Val Ile His Glu Cys Lys Ile Phe Asn Gly Glu His Leu Arg Tyr
    50                  55                  60

<210> SEQ ID NO 337
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 337

Met Ala Lys Thr Leu Lys Phe Val Tyr Gly Leu Val Leu Phe Leu Tyr
1               5                   10                  15

Leu Phe Leu Ile Glu Lys Gly Val Asp Gly Lys Thr Phe Leu Met Ala
            20                  25                  30

Glu Tyr Ile Lys Cys Asp Thr Asp Ala Asp Cys Pro Ile Val Ile His
        35                  40                  45

His Ser Phe Tyr Lys Cys Ile Asp Asn Leu Cys Lys Arg Phe Arg Arg
    50                  55                  60

Gln Lys His Leu Val
65

<210> SEQ ID NO 338
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 338

Met Ala Gln Leu Ile Ile Phe Val Tyr Ala Leu Met Val Phe Leu Ser
1               5                   10                  15

Ile Phe Leu Val Glu Ser Tyr Lys Thr Lys Thr Pro Cys Lys Ser Leu
            20                  25                  30

Asn Asp Cys Pro Lys Ala Ile Lys Pro Ile Phe Val Lys Cys Leu Gly
        35                  40                  45

Asn Ile Cys Gln Tyr Ser Ile Gly Arg Ile
    50                  55

<210> SEQ ID NO 339
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 339

Met Ala Asn Asp Leu Lys Phe Ile Tyr Val Ile Ser Phe Leu Ser
1               5                   10                  15

Met Phe Leu Val Thr Lys Glu Val Asp Gly Ala Phe Ala Gly Trp Ile
            20                  25                  30

Lys Cys Lys Val Asp Glu Asp Cys Pro Asn Val Phe Thr Tyr Ser Tyr
        35                  40                  45

Tyr Lys Cys Val Asn Glu Leu Cys Glu Ile Phe Leu Arg Glu Ile Pro
    50                  55                  60

Lys Lys Pro Tyr Met
65

<210> SEQ ID NO 340
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 340

Met Ala Lys Thr Leu Lys Phe Leu Cys Gly Leu Val Leu Phe Val Tyr
1               5                   10                  15

```
Leu Phe Phe Ile Lys Lys Asp Val Ala Gly Asn Thr Phe Leu Met Ala
             20                  25                  30

Asp Asn Ile Glu Cys Asp Thr Asp Ala Gly Cys Pro Lys Met Val His
         35                  40                  45

His Ile Phe Tyr Lys Cys Ile Asp Asn Lys Cys Lys Gln Phe Arg Arg
     50                  55                  60

Ser
 65

<210> SEQ ID NO 341
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 341

Met Ala Lys Ile Phe Lys Phe Ile Tyr Gly Leu Val Ile Phe Leu Tyr
 1               5                  10                  15

Leu Phe Leu Ile Gln Lys Glu Val Ala Gly Tyr Ile Gln Cys Asp Phe
             20                  25                  30

Asp Ala Asp Cys Pro Glu Met Phe Arg His Ile Phe Tyr Leu Cys Ile
         35                  40                  45

Asp Lys Leu Cys Arg Gln Phe Val Thr Leu
     50                  55

<210> SEQ ID NO 342
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 342

Met Thr Gln Ile Leu Leu Phe Val Tyr Phe Phe Ile Ile Phe Leu Ser
 1               5                  10                  15

Leu Ser Phe Val Val Thr Ser Tyr Arg Thr Arg Ile Pro Cys Val Ser
             20                  25                  30

Asp Tyr Asp Cys Pro Lys Ala Ser Tyr Pro Leu Phe Ile Lys Cys Ile
         35                  40                  45

Tyr Asn Phe Cys Glu Ile Trp Gly Ser Pro
     50                  55

<210> SEQ ID NO 343
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 343

Met Gln Arg Arg Thr Asn Met Thr Gln Ile Val Ile Leu Phe Tyr Val
 1               5                  10                  15

Leu Ile Ile Phe Leu Ile Leu Pro Ile Ser Cys Val Ser Asp Asp
             20                  25                  30

Asp Cys Pro Lys Val Pro Tyr Pro Leu Tyr Ile Lys Cys Glu Asp Asn
         35                  40                  45

Phe Cys Asp Ile Trp Ala Ser Pro Tyr
     50                  55

<210> SEQ ID NO 344
```

-continued

```
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 344

Met Ala Gln Ile Leu Met Phe Phe Tyr Ser Leu Ile Ile Phe Phe Phe
1               5                   10                  15

Leu Phe Leu Val Glu Thr Lys Arg Thr Asn Ile Pro Cys Phe Ser Asp
            20                  25                  30

Asp Asp Cys Pro Lys Thr Ser Pro Pro Leu Val Leu Lys Cys Asp Asp
        35                  40                  45

Tyr Phe Cys Arg Tyr Phe Arg Glu Lys Asn Leu Ile
    50                  55                  60

<210> SEQ ID NO 345
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 345

Met Ala Lys Thr Leu Lys Phe Val Tyr Val Val Ile Leu Phe Ile Ser
1               5                   10                  15

Ile Phe Leu Val Leu Thr Val Tyr Asp Ser Lys Tyr Phe Gln Ile Ala
            20                  25                  30

Ser Pro Cys Val Asn Asp Lys Asp Cys Pro Arg Phe Lys Asn Asn Asn
        35                  40                  45

Val Arg Cys Arg Lys Gly Phe Cys Val Asn Leu Cys Asn
    50                  55                  60

<210> SEQ ID NO 346
<211> LENGTH: 73
<212> TYPE: PRT
<213> ORGANISM: Artificial sequence
<220> FEATURE:
<223> OTHER INFORMATION: Peptide derived from Medicago truncatula

<400> SEQUENCE: 346

Met Ala Lys Thr Leu Lys Phe Val Tyr Val Val Ile Leu Phe Ile Ser
1               5                   10                  15

Ile Phe Leu Val Leu Thr Val Tyr Asp Ser Lys Tyr Phe Gln Ile Ala
            20                  25                  30

Ser Pro Cys Val Asn Asp Lys Asp Cys Pro Gln Phe Lys Asn Asn Asn
        35                  40                  45

Val Arg Cys Arg Arg Gly Phe Cys Val Asn Ser Gly Gly Ala Thr Gln
    50                  55                  60

Lys Cys Leu Gly Cys Pro Ser Leu Lys
65                  70

<210> SEQ ID NO 347
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 347

Met Ala Gln Phe Phe Met Phe Val Tyr Ile Leu Ile Ile Phe Leu Ser
1               5                   10                  15
```

```
Ser Phe Leu Ile Glu Ala Ser Thr Ala Ala Thr Pro Cys Thr Ser Asp
            20                  25                  30

Lys Asp Cys Arg Leu Glu Arg Tyr Asn Val Trp Cys Ile Asn Gly Tyr
        35                  40                  45

Cys Lys Tyr Lys Phe Thr Pro Ile Asp
    50                  55

<210> SEQ ID NO 348
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 348

Met Ala Gln Met Leu Met Phe Val Tyr Thr Leu Ile Ile Phe Leu Ser
1               5                   10                  15

Leu Phe Leu Val Ile Thr Asn Ser Val Arg Ile Pro Cys Val Thr Val
            20                  25                  30

Ala Asp Cys Pro Pro Thr Ile Leu Pro Val Phe Tyr Glu Cys Ile Asp
        35                  40                  45

Lys Phe Cys Met Leu His Ile Glu
    50                  55

<210> SEQ ID NO 349
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 349

Met Phe Leu Tyr Ala Leu Ile Thr Phe Leu Phe Leu Phe Leu Val Glu
1               5                   10                  15

Thr Ser Thr Thr Asn Thr Lys Thr Ile Pro Cys Lys Phe Asp Asn
            20                  25                  30

Asp Cys Pro Glu Ile Ser Tyr Pro Leu Ile Leu Met Cys Ile Asp Asp
        35                  40                  45

Phe Cys Glu Tyr Leu Leu Ala
    50                  55

<210> SEQ ID NO 350
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 350

Met Val Glu Thr Leu Lys Leu Val Tyr Val Leu Ile Ile Phe Tyr Ser
1               5                   10                  15

Ile Phe Leu Gly Ile Ile Val Cys Asn Ser Ser Thr Ile Met Tyr Tyr
            20                  25                  30

Asp Val Pro Cys Glu Lys Asp Lys Asp Cys Pro Ala Pro Pro Arg Phe
        35                  40                  45

Asn Ile Arg Cys Arg Lys Gly Tyr Cys Val Arg Ile
    50                  55                  60

<210> SEQ ID NO 351
<211> LENGTH: 59
<212> TYPE: PRT
<213> ORGANISM: Artificial sequence
```

<220> FEATURE:
<223> OTHER INFORMATION: Peptide derived from Medicago truncatula

<400> SEQUENCE: 351

Met Thr Gln Ile Leu Leu Phe Val His Val Leu Ile Ser Phe Leu Ser
1               5                   10                  15

Leu Leu Leu Ile Val Thr Asn Ser Val Glu Ile Pro Glu Thr Pro Cys
                20                  25                  30

Glu Ser Asp Ala Glu Cys Pro Tyr Tyr Ser Pro Ser Leu Tyr Ala Arg
            35                  40                  45

Cys Ile Asp Gly Phe Cys Thr Leu Phe Leu Ser
        50                  55

<210> SEQ ID NO 352
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 352

Met Gln Arg Lys Lys Asn Met Gly Gln Ile Leu Ile Phe Val Phe Ala
1               5                   10                  15

Leu Ile Asn Phe Leu Ser Pro Ile Leu Val Glu Met Thr Thr Thr Ala
                20                  25                  30

Thr Ile Pro Cys Thr Ser Ile Asp Asp Cys Pro Lys Met Pro Leu Val
            35                  40                  45

Val Lys Cys Ile Asp Asn Phe Cys Asn Tyr Phe Glu Ile Lys
        50                  55                  60

<210> SEQ ID NO 353
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 353

Met Val Glu Leu Leu Lys Phe Val Tyr Val Met Ile Leu Phe Leu Phe
1               5                   10                  15

Leu Phe Phe Val Thr Thr Glu Ala Cys Gly Gly Lys Thr His Tyr Ser
                20                  25                  30

Glu Ile Ile Glu Cys Lys Asn Asp Ala Asp Cys Pro Ile Gly Tyr Lys
            35                  40                  45

Cys Ile Asp Glu Met Cys Lys Tyr Gly
        50                  55

<210> SEQ ID NO 354
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 354

Met Val Glu Thr Leu Lys Tyr Val Tyr Val Met Phe Leu Phe Leu Ser
1               5                   10                  15

Ile Phe Gln Leu Met Val Val Tyr Asp Ser Ile Tyr Phe Arg Lys Pro
                20                  25                  30

Pro Pro Cys Ile Thr Asp Lys Asp Cys Pro Gln Met Lys Ile Asn Asn
            35                  40                  45

```
Val Arg Cys Arg Lys Gly Phe Cys Ile Gln Ile His Lys Phe Thr Pro
        50                  55                  60

<210> SEQ ID NO 355
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 355

Met Gln Ile Gly Lys Asn Met Val Glu Thr Leu Lys Phe Val Tyr Val
1               5                   10                  15

Ile Leu Leu Phe Leu Ser Ile Phe Leu Phe Asn Lys Ser Pro Phe Ser
                20                  25                  30

Gln Ile Met Phe Ser Asp Cys Lys Thr Asp Lys Asp Cys Pro Gln Phe
            35                  40                  45

Arg Arg Ala Asn Ile Arg Cys Arg Lys Gly Gln Cys Val Lys Leu
        50                  55                  60

<210> SEQ ID NO 356
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 356

Met Ala His Ile Leu Met Phe Thr Tyr Val Leu Ile Ile Phe Leu Phe
1               5                   10                  15

Ser Phe Arg Ser Met Thr Phe Leu Thr Gln Cys Lys Phe Ser Cys Lys
                20                  25                  30

Thr Ile Phe Asn Cys Pro Ala Leu Val Tyr His Gln His Ala Ser Cys
            35                  40                  45

Leu Asp Gly Phe Cys Trp Tyr Glu Glu Lys Phe Glu Asp Glu
        50                  55                  60

<210> SEQ ID NO 357
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 357

Met Thr Lys Thr Met Lys Phe Leu Tyr Val Leu Ile Ile Phe Ile Ser
1               5                   10                  15

Ile Phe Val Val Ala Ser Val Tyr Asp Ser Ile Pro Tyr Val Asn Ser
                20                  25                  30

Gly Pro Cys Val Thr Asp Lys Asp Cys Pro Lys Val Ser Gln Tyr Asn
            35                  40                  45

Ile Arg Cys Arg Lys Gly Gln Cys Ala Arg Ile Arg Val
        50                  55                  60

<210> SEQ ID NO 358
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 358

Met Thr Thr Ile Val Asn Phe Val Cys Gly Met Ile Ile Phe Leu Ser
```

```
                 1               5                  10                 15
Glu Phe Met Val Ala Thr Asn Phe Lys Arg Lys Gln Ile Pro Phe Tyr
                20                 25                 30

Phe Phe Ile Arg Glu Phe Tyr Pro Cys Phe Ile Asp Gly Asn Cys Pro
                35                 40                 45

Arg Asn Met Cys Lys Val Tyr Gln Ile Pro Lys Cys Val Gly Gly Leu
                50                 55                 60

Cys Arg Cys Ile Pro Leu Arg Cys Gly Arg Trp Glu Lys
65                 70                 75

<210> SEQ ID NO 359
<211> LENGTH: 77
<212> TYPE: PRT
<213> ORGANISM: Artificial sequence
<220> FEATURE:
<223> OTHER INFORMATION: Peptide derived from Medicago truncatula

<400> SEQUENCE: 359

Met Pro Lys Ile Met Glu Phe Val Tyr Val Met Ile Ile Phe Leu Ser
1               5                  10                 15

Ile Phe Val Val Ile Thr Asn Val Asn Ala His Ile Glu Cys Lys Asn
                20                 25                 30

Asp Phe Asp Cys Pro Lys Asn Met Cys Leu Ala Pro Arg Val Ala Trp
                35                 40                 45

Cys Val Asn Asn Lys Cys Glu Cys Val Leu Thr Tyr Gly Pro Lys Tyr
                50                 55                 60

Ser Thr Met Lys Glu Lys Leu Leu Gln Lys Glu Lys Ile
65                 70                 75

<210> SEQ ID NO 360
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 360

Met Asn Lys Ile Leu Lys Phe Val Tyr Glu Met Ile Leu Phe Leu Ser
1               5                  10                 15

Leu Phe His Leu Ala Arg Glu Val Pro His Thr Asp Ile Pro Cys Glu
                20                 25                 30

Pro Asp Ala Asp Cys Pro Lys Ser Leu His Glu Tyr Phe Glu Met Lys
                35                 40                 45

Cys Ile Asp Lys Lys Cys Glu Trp Ser Arg Lys Thr Ser Leu Ile Pro
                50                 55                 60

<210> SEQ ID NO 361
<211> LENGTH: 83
<212> TYPE: PRT
<213> ORGANISM: Artificial sequence
<220> FEATURE:
<223> OTHER INFORMATION: Peptide derived from Medicago truncatula

<400> SEQUENCE: 361

Met Gln Arg Gly Lys His Met Val Glu Ile Leu Glu Phe Val Tyr Ala
1               5                  10                 15

Met Ile Leu Phe Leu Pro Leu Phe Leu Val Ile Thr Glu Val Asp Gly
                20                 25                 30

Val Asp Ile Tyr Cys Glu Thr Asp Ala Asp Cys Pro Gln Ile Thr Asp
                35                 40                 45
```

Trp Phe Tyr Val Val Lys Cys Val Asp His Lys Cys Glu Leu Thr Lys
50                  55                  60

Lys Leu Arg Arg Leu Tyr Glu Tyr Gln Thr Gln Lys Ser Ala Glu Thr
65                  70                  75                  80

Pro Tyr Ile

<210> SEQ ID NO 362
<211> LENGTH: 81
<212> TYPE: PRT
<213> ORGANISM: Artificial sequence
<220> FEATURE:
<223> OTHER INFORMATION: Peptide derived from Medicago truncatula

<400> SEQUENCE: 362

Met Thr Gln Ile Leu Lys Leu Val Tyr Ile Val Ile Leu Phe Cys Phe
1               5                   10                  15

His Ile Cys Phe Val Ala Glu Ala Glu Gln Cys Val Ser Asp Ala Asp
                20                  25                  30

Cys Gln Ile Lys Phe Pro Gly Pro Arg Gln His Leu Leu Arg Cys Thr
            35                  40                  45

Gln Gly Asn Cys Val Met Leu Val Gly Gln Gly Lys Asn Tyr Phe Ser
50                  55                  60

Ile Met Ser Lys Thr Leu Phe Ser Leu Leu Val Ile Ile Phe Leu Leu
65                  70                  75                  80

Leu

<210> SEQ ID NO 363
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 363

Met Pro Lys Ser Leu Lys Phe Val Tyr Thr Met Ile Leu Phe Ile Phe
1               5                   10                  15

Leu Phe Leu Ile Thr Lys Asn Val Asp Ala Leu His Cys Glu Tyr
                20                  25                  30

Asp Asp Asp Cys Pro Lys Ser Thr Ser Lys Arg Thr Tyr Arg Cys Ile
            35                  40                  45

Asn Lys Lys Cys Arg Ser Tyr Phe Thr Arg Val Glu Lys
50                  55                  60

<210> SEQ ID NO 364
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 364

Met Asn Lys Asn Met Pro Gln Ile Leu Met Phe Val Tyr Thr Phe Ile
1               5                   10                  15

Ile Phe Phe Ser Pro Phe Val Val Thr Asn Gly Thr Thr Ser Cys
                20                  25                  30

Ile Thr Asp Asp Cys Pro Lys Ala Val Ser Phe Leu Val Phe Lys
            35                  40                  45

Cys Ile Asp Asn Ile Cys Val Arg Val Glu Ile Leu
50                  55                  60

-continued

```
<210> SEQ ID NO 365
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 365

Met Ala Lys Ile Leu Lys Phe Val Tyr Val Pro Ile Leu Tyr Leu Ser
1               5                   10                  15

Ile Leu Leu Val Leu Thr Ile Tyr Asp Gln Val Tyr Phe Asn Tyr Asn
            20                  25                  30

Pro Pro Cys Val Ser Asp Lys Asp Cys Pro Ser Pro Lys Ser Pro Lys
        35                  40                  45

Ser Asn Ile Arg Cys Arg Gln Gly Tyr Cys Val Asn Leu Tyr Ser
    50                  55                  60

<210> SEQ ID NO 366
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 366

Met Ala Gln Leu His Lys Leu Ile Tyr Ala Leu Thr Ile Phe Leu Ser
1               5                   10                  15

Leu Phe Ile Val Gly Ala Val Arg Ile Pro Arg Pro Leu Ile Asp Pro
            20                  25                  30

Leu Asn Cys His Ile Asp Ile His Cys Ile Tyr Lys Glu Cys Arg Arg
        35                  40                  45

Pro Phe Lys Pro Ser Cys Leu Asn Phe Lys Cys Asp Cys Gly Lys Glu
    50                  55                  60

<210> SEQ ID NO 367
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 367

Met Arg Ile Gly Lys Lys Met Val Glu Thr Leu Lys Leu Ile Tyr Val
1               5                   10                  15

Ile His Leu Phe Leu Ser Ile Phe Leu Phe Thr Asn Ser Pro Phe Gly
            20                  25                  30

Gln Ile Ile Phe Arg Gln Cys Lys Thr Asp Lys Asp Cys Pro Lys Leu
        35                  40                  45

Gly Arg Ala Asn Ile Arg Cys Arg Glu Gly Tyr Cys Val Arg Ile
    50                  55                  60

<210> SEQ ID NO 368
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 368

Met Ala Gln Ile Tyr Met Phe Val Tyr Val Leu Ile Ile Phe Leu Ser
1               5                   10                  15

Leu Phe Leu Val Ile Ile Asn Cys Thr Pro Ile Pro Cys Asn Thr Pro
            20                  25                  30
```

```
Ala Asp Cys Pro Lys Arg Val Cys Ile Tyr Pro Leu Arg Ala Lys Cys
        35                  40                  45

Ile Asn Phe Asn Cys Glu Cys Asp Tyr Val Lys Lys
 50                  55                  60

<210> SEQ ID NO 369
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 369

Met Thr Lys Thr Leu Lys Phe Ile Leu Thr Met Ile Leu Leu Leu Ser
1               5                  10                  15

Leu Phe Leu Val Ala Glu Ser Gly Asp Ile Pro Cys Glu Ser Arg Glu
                20                  25                  30

Gln Cys Pro Asn Thr Ala Thr Arg Arg Tyr Ala Cys Leu Asn Lys Leu
            35                  40                  45

Cys Tyr Cys Tyr Asp Asn Asn Tyr Pro Asn Gly Trp Asn Pro Phe Glu
 50                  55                  60

Pro
65

<210> SEQ ID NO 370
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 370

Met Phe Asn Thr Leu Thr Phe Ala Phe Val Ile Ile Leu Leu Val Thr
1               5                  10                  15

Leu Phe Leu Val Pro Lys Asn Val Asp Ala Phe Val Lys Cys Glu Thr
                20                  25                  30

Thr Asp Asp Cys Pro Lys Ser Asp Tyr Ile Arg Gln Tyr Glu Cys Val
            35                  40                  45

Asn Asn Trp Cys Arg Leu Ala Arg Leu His Glu Phe Gln Pro Lys Lys
 50                  55                  60

Ser Thr Leu Thr Ser
65

<210> SEQ ID NO 371
<211> LENGTH: 108
<212> TYPE: PRT
<213> ORGANISM: Artificial sequence
<220> FEATURE:
<223> OTHER INFORMATION: Peptide derived from Medicago truncatula

<400> SEQUENCE: 371

Met Thr Glu Ile Val Lys Phe Ile Tyr Leu Met Ile Ile Phe Leu Ser
1               5                  10                  15

Leu Phe Ile Val Ala Met Asn Val Asp Gly Phe Thr Phe Ser Ile Leu
                20                  25                  30

Cys Gln Val Asn Ser Asp Cys Leu Gly Glu Ile Cys Leu Pro Pro Lys
            35                  40                  45

Thr His Trp Cys Asn Lys Ile Leu Leu Glu Ile Tyr Ile Ser Cys His
 50                  55                  60

Leu Val Thr Met Leu Glu Pro Asn Asn Leu Tyr Leu Leu Pro Phe Leu
```

```
                65                  70                  75                  80
Ile Ser Trp Thr Arg Asn Asn Leu Tyr Ile Ile Leu Gly Leu Ser Leu
                    85                  90                  95

Phe Ser Arg Thr Asn Ser Leu Val Leu Ser Trp Arg
                100                 105
```

<210> SEQ ID NO 372
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 372

```
Met Gln Arg Glu Asn Asn Met Ala Lys Thr Ile Lys Phe Val Tyr Thr
1               5                   10                  15

Met Ile Leu Phe Leu Ser Leu Phe Ile Val Ala Lys Glu Val His Ala
                20                  25                  30

Tyr Pro Gly Cys Glu Thr Asp Ala Glu Cys Pro Lys Ile Tyr Glu Leu
            35                  40                  45

Tyr Pro Leu Ile Tyr Lys Cys Glu Asn Lys Phe Cys Ile Leu Ser Gln
        50                  55                  60

Val Leu Pro Tyr Ile Val
65                  70
```

<210> SEQ ID NO 373
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 373

```
Met Lys Ile Gly Lys Asn Met Ala Glu Thr Leu Lys Phe Val Tyr Val
1               5                   10                  15

Ile Leu Phe Ile Ser Leu Phe Leu Met Ile Ile Val Ser Asp Ser Phe
                20                  25                  30

Asn Pro Leu Ile Arg Gln Tyr Cys Val Thr Asp Lys Asp Cys Pro Lys
            35                  40                  45

Phe Lys Lys Tyr Asn Ile Arg Cys Arg Lys Gly Phe Cys Val Gln Val
        50                  55                  60

Asn Gly Gly
65
```

<210> SEQ ID NO 374
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 374

```
Met Thr Lys Ile Ile Lys Phe Val Tyr Ala Leu Val Leu Phe Leu Ser
1               5                   10                  15

Leu Phe Ile Val Ser Gln Ala Ala Gln Asn Asp Trp Met Lys Cys Lys
                20                  25                  30

Thr Asp Asp Glu Cys Pro Lys Val Ser Asn Pro Leu Tyr Phe Lys
            35                  40                  45

Cys Ile Asp Arg Gly Cys Arg Ile Val Ile Lys Met Arg Phe
        50                  55                  60
```

-continued

<210> SEQ ID NO 375
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 375

Met Ala Thr Ile Leu Lys Ile Val Tyr Ala Met Ile Leu Phe Ile Ser
1               5                   10                  15

Leu Phe Leu Val Ala Met Asn Val Asp Ala Tyr Val Glu Cys Glu Thr
            20                  25                  30

Asp Ala Asp Cys Gln Pro Asn Met Cys Lys Trp Pro Phe Ile Val Gln
        35                  40                  45

Cys Tyr Lys Asn Val Cys Ile Cys Val His His Thr Asn Pro Tyr Leu
    50                  55                  60

<210> SEQ ID NO 376
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 376

Met Val Gln Ile Leu Lys Phe Val Cys Val Arg Ile Leu Phe Ile Ser
1               5                   10                  15

Leu Phe Leu Ile Ala Thr Lys Phe Gly Val Ala Ser Asp Glu Cys Gln
            20                  25                  30

Ile Asp Ala Asp Cys Pro Lys Ser Gly Asn Leu Phe Tyr Ile Tyr Lys
        35                  40                  45

Cys Ile Asn His Lys Cys Glu Leu Val Ala Ala His Leu Arg Phe Tyr
    50                  55                  60

<210> SEQ ID NO 377
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 377

Met Thr Asn Tyr Ile Val Ile Phe Phe Leu Ala Leu Phe Leu Ile Val
1               5                   10                  15

Ile Asp Val Ser Ala Ile Leu Glu Cys Ile Phe Asp Ile Asp Cys Pro
            20                  25                  30

Thr Lys Lys Cys Ala Pro Pro Leu Val Ala Lys Cys Asp Met Tyr Glu
        35                  40                  45

Cys Tyr Cys Arg Cys Pro Pro Asn Asn
    50                  55

<210> SEQ ID NO 378
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 378

Met Ala Gln Ile Gln Lys Phe Val Tyr Thr Leu Ile Met Phe Leu Ser
1               5                   10                  15

Leu Phe Val Met Val Thr Asn Gly Met Val Ser Thr Asn Ala Tyr Ile

```
                    20                  25                  30
His Arg Cys Ile His Gln Asp Asp Cys Pro Lys Tyr Met Cys Glu Ile
        35                  40                  45

Ser Val Leu Pro Glu Cys Ile Asn Gly Phe Cys Thr Cys Val
    50                  55                  60

<210> SEQ ID NO 379
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 379

Met Ser Gln Ile Leu Lys Phe Phe Ala Thr Val Leu Ile Phe Ala
1               5                   10                  15

Leu Phe Leu Ser Ala Thr Asn Gly Gln Lys Phe Asn Glu Cys Tyr Glu
                20                  25                  30

Asp Thr Asp Cys Pro Ile Gln Met Cys Gly Tyr Pro Phe Asn Val Asp
            35                  40                  45

Cys Val Gly Asn Lys Cys Thr Cys Val Tyr Asn Pro
    50                  55                  60

<210> SEQ ID NO 380
<211> LENGTH: 89
<212> TYPE: PRT
<213> ORGANISM: Artificial sequence
<220> FEATURE:
<223> OTHER INFORMATION: Peptide derived from Medicago truncatula

<400> SEQUENCE: 380

Met Gln Lys Lys Gly Lys Tyr Met Ala Lys Leu Val Thr Phe Val Tyr
1               5                   10                  15

Val Met Ile Tyr Phe Leu Ser Leu Phe Leu Val Thr Lys Gly Ala Tyr
                20                  25                  30

Tyr Glu Cys Ser Asn Asp Ser Ala Cys Gln Ala Thr Thr Lys Cys Val
            35                  40                  45

Leu Pro Arg Val Pro Arg Cys Ile Lys Tyr Lys Cys Leu Cys Gly Asn
    50                  55                  60

Ser Asn Gly Ser Gly Asn Arg Trp Ser Thr Arg Pro Asn Arg Ile Gln
65                  70                  75                  80

Lys Gly Ser Thr Glu Ser Asn Tyr Phe
                85

<210> SEQ ID NO 381
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 381

Met Asp Lys Thr Leu Lys Phe Ile Tyr Ala Met Phe Ser Cys Leu Tyr
1               5                   10                  15

Leu Phe Met Val Thr Lys Glu Val Tyr Val Ile Tyr Ile Phe Phe His
                20                  25                  30

Phe Leu Ile Leu Ala Lys Ser Ile Cys Lys Val Asp Asp Cys Pro
            35                  40                  45

Gln Arg Phe Val Met Tyr Pro Leu Met Phe Met Cys Ile Lys Asn Ile
    50                  55                  60
```

Cys Arg Leu Val Asn Glu
65                  70

<210> SEQ ID NO 382
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 382

Met Ala Gln Leu Leu Lys Phe Val Tyr Ala Ile Ile Phe Leu Phe Ser
1               5                   10                  15

Leu Cys Leu Ala Ala Thr Lys Glu Lys Phe His Ser Cys Val Asn Ala
            20                  25                  30

Asn Asp Cys Pro Tyr Asp Phe Cys Ser Pro Lys Tyr Ala Lys Cys
        35                  40                  45

Val Tyr Asn Ser Cys Tyr Cys Glu Asp Gln Gly Arg Leu
    50                  55                  60

<210> SEQ ID NO 383
<211> LENGTH: 73
<212> TYPE: PRT
<213> ORGANISM: Artificial sequence
<220> FEATURE:
<223> OTHER INFORMATION: Peptide derived from Medicago truncatula

<400> SEQUENCE: 383

Met Gln Lys Arg Glu Asn Met Thr Val Ile Val Lys Phe Val Cys Val
1               5                   10                  15

Met Ile Ile Phe Leu Ser Leu Cys Val Phe Ser Met His Ile Glu Thr
            20                  25                  30

Val Thr Thr Cys Ile Tyr Asp Ser Asp Cys Pro Glu Asp Met Cys Tyr
        35                  40                  45

Pro Pro Lys Lys Ser Phe Cys Ser Thr Phe Glu Ile Leu Ser Ile Glu
    50                  55                  60

Arg Lys Val Gly Val Cys Glu Cys Ile
65                  70

<210> SEQ ID NO 384
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 384

Met Asn Thr Ile Pro Lys Phe Val Tyr Ile Thr Ile Leu Phe Ile Ser
1               5                   10                  15

Leu Leu Leu Val Val Thr Gly Ala Val Arg Lys Pro Glu Cys Arg Gln
            20                  25                  30

Asn Ser Asp Cys Pro Pro Tyr Phe Cys Ile Lys Pro Thr Val Pro Lys
        35                  40                  45

Cys Ile Lys Phe Lys Cys Leu Cys Lys
    50                  55

<210> SEQ ID NO 385
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 385

Met Ala Glu Ile Leu Lys Phe Val Cys Phe Met Ile Ile Phe Leu Ser
1               5                   10                  15

Ser Phe Ile Val Ser Glu Ser Leu Asn Gly Asn Arg His Gly Lys Asp
            20                  25                  30

Arg Cys Phe Lys Asp Ser Asp Cys Pro Lys Tyr Met Cys Pro Ser Ser
        35                  40                  45

Leu Val Ala Lys Cys Ile Lys Lys Leu Cys Ser Cys Arg Lys Pro Gly
    50                  55                  60

Leu Gln Ile Gln Leu Asn Pro Lys
65                  70

<210> SEQ ID NO 386
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 386

Met Ala Glu Ser Phe Lys Phe Ile Cys Val Ile Ile Phe Leu Cys
1               5                   10                  15

Ser Phe Ile Ala Ala Lys Asn Ile Asp Glu Lys Cys Phe Arg Asp Asp
            20                  25                  30

Asp Cys Ala Lys Asn Met Cys Pro Ser Tyr Leu Val Val Lys Cys Val
        35                  40                  45

Asn Gly Ile Tyr Lys Cys Val Arg Pro
    50                  55

<210> SEQ ID NO 387
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 387

Met Val Glu Ile Gln Lys Leu Val Tyr Val Leu Ile Leu Phe Leu Ser
1               5                   10                  15

Ile Phe Leu Glu Met Ile Val Ser Asn Cys Thr Phe Ile Gly Phe Gln
            20                  25                  30

Asp Asn Pro Cys Lys Thr Asp Asn Asp Cys Arg Lys Val Arg Gly Val
        35                  40                  45

Asn Leu Arg Cys Arg Asn Gly His Cys Val Met Ile Leu Gln
    50                  55                  60

<210> SEQ ID NO 388
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 388

Met Ala Glu Ile Val Lys Tyr Val Tyr Val Ile Ile Ile Phe Leu Ser
1               5                   10                  15

Thr Ile Leu Val Ala Thr Asn Ile Glu Gly Thr Met Ser Cys Phe His
            20                  25                  30

Asp Ala Asp Cys Val His Lys Arg Cys Gln Leu Pro Gln Ile Pro Lys
        35                  40                  45

-continued

Cys Val Gly Lys Lys Cys Arg Cys Arg Gly Gln Tyr Gln Ala Asn Pro
            50                  55                  60

Met Gly
65

<210> SEQ ID NO 389
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 389

Met Ala Glu Phe Leu His Met Thr Tyr Val Met Ile Ile Phe Ile Phe
1               5                   10                  15

Leu Phe Leu Ser Leu Ile Asp Ala Glu Val His Arg Cys Ile Glu Tyr
            20                  25                  30

Thr Asp Cys Pro Glu Asp Met Cys His Leu Pro Leu Val Val Val Cys
        35                  40                  45

His Asp His Ile Cys Lys Cys Leu Arg Leu Pro
    50                  55

<210> SEQ ID NO 390
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 390

Met Ala Lys Ile Ile Lys Ile Val Tyr Val Met Ile Val Phe Phe Phe
1               5                   10                  15

Ile Phe Leu Ser Val Thr Asn Ser Ser Ala Phe Ser Gly Cys Met Asn
            20                  25                  30

Asp Ser Asp Cys Pro Asp Leu Phe Cys Leu Pro Pro Leu Asp Met Lys
        35                  40                  45

Cys His Glu Leu Val Cys Lys Cys Arg
    50                  55

<210> SEQ ID NO 391
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 391

Met Lys Asn Met Ser Ala Ile Ile Lys Phe Ile Tyr Ala Met Ser Leu
1               5                   10                  15

Ile Leu Phe Ile Ala Asn Glu His Tyr Arg Glu Leu Ile Cys Lys Thr
            20                  25                  30

Asp Asp Asn Cys Pro Arg Arg Gly Thr Asn Lys Tyr Phe Ile His Lys
        35                  40                  45

Cys Ile Asp Tyr Arg Cys Gln Trp Ile Pro Arg
    50                  55

<210> SEQ ID NO 392
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 392

Met Gln Arg Arg Lys Asn Met Ala Gln Ile Leu Phe Tyr Val Tyr Ala
1               5                   10                  15

Leu Ile Ile Leu Phe Ser Pro Ser Leu Val Val Pro Leu Lys Val Ile
            20                  25                  30

Ile Pro Ser Ser Thr Cys Asp Ser Asp Tyr Asp Cys Leu Arg Tyr Glu
        35                  40                  45

Glu Ala Leu Asn Val Ile Thr Cys Cys Asn Asn Gly Leu Cys Val Met
    50                  55                  60

Phe Cys Pro Asp Phe Asp
65                  70

<210> SEQ ID NO 393
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 393

Met Thr Asn Ile Ile Lys Phe Val Lys Val Met Ile Tyr Phe Leu Ser
1               5                   10                  15

Ile Phe Leu Ile Ser Thr Tyr Phe Lys Val Lys Leu Ser Cys Phe Glu
            20                  25                  30

Asp Ser Asp Cys Pro Tyr Asp Met Cys Tyr Ala Gly Phe Gln Pro Lys
        35                  40                  45

Cys Val Asn Gly Trp Cys Asp Cys
    50                  55

<210> SEQ ID NO 394
<211> LENGTH: 78
<212> TYPE: PRT
<213> ORGANISM: Artificial sequence
<220> FEATURE:
<223> OTHER INFORMATION: Peptide derived from Medicago truncatula

<400> SEQUENCE: 394

Met Thr Asn Ser Ile Lys Phe Val Tyr Val Met Met Tyr Phe Leu Ser
1               5                   10                  15

Ile Phe Leu Ile Ser Thr Tyr Phe Glu Thr Lys Leu Asn Cys Ile Asp
            20                  25                  30

Asp Ser Asp Cys Pro Tyr Asp Met Cys Asp Pro Gly Leu Leu Pro Arg
        35                  40                  45

Cys Leu Asn Gly Trp Cys Asp Cys Ser Arg Phe Gln Pro Trp Pro Met
    50                  55                  60

Asp Ser Met Ser Ser Asn Leu Arg Glu Phe Thr Leu Pro Asn
65                  70                  75

<210> SEQ ID NO 395
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 395

Met Ser Lys Asn Ile Leu Phe Asn Cys Ala Ile Ile Leu Phe Leu Ser
1               5                   10                  15

Leu Phe Leu Val Thr Tyr Phe Glu Arg Phe Gly Pro Cys Ser Ser Asp
            20                  25                  30

Ser Asp Cys Pro Ser Phe Leu Cys Asp His Asp Gly Val Met Lys Cys
            35                  40                  45

Phe Ser Asn Gly Cys Ser Cys Val Asp Pro Ser Asp
         50                  55                  60

<210> SEQ ID NO 396
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 396

Met Val Lys Ile Leu Lys Phe Ile His Ile Met Ile Ile Phe Leu Ile
1               5                   10                  15

Phe Ile Ile Val Thr Asn Ala Ser Asn Pro Cys Val Ser Thr Arg Asp
            20                  25                  30

Cys Thr Thr His Thr Cys Asn Pro Pro Leu Val Ala Arg Cys Ile Asn
            35                  40                  45

Leu Arg Cys Tyr Cys Gly Tyr Lys
         50                  55

<210> SEQ ID NO 397
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 397

Met Gly Gly Ile Ile Lys Ile Val Tyr Ala Phe Val Ile Phe Ile Ser
1               5                   10                  15

Leu Ile Leu Ile Val Thr Ser Asn Val His Ser Leu Leu Pro Cys Gly
            20                  25                  30

Thr Asp Asp Asp Cys Ala Asn Asp Pro Cys Ile His Pro Glu Tyr Pro
            35                  40                  45

His Cys His Thr Glu Gln Cys His Cys Val
         50                  55

<210> SEQ ID NO 398
<211> LENGTH: 107
<212> TYPE: PRT
<213> ORGANISM: Artificial sequence
<220> FEATURE:
<223> OTHER INFORMATION: Peptide derived from Medicago truncatula

<400> SEQUENCE: 398

Met Lys Tyr Val Tyr Ala Met Ile Leu Phe Ile Ser Leu Phe Leu Ile
1               5                   10                  15

Ala Met Asn Val His Ala Leu Tyr Val Cys Arg Ser Val Ser Asp Cys
            20                  25                  30

Pro Glu Asn Phe Cys Val Pro Pro Leu Thr Ile Gln Cys Ile Asn Tyr
            35                  40                  45

Thr Cys Ile Cys Asp Asp Pro Tyr Gly Pro Glu Tyr Asp Asn
         50                  55                  60

Asn Asp Asp Phe Val Thr Leu Asn Arg Glu Lys Ala Lys Ile Lys Asn
65                  70                  75                  80

Glu Glu Met Met Met Arg Glu Arg Asp Met Met Ile Glu Ile Glu Thr
                85                  90                  95

Tyr Ser Val Ala Asp Asp Leu Asp Pro His Leu
                100                 105

<210> SEQ ID NO 399
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 399

Met Gln Lys Lys Lys Asn Met Ala Gln Met His Leu Phe Val Tyr Ile
1               5                   10                  15

Phe Ile Ile Ile Leu Ser Leu Phe Ile Ala Val Thr Asn Ala Leu Ile
                20                  25                  30

Phe Cys Phe Glu Asp Ile Asn Cys Pro Phe Asp Lys Cys Phe Pro Gln
            35                  40                  45

Leu Pro Lys Cys Ile Asn Ser Phe Cys Glu Cys Val
    50                  55                  60

<210> SEQ ID NO 400
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 400

Met Ser Met Thr Ile Lys Phe Leu Tyr Ala Met Thr Leu Phe Leu Phe
1               5                   10                  15

Leu Phe His Ile Glu Lys Ser Ser Ala Leu Ile Asp Cys Lys Thr Val
                20                  25                  30

Asp Asp Cys Pro Ser Ser Trp Thr Lys Ile Tyr Lys Cys Ile Asp Asn
            35                  40                  45

Lys Cys Arg Tyr Ser Val Val Lys Gly Leu Ile Ile
    50                  55                  60

<210> SEQ ID NO 401
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 401

Met Ser Lys Thr Ile Lys Phe Leu Tyr Ala Ile Thr Leu Phe Leu Phe
1               5                   10                  15

Leu Phe Leu Ile Glu Lys Asn Asn Val Leu Ile Asp Cys Lys His Val
                20                  25                  30

Arg Asp Cys Pro Lys Gly Ile Trp Arg Ser Cys Arg Tyr Lys Cys Ile
            35                  40                  45

Asp Asn Lys Cys Val Phe Thr Tyr Trp Pro His
    50                  55

<210> SEQ ID NO 402
<211> LENGTH: 75
<212> TYPE: PRT
<213> ORGANISM: Artificial sequence
<220> FEATURE:
<223> OTHER INFORMATION: Peptide derived from Medicago truncatula

<400> SEQUENCE: 402

Met Thr His Lys Leu Val Tyr Ala Ile Ile Leu Phe Ile Phe Leu Phe
1               5                   10                  15

```
Leu Val Ala Asn Asn Val Glu Gly Tyr Ile Leu Cys Lys Thr Val Asn
                20                  25                  30

Asp Cys Pro Asn Thr Arg Asn Leu Arg Tyr Arg Cys Ile Asp Gly
        35                  40                  45

Lys Cys Lys Ser His Arg Val Leu Tyr Glu Trp Asp Glu Ser His Thr
 50                  55                  60

Gln Asp Ile Thr Ile Thr Pro Cys Ile Glu Glu
 65                  70                  75

<210> SEQ ID NO 403
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 403

Met Thr Glu Ile Leu Lys Phe Val Cys Val Met Ile Ile Phe Leu Ser
 1               5                  10                  15

Ser Phe Ile Val Ser Gln Asn Ile Asp Ser Gly Gly Asn Arg Arg Cys
                20                  25                  30

Phe Arg Asp Ser Asp Cys Pro Lys Asn Met Cys Pro Ser Tyr Leu Val
        35                  40                  45

Val Lys Cys Leu Arg Ser Asn Cys Lys Cys Val Arg Pro Gly Leu Gln
 50                  55                  60

Val Arg Leu Asn Pro Asn
 65                  70

<210> SEQ ID NO 404
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 404

Met Ala Glu Ile Leu Lys Phe Ile Cys Phe Met Ile Ile Phe Leu Ser
 1               5                  10                  15

Ser Phe Ile Val Ser Glu Ser Leu Asn Gly His Gly Arg Asn Arg Cys
                20                  25                  30

Phe Arg Asp Ser Asp Cys Pro Lys Val Met Cys Pro Ser Tyr Leu Val
        35                  40                  45

Thr Lys Cys Phe Lys Lys His Cys Arg Cys Arg Lys Pro Gly Leu Gln
 50                  55                  60

Val Gln Leu Asn Pro Lys
 65                  70

<210> SEQ ID NO 405
<211> LENGTH: 79
<212> TYPE: PRT
<213> ORGANISM: Artificial sequence
<220> FEATURE:
<223> OTHER INFORMATION: Peptide derived from Medicago truncatula

<400> SEQUENCE: 405

Met Ser Thr Ile Val Asn Tyr Val Cys Ser Met Met Ile Ile Cys Leu
 1               5                  10                  15

Phe Gln Phe Thr Val Ala Thr Asn Phe Glu Arg Lys Gln Ile Ser Phe
                20                  25                  30

Ser Phe Phe Met Lys Glu Tyr Trp Pro Cys Val Thr Asp Asp Asp Cys
        35                  40                  45
```

```
Pro Ser Asp Leu Cys Lys Lys Val Asp Gln Ile Pro Lys Cys Val Gly
    50                  55                  60

Gly Leu Cys Lys Cys Phe Pro Ile Arg Phe Gly Gln Trp Glu Arg
65                  70                  75
```

<210> SEQ ID NO 406
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 406

```
Met Ala Glu Ile Phe Lys Val Phe Tyr Thr Leu Ile Ile Phe Ala Ser
1               5                   10                  15

Leu Tyr Tyr Val Val Ala Leu Val Gln Asn Glu Cys Val Thr Asp Gly
            20                  25                  30

Asp Cys Arg Arg Leu Tyr Pro His Leu Ile Pro Arg Tyr Pro Met Cys
        35                  40                  45

Asn Glu Gly Thr Cys Val Cys Ile Phe Glu
    50                  55
```

<210> SEQ ID NO 407
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 407

```
Met Ala Gln Ile Phe Lys Phe Val Tyr Val Met Ile Ile Phe Ile Tyr
1               5                   10                  15

Leu Phe Leu Val Leu Thr Asn Val Asp Ala Gly Ile Arg Cys His Asp
            20                  25                  30

Val Ser Glu Cys Pro Lys Gly Leu Tyr Cys Asn Val Gly Ser His Met
        35                  40                  45

Glu Cys Val Lys His Gln Cys Lys Cys Ile Lys Asn Phe Glu Pro Ile
    50                  55                  60

Asp Leu Ala
65
```

<210> SEQ ID NO 408
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 408

```
Met Ala Glu Thr Phe Lys Phe Val Tyr Ile Val Ile Leu Leu Val Ser
1               5                   10                  15

Leu Cys Leu Val Val Val Asp Gly Ile Arg Thr Tyr Arg Glu Cys Glu
            20                  25                  30

Asn Ala Ser Asp Cys Tyr Ser Ile Tyr Trp Arg Ala Pro Tyr Gly Thr
        35                  40                  45

Met Arg Cys Val Lys Gly His Cys Lys Gln Ile Lys Asp Val Lys Val
    50                  55                  60

Met Lys Phe Leu Tyr Cys Val
65                  70
```

<210> SEQ ID NO 409
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 409

```
Met Thr His Ile Ser Met Phe Val Tyr Ser Leu Ile Ile Phe Leu Ser
1               5                   10                  15

Ile Tyr Leu Val Val Thr Asp Gly Ile Ile Leu Cys Lys Asp His Phe
            20                  25                  30

Asp Cys Tyr Glu Asn Ile Arg Lys Leu Arg Cys Asp Phe Asp Thr Glu
        35                  40                  45

Lys Pro Phe Cys Ile Ser Leu Asn Val Cys Gln Cys Ile Lys Gln
    50                  55                  60
```

<210> SEQ ID NO 410
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 410

```
Met Ala Glu Phe Val Lys Phe Val Tyr Val Met Ile Ile Phe Ile Phe
1               5                   10                  15

Leu Cys Leu Val Val Glu Asn Ile Asp Gly Phe Arg Cys Leu Arg Asn
            20                  25                  30

Leu Asp Cys Pro Asp Ser Met Cys Ser Ser Ala Tyr Thr Pro Arg Cys
        35                  40                  45

Arg His Arg Thr Cys Val Cys Leu Asn Asn Asp Glu Ile Lys Ile Leu
    50                  55                  60
```

<210> SEQ ID NO 411
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 411

```
Met Lys Met Glu Glu Asn Arg Ala Lys Thr Phe Lys Phe Val Tyr Gly
1               5                   10                  15

Met Val Ile Phe Leu Tyr Leu Tyr His Val Ala Lys Arg Val Glu Ala
            20                  25                  30

Ala Ile Pro Cys Ile Thr Asp Ala Asn Cys Pro Cys Val Phe Pro Leu
        35                  40                  45

Lys Pro Arg Cys Asn Phe Gly Tyr Cys Ile Cys Glu Glu Met Ile Pro
    50                  55                  60
```

<210> SEQ ID NO 412
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 412

```
Met Ala Glu Ile Val Lys Phe Ile Tyr Val Met Ile Ile Phe Leu Tyr
1               5                   10                  15

Leu Phe Leu Val Ser Thr Asn Ile Glu Ala Arg Gln Gly Cys Lys Ile
            20                  25                  30
```

```
Asp Tyr Asp Cys Ile Lys Val Val Cys Lys Asp Gly His Ala Ala Arg
            35                  40                  45

Cys Ile Met Arg Arg Cys Glu Cys Val Glu Ile Leu Asn Pro Ile Asp
 50                  55                  60

Leu Gly Ser Thr
 65
```

<210> SEQ ID NO 413
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 413

```
Met Ala Lys Ile Val Lys Phe Val Tyr Val Thr Ile Ile Phe Leu Tyr
 1               5                   10                  15

Met Phe His Ile Ser Thr Asn Ile Glu Ala Gly Asn Tyr Lys Cys Gln
            20                  25                  30

Thr Asn Tyr Asp Cys Leu Arg Met Trp Cys Pro Ile Gly Ile Ser Pro
            35                  40                  45

Arg Cys Ile Lys Arg Arg Cys Lys Cys Ile Glu Thr Leu Val Gln
 50                  55                  60
```

<210> SEQ ID NO 414
<211> LENGTH: 75
<212> TYPE: PRT
<213> ORGANISM: Artificial sequence
<220> FEATURE:
<223> OTHER INFORMATION: Peptide derived from Medicago truncatula

<400> SEQUENCE: 414

```
Met Ala Gly Thr Leu Asn Phe Val Tyr Ala Met Ile Leu Phe Ile Ser
 1               5                   10                  15

Leu Phe Leu Val Ala Gly Gly Glu Glu Ile Ile Ile Lys Cys Gln
            20                  25                  30

Thr Ala Lys Asp Cys Pro Asp Ile Tyr Asn Leu Phe Pro Leu Val Tyr
            35                  40                  45

Lys Cys Ile Asp Asn Ile Cys Val Asp Val Arg Leu Glu Pro Pro Tyr
 50                  55                  60

Asp Met Ser Ile Ser Pro Lys Ser Val His Lys
 65                  70                  75
```

<210> SEQ ID NO 415
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 415

```
Met Val Lys Ile Ala Lys Phe Leu Tyr Val Leu Ile Ile Ser Leu Ser
 1               5                   10                  15

Leu Phe Leu Phe Ala Ile Thr Val Asp Gly Ala Tyr Val Thr Arg Phe
            20                  25                  30

Trp Cys Tyr Arg Asp Leu Asp Cys Arg Lys Asp Met Cys Lys Pro Pro
            35                  40                  45

Phe Asn Pro Arg Cys His Asn His Ile Cys Ile Cys Arg Leu Trp Gly
 50                  55                  60

Leu
```

-continued

<210> SEQ ID NO 416
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 416

Met Ala Lys Thr Ile Lys Phe Val Asn Leu Leu Ile Leu Phe Ile Phe
1               5                   10                  15

Thr Phe Leu Val Val Ala Asp Ala Ser Ala Thr Thr Arg Cys Val Arg
            20                  25                  30

Asn Ser Asp Cys Arg His His Ile Cys Met Tyr Pro Leu Val Pro Arg
        35                  40                  45

Cys Lys Tyr Pro Leu Cys Arg Cys Val
    50                  55

<210> SEQ ID NO 417
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 417

Met Val Lys Ile Ile Lys Tyr Val Asn Leu Leu Ile Leu Phe Ile Ser
1               5                   10                  15

Ile Phe Leu Val Val Thr Asp Val Ser Ala His Lys Arg Cys Arg Val
            20                  25                  30

Asp Phe Asp Cys Arg Met Arg Met Cys Val Tyr Pro Thr Val Ser Val
        35                  40                  45

Cys Ile Asp Arg Leu Cys Arg Cys Arg Arg Pro Pro Asn Met
    50                  55                  60

<210> SEQ ID NO 418
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 418

Met Val Lys Ile Ile Lys Tyr Val Asn Leu Leu Ile Leu Phe Ile Ser
1               5                   10                  15

Ile Phe Leu Val Val Thr Asp Val Ser Ala Gln Lys Arg Cys Lys Glu
            20                  25                  30

Asp Phe Asp Cys Arg Ile Arg Ser Cys Ala Tyr Pro Leu Ile Pro Val
        35                  40                  45

Cys Ile Asp Pro Phe Cys Arg Cys Arg Arg Ala Ser Ile
    50                  55                  60

<210> SEQ ID NO 419
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 419

Met Gly Lys Ile Ile Lys Phe Val Asn Leu Ser Ile Leu Phe Ile Phe
1               5                   10                  15

```
Met Phe Leu Val Val Val Asp Val Asn Ala Glu Arg Thr Cys Lys Glu
            20                  25                  30

Asp Phe Asp Cys Arg Met Arg Tyr Cys Val Tyr Pro Thr Ile Pro Leu
            35                  40                  45

Cys Asp Val Lys His Cys Arg Cys Arg Arg Pro Pro Asn Leu
50                  55                  60

<210> SEQ ID NO 420
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 420

Met Ala Lys Val Leu Lys Leu Val Asn Val Met Ile Ile Phe Leu Ala
1               5                   10                  15

Leu Val Leu Val Ala Met Asn Val Asn Ala Asp Val Ile Asn Cys Thr
            20                  25                  30

Gln Asp Ser Asp Cys Gln Ser Ile Gly Cys Leu Ser His Leu Lys Pro
            35                  40                  45

Lys Cys Thr Met Leu Gly Phe Phe Asn Ala Phe Val Gly Ile Cys
50                  55                  60

Glu Cys Asp Gln Val Met
65                  70

<210> SEQ ID NO 421
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 421

Met Ala Lys Ile Leu Met Phe Val Tyr Ala Leu Ile Ile Phe Ile Ser
1               5                   10                  15

Leu Val Ile Thr Gly Arg Ser Thr Ile Asn Val Met Cys Tyr Tyr Asp
            20                  25                  30

His Asp Cys Pro Phe Val Leu Asp His Ile Ala Glu Cys Lys Gly Gly
            35                  40                  45

Val Cys Glu Tyr Thr Ala Phe Phe Tyr Glu
50                  55

<210> SEQ ID NO 422
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 422

Met Gln Arg Lys Lys Leu Met Ala Gln Ile His Leu Cys Val Tyr Ala
1               5                   10                  15

Leu Ile Ile Phe Leu Ser Pro Phe Leu Ala Leu Thr Asn Asp Arg Ile
            20                  25                  30

Val Tyr His Gly Cys Tyr Ser Asp Asp Gln Cys Pro Asn Glu Cys Pro
            35                  40                  45

Ala Ile Leu Met Arg Cys Ile His Ser Leu Cys Val Glu Phe Ile Lys
50                  55                  60

Thr Asp Pro Leu Phe Ile
```

<210> SEQ ID NO 423
<211> LENGTH: 76
<212> TYPE: PRT
<213> ORGANISM: Artificial sequence
<220> FEATURE:
<223> OTHER INFORMATION: Peptide derived from Medicago truncatula

<400> SEQUENCE: 423

Met Gln Arg Met Glu His Thr Thr Lys Ile Gln Phe Cys Val Tyr Val
1               5                   10                  15

Leu Ile Ile Phe Leu Ser Leu Phe Leu Val Val Thr Asn Gly Asp Lys
            20                  25                  30

Pro Arg Tyr Thr Pro Arg Asn Ala Val Lys Ile Ala Glu Cys Val Ser
        35                  40                  45

Tyr Thr Asp Cys Gln Gly Gly Cys Pro Ala Cys Tyr Met Arg Cys Ile
    50                  55                  60

Asp Gly Gln Cys Glu Pro Phe Ile Ile Lys Phe Ile
65                  70                  75

<210> SEQ ID NO 424
<211> LENGTH: 70
<212> TYPE: PRT
<213> ORGANISM: Artificial sequence
<220> FEATURE:
<223> OTHER INFORMATION: Peptide derived from Medicago truncatula

<400> SEQUENCE: 424

Met Gln Arg Met Glu His Met Thr Lys Ile Gln Phe Gly Val Tyr Val
1               5                   10                  15

Leu Ile Ile Phe Leu Ser Leu Phe Leu Val Lys Val Tyr Glu Cys Tyr
            20                  25                  30

Asn Tyr Ile Asp Cys Pro Val Gly Cys Arg Ala Cys Tyr Met Arg Cys
        35                  40                  45

Ile Asp Gly Gln Cys Ile Pro Phe Ile Lys Lys Leu Ile Leu Phe His
    50                  55                  60

Leu Tyr Val Ile Val Glu
65                  70

<210> SEQ ID NO 425
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 425

Met Ala Gln Ile Leu Met Phe Ile Tyr Asp Leu Ile Ile Phe Leu Ser
1               5                   10                  15

Ile Phe Ile Ile Val Thr Asn Gly Gly Leu Ile Pro Cys Val Ser Asp
            20                  25                  30

Ala Asp Cys Pro Glu Glu Leu Ala Leu Val Met Lys Cys Ile Asn Lys
        35                  40                  45

Leu Cys Glu Leu Val Met Glu
    50                  55

<210> SEQ ID NO 426
<211> LENGTH: 64
<212> TYPE: PRT
<213> ORGANISM: Artificial sequence
<220> FEATURE:

<223> OTHER INFORMATION: Peptide derived from Medicago truncatula

<400> SEQUENCE: 426

Met Ile Lys Asp Val Lys Phe Val Tyr Val Met Ile Ile Phe Leu Ser
1               5                   10                  15

Leu Phe Leu Val Ala Met Ser Ile Asp Asp Ser His Cys Pro His Asp
            20                  25                  30

Ile Cys Pro Phe His Leu Lys Pro Lys Cys Ile Phe Thr Lys Val Val
        35                  40                  45

Gly Gln Lys Phe Phe Ser Phe Ser Leu Asp Gly Lys Cys Gly Cys Met
    50                  55                  60

<210> SEQ ID NO 427
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 427

Met Ala Glu Ile Leu Lys Phe Val Tyr Ile Ile Ile Ile Phe Leu Phe
1               5                   10                  15

Ile Thr Glu Ile Lys Gly Asp Lys Phe Val Phe Asp Lys Asn Gly Ala
            20                  25                  30

Asp Arg Cys Arg Ser Ile Leu Asp Cys Pro Gln Asp Lys Cys Phe Pro
        35                  40                  45

Leu Leu Thr Leu Val Cys Val Asn Phe Ala Cys Asp Cys Leu His Val
    50                  55                  60

<210> SEQ ID NO 428
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 428

Met Asn Lys Thr Leu Lys Phe Val Tyr Val Leu Ile Leu Phe Ile Ser
1               5                   10                  15

Leu Ser Ile Val Ser Lys Ser Val Ala Gln Tyr Asn Ile Gly Cys Lys
            20                  25                  30

Thr Asp Asp Asp Cys Gln Lys Tyr Tyr Thr Lys Met Phe Gly Met Lys
        35                  40                  45

Cys Phe Lys Ser Trp Cys Ile Thr Gly Ile Leu Asp
    50                  55                  60

<210> SEQ ID NO 429
<211> LENGTH: 73
<212> TYPE: PRT
<213> ORGANISM: Artificial sequence
<220> FEATURE:
<223> OTHER INFORMATION: Peptide derived from Medicago truncatula

<400> SEQUENCE: 429

Met Thr Lys Thr Leu Gly Ile Val Tyr Ala Ile Ile Leu Phe Ile Ser
1               5                   10                  15

Leu Phe Leu Val Leu Gln Asn Thr Glu Phe Glu Asp Tyr Tyr Tyr Ile
            20                  25                  30

Glu Cys Gln Arg Asp Phe Asp Cys Pro Gln Leu Asn Ser Glu Ile Phe
        35                  40                  45

Ala Phe Lys Cys Ile Glu Lys Leu Cys Lys Leu Glu Phe Ile Tyr Gln

```
                 50                  55                  60

Gln Ala Pro Phe Leu Leu Gly Gln Val
 65                  70

<210> SEQ ID NO 430
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 430

Met Ala His Leu Lys Phe Val Tyr Val Met Ile Leu Phe Leu Phe Leu
  1               5                  10                  15

Phe Leu Ile Thr Lys Asn Ile Glu Ala Tyr Lys Cys Asn Ile Asp Val
                 20                  25                  30

Asp Cys Pro Ile Thr Pro Ser Pro Lys Phe Lys Trp Lys Cys Ile Asn
             35                  40                  45

Lys Arg Cys Leu Tyr Ile Arg Phe Asp Glu Ile Trp Thr Ser Asp Pro
         50                  55                  60

Arg Glu
 65

<210> SEQ ID NO 431
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 431

Met Ala Lys Thr Leu Lys Phe Ser Tyr Pro Met Ile Leu Phe Ile Phe
  1               5                  10                  15

Leu Phe Leu Val Ala Tyr Lys Ile Glu Ala Leu Thr Lys Cys Glu Thr
                 20                  25                  30

Asp Ala Asn Cys Pro Glu Ile Ser Ile Phe Ser Pro Phe Phe Tyr Lys
             35                  40                  45

Cys Ile Asn Asn Gly Cys Val Leu Ile Met Leu
         50                  55

<210> SEQ ID NO 432
<211> LENGTH: 65
<212> TYPE: PRT
<213> ORGANISM: Artificial sequence
<220> FEATURE:
<223> OTHER INFORMATION: Peptide derived from Medicago truncatula

<400> SEQUENCE: 432

Met Thr Lys Thr Leu Lys Phe Val Tyr Ser Ile Ile Leu Phe Ile Thr
  1               5                  10                  15

Leu Phe Leu Val Ala Lys Asn Val Asp Ala Leu Lys Lys Cys Ile Thr
                 20                  25                  30

Phe Glu Asp Cys Pro Ile Ser Lys Thr Arg Val Tyr Lys Cys Leu His
             35                  40                  45

Gly Glu Cys Arg Tyr Thr Ile Pro Tyr Ile Pro Lys Val Pro Lys Val
         50                  55                  60

Lys
 65

<210> SEQ ID NO 433
<211> LENGTH: 71
```

<212> TYPE: PRT
<213> ORGANISM: Artificial sequence
<220> FEATURE:
<223> OTHER INFORMATION: Peptide derived from Medicago truncatula

<400> SEQUENCE: 433

Met Ser Gln Ile Leu Thr Phe Val Tyr Ala Met Ile Leu Phe Ile Ser
1               5                   10                  15

Ile Phe Leu Val Ala Ala Glu Val Asp Trp Ile Tyr His Leu Cys Asp
                20                  25                  30

Thr Asp Thr Asp Cys Pro Glu His Trp Ser Lys Phe Ile Tyr Lys
            35                  40                  45

Cys Val Asn His Val Cys Asp Ser Ile Ser Lys Val Thr Thr Asp Ser
    50                  55                  60

Lys Glu Tyr Lys Asn Phe Pro
65                  70

<210> SEQ ID NO 434
<211> LENGTH: 84
<212> TYPE: PRT
<213> ORGANISM: Artificial sequence
<220> FEATURE:
<223> OTHER INFORMATION: Peptide derived from Medicago truncatula

<400> SEQUENCE: 434

Met Ala Lys Leu Leu Thr Phe Val Tyr Val Met Ile Tyr Phe Leu Ser
1               5                   10                  15

Leu Phe Leu Val Thr Lys Gly Ala His Val Glu Cys His Asn Asp Ser
                20                  25                  30

Ala Cys Glu Lys Thr Val Lys Cys Met Leu Pro Arg Ile Pro Arg Cys
            35                  40                  45

Ile Lys Tyr Gln Cys Leu Cys Gly Tyr Ser Asp Asp Pro Gly Asn Arg
    50                  55                  60

Trp Ser Thr Arg Pro Lys Arg Ile Gln Lys Gly Ser Thr Glu Arg Lys
65                  70                  75                  80

Gly Phe Leu Tyr

<210> SEQ ID NO 435
<211> LENGTH: 66
<212> TYPE: PRT
<213> ORGANISM: Artificial sequence
<220> FEATURE:
<223> OTHER INFORMATION: Peptide derived from Medicago truncatula

<400> SEQUENCE: 435

Met Asp Lys Thr Leu Lys Tyr Met Tyr Thr Leu Ile Ser Phe Ile Ser
1               5                   10                  15

Leu Phe Phe Ile Ala Lys Asn Asp Ala Val Tyr Ile Lys Cys Lys Thr
                20                  25                  30

Asp Ala Asp Cys Pro Lys Ser Glu Ser Thr Ile Phe Ala Met Lys Cys
            35                  40                  45

Asn Asn Tyr Arg Cys Ile Tyr Asp Tyr Ile His Lys Arg Asn Ser Tyr
    50                  55                  60

Ala Thr
65

<210> SEQ ID NO 436
<211> LENGTH: 72
<212> TYPE: PRT
<213> ORGANISM: Artificial sequence
<220> FEATURE:

-continued

<223> OTHER INFORMATION: Peptide derived from Medicago truncatula

<400> SEQUENCE: 436

Met Pro Ser Phe Leu Lys Phe Val Tyr Ala Ile Ile Leu Phe Val Ser
1               5                   10                  15

Leu Phe Leu Ala Ala Thr Asn Val Asn Ala Thr Tyr Asp Ala Tyr Asp
            20                  25                  30

Glu Cys Gln Thr Glu Leu Asp Cys Pro Lys Asn Ile Asp Cys Val Tyr
        35                  40                  45

Pro Lys Ser Met Lys Cys Ile Asp Lys Lys Cys Ile Cys Val Gly Ala
    50                  55                  60

Arg Met Ile Ile Pro Arg Val Leu
65                  70

<210> SEQ ID NO 437
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 437

Met Val Ala Ile Leu Lys Phe Ile Tyr Ser Ile Leu Phe Ile Phe
1               5                   10                  15

Leu His Leu Val Ser Thr Asn Gly Tyr Arg Asn Ile Lys Tyr Cys Phe
            20                  25                  30

Ile Asp Thr Asp Cys Pro Arg Ser Met Cys His Tyr Pro Glu Ile Val
        35                  40                  45

Arg Cys Val Asp Gln Cys Lys Cys Val Arg Ile Met Pro
    50                  55                  60

<210> SEQ ID NO 438
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 438

Met Thr Glu Ile Leu Lys Leu Phe Tyr Ala Met Ile Leu Phe Ala Ser
1               5                   10                  15

Leu Phe Leu Val Ala Met Glu Ile Gly Glu Ser Phe Gly Cys Thr Glu
            20                  25                  30

His Arg His Cys Glu Ile Ala Met Cys Lys Phe Pro Phe Ile Val Arg
        35                  40                  45

Cys Ser Met Asn Glu Cys Asn Cys Glu Arg Val His Tyr Leu Ile
    50                  55                  60

<210> SEQ ID NO 439
<211> LENGTH: 69
<212> TYPE: PRT
<213> ORGANISM: Artificial sequence
<220> FEATURE:
<223> OTHER INFORMATION: Peptide derived from Medicago truncatula

<400> SEQUENCE: 439

Met Thr Ile Lys Thr Leu Lys Phe Val Tyr Val Ile Ile Leu Phe Phe
1               5                   10                  15

Ser Leu Phe Leu Val Ala Lys Asn Glu Pro Glu Pro Lys Phe Ile Glu
            20                  25                  30

Cys Val Thr Asp Ala Asp Cys Leu Asn Ser Gln Ser Lys Met Tyr Ala

-continued

```
                35                  40                  45
Leu Ile Cys Glu Lys Asn Arg Cys Ile Tyr Glu Phe Leu Lys Ser Met
 50                  55                  60

His Tyr Asn Leu Ser
 65

<210> SEQ ID NO 440
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 440

Met Gln Asn Ala Lys Asn Met Thr Glu Ile Leu Lys Phe Val Tyr Val
 1               5                  10                  15

Met Phe Leu Phe Ile Ser Met Phe Ile Val Thr Thr Glu Val Gly Gly
                20                  25                  30

Glu Cys Ile Asn Asp Ile Asp Cys Pro Gln Thr Gly Asn Leu Phe Tyr
            35                  40                  45

Val Phe Ile Cys Lys Asn Arg Ile Cys Glu Leu Ile Asn Lys Tyr Pro
 50                  55                  60

Gln Asn Leu
 65

<210> SEQ ID NO 441
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 441

Met Val Gln Leu Leu Lys Phe Val Tyr Ala Met Ile Leu Phe Ile Ser
 1               5                  10                  15

Ile Val Phe Leu Ile Arg Thr Gln Leu Ser Asp Ile Tyr Glu Glu Cys
                20                  25                  30

Glu Thr Asp Asp Tyr Cys Pro Lys Tyr Arg Asp Leu Leu Tyr Val Phe
            35                  40                  45

Lys Cys Ile Asp Lys Arg Cys Glu Leu Val Glu Ala His Ala
 50                  55                  60

<210> SEQ ID NO 442
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 442

Met Asn Lys Ile Leu Lys Phe Val Tyr Glu Met Ile Leu Phe Leu Ser
 1               5                  10                  15

Leu Phe His Leu Ala Arg Glu Val His Asp Val Ala Thr His Thr Asp Ile
                20                  25                  30

Pro Cys Glu Pro Asp Ala Asp Cys Pro Lys Ser Leu His Glu Tyr Phe
            35                  40                  45

Glu Met Lys Cys Ile Asp Lys Lys Cys Glu Trp Ser Arg Lys Thr Ser
 50                  55                  60

Leu Ile Pro
 65
```

-continued

<210> SEQ ID NO 443
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 443

Met Thr Glu Thr Leu Lys Phe Phe Tyr Ala Met Ile Leu Phe Leu Ser
1               5                   10                  15

Leu Phe Leu Ile Thr Thr Asn Val Gly Gly Ser Tyr Tyr Gly Cys Glu
            20                  25                  30

Thr Asp Ala Asp Cys Pro Arg Ser Met Asn Lys Asp Phe Tyr Leu Lys
        35                  40                  45

Cys Val Asp Lys Lys Cys Glu Trp Thr Ala Lys Ile
    50                  55                  60

<210> SEQ ID NO 444
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 444

Met Val Glu Ile His Lys Phe Val Phe Ala Met Ile Gln Phe Ile Ser
1               5                   10                  15

Leu Phe Leu Ile Thr Ile Glu Val Gly Arg Leu Arg Tyr Gly Cys Glu
            20                  25                  30

Thr Asp Ala Asp Cys Pro Arg Tyr Thr His Asn Asn Phe Ser Leu Lys
        35                  40                  45

Cys Ile Asn Lys Lys Cys Glu Trp Ser Ala Lys Leu His
    50                  55                  60

<210> SEQ ID NO 445
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 445

Met Ala Glu Ile Ile Lys Phe Val Tyr Val Met Ile Leu Phe Leu Phe
1               5                   10                  15

Leu Phe Leu Val Ala Ala Glu Asp Ile Gly Gly Asn Cys Glu Cys Ile
            20                  25                  30

Arg Asp Glu Asp Cys Phe Lys Gln Lys Arg Asp Glu Asp Cys His Lys
        35                  40                  45

Glu Tyr Cys Met Ile Phe Tyr Val His Lys Cys Glu Asn Tyr Lys Cys
    50                  55                  60

Val Cys Ala Gly Met Phe Asn
65                  70

<210> SEQ ID NO 446
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 446

Met Thr Thr Ile Leu Lys Phe Ala Tyr Ile Met Ile Thr Cys Leu Phe

```
                1               5                  10                 15
Leu Leu His Ile Ala Ala Gln Glu Val Leu Gln Tyr Glu Leu Phe Asp
                               20                 25                 30

Cys Asn Glu Asp Arg Asp Cys Asp Asn Val Ile Cys Val Ala Gly Gly
            35                 40                 45

Ile Pro Lys Cys Ile Thr Pro Phe Cys Phe Cys Phe
        50                 55                 60

<210> SEQ ID NO 447
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 447

Met Gln Arg Val Lys Asn Met Ala Glu Thr Leu Lys Phe Val Tyr Val
1               5                  10                 15

Leu Ile Leu Phe Ile Ser Ile Phe Leu Val Val Ile Gly Cys Asp Ser
                20                 25                 30

Ile Tyr Tyr Pro Ile Ser Arg Pro Cys Lys Thr Asp Lys Asp Cys Pro
            35                 40                 45

Asn Arg Lys Asn Tyr Lys Gly Lys Cys Arg Lys Gly Phe Cys Met Ser
        50                 55                 60

Ser Arg Leu Arg
65

<210> SEQ ID NO 448
<211> LENGTH: 81
<212> TYPE: PRT
<213> ORGANISM: Artificial sequence
<220> FEATURE:
<223> OTHER INFORMATION: Peptide derived from Medicago truncatula

<400> SEQUENCE: 448

Met Ala Glu Thr Leu Lys Ile Val Tyr Ile Val Ile Leu Leu Val Ser
1               5                  10                 15

Leu Cys Leu Val Val Asp Gly Ile Ser Ile Tyr Val Arg Cys Ala
                20                 25                 30

Ser Thr Asn Glu Cys Tyr Thr Thr Phe Lys Phe Ala Pro Leu Gly Ser
            35                 40                 45

Met Arg Cys Val Glu Gly Tyr Cys Lys His Leu Lys Asp Phe Lys Val
        50                 55                 60

Lys Thr Pro Leu Gln Ile Lys Glu Ile Thr Pro Leu Leu His Phe
65                 70                 75                 80

Pro

<210> SEQ ID NO 449
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 449

Met Ala Lys Thr Leu Lys Phe Val Tyr Val Met Ile Leu Phe Thr Ser
1               5                  10                 15

Leu Phe Leu Phe Ala Lys Asn Val Val Gly Tyr Ile Asn Cys Lys Thr
                20                 25                 30

Asp Asp Asp Cys Pro Lys Leu Glu Ser Arg Met Val Val Leu Lys Cys
```

```
                       35                  40                  45
Thr Asn Ser Arg Cys Ala Ala Val Ile Leu His
    50                  55

<210> SEQ ID NO 450
<211> LENGTH: 82
<212> TYPE: PRT
<213> ORGANISM: Artificial sequence
<220> FEATURE:
<223> OTHER INFORMATION: Peptide derived from Medicago truncatula

<400> SEQUENCE: 450

Met Gln Met Gly Glu Ser Met Ala Lys Ile Val Lys Phe Val Tyr Phe
1               5                   10                  15

Val Ile Ile Phe Ala Ser Pro Phe Val Val Ala Asn His Glu Ile Ser
            20                  25                  30

Gly Trp Ile Thr Glu Leu Pro Phe Gly Met Cys Thr Ser Ile Leu Asp
        35                  40                  45

Cys Pro Met Asp Ser Cys Thr His Pro Gln Gln Pro Trp Cys Glu Leu
    50                  55                  60

His Gly Val Pro Ile Leu Tyr His Gly Ser Glu Ile Gly Leu Cys Ile
65                  70                  75                  80

Cys Ile

<210> SEQ ID NO 451
<211> LENGTH: 82
<212> TYPE: PRT
<213> ORGANISM: Artificial sequence
<220> FEATURE:
<223> OTHER INFORMATION: Peptide derived from Medicago truncatula

<400> SEQUENCE: 451

Met Gln Arg Gly Glu Ser Met Gly Lys Ile Val Lys Phe Val Tyr Phe
1               5                   10                  15

Met Ile Ile Phe Ile Ser Pro Phe Val Val Ala Asn His Ala Ile Ser
            20                  25                  30

Gly Leu Leu Pro Lys Leu Pro Phe Gly Cys Cys Thr Ser Asn Leu Asp
        35                  40                  45

Cys Pro Arg His Met Cys Thr His Pro Gln Gln Pro Trp Cys Ile Phe
    50                  55                  60

Tyr Gly Asn Arg Ile Met Tyr Arg Gly Ser Arg Leu Gly Ile Cys Lys
65                  70                  75                  80

Cys Ser

<210> SEQ ID NO 452
<211> LENGTH: 83
<212> TYPE: PRT
<213> ORGANISM: Artificial sequence
<220> FEATURE:
<223> OTHER INFORMATION: Peptide derived from Medicago truncatula

<400> SEQUENCE: 452

Met Gln Thr Gly Glu Ser Met Thr Lys Ile Ile Lys Phe Val Tyr Phe
1               5                   10                  15

Met Thr Ile Phe Ile Ser Pro Phe Val Val Ala Ser Leu His Glu Ile
            20                  25                  30

Ser Gly Tyr Val Leu Gly Leu Pro Ala Gly Tyr Cys Thr Ser Asn His
        35                  40                  45

His Cys Pro Val Tyr Asn Cys Thr His Pro Lys Gln Pro Trp Cys Lys
    50                  55                  60
```

```
Leu Val Arg Leu Gln Leu Leu Phe His Gly Ser Ile Gly Leu Cys
 65                  70                  75                  80

Asp Cys Ile

<210> SEQ ID NO 453
<211> LENGTH: 67
<212> TYPE: PRT
<213> ORGANISM: Artificial sequence
<220> FEATURE:
<223> OTHER INFORMATION: Peptide derived from Medicago truncatula

<400> SEQUENCE: 453

Met Ala Glu Ile Val Lys Phe Val Tyr Val Met Ile Ile Phe Leu Ser
  1               5                  10                  15

Leu Phe Leu Val Ser Ile His Ile Asn Ala Leu Asn Glu Cys Thr Gln
                 20                  25                  30

Asp Tyr Asp Cys Pro Ile Glu Met Cys Pro Phe Pro Phe Gln Pro Lys
             35                  40                  45

Cys Ile Met Leu Lys Asn Leu Ser Ile Phe Ser Asn Ser Gly Ile Cys
 50                  55                  60

Ser Cys Thr
 65

<210> SEQ ID NO 454
<211> LENGTH: 63
<212> TYPE: PRT
<213> ORGANISM: Artificial sequence
<220> FEATURE:
<223> OTHER INFORMATION: Peptide derived from Medicago truncatula

<400> SEQUENCE: 454

Met Gly Thr Ile His Lys Phe Leu Tyr Ala Met Ile Leu Phe Ile His
  1               5                  10                  15

Ile Thr Leu Val Val Ser Gly Asn Phe Phe Glu Phe Phe His Lys Cys
                 20                  25                  30

Thr Gln Asp Ser Asp Cys Pro Ser Leu Leu Cys Arg Asn Lys Ser Glu
             35                  40                  45

Leu Pro Lys Cys Ile Ala Gly Phe Met Cys Arg Cys Pro Asn Val
 50                  55                  60

<210> SEQ ID NO 455
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 455

Met Ala Asp Val Leu Lys Phe Val Tyr Ile Val Phe Leu Phe Val Ser
  1               5                  10                  15

Gln Phe Cys Ala Glu Pro Asp Asp Asn Gln Lys Asn Cys Val Ser Asp
                 20                  25                  30

Ser Asp Cys Tyr Lys Lys Phe His Leu Pro Arg His Phe Ile Met Lys
             35                  40                  45

Cys Ile Lys Asn Arg Cys Thr Phe Val
 50                  55

<210> SEQ ID NO 456
<211> LENGTH: 47
<212> TYPE: PRT
<213> ORGANISM: Artificial sequence
```

```
<220> FEATURE:
<223> OTHER INFORMATION: Peptide derived from Medicago truncatula

<400> SEQUENCE: 456

Met Ile Ile Phe Leu Phe Ile Phe Val Ala Met Leu Val Lys Val
1               5                   10                  15

Ser His Ser His Cys Val Ile Asp Ala His Cys Pro Arg Asn Met Cys
            20                  25                  30

Gly Phe His Phe Pro Pro Arg Cys Val Glu Gly Asp Cys Val Cys
        35                  40                  45

<210> SEQ ID NO 457
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 457

Met Thr Lys Thr Phe Lys Phe Val Ile Ala Thr Ile Leu Phe Leu Thr
1               5                   10                  15

Leu Phe Phe Ile Val Lys Asn Val Asp Ala Gln Val Lys Cys Lys Thr
            20                  25                  30

Val Lys Asp Cys Pro Ile Arg Arg Asn Arg Lys Tyr Tyr Cys Leu Phe
        35                  40                  45

Gly Ile Cys Lys Tyr Asp Val Met
    50                  55

<210> SEQ ID NO 458
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 458

Met Ser Glu Ile Ile Lys Phe Val Tyr Ala Met Phe Ile Phe Ile Phe
1               5                   10                  15

Met Phe Thr Val Ala Thr Glu Thr Asp Ala Leu Cys Asp Ser Asn Arg
            20                  25                  30

Asp Cys Arg Gly Tyr His Cys Asn Trp Pro Lys Phe Pro Ile Cys Val
        35                  40                  45

Arg Met Ile Cys Glu Cys Ile
    50                  55

<210> SEQ ID NO 459
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 459

Met Thr Ile Ile Ile Lys Phe Val Tyr Ile Met Ile Leu Leu Phe Phe
1               5                   10                  15

Pro Phe Leu Val Val Ser Gln Ile Phe Pro Lys Trp Cys Leu Tyr Asp
            20                  25                  30

Lys Asp Cys Pro Gln Asn Met Cys Arg Pro Gly Arg Ile Pro Lys Cys
        35                  40                  45

Ile Phe Gly His Cys Asn Cys Val Lys Gln Arg Ser
    50                  55                  60
```

```
<210> SEQ ID NO 460
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 460

Met Ile Lys Phe Leu Lys Phe Val Tyr Gly Met Ile Ile Leu Ile Ser
1               5                   10                  15

Leu Phe Phe Ala Val Arg Asp Val Ser Ala Ala Pro Pro Val Tyr Cys
            20                  25                  30

Ile Glu Asp Glu Asp Cys Tyr Asp Leu Cys Thr Ser Pro Leu Val Glu
        35                  40                  45

Ile Cys Thr Asn Tyr Gln Cys Ile Cys Leu Lys Arg Phe
    50                  55                  60

<210> SEQ ID NO 461
<211> LENGTH: 59
<212> TYPE: PRT
<213> ORGANISM: Artificial sequence
<220> FEATURE:
<223> OTHER INFORMATION: Peptide derived from Medicago truncatula

<400> SEQUENCE: 461

Met Val Glu Leu Val Lys Phe Val Tyr Val Met Ile Thr Leu Leu Ser
1               5                   10                  15

Ile Val Val Val Ala Lys Asn Ser Gln Gly Asn Lys Glu Asn Ile Cys
            20                  25                  30

Phe Lys Asp Ala Asp Cys Pro Gln Asp Ile Cys Ser Tyr Pro Phe Lys
        35                  40                  45

Pro Lys Cys Asn Ile Tyr Gly Tyr Cys Ser Cys
    50                  55

<210> SEQ ID NO 462
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 462

Met Ala Gly Asn Leu Lys Ile Val Tyr Ala Leu Met Ile Leu Val Ser
1               5                   10                  15

Leu Ile Leu Val Val Thr Ser His Ser Phe Leu Pro Cys Val Thr Lys
            20                  25                  30

Asp Asp Cys Ala Tyr Asp Glu Cys Ile Ser Pro Arg Lys Pro Thr Cys
        35                  40                  45

Tyr Leu Glu Thr Cys His Cys Leu
    50                  55

<210> SEQ ID NO 463
<211> LENGTH: 68
<212> TYPE: PRT
<213> ORGANISM: Artificial sequence
<220> FEATURE:
<223> OTHER INFORMATION: Peptide derived from Medicago truncatula

<400> SEQUENCE: 463

Met Ala Glu Ile Gly Lys Tyr Ile Tyr Val Ile Ile Phe Ile Ser
1               5                   10                  15

Leu Phe Phe Ile Thr Met Ser Val Glu Gly Trp Arg Cys Lys Lys Thr
```

-continued

```
                20                  25                  30

Asp Asp Cys Ile Lys Ile Glu Phe Cys Lys Phe Pro Lys Ile Ala Arg
            35                  40                  45

Cys Thr Lys Pro Lys Phe Leu Phe Leu Glu Phe Gly Thr Gly Phe Cys
 50                  55                  60

Thr Cys Asp Asp
 65

<210> SEQ ID NO 464
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 464

Ala Phe Glu Arg Thr Glu Thr Arg Met Leu Thr Ile Pro Cys Thr Ser
 1               5                  10                  15

Asp Ala Asn Cys Pro Lys Val Ile Ser Pro Cys His Thr Lys Cys Phe
            20                  25                  30

Asp Gly Phe Cys Gly Trp Tyr Ile Glu Gly Ser Tyr Glu Gly Pro
        35                  40                  45

<210> SEQ ID NO 465
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 465

Ala Phe Glu Thr Thr Glu Pro Met Leu Thr Thr Tyr Leu Ile Leu Cys
 1               5                  10                  15

Val Ser Glu Ala Asp Cys Pro Lys Val Val Lys Pro Asn Tyr Thr Met
            20                  25                  30

Cys Ala Gly Gly Ile Cys Trp Gln Ser Val Gln Gly Ser Asn Gln Gly
        35                  40                  45

Pro

<210> SEQ ID NO 466
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 466

Ala Leu Glu Arg Thr Arg Thr Thr Met Leu Thr Ser Tyr Asn Ile Gly
 1               5                  10                  15

Cys Lys Ser Asp Ala Asp Cys Pro Lys Ala Ile Glu Pro His Tyr Thr
            20                  25                  30

Arg Cys Val Asp Gly His Cys Trp Leu Tyr Phe Gly Glu Gly Pro Lys
        35                  40                  45

Leu His Asn
     50

<210> SEQ ID NO 467
<211> LENGTH: 46
<212> TYPE: PRT
<213> ORGANISM: Artificial sequence
<220> FEATURE:
<223> OTHER INFORMATION: Peptide derived from Medicago truncatula
```

-continued

<400> SEQUENCE: 467

Trp Phe Lys Arg Thr Glu Thr Gly Glu Ile Ile Trp Val Val Arg Cys
1               5                   10                  15

Val Thr Asp Thr Asp Cys Pro Lys Met Gly Glu Pro Gln Tyr Phe Lys
            20                  25                  30

Cys Leu Asn Gly Val Cys Leu Glu His Ile Arg Glu Leu Pro
        35                  40                  45

<210> SEQ ID NO 468
<211> LENGTH: 50
<212> TYPE: PRT
<213> ORGANISM: Artificial sequence
<220> FEATURE:
<223> OTHER INFORMATION: Peptide derived from Medicago truncatula

<400> SEQUENCE: 468

Ala Leu Glu Arg Thr Glu Thr Thr Met His Asn Val Gln Pro Ser His
1               5                   10                  15

Phe Ile Pro Cys Phe Thr Ala Ala Asp Cys Pro Met Ile Asp Glu Pro
            20                  25                  30

His Tyr Ile Glu Cys Val Thr Gly Phe Cys Trp Ala Leu Met Arg Asn
        35                  40                  45

Leu His
    50

<210> SEQ ID NO 469
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 469

Lys Lys Thr Asp Ile Pro Cys Asp Ser Arg Asn Asp Cys Pro Gln Gln
1               5                   10                  15

Ile Leu Pro Arg Tyr Val Leu Cys Val Asn Gly Leu Cys Arg Ile Tyr
            20                  25                  30

Phe Pro

<210> SEQ ID NO 470
<211> LENGTH: 50
<212> TYPE: PRT
<213> ORGANISM: Artificial sequence
<220> FEATURE:
<223> OTHER INFORMATION: Peptide derived from Medicago truncatula

<400> SEQUENCE: 470

Ala Tyr Glu Arg Thr Glu Pro Ile Met His Asn Gly Glu Pro Ile Asn
1               5                   10                  15

Leu Ile Pro Cys Val Thr Val Ala Asp Cys Pro Arg Met Asp Glu Pro
            20                  25                  30

Leu His Met Thr Cys Leu Val Gly Ala Cys Trp Pro Cys Ile Arg Ser
        35                  40                  45

Leu Tyr
    50

<210> SEQ ID NO 471
<211> LENGTH: 47
<212> TYPE: PRT
<213> ORGANISM: Artificial sequence
<220> FEATURE:

-continued

<223> OTHER INFORMATION: Peptide derived from Medicago truncatula

<400> SEQUENCE: 471

Val Phe Lys Arg Thr Glu Thr Gly Glu Ile Ile Trp Thr Leu Pro Cys
1               5                   10                  15

Ala Thr Asp Thr Asp Cys Pro Lys Met Gly Pro Met Tyr Phe Lys
            20                  25                  30

Cys Leu Asn Gly Phe Cys Leu Glu His Ile Arg Glu Leu His Asp
        35                  40                  45

<210> SEQ ID NO 472
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 472

Gln Glu Cys Lys Asp Asp Gly Asp Cys Pro Thr Asn Met Cys Leu Pro
1               5                   10                  15

Ser Leu Val Ser Lys Cys Ile Asn Phe Ile Cys Glu Cys Thr His Ser
            20                  25                  30

Met Ser Thr Asp
        35

<210> SEQ ID NO 473
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 473

Arg Ser Phe Pro Ser Ser Phe Val Ser Pro Lys Ser Tyr Thr Ser Glu
1               5                   10                  15

Ile Pro Cys Lys Ala Thr Arg Asp Cys Pro Tyr Glu Leu Tyr Tyr Glu
            20                  25                  30

Thr Lys Cys Val Asp Ser Leu Cys Thr Tyr Trp
        35                  40

<210> SEQ ID NO 474
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 474

Lys Gln Thr Asn Ile Pro Cys Lys Ser Ala Glu Asp Cys Pro Lys Pro
1               5                   10                  15

Ile Tyr Pro Arg Tyr Val Leu Cys Ser Tyr Gly Phe Cys Arg Ile Phe
            20                  25                  30

Phe Pro

<210> SEQ ID NO 475
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 475

Ala Met Phe Glu Leu Thr Lys Ser Thr Ile Arg Cys Val Thr Asp Ala

```
1               5                  10                 15
Asp Cys Pro Asn Val Val Lys Pro Leu Lys Pro Lys Cys Val Asp Gly
            20                  25                 30

Phe Cys Glu Tyr Thr
        35
```

<210> SEQ ID NO 476
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 476

```
Arg Glu Pro Thr Lys Ile Pro Cys Val Ser Asp Ser Asp Cys His Lys
1               5                  10                 15

Val Lys Lys Pro Leu Leu Leu Thr Cys Ile Asp Gly Ile Cys Gln Tyr
            20                  25                 30

Thr Leu Glu Ala Thr Pro Phe Asp
        35                  40
```

<210> SEQ ID NO 477
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 477

```
Arg Lys Gly Gly Pro Pro Gly Gly Arg Thr Tyr Ile Pro Cys Ile Ser
1               5                  10                 15

Asp Asp Asp Cys Ile Val Ala Gln Pro Pro Tyr Val Leu Leu Cys Val
            20                  25                 30

Asn Asn Phe Cys Thr Tyr Phe Lys Asp Asp Leu Pro Gln Arg
        35                  40                  45
```

<210> SEQ ID NO 478
<211> LENGTH: 72
<212> TYPE: PRT
<213> ORGANISM: Artificial sequence
<220> FEATURE:
<223> OTHER INFORMATION: Peptide derived from Medicago truncatula

<400> SEQUENCE: 478

```
Ala Gln Ile Tyr Ile Thr Phe Phe Thr Ile Phe Ser Ile Phe Val Phe
1               5                  10                 15

Tyr Thr Thr Phe Tyr His Leu Thr Leu Thr Thr Phe Phe Ser Phe His
            20                  25                 30

Asn Ala Gly Tyr Leu Pro Cys Ser Ser Asp Asp Cys Pro Lys Glu
        35                  40                  45

Met Lys Pro Val Val Lys Cys Ile His Asn Phe Cys Glu His Phe
    50                  55                  60

Met Val Gly Glu Tyr Glu Gly Pro
65                  70
```

<210> SEQ ID NO 479
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 479

-continued

Phe Phe Cys Gly Leu Ala Glu Thr Lys Arg Thr Asn Ile Pro Cys Phe
1               5                   10                  15

Ser Asp Asp Cys Pro Lys Thr Cys Pro Pro Leu Val Phe Glu Val
            20                  25                  30

Arg

<210> SEQ ID NO 480
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 480

Glu Lys Thr His Val Arg Cys Ile Thr Ala Asp Cys Pro Lys Val
1               5                   10                  15

Glu Arg Pro Leu Lys Met Lys Cys Ile Gly Asn Tyr Cys His Tyr Phe
            20                  25                  30

Leu Asn Asn Phe
        35

<210> SEQ ID NO 481
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 481

Tyr Tyr Pro Cys Asn Thr Asp Ser Asp Cys Pro Gln Asn Met Cys Pro
1               5                   10                  15

Pro Asp Met Glu Pro Arg Cys Trp Thr Gly Tyr Cys Ser Ser Cys Tyr
            20                  25                  30

Ile Arg Trp Gly Lys
        35

<210> SEQ ID NO 482
<211> LENGTH: 79
<212> TYPE: PRT
<213> ORGANISM: Artificial sequence
<220> FEATURE:
<223> OTHER INFORMATION: Peptide derived from Medicago truncatula

<400> SEQUENCE: 482

Leu Thr Val Pro Cys Glu Asn Pro Thr Thr Cys Pro Glu Asp Phe Cys
1               5                   10                  15

Thr Pro Pro Met Ile Thr Arg Cys Ile Asn Phe Ile Cys Leu Cys Asp
            20                  25                  30

Gly Pro Glu Tyr Ala Glu Pro Glu Tyr Asp Gly Pro Val Glu Glu Tyr
        35                  40                  45

Asp His Lys Gly Asp Phe Leu Ser Val Lys Pro Lys Val Ile Asn Glu
    50                  55                  60

Asn Met Met Met Arg Glu Arg His Met Ile Lys Glu Ile Glu Val
65                  70                  75

<210> SEQ ID NO 483
<211> LENGTH: 38
<212> TYPE: PRT
<213> ORGANISM: Artificial sequence
<220> FEATURE:
<223> OTHER INFORMATION: Peptide derived from Medicago truncatula

```
-continued

<400> SEQUENCE: 483

Ala Phe Val Pro Asn Ser Gly Pro Cys Thr Thr Asp Lys Asp Cys Lys
1               5                   10                  15

Gln Val Lys Gly Tyr Ile Ala Arg Cys Arg Lys Gly Tyr Cys Met Gln
            20                  25                  30

Ser Val Lys Arg Thr Trp
        35

<210> SEQ ID NO 484
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 484

Arg Val Cys Lys Ser Asp Lys Asp Cys Lys Asp Ile Ile Ile Tyr Arg
1               5                   10                  15

Tyr Ile Leu Lys Cys Arg Asn Gly Glu Cys Val Lys Ile Lys Ile
            20                  25                  30

<210> SEQ ID NO 485
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 485

Ile Asn Lys Cys Ser Gln Asp Ser His Cys Pro Lys Asp Met Cys Lys
1               5                   10                  15

Lys Pro Ser Lys Pro Arg Cys Val Val Ser Pro Lys Leu Pro Leu Ser
            20                  25                  30

Ser Lys Ser Gly Val Cys Thr Cys Val
        35                  40

<210> SEQ ID NO 486
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 486

Ile Arg Asp Lys Cys Phe Arg Pro Ser Asp Cys Pro Pro Ser Met Tyr
1               5                   10                  15

Cys Asp Ala Gly Phe Gln Ile Gly Cys Val Arg Lys Ile Cys Thr Cys
            20                  25                  30

Leu Arg Ile Leu Ala Pro Ile Asp Phe Val Pro Thr
        35                  40

<210> SEQ ID NO 487
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 487

Ala Tyr Ile Ile Glu Cys Gln Thr Asp Asp Cys Pro Lys Ser Gln
1               5                   10                  15

Leu Glu Met Phe Ala Trp Lys Cys Val Lys Asn Gly Cys His Leu Phe
            20                  25                  30
```

```
Gly Met Tyr Glu Asp Asp Asp Pro
        35                  40
```

<210> SEQ ID NO 488
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 488

```
Asp Asp Val Val Phe Gln Tyr Val Phe Asp Gly Cys Arg Ile Asp Ala
1               5                   10                  15

Asp Cys Pro Ile Ser Gly Leu Gln Leu Leu Lys Trp Met Cys Ile Asn
            20                  25                  30

Asn Glu Cys Glu Phe Asn His Val Arg Pro Arg Tyr Val
        35                  40                  45
```

<210> SEQ ID NO 489
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 489

```
Leu Tyr Ile Ile Glu Cys Lys Thr Asp Ala Asp Cys Pro Ile Ser Lys
1               5                   10                  15

Leu Asn Met Tyr Asn Trp Arg Cys Ile Lys Ser Ser Cys His Leu Tyr
            20                  25                  30

Lys Val Ile Gln Phe Met Val
        35
```

<210> SEQ ID NO 490
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 490

```
Lys Phe Thr Arg Cys Phe Arg Asp Ser Asp Cys Pro Lys Thr Leu Cys
1               5                   10                  15

His Ser Pro Gly Lys Ala Lys Cys Met His His Ser Ile Cys Lys Cys
            20                  25                  30

Ile Phe Phe Gly Tyr Asn Ile
        35
```

<210> SEQ ID NO 491
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 491

```
Tyr Thr Asp Glu Cys Ser Thr Asp Ala Asp Cys Glu Tyr Ile Leu Cys
1               5                   10                  15

Leu Phe Pro Ile Ile Lys Arg Cys Ile His Asn His Cys Lys Cys Val
            20                  25                  30

Pro Met Gly Ser Ile Glu Pro Met Ser Thr Ile Pro Asn Gly Val His
        35                  40                  45
```

-continued

Lys Phe His Ile Ile Asn Asn
    50                  55

<210> SEQ ID NO 492
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 492

Glu Leu Ile Lys Cys Thr Met Asp Ala Asp Cys Pro Thr Ser Leu Asn
1               5                   10                  15

Arg Lys Trp Leu Cys Ile Asn Asn Ile Cys Arg Lys Met Cys Val Thr
            20                  25                  30

Asn Val

<210> SEQ ID NO 493
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 493

Ala Phe Leu Pro Thr Ser Arg Asn Cys Ile Thr Asn Lys Asp Cys Arg
1               5                   10                  15

Gln Val Arg Asn Tyr Ile Ala Arg Cys Arg Lys Gly Gln Cys Leu Gln
            20                  25                  30

Ser Pro Val Arg
        35

<210> SEQ ID NO 494
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 494

Gln Ile Arg Cys Asn Asp Ala Phe Glu Cys Arg Arg Ser Ala Ile Cys
1               5                   10                  15

Asn Phe Pro Asn Lys Trp Lys Cys Asn Asp His Lys Cys Glu Cys Val
            20                  25                  30

<210> SEQ ID NO 495
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 495

Phe Pro Asp Lys Ile Phe Ile Gly Asp Cys Lys Thr Asp Lys Asp Cys
1               5                   10                  15

Lys Pro Lys Arg Gly Val Asn Phe Arg Cys Arg Lys Gly Lys Cys Tyr
            20                  25                  30

Pro Arg

<210> SEQ ID NO 496
<211> LENGTH: 36
<212> TYPE: PRT
<213> ORGANISM: Artificial sequence
<220> FEATURE:

<223> OTHER INFORMATION: Peptide derived from Medicago truncatula

<400> SEQUENCE: 496

Ala Phe Val Ala Asn Thr Glu Thr Cys Ile Thr Asp Lys Asp Cys Pro
1               5                   10                  15

Asn Gly Arg Asn Tyr Ile Gly Arg Cys Arg Lys Gly His Cys Gln Gln
            20                  25                  30

Arg Leu Val Arg
        35

<210> SEQ ID NO 497
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 497

Ile His Asp Gln Val Tyr Phe Asn Asn Ser Pro Pro Cys Val Thr
1               5                   10                  15

Asp Lys Asp Cys Pro Arg Pro Gln Phe Arg Lys Ser Asn Val Arg Cys
            20                  25                  30

Arg Asn Gly His Cys Val Asn Leu Gly Asn
        35                  40

<210> SEQ ID NO 498
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 498

Ser Phe Leu Gly Thr Phe Ile Ser Ser Cys Lys Arg Asp Lys Asp Cys
1               5                   10                  15

Pro Lys Leu Tyr Gly Ala Asn Phe Arg Cys Arg Lys Gly Thr Cys Val
            20                  25                  30

Pro Pro Ile
        35

<210> SEQ ID NO 499
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 499

Tyr Phe Asn Asp Pro Arg Pro Cys Val Ser Asp Lys Asp Cys Pro Arg
1               5                   10                  15

Pro Lys Phe Gln Lys Ser Asn Val Arg Cys Arg Lys Gly Tyr Cys Val
            20                  25                  30

Asn Leu Asp Gly
        35

<210> SEQ ID NO 500
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 500

-continued

Asn Asn Ser Pro Pro Cys Val Thr Asp Lys Asp Cys Pro Arg Pro Gln
1               5                   10                  15

Phe Arg Lys Ser Asn Val Arg Cys Arg Asn Gly Tyr Cys Val Asn Leu
            20                  25                  30

Gly Asn

<210> SEQ ID NO 501
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 501

Ser Asn Tyr Ser Pro Thr Pro Phe Pro Cys Leu Thr Asp Lys Asp Cys
1               5                   10                  15

Thr Arg Arg Lys Gly Phe Ser Val Thr Cys Arg Lys Gly Phe Cys Val
            20                  25                  30

Glu Phe Lys His Phe
        35

<210> SEQ ID NO 502
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 502

Thr Thr Pro Thr Pro Cys Arg Thr Asp Gln Asp Cys Pro Arg Lys Lys
1               5                   10                  15

Lys Phe Ser Val Thr Cys Arg Lys Gly Phe Cys Ala Glu Ile Arg His
            20                  25                  30

Val Tyr

<210> SEQ ID NO 503
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 503

Val Thr Ser Pro Trp Val Leu Lys Gln His Cys Val Thr Asp Lys Asp
1               5                   10                  15

Cys Pro Gln Met Gly Lys Ile Lys Ile Arg Cys Arg Asn Gly Glu Cys
            20                  25                  30

Val Gln Gly Phe
        35

<210> SEQ ID NO 504
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 504

Gln Ile Ile Phe Ser Glu Cys Lys Thr Asp Lys Asp Cys Pro Lys Tyr
1               5                   10                  15

Gln Arg Ala Asn Ile Arg Cys Arg Lys Gly Gln Cys Val Arg Ile
            20                  25                  30

-continued

```
<210> SEQ ID NO 505
<211> LENGITH: 36
<212> TYPE: PRT
<213> ORGANISM: Artificial sequence
<220> FEATURE:
<223> OTHER INFORMATION: Peptide derived from Medicago truncatula

<400> SEQUENCE: 505

Thr Tyr Leu Pro Thr Thr Arg Ile Cys Ile Thr Asp Lys Asp Cys Pro
1               5                   10                  15

Ser Val Lys Asn Tyr Ile Gly Arg Cys Arg Lys Gly Tyr Cys Gln Ala
            20                  25                  30

Ser Lys Leu Arg
        35

<210> SEQ ID NO 506
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 506

Asn Ser Ser Phe Ser His Phe Phe Glu Gly Ala Cys Lys Ser Asp Lys
1               5                   10                  15

Asp Cys Pro Lys Leu His Arg Ser Asn Val Arg Cys Arg Lys Gly Gln
            20                  25                  30

Cys Val Gln Ile
        35

<210> SEQ ID NO 507
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 507

Ala Phe Ile Gln Leu Ser Lys Pro Cys Ile Ser Asp Lys Glu Cys Ser
1               5                   10                  15

Ile Val Lys Asn Tyr Arg Ala Arg Cys Arg Lys Gly Tyr Cys Val Arg
            20                  25                  30

Arg Arg Ile Arg
        35

<210> SEQ ID NO 508
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 508

Phe Ile Phe Leu Pro Cys Ile Thr Asp Lys Asp Cys Gln Thr Leu Lys
1               5                   10                  15

Lys Asn Lys Gly Lys Gly Arg Cys Arg Lys Gly Phe Cys Val Asp Gly
            20                  25                  30

Leu Ile Gly
        35

<210> SEQ ID NO 509
<211> LENGTH: 31
<212> TYPE: PRT
```

<213> ORGANISM: Artificial sequence
<220> FEATURE:
<223> OTHER INFORMATION: Peptide derived from Medicago truncatula

<400> SEQUENCE: 509

Lys Thr Phe Asp Arg Ala Cys Lys Thr Asp Asp Cys Pro Lys Leu
1               5                   10                  15

Arg Gly Val Asn Val Arg Cys Arg Lys Asp Gln Cys Val Thr Val
            20                  25                  30

<210> SEQ ID NO 510
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 510

Ser Phe Phe Pro Ser Ser Pro Val Cys Lys Thr Asp Lys Asp Cys Pro
1               5                   10                  15

Gln Leu Arg Gly Tyr Thr Ala Arg Cys Arg Lys Thr Gln Cys Leu Leu
            20                  25                  30

Ile Pro Arg Gly
        35

<210> SEQ ID NO 511
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 511

His Phe His Val Ser Arg Pro Cys Met Thr Asp Asp Cys Ala Pro
1               5                   10                  15

Glu Lys Tyr Tyr Asn Ile Arg Cys Arg Lys Gly Phe Cys Val Gln Ile
            20                  25                  30

Arg Lys Tyr
        35

<210> SEQ ID NO 512
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 512

Ala Tyr Phe Pro Asn Ser Arg Pro Cys Lys Thr Asp Lys Asn Cys Ala
1               5                   10                  15

Gln Val Lys Asn Tyr Ile Ser Lys Cys Leu Lys Gly Leu Cys Val Gln
            20                  25                  30

Glu Glu

<210> SEQ ID NO 513
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 513

Ala Tyr Leu Pro Leu Ser Arg Ser Cys Ile Thr Asp Lys Asp Cys Ser
1               5                   10                  15

```
Arg Val Lys Asn Tyr Asn Ala Arg Cys Arg Lys Gly Tyr Cys Gln Tyr
            20                  25                  30

Leu Gln Tyr
        35

<210> SEQ ID NO 514
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 514

Glu Glu Asp Ile Gly Gly His Leu Glu Cys Val Glu Asp Glu Asp Cys
1               5                   10                  15

Met Glu Glu Ser Cys Pro Ile Phe Ser Val His Lys Cys Lys Asn Ser
            20                  25                  30

Gly Cys Glu Cys Asp Glu Met Phe Arg
        35                  40

<210> SEQ ID NO 515
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 515

Asn Pro Tyr Ile Ile Asn Ile Val Cys Lys Thr Asp Lys Asp Cys Pro
1               5                   10                  15

Lys Val Gln Gly Ala Asn Ile Lys Cys Arg Ser Gly Lys Cys Val Gln
            20                  25                  30

Ala

<210> SEQ ID NO 516
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 516

Lys Arg Ile Pro Cys Lys Asp Asn Asp Cys Asn Asn Asn Trp Gln
1               5                   10                  15

Leu Leu Ala Cys Arg Phe Glu Arg Glu Val Pro Arg Cys Ile Asn Ser
            20                  25                  30

Ile Cys Lys Cys Met Pro Met
        35

<210> SEQ ID NO 517
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 517

Met Leu Val Thr Cys Glu Asp His Phe Asp Cys Arg Gln Asn Val Gln
1               5                   10                  15

Gln Val Gly Cys Ser Phe Arg Glu Ile Pro Gln Cys Ile Asn Ser Ile
            20                  25                  30

Cys Lys Cys Met Lys Gly
```

35

<210> SEQ ID NO 518
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 518

Val Asn Asp Cys Ile Arg Ile His Cys Lys Asp Asp Phe Asp Cys Ile
1               5                   10                  15

Glu Asn Arg Leu Gln Val Gly Cys Arg Leu Gln Arg Glu Lys Pro Arg
            20                  25                  30

Cys Val Asn Leu Val Cys Arg Cys Leu Arg Arg
        35                  40

<210> SEQ ID NO 519
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 519

Val Phe Val Ser Cys Asn Ser His Ile His Cys Arg Val Asn Asn His
1               5                   10                  15

Lys Ile Gly Cys Asn Ile Pro Glu Gln Tyr Leu Leu Cys Val Asn Leu
            20                  25                  30

Phe Cys Leu Trp Leu Asp Tyr
        35

<210> SEQ ID NO 520
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 520

Arg Pro Val Ser Cys Lys Asp His Tyr Asp Cys Arg Arg Lys Val Lys
1               5                   10                  15

Ile Val Gly Cys Ile Phe Pro Gln Glu Lys Pro Met Cys Ile Asn Ser
            20                  25                  30

Met Cys Thr Cys Ile Arg Glu Ile Val Pro
        35                  40

<210> SEQ ID NO 521
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 521

Gly Leu Phe Arg Cys Lys Val Asp Ile Asp Cys Pro Gln Ile Leu Cys
1               5                   10                  15

Phe Asp Glu Gln Ile Ala Lys Cys Ile Ala Arg Met Cys Glu Cys Asp
            20                  25                  30

Tyr Glu

<210> SEQ ID NO 522
<211> LENGTH: 35

```
<212> TYPE: PRT
<213> ORGANISM: Artificial sequence
<220> FEATURE:
<223> OTHER INFORMATION: Peptide derived from Medicago truncatula

<400> SEQUENCE: 522

Asp Phe Pro Cys Lys Thr Lys Asp Asp Cys Ala Gln Gln Ile Asp Tyr
1               5                   10                  15

Ile Ala Glu Cys Ile Ile Gly Phe Cys Arg Tyr Phe Thr Pro Phe Glu
                20                  25                  30

His Pro Phe
        35

<210> SEQ ID NO 523
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 523

Arg Asn Lys Thr Cys Asn Tyr Ser Ser Glu Cys Leu Phe His Asn Cys
1               5                   10                  15

Pro Leu Gly Trp Val Met Lys Cys Phe Thr Tyr Phe Cys Ala Cys Ser
                20                  25                  30

Arg Leu

<210> SEQ ID NO 524
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 524

Asp Phe Pro Cys Lys Thr Lys Val Asp Cys Pro Gln His Lys Lys Tyr
1               5                   10                  15

Ile Ala Glu Cys Ile Phe Gly Phe Cys Arg His Phe Lys Pro Leu Glu
                20                  25                  30

His Pro Phe
        35

<210> SEQ ID NO 525
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 525

Val Lys Ile Pro Cys Val Lys Asp Thr Asp Cys Pro Thr Leu Pro Cys
1               5                   10                  15

Pro Leu Tyr Ser Lys Cys Val Asp Gly Phe Cys Lys Met Leu Ser Ile
                20                  25                  30

<210> SEQ ID NO 526
<211> LENGTH: 29
<212> TYPE: PRT
<213> ORGANISM: Artificial sequence
<220> FEATURE:
<223> OTHER INFORMATION: Peptide derived from Medicago truncatula

<400> SEQUENCE: 526

Ile Pro Cys Lys Thr Lys Val Asp Cys Pro Gln Gln Ile Tyr Tyr Val
```

```
1               5                  10                 15

Val Glu Cys Leu Asp Gly Phe Cys Asp Tyr Trp Arg Asp
        20                  25

<210> SEQ ID NO 527
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 527

Pro Arg Ile Lys Cys Asn Thr Glu Ala Asp Cys Pro Gln Arg Phe Asp
1               5                  10                 15

Asn Ile Val Glu Cys Leu Phe Gly Ile Cys His Phe Tyr Ile Lys
            20                  25                 30

<210> SEQ ID NO 528
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 528

Asp Leu Ser Pro Cys Leu Arg Ser Gly Asp Cys Ser Lys Asp Glu Cys
1               5                  10                 15

Pro Ser His Leu Val Pro Lys Cys Ile Gly Leu Thr Cys Tyr Cys Ile
            20                  25                 30

<210> SEQ ID NO 529
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 529

Asp Arg Ile Pro Cys Ile Asp Asp Met Asp Cys Pro Asp Met Phe Pro
1               5                  10                 15

Ser Leu Asn Thr Gln Cys Ile Asp Asn Phe Cys Asp Val Val Leu Gly
            20                  25                 30

Tyr Asn

<210> SEQ ID NO 530
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 530

Lys Gln Thr Asn Ile Pro Cys Glu Asn Lys Arg Asp Cys Pro Gln Pro
1               5                  10                 15

Leu Tyr Pro Lys Phe Val Thr Cys Phe Glu Gly Leu Cys Arg Met His
            20                  25                 30

Tyr Pro Leu Lys Lys Ile
        35

<210> SEQ ID NO 531
<211> LENGTH: 38
<212> TYPE: PRT
<213> ORGANISM: Artificial sequence
<220> FEATURE:
```

<223> OTHER INFORMATION: Peptide derived from Medicago truncatula

<400> SEQUENCE: 531

Ile Lys Ile Phe Thr Glu His Arg Cys Arg Thr Asp Ala Asp Cys Pro
1               5                   10                  15

Ala Arg Glu Leu Pro Glu Tyr Leu Lys Cys Gln Gly Gly Met Cys Arg
            20                  25                  30

Leu Leu Ile Lys Lys Asp
        35

<210> SEQ ID NO 532
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 532

Gln Ile Thr Lys Leu Pro Cys Val Thr Val Asp Asp Cys Pro Lys Val
1               5                   10                  15

Glu Lys Pro Ile Pro Met Val Ala Lys Cys Phe Gly Lys Arg Phe Ser
            20                  25                  30

Arg His Cys His Tyr Phe Tyr Phe
        35                  40

<210> SEQ ID NO 533
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 533

Ser Ile Lys Thr Lys Ile Ala Cys Val Thr Asp Asn Asp Cys Pro Arg
1               5                   10                  15

Ala Ile Lys Pro Val Val Met Trp Cys Ile Asn Asn Tyr Cys His Tyr
            20                  25                  30

Tyr Leu Tyr Gly Tyr Gln
        35

<210> SEQ ID NO 534
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 534

Ser Ile Pro Cys Lys Thr Arg Thr Gln Cys Pro Glu Lys Met Cys Arg
1               5                   10                  15

Leu Pro Lys Phe Val Trp Cys Ile Asp Gly Ser Cys Val Cys Ala
            20                  25                  30

<210> SEQ ID NO 535
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 535

Ala Gln Phe Leu Cys Ser Asp Asp Ser Asp Cys Pro Arg Asp Leu Cys
1               5                   10                  15

```
Val Arg Asn Ser Leu Thr Leu Arg Cys Val Asn Tyr Ile Cys Gln Cys
            20                  25                  30
Arg

<210> SEQ ID NO 536
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 536

Glu Lys Leu Asp Ile Arg Cys Ala Thr Val Asp Cys Pro Lys Val
1               5                   10                  15

Thr Lys Pro Val Val Met Met Cys Thr Gly Lys Phe Cys His Tyr Phe
            20                  25                  30

Phe Val Arg Lys Gln Ile Leu
        35

<210> SEQ ID NO 537
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 537

Glu Leu Glu Ile Arg Cys Val Ser Asp Ala Asp Cys Pro Leu Phe Pro
1               5                   10                  15

Leu Pro Leu His Asn Arg Cys Ile Asp Asp Val Cys His Leu Phe Thr
            20                  25                  30

Ser

<210> SEQ ID NO 538
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 538

Asp Arg Ile Pro Cys Ala Thr Asp Ala Asp Gly Pro Pro Lys Ile Leu
1               5                   10                  15

Pro Ile Ile His Lys Cys Ile Asn Asn Phe Cys Lys Leu Lys Leu Tyr
            20                  25                  30

Asn

<210> SEQ ID NO 539
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 539

Asp Arg Ile Pro Cys Val Thr Asn Gly Asp Cys Pro Val Met Arg Leu
1               5                   10                  15

Pro Leu Tyr Met Arg Cys Ile Thr Tyr Ser Cys Glu Leu Phe Phe Asp
            20                  25                  30

Gly Pro Asn Leu Cys Ala Val Glu Arg Ile
        35                  40
```

```
<210> SEQ ID NO 540
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 540

Ser Ile His Cys Val Ser Val Asp Asp Cys Pro Lys Val Glu Lys Pro
1               5                   10                  15

Ile Thr Met Lys Cys Ile Asn Asn Tyr Cys Lys Tyr Phe Val Asp His
            20                  25                  30

Lys Leu

<210> SEQ ID NO 541
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 541

Asn Met Val Val Leu Gly Cys Val Ser Asp Asp Cys Pro Lys Val
1               5                   10                  15

Pro Leu Pro Arg Phe Leu Lys Cys Ile Ala Asn Leu Cys Cys Leu Val
            20                  25                  30

Arg Lys Lys Asp Leu
        35

<210> SEQ ID NO 542
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 542

Ala Phe Val Lys Cys Glu Thr Asp Asp Cys Pro Lys Tyr Asn Gly
1               5                   10                  15

Phe Arg Lys Tyr Glu Cys Val Asn Asn Trp Cys Arg Leu Thr Gly Leu
            20                  25                  30

His

<210> SEQ ID NO 543
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 543

Val Leu Ile Asp Cys Lys Thr Val Lys Asp Cys Pro Thr Ser Tyr Thr
1               5                   10                  15

Lys Ile Tyr Arg Cys Lys Asp Asn Lys Cys Arg Phe Ser Phe Val Ile
            20                  25                  30

Gly Leu

<210> SEQ ID NO 544
<211> LENGTH: 34
<212> TYPE: PRT
<213> ORGANISM: Artificial sequence
<220> FEATURE:
<223> OTHER INFORMATION: Peptide derived from Medicago truncatula
```

-continued

<400> SEQUENCE: 544

His Phe Gly Cys Glu Thr Asp Ala Asp Cys Pro Arg Ser Thr Asp Lys
1               5                   10                  15

Asn Phe Phe Leu Arg Cys Ile Asn Lys Lys Cys Glu Trp Ala Ala Lys
            20                  25                  30

Arg His

<210> SEQ ID NO 545
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 545

Asp Ile Leu Cys Lys Val His Glu Asp Cys Pro Gln Lys Ser Thr His
1               5                   10                  15

Lys Tyr Tyr Cys Ile Asp Asp Gly Cys Phe Leu Tyr Tyr Trp Glu Ala
            20                  25                  30

Pro

<210> SEQ ID NO 546
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 546

Tyr Ile Ala Cys Gln Ser Glu Ile Asp Cys Pro Pro Asn Tyr Ser Phe
1               5                   10                  15

Leu Phe Ala Ile Arg Cys Ile Lys Gln Lys Cys Val Thr Val Gly Arg
            20                  25                  30

Tyr Leu

<210> SEQ ID NO 547
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 547

Phe Ala Thr Gly Met Pro Cys Lys Thr Asp Lys Glu Cys Pro Asn Thr
1               5                   10                  15

Ser Thr His Lys Tyr Lys Cys Ile Asn Asp Asp Cys Phe Cys Phe Tyr
            20                  25                  30

Ile Tyr Trp Pro Leu Gly Asn Ser Leu Val
        35                  40

<210> SEQ ID NO 548
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 548

Phe Phe Val Asp Ile Met Cys Lys Val His Glu Asp Cys Pro Gln Lys
1               5                   10                  15

Ser Thr His Lys Tyr Tyr Cys Val Asp Asp Lys Cys Phe Leu Tyr Tyr
            20                  25                  30

```
Trp Glu Gly Lys Pro
        35

<210> SEQ ID NO 549
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 549

Tyr Val Asn Cys Glu Thr Asp Ala Asp Cys Pro Pro Ser Thr Arg Val
1               5                   10                  15

Lys Arg Phe Lys Cys Val Lys Gly Glu Cys Arg Trp Thr Arg Met Ser
            20                  25                  30

Tyr Ala

<210> SEQ ID NO 550
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 550

Asp Ile Val Cys Ile Thr Asp Asn Asp Cys Pro Pro Asn Thr Leu Val
1               5                   10                  15

Gln Gly Tyr Arg Cys Ile Asp Gly Lys Cys Glu Ser Val Phe Leu Ser
            20                  25                  30

Tyr Arg

<210> SEQ ID NO 551
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 551

Ile Asp Ile Phe Val Cys Gln Thr Asp Ala Asp Cys Pro Lys Ser Glu
1               5                   10                  15

Leu Ser Met Tyr Thr Trp Lys Cys Ile Asp Asn Glu Cys Asn Leu Phe
            20                  25                  30

Lys Val Met Gln Gln Met Val
        35

<210> SEQ ID NO 552
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 552

Ala Glu Leu Gly Gly Pro Cys Arg Ser Asp Glu Glu Cys Pro Gln Leu
1               5                   10                  15

Ser Leu Arg Phe Phe Ala Ile Lys Cys Arg Glu Asn Val Cys Ile Tyr
            20                  25                  30

Val Asp Leu Asp Pro Tyr Lys Pro Arg Ala Glu Lys Asn Gln Phe Leu
        35                  40                  45

His
```

-continued

<210> SEQ ID NO 553
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 553

Ser Asp Asp Glu Cys Lys Ile Asp Gly Asp Cys Pro Ile Ser Trp Gln
1               5                   10                  15

Lys Phe His Thr Tyr Lys Cys Ile Asn Gln Lys Cys Lys Trp Val Leu
            20                  25                  30

Arg Phe His Glu Tyr
        35

<210> SEQ ID NO 554
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 554

Lys Leu Thr Gly Cys Glu Val Asp Gly Asp Cys Pro Lys Val Phe Lys
1               5                   10                  15

Leu Lys Val Met Ile Leu Phe Ile Lys Cys Ile Asn Asn Lys Cys Val
            20                  25                  30

Arg Gly Leu Leu Ser Gln Thr Gly Thr Gln Cys Pro Asp Phe Phe Phe
        35                  40                  45

Leu Lys Arg Thr Leu Pro Arg Phe Tyr Phe
    50                  55

<210> SEQ ID NO 555
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 555

Gln Asn Leu Met Lys Cys Asn Thr Asp Asp Glu Cys Pro Lys Phe Asp
1               5                   10                  15

Asp Lys Phe Pro Leu Ser Phe Lys Cys Ile Asn Asp Gly Cys Arg Met
            20                  25                  30

Val Ile Asn Asp Lys Tyr Lys His Lys Thr Val Gln Lys Leu Leu
        35                  40                  45

<210> SEQ ID NO 556
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 556

Tyr Tyr Tyr Lys Cys Phe Lys Asp Ser Asp Cys Val Lys Leu Leu Cys
1               5                   10                  15

Arg Ile Pro Leu Arg Pro Lys Cys Met Tyr Arg His Ile Cys Lys Cys
            20                  25                  30

Lys Val Val Leu Thr Gln Asn Asn Tyr Val Leu Thr
        35                  40

```
<210> SEQ ID NO 557
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 557

Phe Gln Pro Cys Val Thr Thr Ala Asp Cys Met Lys Thr Leu Lys Thr
1               5                   10                  15

Asp Glu Asn Ile Trp Tyr Glu Cys Ile Asn Asp Phe Cys Ile Pro Phe
            20                  25                  30

Pro Ile Pro Lys Gly Arg Lys
        35

<210> SEQ ID NO 558
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 558

Glu Leu Val Cys Asp Thr Asp Asp Cys Leu Lys Phe Phe Pro Asp
1               5                   10                  15

Asn Pro Tyr Pro Met Glu Cys Ile Asn Ser Ile Cys Leu Ser Leu Thr
            20                  25                  30

Asp

<210> SEQ ID NO 559
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 559

Asp Asp Val Lys Ile Lys Cys Val Val Ala Ala Asn Cys Pro Asp Leu
1               5                   10                  15

Met Tyr Pro Leu Val Tyr Lys Cys Leu Asn Gly Ile Cys Val Gln Phe
            20                  25                  30

Thr Leu Thr Phe Pro Phe Val
        35

<210> SEQ ID NO 560
<211> LENGTH: 28
<212> TYPE: PRT
<213> ORGANISM: Artificial sequence
<220> FEATURE:
<223> OTHER INFORMATION: Peptide derived from Medicago truncatula

<400> SEQUENCE: 560

Asn Ile His Lys Ile Gly Cys Lys Thr Ser Glu Asp Cys Pro Tyr Leu
1               5                   10                  15

Gly Lys Cys Ile Glu Asp Phe Cys Gln Phe Lys Lys
            20                  25

<210> SEQ ID NO 561
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 561
```

```
Ala Glu Arg Ile Tyr Arg Cys Leu Asp His Ser His Cys Pro Thr Phe
1               5                   10                  15

Met Cys Ser Pro Gly Leu Lys Pro Lys Cys Met Asn Pro Lys Val Cys
                20                  25                  30

Lys Cys Val Pro Val Gln Ser Arg Lys Tyr Tyr Ala Leu Thr
            35                  40                  45
```

<210> SEQ ID NO 562
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 562

```
Ile Asp Pro Pro His His Ile Thr Asn His Glu Ile Pro Cys Lys Tyr
1               5                   10                  15

Asn His Asp Cys Pro Thr Ile Leu Asp Tyr Ile Ser Ile Cys Pro Tyr
                20                  25                  30

His Tyr Cys Glu Phe Trp Arg Thr Tyr
            35                  40
```

<210> SEQ ID NO 563
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 563

```
Leu Tyr Ile Gly Cys Glu Thr Asp Arg Asp Tyr Pro Pro Leu Ala Asn
1               5                   10                  15

Lys Thr Phe Tyr Leu Lys Cys Ile Asp Lys Lys Cys Glu Trp Thr Val
                20                  25                  30

Thr Asp Ser Leu Ser Thr Arg Ser Gly Arg Met Gln Lys Leu Ser Ile
            35                  40                  45
```

<210> SEQ ID NO 564
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 564

```
Lys Lys Ile Tyr Cys Glu Asn Ala Ala Ser Cys Pro Arg Leu Met Tyr
1               5                   10                  15

Pro Leu Val Tyr Lys Cys Leu Asp Asn Lys Cys Val Lys Phe Met Met
                20                  25                  30

Lys Ser Arg Phe Val
            35
```

<210> SEQ ID NO 565
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 565

```
Ile Ile Arg Cys Phe His Asp Ala Asp Cys Val His Lys Ile Cys His
1               5                   10                  15
```

```
Pro Pro Gln Ile Arg Lys Cys Val Ser Lys Ile Cys Lys Cys Arg Leu
        20                  25                  30

Met Ile Thr Gln Lys Asp Tyr Val Leu Thr
        35                  40
```

<210> SEQ ID NO 566
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 566

```
Lys Pro Phe Leu Thr Arg Pro Tyr Pro Cys Asn Thr Gly Ser Asp Cys
1               5                   10                  15

Pro Gln Asn Met Cys Pro Pro Gly Tyr Lys Pro Gly Cys Glu Asp Gly
            20                  25                  30

Tyr Cys Asn His Cys Tyr Lys Arg Trp
        35                  40
```

<210> SEQ ID NO 567
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 567

```
Glu Pro Gly Gly His Arg Cys Ser Thr Asp Ser Phe Cys Pro Pro Asn
1               5                   10                  15

Met Cys Pro Pro Gly Met Thr Pro Lys Cys Val Arg Phe Arg Cys Lys
            20                  25                  30

Cys Val Pro Ile Gly Trp Lys Asn Leu Ser His Val Leu Ala
        35                  40                  45
```

<210> SEQ ID NO 568
<211> LENGTH: 58
<212> TYPE: PRT
<213> ORGANISM: Artificial sequence
<220> FEATURE:
<223> OTHER INFORMATION: Peptide derived from Medicago truncatula

<400> SEQUENCE: 568

```
Glu Gln Tyr Cys Val Asp Asp Ala Asp Cys Gln Lys Leu Tyr Pro Phe
1               5                   10                  15

His Arg Gln Leu Ser Leu Lys Cys Ile Arg Ala Phe Cys Val Lys Leu
            20                  25                  30

Val Gly Gln Ala Asn Asp Asp Leu Phe Pro Ser Thr Val His Ala Ala
        35                  40                  45

Asp Ala Thr Gly Leu Gly Ile Asp Ala Lys
    50                  55
```

<210> SEQ ID NO 569
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 569

```
Gln Cys Ile Tyr Pro Ala Cys Phe Lys Asp His Met Cys Arg Gln Leu
1               5                   10                  15

Lys Cys Ser Pro Gly Arg Thr Pro Lys Cys Val Asn Tyr Gln Cys Arg
```

```
                20              25                  30
Cys Ser Pro Gln Ala Leu Gly Ser Tyr His Leu Leu Thr
        35                  40                  45

<210> SEQ ID NO 570
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 570

Ala Leu Ile Glu Cys Gln Ile Asp Asp Cys Pro Pro Ile Lys Phe
1               5                   10                  15

Ala Lys Tyr Leu Cys Ile Asn Tyr Lys Cys Arg Lys Ile Cys Leu Gly
            20                  25                  30

Glu

<210> SEQ ID NO 571
<211> LENGTH: 52
<212> TYPE: PRT
<213> ORGANISM: Artificial sequence
<220> FEATURE:
<223> OTHER INFORMATION: Peptide derived from Medicago truncatula

<400> SEQUENCE: 571

Glu Glu Ile Ile Ile Ile Lys Cys Gln Thr Ala Lys Asp Cys Pro Asp
1               5                   10                  15

Ile Tyr Asn Leu Phe Pro Leu Val Tyr Lys Cys Ile Asp Asn Ile Cys
            20                  25                  30

Val Asp Val Lys Leu Glu Pro Pro Tyr Asp Met Ser Ile Thr Pro Asn
        35                  40                  45

Ser Val His Lys
    50

<210> SEQ ID NO 572
<211> LENGTH: 29
<212> TYPE: PRT
<213> ORGANISM: Artificial sequence
<220> FEATURE:
<223> OTHER INFORMATION: Peptide derived from Medicago truncatula

<400> SEQUENCE: 572

Lys His Asp Tyr His Met Phe Phe Gln Arg Ile Pro Cys Pro Lys Asp
1               5                   10                  15

Lys Ile Leu Asp Cys Asn Leu Leu Glu Cys Trp Cys Lys
            20                  25

<210> SEQ ID NO 573
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 573

Arg Ile Pro Cys Val Ser Arg Asn Asp Cys Pro Lys Arg Pro Tyr Pro
1               5                   10                  15

Leu Phe Met Lys Cys Ile Asp Asn Phe Cys Glu Ile Trp Lys Ile Gly
            20                  25                  30

Lys Glu
```

```
<210> SEQ ID NO 574
<211> LENGTH: 73
<212> TYPE: PRT
<213> ORGANISM: Artificial sequence
<220> FEATURE:
<223> OTHER INFORMATION: Peptide derived from Medicago truncatula

<400> SEQUENCE: 574

Ile Tyr Ile Thr Phe Lys Lys Phe Ile Ile Asp Phe Ile His Asn Val
1               5                   10                  15

Tyr His Pro Ser Ile Thr Ser Asn Phe Ser Leu Phe Asn Asn Ala Gly
            20                  25                  30

Asp Ile Pro Asn Asn Ser Asn Arg Asn Ser Pro Lys Glu Asp Val Phe
        35                  40                  45

Cys Asn Ser Asn Asp Asp Cys Pro Thr Ile Leu Tyr Tyr Val Ser Lys
    50                  55                  60

Cys Val Tyr Asn Phe Cys Glu Tyr Trp
65                  70

<210> SEQ ID NO 575
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 575

Lys Thr Ile Cys Ile Gly Asp Ser Asp Cys Arg Asn Glu Arg Cys Met
1               5                   10                  15

Pro Gly Ile Lys Pro Val Cys Ser Glu Gly Trp Cys Asp Cys Ile Gly
            20                  25                  30

Phe Ile Pro
        35

<210> SEQ ID NO 576
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 576

Tyr Val Trp Cys Glu Thr Val Glu Asp Cys Phe Lys Ser Gln Tyr Phe
1               5                   10                  15

Ile Phe Asp Cys Ile Asn Asn Gln Cys Ile Asn Val Gly Lys Asn Pro
            20                  25                  30

Lys Glu Pro Arg Tyr Pro Gly Ile Pro Arg Asp Gln
        35                  40

<210> SEQ ID NO 577
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 577

Arg Glu Lys Val Asn Cys Leu Asp Asp Ala Asp Cys Leu Glu Val Ser
1               5                   10                  15

Cys Leu Asn Gly Ser Asn Ala Glu Cys Val Gly Asn Ser Cys Val Cys
            20                  25                  30

Val Phe Val Phe Tyr Arg Glu Asn Phe Asp Glu Gln Phe Arg Arg
        35                  40                  45
```

<210> SEQ ID NO 578
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 578

Ser Val Pro Cys Leu Thr Ser Phe Gly Cys Pro Arg Ser Thr Cys Tyr
1               5                   10                  15

Pro Pro Ser Thr Pro Asn Cys Ile Leu Arg Ile Cys Glu Cys Ile
            20                  25                  30

<210> SEQ ID NO 579
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 579

Glu Glu Trp Asn Ser His Ser Trp Asn Ser Glu Phe Tyr Leu Lys Lys
1               5                   10                  15

Ser Cys Ser Ser Asp Phe Asp Cys Pro Arg Thr Met Cys Ile Lys Leu
            20                  25                  30

Ser Leu Ala Arg Cys Phe Asn Asp Phe Cys His Cys Tyr
        35                  40                  45

<210> SEQ ID NO 580
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 580

Gln Thr Glu Pro Pro Gly Pro Leu Ile Pro Cys Glu Phe Asp Tyr Asp
1               5                   10                  15

Cys Pro Leu Ile Asp Cys Ile Arg Thr Ser Asp Ser Arg Cys Ile Asn
            20                  25                  30

Gly Asn Cys His Cys Arg Glu
        35

<210> SEQ ID NO 581
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 581

Arg Ile Met Val Val Asn Pro Asn Asn Pro Cys Val Thr Asp Ala Asp
1               5                   10                  15

Cys Gln Arg Tyr Arg His Lys Leu Ala Thr Arg Met Val Cys Asn Ile
            20                  25                  30

Gly Phe Cys Leu Met Asp Phe Thr His Asp Pro Tyr Ala Pro Ser Leu
        35                  40                  45

Pro

<210> SEQ ID NO 582
<211> LENGTH: 34
<212> TYPE: PRT

```
-continued

<213> ORGANISM: Artificial sequence
<220> FEATURE:
<223> OTHER INFORMATION: Peptide derived from Medicago truncatula

<400> SEQUENCE: 582

Gln Met Ile Asn Phe Arg Gly Cys Lys Arg Asp Lys Asp Cys Pro Gln
1               5                   10                  15

Phe Arg Gly Val Asn Ile Arg Cys Arg Ser Gly Phe Cys Thr Pro Ile
            20                  25                  30

Asp Ser

<210> SEQ ID NO 583
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 583

Lys Arg Asn Tyr Gln Cys Asp Pro Cys Phe Gly His Pro Asp Asp Met
1               5                   10                  15

Ile Asn Phe Cys Pro Pro Gly Thr Ala Pro Lys Cys Phe His Gly Leu
            20                  25                  30

Ile Lys Cys Val Pro Ile Met Arg Gly Thr Asn Arg Met Phe Ala
        35                  40                  45

<210> SEQ ID NO 584
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 584

Leu Phe Glu Cys Asn Arg Asp Phe Val Cys Gly Asn Asp Asp Glu Cys
1               5                   10                  15

Val Tyr Pro Tyr Ala Val Gln Cys Ile His Arg Tyr Cys Lys Cys Leu
            20                  25                  30

Lys Ser Arg Asn
        35

<210> SEQ ID NO 585
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 585

Thr Arg Cys Asn Arg Asp Glu Asp Cys Pro Phe Ile Cys Thr Gly Pro
1               5                   10                  15

Gln Ile Pro Lys Cys Val Ser His Ile Cys Phe Cys Leu Ser Ser Gly
            20                  25                  30

Lys Glu Ala Tyr
        35

<210> SEQ ID NO 586
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 586
```

```
Ile Pro Cys Asn Asp Asp Val Asp Cys Pro Gln Thr Leu Cys Glu Gln
1               5                   10                  15

Leu Ile Ala Asp Phe Lys Tyr Met Ile Asp Phe Lys Ser Glu Cys Val
            20                  25                  30

Ser Arg Met Cys Ala Cys Thr Gly Ser Pro Val
            35                  40
```

<210> SEQ ID NO 587
<211> LENGTH: 30
<212> TYPE: PRT
<213> ORGANISM: Artificial sequence
<220> FEATURE:
<223> OTHER INFORMATION: Peptide derived from Medicago truncatula

<400> SEQUENCE: 587

```
Ala Val His Lys Glu Cys Lys Thr Asp Val Asp Cys Arg Gln Ile Trp
1               5                   10                  15

Phe Val Thr Lys Cys Ile Asn His Glu Cys Gln Pro Ile Leu
            20                  25                  30
```

<210> SEQ ID NO 588
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 588

```
His Ala Cys Thr Val Asn Ala Asp Cys Glu Gln Ser Met Cys Asp Pro
1               5                   10                  15

Phe Cys Val Gly Gly Tyr His Phe Thr Pro Ile Cys Val Ile Gly Trp
            20                  25                  30

Cys Val Cys Val Gly Asn Arg Val Ala Pro Val Leu
            35                  40
```

<210> SEQ ID NO 589
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 589

```
His Ile Pro Cys Val His His Asp Asp Cys Pro Lys Arg Pro Tyr Pro
1               5                   10                  15

Arg Phe Met Lys Cys Val Asp Asn Phe Cys Glu Thr Trp Ile Ile Gly
            20                  25                  30

Trp Glu
```

<210> SEQ ID NO 590
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 590

```
Asn Ile Pro Cys Asn Ser Asp Ser Asp Cys Trp Lys Ile Tyr Tyr
1               5                   10                  15

Thr Tyr Arg Cys Asn Asp Gly Phe Cys Val Tyr Lys Ser Ile Asp Pro
            20                  25                  30

Ser Thr Ile Pro Gln Tyr Met Thr Asp Leu Ile Phe Pro Arg
```

-continued

```
<210> SEQ ID NO 591
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 591

Arg Gln Thr Asp Ile Pro Cys Lys Ser Asp Asp Ala Cys Pro Arg Val
1               5                   10                  15

Ser Ser His His Ile Glu Cys Val Lys Gly Phe Cys Thr Tyr Trp Lys
            20                  25                  30

Leu Asp

<210> SEQ ID NO 592
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 592

Glu Met Thr Thr Thr Thr Ile Pro Cys Thr Phe Ile Asp Asp Cys Pro
1               5                   10                  15

Lys Met Pro Leu Val Val Lys Cys Ile Asp Asn Phe Cys Asn Tyr Phe
            20                  25                  30

Glu Ile Lys
        35

<210> SEQ ID NO 593
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 593

Tyr His Leu Cys Lys Thr Arg Phe Asp Cys Pro Arg Thr Tyr Leu Leu
1               5                   10                  15

Phe Phe Pro Arg Met Trp Lys Cys Ile Asn Arg Arg Cys Arg Tyr Val
            20                  25                  30

Tyr Phe Phe Glu
        35

<210> SEQ ID NO 594
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 594

Gly Met Arg Cys Asn His Val Ser Asp Cys Pro Lys Asp Thr Phe Cys
1               5                   10                  15

Trp Leu Asp Ser His Met Gln Cys Ile Lys His Gln Cys Lys Cys Val
            20                  25                  30

Arg Ile Phe Glu Pro Ile Asp Pro Ala
        35                  40

<210> SEQ ID NO 595
<211> LENGTH: 34
```

```
<212> TYPE: PRT
<213> ORGANISM: Artificial sequence
<220> FEATURE:
<223> OTHER INFORMATION: Peptide derived from Medicago truncatula

<400> SEQUENCE: 595

Tyr Ile Val Cys Ile Thr Asp Asn Asp Cys Pro Glu Asn Thr Glu Val
1               5                   10                  15

Arg Gln Tyr Glu Cys Ile Glu Gly Arg Cys Arg Leu Ser Arg Val Leu
            20                  25                  30

Asn Pro

<210> SEQ ID NO 596
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 596

Gly Ile Arg Cys Arg Asn Val Tyr Asp Cys Pro Lys Ala Thr Tyr Cys
1               5                   10                  15

Arg Ala Gly Ser His Arg Val Gln Cys Ile Lys His Gln Cys Lys Cys
            20                  25                  30

Val Arg Ile Phe Glu Ser Ile Asp Pro Ala
        35                  40

<210> SEQ ID NO 597
<211> LENGTH: 54
<212> TYPE: PRT
<213> ORGANISM: Artificial sequence
<220> FEATURE:
<223> OTHER INFORMATION: Peptide derived from Medicago truncatula

<400> SEQUENCE: 597

Cys Glu Asp Asp Ser Asp Cys Pro Gln Ile Phe Asn Phe His Pro Phe
1               5                   10                  15

Ile Cys Lys Cys Ile Asn Asn Glu Cys Glu Lys Val Ile Leu Gln Lys
            20                  25                  30

Gly Tyr Met Ser Met Lys Pro Lys Ile Leu His Lys Arg Tyr Thr Arg
        35                  40                  45

Lys Asn Glu Phe Leu His
    50

<210> SEQ ID NO 598
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 598

Ser Asp Glu Cys Val Lys Val Ser Asp Cys Ser Pro Thr Lys Tyr Cys
1               5                   10                  15

Leu Pro Gly Arg Arg Met Ile Cys Ser Lys Gly Lys Cys Lys Cys Leu
            20                  25                  30

Arg Asn Met Phe Ile Pro Ile Pro Glu
        35                  40

<210> SEQ ID NO 599
<211> LENGTH: 34
<212> TYPE: PRT
<213> ORGANISM: Artificial sequence
```

-continued

```
<220> FEATURE:
<223> OTHER INFORMATION: Peptide derived from Medicago truncatula

<400> SEQUENCE: 599

Tyr Val Val Cys Arg Thr Val Asp Asp Cys Pro Pro Asp Thr Arg Asp
1               5                   10                  15

Leu Arg Tyr Arg Cys Leu Asn Gly Lys Cys Lys Ser Tyr Arg Leu Ser
            20                  25                  30

Tyr Gly

<210> SEQ ID NO 600
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 600

Met Thr Leu Arg Pro Cys Leu Thr Asp Lys Asp Cys Pro Arg Met Pro
1               5                   10                  15

Pro His Asn Ile Lys Cys Arg Lys Gly His Cys Val Pro Ile Gly Lys
            20                  25                  30

Pro Phe Lys
        35

<210> SEQ ID NO 601
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 601

Asn Ile Arg Cys Val Ser Asp Asp Cys Pro Lys Val Ile Lys Pro
1               5                   10                  15

Leu Val Met Lys Cys Ile Gly Asn Tyr Cys Tyr Phe Phe Met Ile Tyr
            20                  25                  30

Glu Gly Pro
        35

<210> SEQ ID NO 602
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 602

Leu Val Ile Ile Asp His His Lys Pro Cys Val Ser Asp Thr Asp Cys
1               5                   10                  15

Ala Phe Tyr Leu Asp Ile Pro Pro Thr Val Lys Tyr Cys Ser Asp Gly
            20                  25                  30

Leu Cys Ala Trp Tyr Phe Pro Asp Asn Pro Leu Pro
        35                  40

<210> SEQ ID NO 603
<211> LENGTH: 123
<212> TYPE: PRT
<213> ORGANISM: Artificial sequence
<220> FEATURE:
<223> OTHER INFORMATION: Peptide derived from Medicago truncatula

<400> SEQUENCE: 603
```

```
Asn Lys Ile Ala Ile Tyr Cys Val Ser Asp Asp Cys Leu Lys Thr
1               5                   10                  15

Phe Thr Pro Leu Asp Leu Lys Cys Val Asp Asn Val Cys Glu Phe Asn
            20                  25                  30

Leu Arg Cys Lys Gly Lys Cys Gly Glu Arg Asp Glu Lys Phe Val Phe
            35                  40                  45

Leu Lys Ala Leu Lys Lys Met Asp Gln Lys Leu Val Leu Glu Glu Gln
    50                  55                  60

Gly Asn Ala Arg Glu Val Lys Ile Pro Lys Lys Leu Leu Phe Asp Arg
65                  70                  75                  80

Ile Gln Val Pro Thr Pro Ala Thr Lys Asp Gln Val Glu Glu Asp Asp
                85                  90                  95

Tyr Asp Asp Asp Glu Glu Glu Glu Glu Glu Asp Asp Val Asp
                100                 105                 110

Met Trp Phe His Leu Pro Asp Val Val Cys His
            115                 120

<210> SEQ ID NO 604
<211> LENGTH: 119
<212> TYPE: PRT
<213> ORGANISM: Artificial sequence
<220> FEATURE:
<223> OTHER INFORMATION: Peptide derived from Medicago truncatula

<400> SEQUENCE: 604

Asn Lys Ile Ala Ile Tyr Cys Val Ser Asp Asp Cys Leu Lys Thr
1               5                   10                  15

Phe Thr Pro Leu Asp Leu Lys Cys Val Asp Asn Val Cys Glu Phe Asn
            20                  25                  30

Leu Arg Cys Lys Gly Lys Cys Gly Glu Arg Asp Glu Lys Val Val Leu
            35                  40                  45

Val Lys Ala Leu Lys Lys Ile Asp Glu Lys Leu Val Leu Glu Glu Gln
    50                  55                  60

Gly Asn Ala Arg Glu Val Lys Ile Thr Lys Lys Leu Leu Phe Asp Gly
65                  70                  75                  80

Ile Pro Thr Pro Ala Thr Lys Asp Gln Val Glu Glu Glu Asp Asp Tyr
                85                  90                  95

Gly Asp Asp Glu Glu Glu Glu Glu Asp Asp Val Asp Met Trp Phe Asn
                100                 105                 110

Leu Pro Asp Val Val Cys Arg
        115

<210> SEQ ID NO 605
<211> LENGTH: 30
<212> TYPE: PRT
<213> ORGANISM: Artificial sequence
<220> FEATURE:
<223> OTHER INFORMATION: Peptide derived from Medicago truncatula

<400> SEQUENCE: 605

Pro Cys Ile Ser Asp Asp Cys Pro Glu Ala Leu Ser Pro Gln Phe
1               5                   10                  15

Pro Lys Cys Ile His Asn Val Cys Val Tyr Phe Val Glu Glu
            20                  25                  30

<210> SEQ ID NO 606
<211> LENGTH: 36
<212> TYPE: PRT
<213> ORGANISM: Artificial sequence
<220> FEATURE:
```

<223> OTHER INFORMATION: Peptide derived from Medicago truncatula

<400> SEQUENCE: 606

Ser Tyr Ile Pro Ile Ser His Pro Cys Thr Thr Val Lys Asp Cys Pro
1               5                   10                  15

Glu Val Lys Asn Tyr Lys Ser Arg Cys Leu Lys Gly Leu Cys Ile Ser
            20                  25                  30

Gly Arg Leu Arg
        35

<210> SEQ ID NO 607
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 607

Ala Tyr Ile Glu Cys Glu Val Asp Asp Cys Pro Lys Pro Met Lys
1               5                   10                  15

Asn Ser His Pro Asp Thr Tyr Tyr Lys Cys Val Lys His Arg Cys Gln
            20                  25                  30

Trp Ala Trp Lys
        35

<210> SEQ ID NO 608
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 608

Glu Ala Asp Thr Ser Cys His Ser Phe Asp Asp Cys Pro Trp Val Ala
1               5                   10                  15

His His Tyr Arg Glu Cys Ile Glu Gly Leu Cys Ala Tyr Arg Ile Leu
            20                  25                  30

Tyr

<210> SEQ ID NO 609
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 609

Leu Glu Thr Ile Glu Cys Glu Thr Asp Gly Asp Cys Pro Arg Ser Met
1               5                   10                  15

Ile Lys Met Trp Asn Lys Asn Tyr Arg His Lys Cys Ile Asp Gly Lys
            20                  25                  30

Cys Glu Trp Ile Lys Lys Leu Pro
        35                  40

<210> SEQ ID NO 610
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 610

Ile Tyr Phe Pro Val Ser Arg Pro Cys Ile Thr Asp Lys Asp Cys Pro

```
                1               5                  10                 15
Asn Met Lys His Tyr Lys Ala Lys Cys Arg Lys Gly Phe Cys Ile Ser
                20                 25                 30

Ser Arg Val Arg
        35

<210> SEQ ID NO 611
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 611

Tyr Ile Pro Gly Ile Val Asn Lys Pro Cys Lys Thr Asp Lys Asp Cys
1               5                   10                  15

Pro Lys Lys Pro Pro His Asn Ile Arg Cys Arg Lys Gly Gln Cys Val
                20                  25                  30

Glu Ile Leu
        35

<210> SEQ ID NO 612
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 612

Lys Ile Arg Cys Val Thr Asp Asp Cys Pro Lys Val Glu Lys Pro
1               5                   10                  15

Leu His Met Tyr Cys Gly Asn His Trp Cys Ala Tyr Lys Leu His Phe
                20                  25                  30

Val

<210> SEQ ID NO 613
<211> LENGTH: 30
<212> TYPE: PRT
<213> ORGANISM: Artificial sequence
<220> FEATURE:
<223> OTHER INFORMATION: Peptide derived from Medicago truncatula

<400> SEQUENCE: 613

Ile Pro Cys Ala Thr Ser Asp Asp Cys Leu Lys Asn Met Cys Arg Pro
1               5                   10                  15

Pro Leu Thr Pro Arg Cys Ile Glu His Asn Cys Lys Cys Lys
                20                  25                  30

<210> SEQ ID NO 614
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 614

Asp Arg Ile Pro Cys Ile Asp Asp Met Asp Cys Pro Asp Met Phe Pro
1               5                   10                  15

Ser Leu Asn Thr Gln Cys Ile Asp Asn Phe Cys Asp Val Val Leu Gly
                20                  25                  30

Tyr Asn
```

```
<210> SEQ ID NO 615
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 615

Lys Glu Asp Asp Ile Glu Cys Val Thr Asp Ala Asp Cys Tyr Glu Lys
1               5                   10                  15

Leu Pro Ala Leu Gln Arg Ala Val Met Lys Cys Ile Gln Gly Phe Cys
            20                  25                  30

Lys Ile His Ile
        35

<210> SEQ ID NO 616
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 616

Asn Ser Ile Pro Cys Thr Thr His Ala Gln Cys Pro Gly Asp Met Cys
1               5                   10                  15

Glu Leu Pro Gln Ile Val Trp Cys Val Val Gly Phe Cys Glu Cys Ala
            20                  25                  30

<210> SEQ ID NO 617
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 617

Tyr Arg Ser Cys Lys Thr Asp Asp Cys Pro Asp Tyr Leu Cys Thr
1               5                   10                  15

Ser Pro Lys Ile Gly Lys Cys Met Asp Asn Asp Cys Tyr Cys Ile
            20                  25                  30

<210> SEQ ID NO 618
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 618

Phe Pro Trp Lys Leu Tyr Pro Cys Val Thr Asp Lys Asp Cys Pro Arg
1               5                   10                  15

Lys Asn Arg His Val Val Lys Cys Arg Lys Gly Tyr Cys Val Gly Val
            20                  25                  30

Gln Ile Ile
        35

<210> SEQ ID NO 619
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 619

Asn Met Val Ile Cys Thr Gln Asp Phe Asp Cys Gln Thr Lys Ile Cys
```

```
            1               5                  10                 15
Pro Phe Asp Leu Gln Pro Lys Cys Thr Ile Leu Phe Glu Phe Leu Leu
                20                 25                 30

Ser Leu Cys Gly Cys Val
        35

<210> SEQ ID NO 620
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 620

Leu Ala Gly Cys Ile Thr Asp Ala Asp Cys Val Ile Lys Lys Cys Ser
1               5                  10                 15

Ser Ser Cys Arg Ile Lys Cys Ile Asp Phe Arg Cys Leu Cys Pro Thr
                20                 25                 30

Gly Phe

<210> SEQ ID NO 621
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 621

Ser Leu Pro Asp Ala Pro Pro Cys Leu Phe Thr Pro Glu Cys Pro Pro
1               5                  10                 15

Asp Met Cys Pro Thr Asp Leu Thr Leu Lys Cys Ile Asn Leu Ser Cys
                20                 25                 30

Gln Cys Thr Ile Glu Tyr Asp Ile Asp Pro Asp Val Val Pro Ser
        35                 40                 45

<210> SEQ ID NO 622
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 622

Ala Ile Leu Glu Cys Arg Glu Asp Ser His Cys Val Thr Lys Ile Lys
1               5                  10                 15

Cys Val Leu Pro Arg Lys Pro Glu Cys Arg Asn Asn Ala Cys Thr Cys
                20                 25                 30

Tyr Lys Gly Gly Phe Ser Phe His His
        35                 40

<210> SEQ ID NO 623
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 623

Asn Arg Phe Leu Tyr Arg Ile Gly Cys Asp Thr Ser Asn Asp Cys Pro
1               5                  10                 15

Ser Tyr Met Cys Pro Pro Pro Leu Ser Pro Arg Cys Thr Lys Phe Tyr
                20                 25                 30
```

Cys Lys Cys Ile
        35

<210> SEQ ID NO 624
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 624

Glu Gln Cys Val Tyr Asp Ala Asp Cys Glu Lys Ile Tyr Pro Leu His
1               5                   10                  15

Arg Gln His Leu Phe Lys Cys Ile Lys Ala Phe Cys Val Arg Ser Ser
            20                  25                  30

<210> SEQ ID NO 625
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 625

Asp Ala Pro Pro Cys Leu Phe Thr Pro Glu Cys Pro Pro Asp Met Cys
1               5                   10                  15

Pro Thr Asp Leu Thr Leu Lys Cys Ile Asn Leu Thr Cys Gln Cys Thr
            20                  25                  30

Ser Glu Tyr Asp Ile Asp
        35

<210> SEQ ID NO 626
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 626

Lys Asp Asp Cys Leu Val Asp Ala Asp Cys Val Thr Leu Val Cys Glu
1               5                   10                  15

Phe Asp Glu Arg Pro Gln Cys Val Ile Asn Thr Cys Arg Cys Arg Pro
            20                  25                  30

Leu Arg Phe Ser Gly Phe Tyr Tyr Glu Gln Leu His
        35                  40

<210> SEQ ID NO 627
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 627

Phe Glu Glu Cys Lys Glu Asp Ala Asp Cys His Pro Val Cys Ser Val
1               5                   10                  15

Pro Gly Cys Ser Asn Ile Cys Thr Leu Pro Asp Val Pro Thr Cys Ile
            20                  25                  30

Asp Asn Asn Cys Phe Cys Ile
        35

<210> SEQ ID NO 628
<211> LENGTH: 40
<212> TYPE: PRT

<213> ORGANISM: Artificial sequence
<220> FEATURE:
<223> OTHER INFORMATION: Peptide derived from Medicago truncatula

<400> SEQUENCE: 628

Leu Lys Ile Phe Cys Ile Asp Val Ala Asp Cys Pro Lys Asp Leu Tyr
1               5                   10                  15

Pro Leu Tyr Lys Cys Ile Tyr Asn Lys Cys Ile Val Phe Thr Arg
            20                  25                  30

Ile Pro Phe Pro Phe Asp Trp Ile
        35                  40

<210> SEQ ID NO 629
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 629

Cys Asn Pro Cys Leu Val Thr Cys Pro Asp Leu Leu Asn Arg Cys
1               5                   10                  15

Pro Pro Gly Met Glu Pro Ile Cys Glu Tyr Gly Val Ile Lys Cys Tyr
            20                  25                  30

Pro Ile Gly Lys Glu Thr Asn Arg Val Leu Thr
        35                  40

<210> SEQ ID NO 630
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 630

Ile Pro Asp Val Leu Pro Cys Leu Phe Ser Asn Glu Cys Pro Pro Asp
1               5                   10                  15

Leu Cys Pro Thr Asp Leu Phe Ala Lys Cys Ile Asn Leu Thr Cys Gln
            20                  25                  30

Cys Thr Ala Glu Tyr Asp Leu Asp
        35                  40

<210> SEQ ID NO 631
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 631

Tyr Pro Phe Gln Glu Cys Lys Val Asp Ala Asp Cys Pro Thr Val Cys
1               5                   10                  15

Thr Leu Pro Gly Cys Pro Asp Ile Cys Ser Phe Pro Asp Val Pro Thr
            20                  25                  30

Cys Ile Asp Asn Asn Cys Phe Cys Thr
        35                  40

<210> SEQ ID NO 632
<211> LENGTH: 38
<212> TYPE: PRT
<213> ORGANISM: Artificial sequence
<220> FEATURE:
<223> OTHER INFORMATION: Peptide derived from Medicago truncatula -continued

```
<400> SEQUENCE: 632

Glu Asp Ile Gly His Ile Lys Tyr Cys Gly Ile Val Asp Asp Cys Tyr
1               5                   10                  15

Lys Ser Lys Lys Pro Leu Phe Lys Ile Trp Lys Cys Val Glu Asn Val
            20                  25                  30

Cys Val Leu Trp Tyr Lys
        35

<210> SEQ ID NO 633
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 633

Asn Ser Ala Phe Ser His Phe Ile Pro Gly Cys Lys Thr Asp Lys Asp
1               5                   10                  15

Cys Pro Lys Phe Tyr Gly Ser Asn Val Arg Cys Arg Lys Gly Lys Cys
            20                  25                  30

Val Gln Leu Gly
        35

<210> SEQ ID NO 634
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 634

Ser Glu Phe Ile Phe Thr Lys Lys Leu Thr Ser Cys Asp Ser Ser Lys
1               5                   10                  15

Asp Cys Arg Ser Phe Leu Cys Tyr Ser Pro Lys Phe Pro Val Cys Lys
            20                  25                  30

Arg Gly Ile Cys Glu Cys Ile
        35

<210> SEQ ID NO 635
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 635

Thr Phe Cys His Asp Asp Ser His Cys Val Thr Lys Ile Lys Cys Val
1               5                   10                  15

Leu Pro Arg Thr Pro Gln Cys Arg Asn Glu Ala Cys Gly Cys Tyr His
            20                  25                  30

Ser Asn Lys Phe Arg
        35

<210> SEQ ID NO 636
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 636

Val Lys Ser Leu Leu Leu Ile Lys Val Arg Ser Phe Ile Pro Cys Gln
1               5                   10                  15
```

Arg Ser Asp Asp Cys Pro Arg Asn Leu Cys Val Asp Gln Ile Ile Pro
            20                  25                  30

Thr Cys Val Trp Ala Lys Cys Lys Cys Lys Asn Tyr Asn Asp
            35                  40                  45

<210> SEQ ID NO 637
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 637

Asn Ile Ile Ser Cys Thr Gln Asp Phe Asp Cys Gln Thr Lys Ile Cys
1               5                   10                  15

Pro Phe His Leu Lys Pro Lys Cys Ile Val Leu Glu Ile Leu Pro His
            20                  25                  30

Ser Leu Ser Gly Gly Ile Cys Gly Cys Asp
            35                  40

<210> SEQ ID NO 638
<211> LENGTH: 52
<212> TYPE: PRT
<213> ORGANISM: Artificial sequence
<220> FEATURE:
<223> OTHER INFORMATION: Peptide derived from Medicago truncatula

<400> SEQUENCE: 638

Glu His Ile Gln Cys Val Ile Asp Asp Cys Pro Lys Ser Leu Asn
1               5                   10                  15

Lys Leu Leu Ile Ile Lys Cys Ile Asn His Val Cys Gln Tyr Val Gly
            20                  25                  30

Asn Leu Pro Asp Phe Ala Ser Gln Ile Pro Lys Ser Thr Lys Met Pro
            35                  40                  45

Tyr Lys Gly Glu
    50

<210> SEQ ID NO 639
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 639

Ile His Ile Gly Cys Asp Lys Asp Arg Asp Cys Pro Lys Gln Met Cys
1               5                   10                  15

His Leu Asn Gln Thr Pro Lys Cys Leu Lys Asn Ile Cys Lys Cys Val
            20                  25                  30

<210> SEQ ID NO 640
<211> LENGTH: 29
<212> TYPE: PRT
<213> ORGANISM: Artificial sequence
<220> FEATURE:
<223> OTHER INFORMATION: Peptide derived from Medicago truncatula

<400> SEQUENCE: 640

Tyr Asn Ser Asp Cys Gln Ser Tyr Pro Cys Asp Leu Gly Glu Ser Arg
1               5                   10                  15

Asn Cys Thr Leu Asn Arg Cys Ile Cys Val Tyr Asn Ile
            20                  25

-continued

<210> SEQ ID NO 641
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 641

Glu Arg Glu Cys Asp Thr Asp Ala Asp Cys Gln Lys Lys Phe Pro Gly
1               5                   10                  15

Ser Asn Gln His Leu Leu Trp Cys Asn Asn Gly Phe Cys Asp Cys Arg
            20                  25                  30

Thr His

<210> SEQ ID NO 642
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 642

Thr Phe Ile His Phe Ser Ile Pro Cys Ile Thr Asp Lys Asp Cys Ser
1               5                   10                  15

Ile Leu Gln Asn Tyr Lys Ala Arg Cys Arg Lys Gly Tyr Cys Leu Arg
            20                  25                  30

Arg Lys Ile Arg
            35

<210> SEQ ID NO 643
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 643

His Gln Ser Ile Asp Asp Val Ile Pro Cys Val Leu Asn Thr Asp Cys
1               5                   10                  15

Pro Arg Asp Met Cys Pro Ile His Leu Phe Pro Lys Cys Ile Asn Leu
            20                  25                  30

Leu Cys Arg Cys Ser Tyr Trp Glu Asp Asn
            35                  40

<210> SEQ ID NO 644
<211> LENGTH: 50
<212> TYPE: PRT
<213> ORGANISM: Artificial sequence
<220> FEATURE:
<223> OTHER INFORMATION: Peptide derived from Medicago truncatula

<400> SEQUENCE: 644

Lys Asn Ile Asp Gly Arg Val Ser Tyr Asn Ser Phe Ile Ala Leu Pro
1               5                   10                  15

Val Cys Gln Thr Ala Ala Asp Cys Pro Glu Gly Thr Arg Gly Arg Thr
            20                  25                  30

Tyr Lys Cys Ile Asn Asn Lys Cys Arg Tyr Pro Lys Leu Leu Lys Pro
        35                  40                  45

Ile Gln
    50

<210> SEQ ID NO 645

<211> LENGTH: 29
<212> TYPE: PRT
<213> ORGANISM: Artificial sequence
<220> FEATURE:
<223> OTHER INFORMATION: Peptide derived from Medicago truncatula

<400> SEQUENCE: 645

Ile Pro Cys Phe Gly Thr Lys Asp Lys Cys Pro Phe Asn Leu Tyr Tyr
1               5                   10                  15

Lys Val Glu Cys Ile Asp Gly Phe Cys Tyr Tyr Pro Val
            20                  25

<210> SEQ ID NO 646
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 646

Ile Thr Ile Ser Asn Ser Ser Phe Gly Arg Ile Val Tyr Trp Asn Cys
1               5                   10                  15

Lys Thr Asp Lys Asp Cys Lys Gln His Arg Gly Phe Asn Phe Arg Cys
            20                  25                  30

Arg Ser Gly Asn Cys Ile Pro Ile Arg Arg
        35                  40

<210> SEQ ID NO 647
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 647

Phe Asn Ser Lys Ile Val Phe Thr Asp Cys Lys Thr Asp Lys Asp Cys
1               5                   10                  15

Gln Asn His Arg Gly Phe Asn Phe Arg Cys Arg Lys Gly Asn Cys Val
            20                  25                  30

Ala Lys Ile Arg
        35

<210> SEQ ID NO 648
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 648

Val Ile Asp Ile Asn Ala Phe Ser Phe Pro Cys Lys Thr Asn Ser Asp
1               5                   10                  15

Cys Pro Ser Tyr Leu Cys His Tyr Pro Lys Asn Pro Glu Cys Val Glu
            20                  25                  30

Arg Glu Cys Ile Cys Trp
        35

<210> SEQ ID NO 649
<211> LENGTH: 30
<212> TYPE: PRT
<213> ORGANISM: Artificial sequence
<220> FEATURE:
<223> OTHER INFORMATION: Peptide derived from Medicago truncatula

<400> SEQUENCE: 649

-continued

```
Ser Ile Pro Cys Glu Thr Thr Ala Asp Cys Pro Val Ala Val Pro Pro
1               5                   10                  15

Glu Tyr Tyr Lys Cys Met Tyr Lys Val Cys Val Leu Ile Arg
            20                  25                  30

<210> SEQ ID NO 650
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 650

Ile Pro Cys Leu Ser Asp Asp Glu Cys Pro Glu Met Ser His Tyr Ser
1               5                   10                  15

Phe Lys Cys Asn Asn Lys Ile Cys Glu Tyr Asp Leu Gly Glu Met Ser
            20                  25                  30

Asp Asp Asp Tyr Tyr Leu Glu Met Ser Arg Glu
        35                  40

<210> SEQ ID NO 651
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 651

Gln Asn Ile Asp Ala Gly Gly Asn Arg Lys Cys Phe Arg Asp Ser Asp
1               5                   10                  15

Cys Pro Lys Phe Met Cys Pro Ser Tyr Leu Ala Val Lys Cys Ile Gly
            20                  25                  30

Arg Leu Cys Arg Cys Gly Arg Pro Glu Leu Gln Val Glu Leu Asn Pro
        35                  40                  45

Lys

<210> SEQ ID NO 652
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 652

Leu Asn Gly Gly Gly Lys Asp Lys Cys Phe Arg Asp Ser Asp Cys Pro
1               5                   10                  15

Lys His Met Cys Pro Ser Ser Leu Val Ala Lys Cys Ile Asn Arg Leu
            20                  25                  30

Cys Arg Cys Arg Arg Pro Glu Leu Gln Val Gln Leu Asn Pro
        35                  40                  45

<210> SEQ ID NO 653
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 653

Lys Thr Gln Phe Leu Pro Asn Tyr Tyr Glu Phe Tyr His Cys Tyr Asn
1               5                   10                  15

His Ser Asp Cys Gln Gly Ser Met Cys Pro Thr Gly Ser Lys Pro Lys
```

-continued

```
                 20                  25                  30
Cys Val Asp Gln Val Cys Glu Cys Ile Leu Ile Arg Met
            35                  40                  45

<210> SEQ ID NO 654
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 654

Phe Gln Leu Phe Asp Asn Thr Asp Thr Ala Thr Cys Ile Thr Asp Ala
1               5                   10                  15

Asp Cys Pro Tyr Asp Gly Lys Cys Ile Asp Gly Phe Cys Arg Phe Asn
            20                  25                  30

Val Lys Asn Asn Asn Gln Val
        35

<210> SEQ ID NO 655
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 655

Met Lys Asn Gly Cys Lys His Thr Gly His Cys Pro Arg Lys Met Cys
1               5                   10                  15

Gly Ala Lys Thr Thr Lys Cys Arg Asn Asn Lys Cys Gln Cys Val
            20                  25                  30

<210> SEQ ID NO 656
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 656

Asp Asp Val Lys Ile Lys Cys Val Ser Ala Ile Asp Cys Met Asp Leu
1               5                   10                  15

Phe Asn Leu Leu Pro Ile Val Tyr Lys Cys Ile Asn Asn Ile Cys Val
            20                  25                  30

Tyr Glu Gln Ser Ser Gln Arg Leu Ile
        35                  40

<210> SEQ ID NO 657
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 657

Glu His Asn Glu Cys Glu Thr Asp Ala Asp Cys Pro Lys His Thr Thr
1               5                   10                  15

Ile Phe Phe Val Met Lys Cys Ile Asp His Ile Cys Arg Cys Met Lys
            20                  25                  30

Thr Ser Ile
        35

<210> SEQ ID NO 658
```

```
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 658

Phe Lys Met Phe Cys Arg Tyr Asp Glu Asp Cys Pro Pro Arg Met Cys
1               5                   10                  15

Arg Leu Pro Gln Val Pro Gln Cys Asn Glu Phe Ile Cys Asp Cys Gly
            20                  25                  30

Met Pro Val Tyr Lys Pro Tyr Gln Asn Lys Tyr Ile Lys Lys
        35                  40                  45

<210> SEQ ID NO 659
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 659

Trp Arg Cys Lys Thr Lys Tyr Asp Cys Ile Lys Ile Arg Phe Cys Lys
1               5                   10                  15

Phe Pro Thr Ile Ala Arg Cys Thr Lys Pro Asp Phe Leu Phe Leu Glu
            20                  25                  30

Tyr Asp Arg Gly Phe Cys Thr Cys Asp Asp
        35                  40

<210> SEQ ID NO 660
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 660

Val Ile Lys Cys Phe Gln Asp Ser Asp Cys Pro Lys Tyr Met Cys Met
1               5                   10                  15

Phe Pro Leu Lys Pro Lys Cys Val Tyr Ile Leu Val Phe Pro Pro Pro
            20                  25                  30

Trp Thr Ala Gln Cys Ile Cys Asp
        35                  40

<210> SEQ ID NO 661
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 661

Ile Lys Leu Ile Lys Cys Thr Val Ser Asp Asp Cys Pro Met Asn Phe
1               5                   10                  15

Arg Cys Pro Pro Asn Thr Phe Val Arg Cys Ile Ser Asp Leu Cys Thr
            20                  25                  30

Cys Arg Ser Leu Leu Asp Glu Gln Ser
        35                  40

<210> SEQ ID NO 662
<211> LENGTH: 34
<212> TYPE: PRT
<213> ORGANISM: Artificial sequence
<220> FEATURE:
```

<223> OTHER INFORMATION: Peptide derived from Medicago truncatula

<400> SEQUENCE: 662

Ser Phe Ser Glu Ile Ile Asp Ser Ala Cys Lys Thr Asp Lys Asp Cys
1               5                   10                  15

Pro Lys Leu His Lys Val Asn Val Arg Cys Arg Lys Gly Lys Cys Val
            20                  25                  30

Ala Ile

<210> SEQ ID NO 663
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 663

Gly Arg Glu Cys His Ala Asn Ser His Cys Val Gly Lys Ile Thr Cys
1               5                   10                  15

Val Leu Pro Gln Lys Pro Glu Cys Trp Asn Tyr Ala Cys Val Cys Tyr
            20                  25                  30

Asp Ser Asn Lys Tyr Arg
        35

<210> SEQ ID NO 664
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 664

Lys Glu Cys Val Thr Asp Val Asp Cys Glu Lys Ile Tyr Pro Gly Asn
1               5                   10                  15

Lys Lys Pro Leu Ile Cys Ser Thr Gly Tyr Cys Tyr Ser Leu Tyr Glu
            20                  25                  30

Glu Pro Pro Arg Tyr His Lys
        35

<210> SEQ ID NO 665
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 665

Leu Glu Thr Gln Ile Val Gln Lys Ala Cys Val Ile Leu Leu Pro Asn
1               5                   10                  15

Arg Ser Val Cys Thr Asn Pro Tyr Val Asn Val Tyr Glu Ser Ser Pro
            20                  25                  30

Lys Glu Ile Met Cys Ile His Glu His Val Cys Leu Pro Tyr Leu Arg
        35                  40                  45

Ala Tyr Thr Asn Tyr Ile Pro Ser
    50                  55

<210> SEQ ID NO 666
<211> LENGTH: 38
<212> TYPE: PRT
<213> ORGANISM: Artificial sequence
<220> FEATURE:
<223> OTHER INFORMATION: Peptide derived from Medicago truncatula -continued

```
<400> SEQUENCE: 666

Lys Glu Cys Val Thr Asp Ala Asp Cys Glu Asn Leu Tyr Tyr Gly Asn
1               5                   10                  15

Lys Trp Pro Leu Ile Cys Ser Asn Ile Gly Tyr Cys Leu Ser Ser Tyr
                20                  25                  30

Glu Glu Pro Pro His Lys
            35

<210> SEQ ID NO 667
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 667

Phe Arg Asp Pro Cys Asn Phe Asp Phe Asp Cys Arg Asn Ser Asn Cys
1               5                   10                  15

Thr Ala Pro Tyr Val Ala Thr Cys Met Tyr Glu His Cys Tyr Cys
                20                  25                  30

<210> SEQ ID NO 668
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 668

Ile Pro Ile Cys Gln Thr Tyr Met Asp Cys Pro Ser Asp Met Cys Thr
1               5                   10                  15

Arg Pro Lys His Ala Tyr Cys Val Ser Tyr Lys Cys Tyr Cys Val
                20                  25                  30

<210> SEQ ID NO 669
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 669

Lys Glu Cys Val Thr Asp Ala Asp Cys Glu Asn Leu Tyr Pro Gly Asn
1               5                   10                  15

Lys Lys Pro Met Phe Cys Asn Asn Thr Gly Tyr Cys Met Ser Leu Tyr
                20                  25                  30

Lys Glu Pro Ser Arg Tyr Met
            35

<210> SEQ ID NO 670
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 670

Leu Lys Cys Lys Thr Val His Asp Cys Pro Lys Ser Gln Val Val Tyr
1               5                   10                  15

Lys Cys Val Gly Asn Tyr Cys Arg Ala Val Lys Ile Arg Arg Trp Asn
                20                  25                  30

Leu Ser
```

<210> SEQ ID NO 671
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 671

Tyr Val Val Met Cys Glu Lys Asp Ser Asp Cys Val Asp Ser Phe Cys
1               5                   10                  15

Val Pro Pro Asn Val Pro Lys Cys Arg Val Val Cys Lys Cys Leu Pro
            20                  25                  30

Lys

<210> SEQ ID NO 672
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 672

Lys Ser Tyr Gly Pro Cys Thr Thr Leu Gln Asp Cys Glu Thr His Asn
1               5                   10                  15

Trp Phe Glu Val Cys Ser Cys Ile Asp Phe Glu Cys Lys Cys Trp Ser
            20                  25                  30

Leu Leu

<210> SEQ ID NO 673
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 673

Met Glu Val Gly Arg Arg Ala Asn Val Glu Cys Glu Ser Asp Lys Asp
1               5                   10                  15

Cys Gln Glu His Trp Ser Glu Phe Phe Ile Ile Gln Cys Ile Asp Asn
            20                  25                  30

Ile Cys Val Pro Ser Glu Arg Pro Leu
        35                  40

<210> SEQ ID NO 674
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 674

Asp Arg Glu Cys Asp Thr Asp Thr Glu Cys Gln Lys Lys Phe Pro Gly
1               5                   10                  15

Val Asn Ala His His Leu Trp Cys Asp Asn Gly Asn Cys Val Ser Tyr
            20                  25                  30

Pro Lys

<210> SEQ ID NO 675
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 675

Tyr Lys Asn Arg Cys Phe Arg Asp Ser Asp Cys Pro Lys Glu Met Cys
1               5                   10                  15

Asn His Pro Lys Ile Pro Lys Cys Val Asn Asn Ala Tyr Cys Lys Cys
            20                  25                  30

Val Val Ala Met Tyr Phe Pro Pro Lys
        35                  40

<210> SEQ ID NO 676
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 676

Gly Gly Asn Glu Cys Val Thr Asp Val Asp Cys Glu Lys Leu Tyr Pro
1               5                   10                  15

Gly Asn Lys Lys Pro Leu Ile Cys Asn Ile Gly Tyr Cys Leu Ser Leu
            20                  25                  30

Tyr Lys Glu Pro Pro Arg Tyr Met
        35                  40

<210> SEQ ID NO 677
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 677

Glu Asn Ile Cys Asp Gly Asp Tyr Asp Cys Asn Pro Asn Glu Trp Trp
1               5                   10                  15

Cys Pro Pro Asn Tyr Val Leu Lys Cys Ile Asn Tyr Gln Cys Ser Cys
            20                  25                  30

Ile Gly Phe Thr Pro Ala Ile Tyr Ala Leu Asp
        35                  40

<210> SEQ ID NO 678
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 678

Glu Asp Phe Pro Phe His Lys Cys Glu Lys Asp Glu Asp Cys Leu Glu
1               5                   10                  15

Ile Cys Ala Asp Asp Gln Met Ala Met Cys Ile Leu Asn Val Cys Phe
            20                  25                  30

Cys Tyr

<210> SEQ ID NO 679
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 679

Gln Glu Val Leu Glu Lys Glu Ile Phe Pro Cys Gln Thr Asp Gly Glu
1               5                   10                  15

```
Cys Asp His Met Cys Val Thr Pro Gly Ile Pro Lys Cys Val Ala Asn
             20                  25                  30

Met Cys Phe Cys Phe Asp Asn Leu
             35                  40

<210> SEQ ID NO 680
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 680

His Arg Phe Leu Ile Tyr Asn Asn Cys Lys Asn Asp Thr Glu Cys Pro
1               5                   10                  15

Asn Asp Cys Gly Pro His Glu Gln Ala Lys Cys Ile Leu Tyr Ala Cys
             20                  25                  30

Tyr Cys Val Glu
             35

<210> SEQ ID NO 681
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 681

Val Ile Phe Glu Cys Ser Glu Asp Ser His Cys Val Thr Lys Ile Lys
1               5                   10                  15

Cys Val Leu Pro Arg Lys Pro Glu Cys Arg Asn Thr Gln Cys Thr Cys
             20                  25                  30

Tyr Arg Gly Tyr Lys Gly Ser Phe Thr Leu His His
             35                  40

<210> SEQ ID NO 682
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 682

Lys Asp Gly Cys Lys Thr Asn Phe Asp Cys Leu Ile Lys Tyr Pro Asp
1               5                   10                  15

His Asn Glu Asp Ile Leu Gln Cys Ile Gly Gly His Cys Leu Cys Leu
             20                  25                  30

Thr Asn

<210> SEQ ID NO 683
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 683

Gln His Pro Phe Thr Pro Cys Thr Asn Ala Asp Cys Lys Cys Arg
1               5                   10                  15

Asn His Lys Arg Pro Asp Cys Leu Trp His Lys Cys Tyr Cys Tyr
             20                  25                  30
```

```
<210> SEQ ID NO 684
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 684

Lys Leu Trp Cys Asp Thr Asp Ala Asp Cys Gln Glu Lys Phe Pro Gly
1               5                   10                  15

Pro Ser Lys Tyr Pro Ile Lys Cys Met Lys Gly Ile Cys Lys Cys Val
            20                  25                  30

Ile Asn

<210> SEQ ID NO 685
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 685

Trp Arg Pro Asp Cys Lys Glu Asn Asn Asp Cys Pro Thr Phe Tyr Cys
1               5                   10                  15

Ala Thr Trp Ile Asn Thr Cys Ile Lys Phe Lys Cys Tyr Cys Ile Arg
            20                  25                  30

Pro Trp Gly
        35

<210> SEQ ID NO 686
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 686

Lys Asp Leu Pro Phe Asn Ile Cys Glu Lys Asp Glu Asp Cys Leu Glu
1               5                   10                  15

Phe Cys Ala His Asp Lys Val Ala Lys Cys Met Leu Asn Ile Cys Phe
            20                  25                  30

Cys Phe

<210> SEQ ID NO 687
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 687

Tyr Phe Ile Pro Asp Ser Gly Pro Cys Val Thr Asn Lys Asp Cys Glu
1               5                   10                  15

Gln Glu Ile Gly Tyr Ile Val Lys Cys Asp Thr Asn Thr Gly Phe Cys
            20                  25                  30

Val Lys Ile Leu Gln Arg Ser
        35

<210> SEQ ID NO 688
<211> LENGTH: 49
<212> TYPE: PRT
<213> ORGANISM: Artificial sequence
<220> FEATURE:
<223> OTHER INFORMATION: Peptide derived from Medicago truncatula
```

```
<400> SEQUENCE: 688

Asp Phe Asp Leu His Asn Asp Ser Tyr Asp Tyr Leu Tyr Glu Phe Gln
1               5                   10                  15

Glu Cys Glu Val Asp Asn Asp Cys Pro Gln Asp Pro Leu Pro Met Lys
            20                  25                  30

Cys Ile Asn Tyr Ile Cys Val Val His Asn Glu Glu Pro Ser Asp Asn
        35                  40                  45

Leu

<210> SEQ ID NO 689
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 689

Asn Phe Glu Asp Ile Ser Ile Glu Cys Met Phe Ser Ile Asp Cys Pro
1               5                   10                  15

Gln Ile Lys Ser Asn Ile Phe Arg Phe Lys Cys Ile Glu Asp Arg Cys
            20                  25                  30

Lys Ile Glu Phe Ile Tyr Gln Arg Lys Lys Tyr Glu Ile
        35                  40                  45

<210> SEQ ID NO 690
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 690

Gln Lys Arg Trp His Gly Cys Lys Glu Asp Arg Asp Cys Asp Asn Ile
1               5                   10                  15

Cys Ser Val His Ala Val Thr Lys Cys Ile Gly Asn Met Cys Arg Cys
            20                  25                  30

Leu Ala Asn Val Lys
        35

<210> SEQ ID NO 691
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 691

Gln Lys Asp Leu Lys Val Phe Thr Cys Gln Arg Asp Glu Asp Cys Lys
1               5                   10                  15

Val Ala Cys Ala Thr Tyr Gly Gly Asp Pro Trp Cys Phe Arg Asn Val
            20                  25                  30

Cys Phe Cys Lys His Tyr Asn Glu Gly Gly Thr Leu His Ala Glu Leu
        35                  40                  45

His

<210> SEQ ID NO 692
<211> LENGTH: 53
<212> TYPE: PRT
<213> ORGANISM: Artificial sequence
<220> FEATURE:
<223> OTHER INFORMATION: Peptide derived from Medicago truncatula
```

```
<400> SEQUENCE: 692

Glu Gln His Phe Val Thr Leu Tyr Lys Lys Glu Lys Cys Ala Leu
1               5                   10                  15

Asp Val Asp Cys Leu Glu Leu Phe Pro Asn Ser Tyr Lys Tyr Leu Met
            20                  25                  30

Lys Cys Val Gly Gly Asp Cys Ile Ser Leu Ser Lys Gly Phe Ser His
        35                  40                  45

Asp Glu Ile Lys Glu
    50

<210> SEQ ID NO 693
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 693

Ala Lys Val Asn Cys Leu Asp Asp Ala Asp Cys Leu Glu Val Leu Cys
1               5                   10                  15

Val Phe Gly Ser Lys Ala Glu Cys Val Val Asn Ile Cys Ile Cys Val
            20                  25                  30

Pro Pro Arg Phe Gly Lys Phe Asp Glu His Phe Arg
        35                  40

<210> SEQ ID NO 694
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 694

Lys Asp Ile Thr Cys Thr Val Ala Gly Asp Cys Pro Asn Phe Phe Val
1               5                   10                  15

Cys Pro Pro Asn Asn Phe Val Arg Cys Ile Arg Asn Leu Cys Lys Cys
            20                  25                  30

Arg Ser Leu Ser Tyr Lys Gln Pro
        35                  40

<210> SEQ ID NO 695
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 695

Glu Asn Ser Gln Pro Cys Asn Leu Ser Val Thr Asp Thr Arg Asp Ile
1               5                   10                  15

Cys Pro Pro Gly Thr Thr Leu Gln Phe Val Tyr Lys Val Cys Arg Cys
            20                  25                  30

Tyr Pro Met Lys Trp Arg Leu Asp His Val Leu Thr
        35                  40

<210> SEQ ID NO 696
<211> LENGTH: 49
<212> TYPE: PRT
<213> ORGANISM: Artificial sequence
<220> FEATURE:
<223> OTHER INFORMATION: Peptide derived from Medicago truncatula
```

<400> SEQUENCE: 696

Ile Cys Glu Cys Glu Glu Asp Ile Asp Cys Pro Arg Thr Trp Cys Phe
1               5                   10                  15

Gly Gln Phe Phe Val Lys Cys Ile Thr Asn Glu Cys Ile Cys Val His
            20                  25                  30

Glu Asp Arg Leu Leu Pro Arg Ile Pro Trp Asp Pro Trp Ile Pro Met
        35                  40                  45

Ile

<210> SEQ ID NO 697
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 697

Asp Thr Asp Pro Phe Ala Phe Cys Ile Lys Asp Ser Asn Cys Gly Gln
1               5                   10                  15

Asp Leu Cys Thr Ser Pro Asn Glu Val Pro Glu Cys Arg Leu Leu Lys
            20                  25                  30

Cys Gln Cys Ile Lys Ser
        35

<210> SEQ ID NO 698
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 698

Lys Ile Leu Glu Lys His Lys Cys Val Thr Asp Gly Val Glu Ile Leu
1               5                   10                  15

Glu Lys Gly Lys Cys Phe Thr Asp Trp Glu Cys Val Arg Asn Ser Trp
            20                  25                  30

Leu Cys Pro Val Asp Leu Val Val Arg Cys Ile Lys Glu Thr Cys Lys
        35                  40                  45

Cys Ile Lys Ile Leu Glu Pro Ile Asn Val Val Pro Thr
    50                  55                  60

<210> SEQ ID NO 699
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 699

Val Ser Lys Leu Ala Gln Ser Cys Ser Glu Asp Phe Glu Cys Tyr Ile
1               5                   10                  15

Lys Asn Pro His Ala Pro Phe Gly Gln Leu Arg Cys Phe Glu Gly Tyr
            20                  25                  30

Cys Gln Arg Leu Asp Lys Pro Thr
        35                  40

<210> SEQ ID NO 700
<211> LENGTH: 59
<212> TYPE: PRT
<213> ORGANISM: Artificial sequence
<220> FEATURE:
<223> OTHER INFORMATION: Peptide derived from Medicago truncatula

```
<400> SEQUENCE: 700

Tyr Asp Asp Cys Tyr Asn His Thr Glu Cys Thr Asn Lys Ile Lys Cys
1               5                   10                  15

Val Pro Pro Arg Ile Ala Gln Cys Phe Arg Phe Lys Cys Asp Cys Ile
            20                  25                  30

Arg Leu Asn Asn Gly Pro Lys Thr Pro Trp Ser Ala Thr Pro Lys Arg
        35                  40                  45

Val His Ile Ser Pro Thr Arg Lys Asn Asp Phe
    50                  55

<210> SEQ ID NO 701
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 701

Glu Glu Ser His Tyr Met Lys Phe Ser Ile Cys Lys Asp Asp Thr Asp
1               5                   10                  15

Cys Pro Thr Leu Phe Cys Val Leu Pro Asn Val Pro Lys Cys Ile Gly
            20                  25                  30

Ser Lys Cys His Cys Lys Leu Met Val Asn
        35                  40

<210> SEQ ID NO 702
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 702

Ile Asn Ser Asp Gly Tyr Leu Glu Cys Thr Thr Asp Tyr Asp Cys Arg
1               5                   10                  15

Glu Glu Trp Leu Cys Pro Pro Asp Met Glu Ala Lys Cys Phe Val Ser
            20                  25                  30

Phe Ala Leu Ala Arg Phe Leu Ser Lys Gly Lys Cys Leu Cys Val
        35                  40                  45

<210> SEQ ID NO 703
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 703

Ile Phe Pro Glu His Asn Glu Cys Arg Thr Ser Phe Asp Cys Arg Lys
1               5                   10                  15

Tyr Phe Cys Gln Leu Pro Leu Arg Pro Thr Cys Asn Tyr Val Glu Ile
            20                  25                  30

Phe Arg His Tyr Tyr Asp Thr Thr Cys Gly Cys Ala
        35                  40

<210> SEQ ID NO 704
<211> LENGTH: 39
<212> TYPE: PRT
<213> ORGANISM: Artificial sequence
<220> FEATURE:
<223> OTHER INFORMATION: Peptide derived from Medicago truncatula
```

```
<400> SEQUENCE: 704

Asp Asp Tyr Leu Lys Tyr Ile Tyr Arg Cys Gln Asn Asp Gly Asp Cys
1               5                   10                  15

Asp Gln Ile Cys Ala Thr His Gly Ile Ser Lys Cys Val Ala Thr Met
            20                  25                  30

Cys Phe Cys Asn Leu Asn Leu
            35

<210> SEQ ID NO 705
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 705

Trp Ser Trp Gly Leu Thr Thr Glu Cys Val Thr Glu Leu Asp Cys Tyr
1               5                   10                  15

Lys Lys Tyr Arg Leu Pro Ala Glu Lys Met Lys Cys Ile Arg Gly
            20                  25                  30

Ser Cys Tyr Arg Val Arg Glu
            35

<210> SEQ ID NO 706
<211> LENGTH: 24
<212> TYPE: PRT
<213> ORGANISM: Artificial sequence
<220> FEATURE:
<223> OTHER INFORMATION: Peptide derived from Medicago truncatula

<400> SEQUENCE: 706

Arg Asn Gly Cys Ile Val Asp Pro Arg Cys Pro Tyr Gln Gln Cys Arg
1               5                   10                  15

Arg Pro Leu Tyr Cys Arg Arg Arg
            20

<210> SEQ ID NO 707
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 707

Tyr Asn Ile Thr Cys Asn Ser Ala Leu Asp Cys Ala Ser Asn Arg Cys
1               5                   10                  15

Ile Leu Pro Gly Met Pro Ile Cys Val Thr Asn Lys Cys Leu Cys Val
            20                  25                  30

<210> SEQ ID NO 708
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 708

Glu Arg Glu Cys Val Thr Asp Ala Asp Cys Gln Lys Lys Leu Pro Phe
1               5                   10                  15

Pro His Ala Asn His Phe Ile Cys Met Asn Gly Leu Cys Ala Leu Val
            20                  25                  30

Phe His Asp
    35
```

```
<210> SEQ ID NO 709
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 709

Arg Pro Cys Val Thr Val Ala Asp Cys Pro Pro Val Lys Lys Pro Leu
1               5                   10                  15
Lys Met Trp Cys Ile Arg Gln Thr Cys Phe Tyr Gly Phe Gly Lys Arg
            20                  25                  30
Pro Asp Leu
        35

<210> SEQ ID NO 710
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 710

Glu Thr Cys Val Thr Val Asp Asp Cys Gln Gly Lys His His Leu Pro
1               5                   10                  15
Pro Gly Tyr His Phe Ile Cys Met Asn Ser Arg Cys Val Leu Ile Tyr
            20                  25                  30
Tyr Asn

<210> SEQ ID NO 711
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 711

Gly Thr Gly Asn Ile Arg Gln Ser Cys Glu Phe Asp Val Asp Cys Glu
1               5                   10                  15
Asn Lys Tyr Cys Pro Pro Ser His Asp Gly Lys Cys Val Trp Glu
            20                  25                  30

<210> SEQ ID NO 712
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 712

Gly Glu Cys Ile Thr Phe Leu Asp Cys Leu His Leu Pro Cys Met Pro
1               5                   10                  15
Thr Glu Thr Gln Leu Cys Val Asp Lys Lys Cys Ile Cys Met Gly Leu
            20                  25                  30
Thr Ile Lys Ser Lys Asn Asn Tyr Ile Thr
        35                  40

<210> SEQ ID NO 713
<211> LENGTH: 33
<212> TYPE: PRT
<213> ORGANISM: Artificial sequence
<220> FEATURE:
<223> OTHER INFORMATION: Peptide derived from Medicago truncatula
```

-continued

```
<400> SEQUENCE: 713

Ser Tyr Pro Cys Lys Ile His Arg Asp Cys Thr Thr Ile Thr Cys Ser
1               5                   10                  15

Tyr Pro Leu Val Pro Arg Cys Leu Ile Gln Lys Cys Tyr Cys Gly Phe
            20                  25                  30

Asn

<210> SEQ ID NO 714
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 714

Glu Lys Cys Val Thr Ala Asp Asp Cys Gln Gly Lys His His Met Pro
1               5                   10                  15

Ala Gly Tyr His Phe Ile Cys Met Asn Ala Arg Cys Val Leu Val Tyr
            20                  25                  30

Tyr Asn

<210> SEQ ID NO 715
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 715

Phe Phe Asp Cys Glu Asn His Asp Cys Lys Asn Lys Ile Lys Tyr
1               5                   10                  15

Val Leu Pro Arg Ile Ala Glu Cys Arg Asp Tyr Lys Cys Asn Cys Phe
            20                  25                  30

Pro Leu Asn Leu Ser Lys Thr Leu Trp Ser Ala Ser Thr Lys Arg Val
            35                  40                  45

His Lys Ser Leu Ala Gln Thr Asn Asp Phe Leu His
        50                  55                  60

<210> SEQ ID NO 716
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 716

Asn Asp Ile Lys Cys Thr Val Ala Gly Asp Cys Pro Asp Phe Phe Arg
1               5                   10                  15

Cys Pro Pro Asn Thr Phe Val Arg Cys Ile Ser Asn Ile Cys Ile Cys
            20                  25                  30

Arg Leu Val Tyr Leu Asn Thr Phe Leu Glu Val Ile Ile Asp Lys Val
            35                  40                  45

Phe Val Phe
    50

<210> SEQ ID NO 717
<211> LENGTH: 37
<212> TYPE: PRT
<213> ORGANISM: Artificial sequence
<220> FEATURE:
<223> OTHER INFORMATION: Peptide derived from Medicago truncatula
```

<400> SEQUENCE: 717

Asn Asp Ile Lys Cys Thr Val Ala Gly Asp Cys Pro Asp Phe Phe Arg
1               5                   10                  15

Cys Pro Pro Asn Thr Phe Val Arg Cys Ile Ser Asn Ile Cys Ile Cys
                20                  25                  30

Arg Ser Leu Ser His
        35

<210> SEQ ID NO 718
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 718

Lys Asp Ile Thr Cys Asn Val Ala Gly Asp Cys Pro Glu Tyr Phe Arg
1               5                   10                  15

Cys Pro Pro Asn Thr Phe Val Arg Cys Val Ser Asn Ile Cys Glu Cys
                20                  25                  30

Arg Gly Leu Ser His Gln Gln Pro
        35                  40

<210> SEQ ID NO 719
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 719

Lys Pro Ala Pro Ile Pro Cys Lys Phe His Ala Asp Cys Pro Ile Met
1               5                   10                  15

Leu Ser Ile Val Val Glu Cys Ile Asn Asn Val Cys Gly Phe Ile Tyr
                20                  25                  30

Ile

<210> SEQ ID NO 720
<211> LENGTH: 107
<212> TYPE: PRT
<213> ORGANISM: Artificial sequence
<220> FEATURE:
<223> OTHER INFORMATION: Peptide derived from Medicago truncatula

<400> SEQUENCE: 720

Ala Gly Lys Lys Phe Leu Cys Leu Ser Asn Phe Leu Ile Tyr Phe Val
1               5                   10                  15

Val Ile Phe Phe Gly Ser His Thr Ile Phe His Leu Val Leu Leu Asn
                20                  25                  30

Ile Leu Phe Ser Phe Ser Ser Glu Asn Ile Glu Cys Glu Val Asp Ala
            35                  40                  45

Asp Cys Pro Lys Ser Gln Val Asn Ser Phe Val Ile Lys Cys Ile Lys
        50                  55                  60

Asn Leu Cys Leu Tyr Thr Lys Ile His Ile Leu Tyr Asp Thr Ile Ser
65                  70                  75                  80

Lys Ser Glu Ser Thr Leu Pro Gln Lys Lys Ser Leu Ile Val His
                85                  90                  95

Leu His Ile Ser Arg Lys Asn Glu Leu Leu His
            100                 105

```
<210> SEQ ID NO 721
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 721

Glu Lys Ile Arg Arg Cys Phe Asn Asp Ala His Cys Pro Pro Asp Met
1               5                   10                  15

Cys Thr Leu Gly Val Ile Pro Lys Cys Ser Arg Phe Thr Ile Cys Ile
            20                  25                  30

Cys

<210> SEQ ID NO 722
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 722

Glu Arg Glu Cys Val Thr Asp Ala Asp Cys Gln Lys Lys Tyr Pro Gly
1               5                   10                  15

Pro Tyr Glu His Leu Leu Lys Cys Val Ser Gly Tyr Cys Val Gly Val
            20                  25                  30

Thr Gly Phe
        35

<210> SEQ ID NO 723
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 723

Asn Ile Phe Phe Cys Ser Thr Asp Glu Asp Cys Thr Trp Asn Leu Cys
1               5                   10                  15

Arg Gln Pro Trp Val Gln Lys Cys Arg Leu His Met Cys Ser Cys Glu
            20                  25                  30

Lys Asn

<210> SEQ ID NO 724
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 724

His Val Leu Val Glu Cys Ile Glu Asn Arg Asp Cys Glu Lys Gly Met
1               5                   10                  15

Cys Lys Phe Pro Phe Ile Val Arg Cys Leu Met Asp Gln Cys Lys Cys
            20                  25                  30

Val Arg Ile His Asn Leu Ile
        35

<210> SEQ ID NO 725
<211> LENGTH: 44
<212> TYPE: PRT
<213> ORGANISM: Artificial sequence
<220> FEATURE:
```

<223> OTHER INFORMATION: Peptide derived from Medicago truncatula

<400> SEQUENCE: 725

His Asp Gln Arg Glu Cys Tyr Thr Asn Tyr Asp Cys Cys Val Lys Tyr
1               5                   10                  15

Ser Cys Pro Tyr Lys His Met Val Lys Cys Val Gly Gly Tyr Cys Leu
            20                  25                  30

Gly Phe Arg Asn Asp Tyr Gly Lys Lys Asn Leu Tyr
        35                  40

<210> SEQ ID NO 726
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 726

Tyr Asp Ser Lys Glu Cys Tyr Ser Asp Ser Asp Trp His Lys Lys Tyr
1               5                   10                  15

Ser Cys Pro Tyr Thr His Met Met Lys Cys Val Gly Gly Tyr Cys
            20                  25                  30

<210> SEQ ID NO 727
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 727

Arg Ile Thr His Asp Pro Ser Thr Arg Ser Thr Val Ser Gly Gly Phe
1               5                   10                  15

Gly Lys Cys Val Arg Asp Ala Asp Cys Val Asp Glu Val Cys Ser Pro
            20                  25                  30

Gly Cys Asn Lys Arg Cys Val Gly Phe Glu Cys Gln Cys Pro Leu
        35                  40                  45

<210> SEQ ID NO 728
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 728

Cys Asn Asp Asp Thr Asp Cys Pro Pro Ser Cys Thr Thr Arg Gly Cys
1               5                   10                  15

Pro Asp Ser Cys Ala Tyr Pro His Val Leu Arg Cys Ile Gly Lys Asn
            20                  25                  30

Cys Val Cys Thr
        35

<210> SEQ ID NO 729
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 729

Asp Pro Met Tyr Cys Phe Asn Asp Asp Cys Arg Glu Leu Lys Cys
1               5                   10                  15

```
Ser His Pro Arg Val Arg Lys Cys Arg Met Phe Leu Cys Arg Cys Glu
            20                  25                  30

Glu Val Asp Lys Glu Asp Glu Lys
        35                  40

<210> SEQ ID NO 730
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 730

Val Thr Ile Cys Asp Ser Asp Gln Asp Cys Arg Arg Tyr Arg Cys Asp
1               5                   10                  15

Pro Pro Glu Tyr Pro Arg Cys Leu Gly Ile Leu Cys Lys Cys Val Tyr
            20                  25                  30

Val Ser Gly
        35

<210> SEQ ID NO 731
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 731

Gln Lys Arg Arg Arg Ser Thr Glu Cys Arg Asn Asp Ser Asp Cys Glu
1               5                   10                  15

Lys Met Val Lys Cys Val Leu Pro Arg Ile Ala Arg Cys Ile Lys Tyr
            20                  25                  30

Arg Cys Gln Cys Arg Asn Phe Leu Glu Ser Phe Glu
        35                  40

<210> SEQ ID NO 732
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 732

Asn Asp Thr Glu Tyr Thr Asp Cys Leu Gln His Ser Asp Cys Gln Ala
1               5                   10                  15

Tyr Ala Cys Glu Leu Pro Phe Lys Pro Asp Cys Leu Met Val Glu Tyr
            20                  25                  30

Ala Pro Gln Phe Phe Arg Leu Ala Cys Gly Cys Val
        35                  40

<210> SEQ ID NO 733
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 733

Glu Lys Gly Thr Ile Val Asp Ile Glu Thr Thr Gly Gln Cys Ala Asp
1               5                   10                  15

Asp Tyr Glu Cys Tyr Arg Leu Phe Ser Cys Pro Arg Glu Val Ala Phe
            20                  25                  30

Lys Cys Ile Asn Gly Trp Cys Lys Cys Ile Leu
```

```
              35                  40

<210> SEQ ID NO 734
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 734

Phe Asp Arg Arg Phe Ile Cys Phe Asp Asn Ser Asp Cys Pro Gln His
1               5                   10                  15

Leu Cys His Glu Leu Ile Ile Pro Arg Cys Lys Ile Gly Val Cys Val
            20                  25                  30

Cys Leu Pro
        35

<210> SEQ ID NO 735
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 735

Val Tyr Leu Cys Glu Asp Asp Glu Asp Cys His Ile Met Pro Cys Met
1               5                   10                  15

Val Pro Glu Tyr Ala Lys Cys Ile Arg Met Ile Cys Gln Cys Cys
            20                  25                  30

<210> SEQ ID NO 736
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 736

Phe Lys Thr Ala Ile Thr Cys Asp Cys Asn Glu Asp Cys Leu Asn Phe
1               5                   10                  15

Phe Thr Pro Leu Asp Asn Leu Lys Cys Ile Asp Asn Val Cys Glu Val
            20                  25                  30

Phe Met

<210> SEQ ID NO 737
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 737

Glu Lys Glu Cys Ile Thr Asp Asp Cys Asn Arg Lys Tyr Pro Met
1               5                   10                  15

His Ala Asn Arg Gly Leu Gln Cys Leu Asn Gly Glu Cys Lys Ser Ser
            20                  25                  30

Arg Ile Ile Lys Ser Arg
        35

<210> SEQ ID NO 738
<211> LENGTH: 20
<212> TYPE: PRT
<213> ORGANISM: Artificial sequence
<220> FEATURE:
```

<223> OTHER INFORMATION: Peptide derived from Medicago truncatula

<400> SEQUENCE: 738

Met Arg Val Leu Cys Gly Arg Asp Gly Arg Cys Pro Lys Phe Met Cys
1               5                   10                  15

Arg Thr Phe Leu
            20

<210> SEQ ID NO 739
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 739

Gly Arg Tyr Thr Thr Pro Trp Cys Val Arg Asp Ile Asp Cys Pro Lys
1               5                   10                  15

Glu Lys Cys Lys His Pro Phe Lys Pro Arg Cys Leu Thr His Ser Cys
            20                  25                  30

Val Cys Arg Leu Trp Gly Ser Gln Asp Val Ile
        35                  40

<210> SEQ ID NO 740
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 740

Lys Asn Ile Cys Ile Asp Asp Val His Cys Gln Lys Tyr Lys Cys Ser
1               5                   10                  15

Pro Gly Leu Tyr Pro Thr Cys Ile Asn Gly Trp Cys Glu Cys Lys
            20                  25                  30

<210> SEQ ID NO 741
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 741

Tyr Glu Lys Ile Ser Cys Gln Asn Asp Phe Asp Cys Pro Glu Ser Met
1               5                   10                  15

Cys Glu Phe Gly Met Ile Arg Arg Cys Ile Ser Tyr Lys Cys Gln Cys
            20                  25                  30

His Glu Ala Tyr
            35

<210> SEQ ID NO 742
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 742

Gln Lys Ile Arg Arg Cys Phe Asn Asp Ala His Cys Pro Pro Asp Met
1               5                   10                  15

Cys Thr Pro Gly Val Ile Pro Lys Cys Lys Phe Thr Ile Cys Lys Cys
            20                  25                  30

<210> SEQ ID NO 743
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 743

Ile Pro Met Ile His Pro Leu Leu Tyr Lys Lys Arg Val Val Pro Asn
1               5                   10                  15

Cys Gln Thr Ile Val Asp Cys Pro Asp Asn Met Cys Thr His Pro Lys
            20                  25                  30

Glu Val Tyr Cys Ile Gly Tyr Arg Cys Tyr Cys Leu Lys
        35                  40                  45

<210> SEQ ID NO 744
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 744

Asn Ile Met Asn Cys Gln Ser Thr Phe Asp Cys Pro Arg Asp Met Cys
1               5                   10                  15

Ser His Ile Arg Asp Val Ile Cys Ile Phe Lys Lys Cys Lys Cys Ala
            20                  25                  30

Gly Gly Arg Tyr Met Pro Gln Val Pro
        35                  40

<210> SEQ ID NO 745
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 745

Ser Ile Pro Asp Val Leu Pro Cys Leu Phe Ser Asn Glu Cys Pro Pro
1               5                   10                  15

Asp Leu Cys Pro Ile Asp Leu Phe Pro Lys Cys Ile Asn Leu Ser Cys
            20                  25                  30

Gln Cys Ser Ala Glu Phe Tyr Asn Ile Asp
        35                  40

<210> SEQ ID NO 746
<211> LENGTH: 30
<212> TYPE: PRT
<213> ORGANISM: Artificial sequence
<220> FEATURE:
<223> OTHER INFORMATION: Peptide derived from Medicago truncatula

<400> SEQUENCE: 746

Lys Val Leu Cys Gly Arg Asp Gly Thr Cys Pro Arg Phe Met Cys Gly
1               5                   10                  15

Pro Gly Ile Ile Pro Lys Cys Val Gly Arg Tyr Cys Glu Cys
            20                  25                  30

<210> SEQ ID NO 747
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 747

Lys Glu Asp Gly Ser Val Glu Cys Ile Ala Asn Ile Asp Cys Pro Gln
1               5                   10                  15

Ile Phe Met Leu Pro Phe Val Met Arg Cys Ile Asn Phe Arg Cys Gln
            20                  25                  30

Ile Val Asn Ser Glu Asp Thr
            35

<210> SEQ ID NO 748
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 748

Trp Thr Cys Val Glu Asp Ser Asp Cys Pro Ala Asn Ile Cys Gln Pro
1               5                   10                  15

Pro Met Gln Arg Met Cys Phe Tyr Gly Glu Cys Ala Cys Val Arg Ser
            20                  25                  30

Lys Phe Cys Thr
            35

<210> SEQ ID NO 749
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 749

Val Ala Ala Phe Leu Arg Cys Asp Phe Asp Leu Asp Cys Pro Pro Lys
1               5                   10                  15

Met Cys Tyr Ser His Leu Tyr Phe Val Pro Met Cys Val Asp Asn His
            20                  25                  30

Cys Asp Cys Thr Gln Trp Lys Asp Ile Ile Pro Thr Ile Pro
        35                  40                  45

<210> SEQ ID NO 750
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 750

Pro Ile Arg Cys Asn Arg Val Ser Asp Cys Pro Lys Ile Arg Cys Asn
1               5                   10                  15

Ile Gly Phe Val Leu Arg Cys Leu Tyr Asn Gln Cys Lys Cys Val Arg
            20                  25                  30

Ile Thr Gln Leu Val Asp Tyr Val Leu Lys
        35                  40

<210> SEQ ID NO 751
<211> LENGTH: 60
<212> TYPE: PRT
<213> ORGANISM: Artificial sequence
<220> FEATURE:
<223> OTHER INFORMATION: Peptide derived from Medicago truncatula

<400> SEQUENCE: 751

Arg Ile Thr His Glu Thr Leu Pro Leu Pro Val Ser Lys Pro Ile Pro

```
                 1               5                  10                 15
Ile Leu Gly Gly Glu Cys Ile Ser Asp Ala Asp Cys Lys His Pro Glu
                    20                  25                  30

Cys Asp Asn Cys Arg Gly Val Cys Leu Asn Ser Arg Cys Ile Cys Met
            35                  40                  45

Ala Arg Ser Gly Trp Thr Tyr Thr Ile Pro Gln Asn
        50                  55                  60

<210> SEQ ID NO 752
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 752

Lys Arg Glu Cys Asp Thr Asn Phe Asp Cys Gln Gln Lys Phe Ser Thr
1               5                   10                  15

Gln Ala Glu Asp Leu Leu Trp Cys Ile Arg Gly Tyr Cys Met Ser Ile
            20                  25                  30

Pro Asn

<210> SEQ ID NO 753
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 753

Leu His Cys Asn Asn Asp Asn Glu Cys Pro Pro Ser Thr Trp Lys Pro
1               5                   10                  15

Phe Val Arg Cys Lys Met Asn Arg Cys Ile Tyr Ser Arg Val Gln Pro
            20                  25                  30

Pro Trp Ala Cys
        35

<210> SEQ ID NO 754
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 754

Leu Ile Glu Glu Cys Val Thr Asp Ala Asp Cys Tyr Lys Ile Tyr Pro
1               5                   10                  15

Glu Ala Ser Phe Leu His Met Phe Cys Ile Asp Gly Val Cys Lys Thr
            20                  25                  30

Pro Ile Pro Leu
        35

<210> SEQ ID NO 755
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 755

Met Asp Ile Val Asp Lys Ile Asp Glu Cys Glu Ser Asn Val Asp Cys
1               5                   10                  15
```

Pro Lys Ser Tyr Ile Ile Asn Trp Asp Lys Asn Tyr Val His Lys Cys
            20                  25                  30

Ile Asn Asn Arg Cys Glu Trp Ile Lys Ile Arg Arg
            35                  40                  45

<210> SEQ ID NO 756
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 756

Asp Leu Gly Cys Val Thr Asp Ala Asp Cys Lys Asp Lys Phe Pro Gly
1               5                   10                  15

Asn Lys Tyr Pro Ile Lys Cys Ile Asn Gly Ile Cys Lys Ser Val Pro
            20                  25                  30

Asn

<210> SEQ ID NO 757
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 757

Glu Cys Ile Ser Asp Thr Asp Cys Asn Val Leu Tyr Pro Met Tyr Ile
1               5                   10                  15

Asn Arg Arg Leu Arg Cys Ile Gln Gly Ile Cys His Thr Thr Thr Ala
            20                  25                  30

Arg Arg Arg
        35

<210> SEQ ID NO 758
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 758

Val Lys Asn Ile Asn Arg Glu Cys Thr Gln Thr Ser Asp Cys Tyr Lys
1               5                   10                  15

Lys Tyr Pro Phe Ile Pro Trp Gly Lys Val Ala Cys Val Lys Gly Arg
            20                  25                  30

Cys Arg Leu Asp Met
        35

<210> SEQ ID NO 759
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 759

Asn Asn Ile Glu Asp Asp Ile Phe Cys Ile Thr Asp Asn Asp Cys Pro
1               5                   10                  15

Pro Asn Thr Leu Val Gln Arg Tyr Arg Cys Ile Asn Gly Lys Cys Asn
            20                  25                  30

Leu Ser Phe Val Ser Tyr Gly
        35

```
<210> SEQ ID NO 760
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 760

Ala Ile His Cys Asn Asp Val Asn Asp Cys Pro Pro Asp Ile Ser Asp
1               5                   10                  15

Pro Phe Val Arg Cys Glu Ser Asn Arg Cys Ile Tyr Ser Arg Leu Glu
            20                  25                  30

Pro Pro Phe Gly Cys
        35

<210> SEQ ID NO 761
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 761

Val Ser Ile Thr Gly Asn Leu Ala Arg Ala Ser Arg Lys Lys Pro Val
1               5                   10                  15

Asp Val Ile Pro Cys Ile Tyr Asp His Asp Cys Pro Arg Lys Leu Tyr
            20                  25                  30

Phe Leu Glu Arg Cys Val Gly Arg Val Cys Lys Tyr Leu
        35                  40                  45

<210> SEQ ID NO 762
<211> LENGTH: 62
<212> TYPE: PRT
<213> ORGANISM: Artificial sequence
<220> FEATURE:
<223> OTHER INFORMATION: Peptide derived from Medicago truncatula

<400> SEQUENCE: 762

Asp Asp Asn Lys Leu Leu Leu Ser Phe Ile Glu Gly Phe Leu Cys
1               5                   10                  15

Phe Lys Asp Ser Asp Cys Pro Tyr Asn Met Cys Pro Ser Pro Leu Lys
            20                  25                  30

Glu Met Cys Tyr Phe Ile Lys Cys Val Cys Gly Val Tyr Gly Pro Ile
        35                  40                  45

Arg Glu Arg Arg Leu Tyr Gln Ser His Asn Pro Met Ile Gln
    50                  55                  60

<210> SEQ ID NO 763
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 763

Glu Lys Glu Cys Ala Asn Asp Ile Asp Cys Tyr Lys Ile Phe Leu Gly
1               5                   10                  15

Pro Pro Leu Ile Pro Met Lys Cys Ile Asp Gly Glu Cys Lys Arg Ile
            20                  25                  30

Thr
```

-continued

<210> SEQ ID NO 764
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 764

Glu Lys Glu Cys Asp Thr Asp Ala Asp Cys Arg Lys Lys Phe Ala Gly
1               5                   10                  15

Ala Asn Gln His Leu Leu Trp Cys Asn Asn Gly Tyr Cys Glu Cys His
            20                  25                  30

Thr His

<210> SEQ ID NO 765
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 765

Ser Tyr Tyr Gly Cys Glu Thr Asp Ala Asp Cys Pro Arg Ser Met Asn
1               5                   10                  15

Lys Asp Phe Tyr Leu Lys Cys Val Asp Lys Lys Cys Glu Trp Thr Ala
            20                  25                  30

Lys Ile

<210> SEQ ID NO 766
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 766

Ala Ile His Glu Cys Arg Ala His Ser His Cys Val Ala Arg Ile Asn
1               5                   10                  15

Cys Val Leu Pro Arg Lys Pro Gln Cys Arg Asn Tyr Ala Cys Gly Cys
            20                  25                  30

Tyr Asp Ser Asn Lys Tyr Arg
        35

<210> SEQ ID NO 767
<211> LENGTH: 45
<212> TYPE: PRT
<213> ORGANISM: Artificial sequence
<220> FEATURE:
<223> OTHER INFORMATION: Peptide derived from Medicago truncatula

<400> SEQUENCE: 767

Gln Glu Ile Glu Asn Gly Ile His Pro Cys Lys Lys Asn Glu Asp Cys
1               5                   10                  15

Asn His Met Cys Val Met Pro Gly Leu Pro Trp Cys His Glu Asn Asn
            20                  25                  30

Leu Cys Phe Cys Tyr Glu Asn Ala Tyr Gly Asn Thr Arg
        35                  40                  45

<210> SEQ ID NO 768
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 768

Tyr Glu Asp Phe Glu Lys Glu Ile Phe Asp Cys Lys Lys Asp Gly Asp
1               5                   10                  15

Cys Asp His Met Cys Val Thr Pro Gly Ile Pro Lys Thr Gly Tyr
            20                  25                  30

Val Cys Phe Cys Phe Glu Asn Leu
        35                  40

<210> SEQ ID NO 769
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 769

Trp Arg Cys Lys Lys Thr Asp Asp Cys Leu Lys Ile Glu Phe Cys Lys
1               5                   10                  15

Phe Pro Lys Ile Ala Arg Gly Thr Lys Pro Lys Phe Leu Phe Phe Glu
            20                  25                  30

Phe Gly Thr Gly Phe Cys Thr Trp Asp Asp
        35                  40

<210> SEQ ID NO 770
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 770

Thr Phe Arg Thr Arg Leu Pro Cys Glu Lys Asp Asp Cys Pro Glu
1               5                   10                  15

Ala Phe Leu Pro Pro Val Met Lys Cys Val Asn Arg Phe Cys Gln Tyr
            20                  25                  30

Glu Ile Leu Glu
        35

<210> SEQ ID NO 771
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 771

Asp Ile Arg Cys Arg Phe Tyr Tyr Asp Cys Pro Arg Leu Glu Tyr His
1               5                   10                  15

Phe Cys Glu Cys Ile Glu Asp Phe Cys Ala Tyr Ile Arg Leu Asn
            20                  25                  30

<210> SEQ ID NO 772
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 772

Tyr Val Asn Cys Glu Thr Asp Ala Asp Cys Pro Pro Ser Thr Arg Val
1               5                   10                  15

Lys Arg Phe Lys Cys Val Lys Gly Glu Cys Arg Trp Thr Arg Met Ser

```
                    20                  25                  30

Tyr Ala

<210> SEQ ID NO 773
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 773

Asp Asp Gly Ser Phe Cys Phe Lys Asp Ser Asp Cys Pro Asp Glu Met
1               5                   10                  15

Cys Pro Ser Pro Leu Lys Glu Met Cys Tyr Phe Leu Gln Cys Lys Cys
                20                  25                  30

Gly Val Asp Thr Ile
            35

<210> SEQ ID NO 774
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 774

Tyr Leu Lys Phe Glu Cys Lys Thr Asp Asp Cys Gln Lys Ser Leu
1               5                   10                  15

Leu Lys Thr Tyr Val Trp Lys Cys Val Lys Asn Glu Cys Tyr Phe Phe
                20                  25                  30

Ala Lys Lys
        35

<210> SEQ ID NO 775
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 775

Leu Pro Ile Ser Cys Lys Asp His Phe Glu Cys Arg Arg Lys Ile Asn
1               5                   10                  15

Ile Leu Arg Cys Ile Tyr Arg Gln Glu Lys Pro Met Cys Ile Asn Ser
                20                  25                  30

Ile Cys Thr Cys Val Lys Leu Leu
            35                  40

<210> SEQ ID NO 776
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 776

Arg Ile Met Val Val Asn Pro Asn Asn Pro Cys Val Thr Asp Ala Asp
1               5                   10                  15

Cys Gln Arg Tyr Arg His Lys Leu Ala Thr Arg Met Ile Cys Asn Gln
                20                  25                  30

Gly Phe Cys Leu Met Asp Phe Thr His Asp Pro Tyr Ala Pro Ser Leu
            35                  40                  45
```

-continued

Pro

<210> SEQ ID NO 777
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 777

```
Ala Arg Leu Val Phe Val Asn Pro Glu Lys Pro Cys Val Thr Asp Ala
1               5                   10                  15

Asp Cys Asp Arg Tyr Arg His Glu Ser Ala Ile Tyr Ser Asp Met Phe
            20                  25                  30

Cys Lys Asp Gly Tyr Cys Phe Ile Asp Tyr His His Asp Pro Tyr Pro
        35                  40                  45
```

<210> SEQ ID NO 778
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 778

```
Asn Val Glu Asp Phe Val Gly Gly Ser Asn Asp Glu Cys Val Tyr Pro
1               5                   10                  15

Asp Val Phe Gln Cys Ile Asn Asn Ile Cys Lys Cys Val Ser His His
            20                  25                  30

Arg Thr
```

<210> SEQ ID NO 779
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 779

```
Leu Ile Glu Cys Glu Ile Asp Leu Asp Cys Pro Lys Ser Tyr Ile Lys
1               5                   10                  15

Leu Trp Asp Arg Asn Tyr Ala His Arg Cys Val Asn Asn Ile Cys Glu
            20                  25                  30

Trp Val Lys Lys Pro Arg Ile Tyr
        35                  40
```

<210> SEQ ID NO 780
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 780

```
Glu Ile Asp Leu Asp Cys Pro Lys Ser Tyr Ile Lys Leu Trp Asp Lys
1               5                   10                  15

Asn Tyr Ala His Arg Cys Val Asn Asn Ile Cys Glu Trp Val Lys Lys
            20                  25                  30

Pro Arg Ile Tyr
        35
```

<210> SEQ ID NO 781
<211> LENGTH: 34

```
<212> TYPE: PRT
<213> ORGANISM: Artificial sequence
<220> FEATURE:
<223> OTHER INFORMATION: Peptide derived from Medicago truncatula

<400> SEQUENCE: 781

Gln Met Ile Asn Phe Ser Gly Cys Lys Arg Asp Lys Asp Cys Pro Gln
1               5                   10                  15
Phe Arg Gly Val Asn Ile Arg Cys Arg Ser Gly Phe Cys Thr Pro Ile
            20                  25                  30
Asp Ser

<210> SEQ ID NO 782
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 782

Ser Phe Ser Gln Ile Phe Asn Ser Ala Cys Lys Thr Asp Lys Asp Cys
1               5                   10                  15
Pro Lys Phe Gly Arg Val Asn Val Arg Cys Arg Lys Gly Asn Cys Val
            20                  25                  30
Pro Ile

<210> SEQ ID NO 783
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 783

Gly Ile Arg Lys Lys Glu Cys Arg Gln Asp Ser Asp Cys Pro Ser Tyr
1               5                   10                  15
Phe Cys Glu Lys Leu Thr Ile Ala Lys Cys Ile His Ser Thr Cys Leu
            20                  25                  30
Cys Lys

<210> SEQ ID NO 784
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 784

Gly Ile Arg Arg Phe Glu Cys Arg Gln Asp Ser Asp Cys Pro Ser Tyr
1               5                   10                  15
Phe Cys Glu Lys Leu Thr Val Pro Lys Cys Phe Trp Ser Lys Cys Tyr
            20                  25                  30
Cys Lys

<210> SEQ ID NO 785
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 785

Leu Tyr Glu Pro Leu Tyr Asn Phe Arg Arg Asp Pro Asp Cys Arg Arg
```

```
                1               5                  10                 15
Asn Ile Asp Cys Pro Ser Tyr Leu Cys Val Ala Pro Lys Val Pro Arg
                        20                 25                 30

Cys Ile Met Phe Glu Cys His Cys Lys Asp Ile Pro Ser Asp His
                35                 40                 45
```

<210> SEQ ID NO 786
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 786

```
Tyr Arg Glu Pro Phe Ser Ser Phe Thr Glu Gly Pro Thr Cys Lys Glu
1               5                  10                 15

Asp Ile Asp Cys Pro Ser Ile Ser Cys Val Asn Pro Gln Val Pro Lys
                        20                 25                 30

Cys Ile Met Phe Glu Cys His Cys Lys Tyr Ile Pro Thr Thr Leu Lys
                35                 40                 45
```

<210> SEQ ID NO 787
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 787

```
Ala Arg Phe Glu Cys Arg Glu Asp Ser His Cys Val Thr Arg Ile Lys
1               5                  10                 15

Cys Val Leu Pro Arg Lys Pro Glu Cys Arg Asn Tyr Ala Cys Gly Cys
                        20                 25                 30

Tyr Asp Ser Asn Lys Tyr Arg
                35
```

<210> SEQ ID NO 788
<211> LENGTH: 52
<212> TYPE: PRT
<213> ORGANISM: Artificial sequence
<220> FEATURE:
<223> OTHER INFORMATION: Peptide derived from Medicago truncatula

<400> SEQUENCE: 788

```
Ala His Phe Pro Cys Val Thr Asp Asp Cys Pro Lys Pro Val Asn
1               5                  10                 15

Lys Leu Arg Val Ile Lys Cys Ile Asp His Ile Cys Gln Tyr Ala Arg
                        20                 25                 30

Asn Leu Pro Asp Phe Ala Ser Glu Ile Ser Glu Ser Thr Lys Met Pro
                35                 40                 45

Cys Lys Gly Glu
        50
```

<210> SEQ ID NO 789
<211> LENGTH: 74
<212> TYPE: PRT
<213> ORGANISM: Artificial sequence
<220> FEATURE:
<223> OTHER INFORMATION: Peptide derived from Medicago truncatula

<400> SEQUENCE: 789

```
Glu Thr Leu Ser Leu Thr His Pro Lys Cys His His Ile Met Leu Pro
1               5                  10                 15
```

```
Ser Leu Phe Ile Thr Glu Val Phe Gln Arg Val Thr Asp Asp Gly Cys
        20                  25                  30

Pro Lys Pro Val Asn His Leu Arg Val Val Lys Cys Ile Glu His Ile
        35                  40                  45

Cys Glu Tyr Gly Tyr Asn Tyr Arg Pro Asp Phe Ala Ser Gln Ile Pro
 50                  55                  60

Glu Ser Thr Lys Met Pro Arg Lys Arg Glu
 65                  70

<210> SEQ ID NO 790
<211> LENGTH: 71
<212> TYPE: PRT
<213> ORGANISM: Artificial sequence
<220> FEATURE:
<223> OTHER INFORMATION: Peptide derived from Medicago truncatula

<400> SEQUENCE: 790

Glu Glu Cys Val Thr Asp Ala Asp Cys Asp Leu Tyr Pro Asp Ile
 1               5                  10                  15

Arg Lys Pro Leu Met Cys Ser Ile Gly Glu Cys Tyr Ser Leu Tyr Lys
        20                  25                  30

Gly Lys Phe Ser Leu Ser Ile Ile Ser Lys Thr Ser Phe Ser Leu Met
        35                  40                  45

Val Tyr Asn Val Val Thr Leu Val Ile Cys Leu Arg Leu Ala Tyr Ile
 50                  55                  60

Ser Leu Leu Leu Lys Phe Leu
 65                  70

<210> SEQ ID NO 791
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 791

Glu Arg Glu Cys Val Thr Asp Asp Asp Cys Lys Leu Tyr Pro Thr
 1               5                  10                  15

Asn Glu Tyr Arg Met Met Cys Asp Ser Gly Tyr Cys Met Asn Leu Leu
        20                  25                  30

Asn Gly Lys Ile Ile Tyr Leu Leu Cys Leu Lys Lys Lys Phe Leu
        35                  40                  45

Ile Ile Ile Ser Val Leu Leu
 50                  55

<210> SEQ ID NO 792
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 792

Val Ser Tyr Phe Ser Tyr Phe Ser Thr Tyr Ile Ile Glu Cys Lys Thr
 1               5                  10                  15

Asp Asn Asp Cys Pro Ile Ser Gln Leu Lys Ile Tyr Ala Trp Lys Cys
        20                  25                  30

Val Lys Asn Gly Cys His Leu Phe Asp Val Ile Pro Met Met Tyr Glu
        35                  40                  45
```

-continued

<210> SEQ ID NO 793
<211> LENGTH: 64
<212> TYPE: PRT
<213> ORGANISM: Artificial sequence
<220> FEATURE:
<223> OTHER INFORMATION: Peptide derived from Medicago truncatula

<400> SEQUENCE: 793

Arg Leu Asn Thr Thr Phe Arg Pro Leu Asn Phe Lys Met Leu Arg Phe
1               5                   10                  15

Trp Gly Gln Asn Arg Asn Ile Met Lys His Arg Gly Gln Lys Val His
            20                  25                  30

Phe Ser Leu Ile Leu Ser Asp Cys Lys Thr Asn Lys Asp Cys Pro Lys
        35                  40                  45

Leu Arg Arg Ala Asn Val Arg Cys Arg Lys Ser Tyr Cys Val Pro Ile
    50                  55                  60

<210> SEQ ID NO 794
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 794

Tyr Leu Cys Val Thr Asp Ser His Cys Pro Pro His Met Cys Pro Pro
1               5                   10                  15

Gly Met Glu Pro Arg Cys Val Arg Arg Met Cys Lys Cys Leu Pro Ile
            20                  25                  30

Gly Trp Arg Lys Tyr Phe Val Pro
        35                  40

<210> SEQ ID NO 795
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 795

Glu Ser Lys Leu Glu Gln Thr Cys Ser Glu Asp Phe Glu Cys Tyr Ile
1               5                   10                  15

Lys Asn Pro His Val Pro Phe Gly His Leu Arg Cys Phe Glu Gly Phe
            20                  25                  30

Cys Gln Gln Leu Asn Gly Pro Ala
        35                  40

<210> SEQ ID NO 796
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 796

His Asn Cys Thr Asp Ile Ser Asp Cys Ser Ser Asn His Cys Ser Tyr
1               5                   10                  15

Glu Gly Val Ser Leu Cys Met Asn Gly Gln Cys Ile Cys Ile Tyr Glu
            20                  25                  30

<210> SEQ ID NO 797
<211> LENGTH: 47
<212> TYPE: PRT
<213> ORGANISM: Artificial sequence

```
<220> FEATURE:
<223> OTHER INFORMATION: Peptide derived from Medicago truncatula

<400> SEQUENCE: 797

Glu Ile Asp Ala Asp Cys Pro Gln Ile Cys Met Pro Pro Tyr Glu Val
1               5                   10                  15

Arg Cys Val Asn His Arg Cys Gly Trp Val Asn Thr Asp Asp Ser Leu
            20                  25                  30

Phe Leu Thr Gln Glu Phe Thr Arg Ser Lys Gln Tyr Ile Ile Ser
        35                  40                  45

<210> SEQ ID NO 798
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 798

Lys Lys Lys Arg Tyr Ile Glu Cys Glu Thr His Glu Asp Cys Ser Gln
1               5                   10                  15

Val Phe Met Pro Pro Phe Val Met Arg Cys Val Ile His Glu Cys Lys
            20                  25                  30

Ile Phe Asn Gly Glu His Leu Arg Tyr
        35                  40

<210> SEQ ID NO 799
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 799

Lys Thr Phe Leu Met Ala Glu Tyr Ile Lys Cys Asp Thr Asp Ala Asp
1               5                   10                  15

Cys Pro Ile Val Ile His His Ser Phe Tyr Lys Cys Ile Asp Asn Leu
            20                  25                  30

Cys Lys Arg Phe Arg Arg Gln Lys His Leu Val
        35                  40

<210> SEQ ID NO 800
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 800

Tyr Lys Thr Lys Thr Pro Cys Lys Ser Leu Asn Asp Cys Pro Lys Ala
1               5                   10                  15

Ile Lys Pro Ile Phe Val Lys Cys Leu Gly Asn Ile Cys Gln Tyr Ser
            20                  25                  30

Ile Gly Arg Ile
        35

<210> SEQ ID NO 801
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 801
```

-continued

Ala Phe Ala Gly Trp Ile Lys Cys Lys Val Asp Glu Asp Cys Pro Asn
1               5                   10                  15

Val Phe Thr Tyr Ser Tyr Tyr Lys Cys Val Asn Glu Leu Cys Glu Ile
                20                  25                  30

Phe Leu Arg Glu Ile Pro Lys Lys Pro Tyr Met
            35                  40

<210> SEQ ID NO 802
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 802

Gly Asn Thr Phe Leu Met Ala Asp Asn Ile Glu Cys Asp Thr Asp Ala
1               5                   10                  15

Gly Cys Pro Lys Met Val His His Ile Phe Tyr Lys Cys Ile Asp Asn
                20                  25                  30

Lys Cys Lys Gln Phe Arg Arg Ser
            35                  40

<210> SEQ ID NO 803
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 803

Tyr Ile Gln Cys Asp Phe Asp Ala Asp Cys Pro Glu Met Phe Arg His
1               5                   10                  15

Ile Phe Tyr Leu Cys Ile Asp Lys Leu Cys Arg Gln Phe Val Thr Leu
                20                  25                  30

<210> SEQ ID NO 804
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 804

Tyr Arg Thr Arg Ile Pro Cys Val Ser Asp Tyr Asp Cys Pro Lys Ala
1               5                   10                  15

Ser Tyr Pro Leu Phe Ile Lys Cys Ile Tyr Asn Phe Cys Glu Ile Trp
                20                  25                  30

Gly Ser Pro
            35

<210> SEQ ID NO 805
<211> LENGTH: 27
<212> TYPE: PRT
<213> ORGANISM: Artificial sequence
<220> FEATURE:
<223> OTHER INFORMATION: Peptide derived from Medicago truncatula

<400> SEQUENCE: 805

Asp Asp Asp Cys Pro Lys Val Pro Tyr Pro Leu Tyr Ile Lys Cys Glu
1               5                   10                  15

Asp Asn Phe Cys Asp Ile Trp Ala Ser Pro Tyr
                20                  25

```
<210> SEQ ID NO 806
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 806

Lys Arg Thr Asn Ile Pro Cys Phe Ser Asp Asp Cys Pro Lys Thr
1               5                   10                  15

Ser Pro Pro Leu Val Leu Lys Cys Asp Asp Tyr Phe Cys Arg Tyr Phe
            20                  25                  30

Arg Glu Lys Asn Leu Ile
        35

<210> SEQ ID NO 807
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 807

Lys Tyr Phe Gln Ile Ala Ser Pro Cys Val Asn Asp Lys Asp Cys Pro
1               5                   10                  15

Arg Phe Lys Asn Asn Asn Val Arg Cys Arg Lys Gly Phe Cys Val Asn
            20                  25                  30

Leu Cys Asn
        35

<210> SEQ ID NO 808
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 808

Val Tyr Asp Ser Lys Tyr Phe Gln Ile Ala Ser Pro Cys Val Asn Asp
1               5                   10                  15

Lys Asp Cys Pro Gln Phe Lys Asn Asn Asn Val Arg Cys Arg Arg Gly
            20                  25                  30

Phe Cys Val Asn Ser Gly Gly Ala Thr Gln Lys Cys Leu Gly Cys Pro
        35                  40                  45

Ser Leu Lys
    50

<210> SEQ ID NO 809
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 809

Ala Thr Pro Cys Thr Ser Asp Lys Asp Cys Arg Leu Glu Arg Tyr Asn
1               5                   10                  15

Val Trp Cys Ile Asn Gly Tyr Cys Lys Tyr Lys Phe Thr Pro Ile Asp
            20                  25                  30

<210> SEQ ID NO 810
<211> LENGTH: 32
<212> TYPE: PRT
```

-continued

<213> ORGANISM: Artificial sequence
<220> FEATURE:
<223> OTHER INFORMATION: Peptide derived from Medicago truncatula

<400> SEQUENCE: 810

Val Arg Ile Pro Cys Val Thr Val Ala Asp Cys Pro Pro Thr Ile Leu
1               5                   10                  15

Pro Val Phe Tyr Glu Cys Ile Asp Lys Phe Cys Met Leu His Ile Glu
            20                  25                  30

<210> SEQ ID NO 811
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 811

Lys Thr Thr Ile Pro Cys Lys Phe Asp Asn Asp Cys Pro Glu Ile Ser
1               5                   10                  15

Tyr Pro Leu Ile Leu Met Cys Ile Asp Asp Phe Cys Glu Tyr Leu Leu
            20                  25                  30

Ala

<210> SEQ ID NO 812
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 812

Ser Thr Ile Met Tyr Tyr Asp Val Pro Cys Glu Lys Asp Lys Asp Cys
1               5                   10                  15

Pro Ala Pro Pro Arg Phe Asn Ile Arg Cys Arg Lys Gly Tyr Cys Val
            20                  25                  30

Arg Ile

<210> SEQ ID NO 813
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 813

Val Glu Ile Pro Glu Thr Pro Cys Glu Ser Asp Ala Glu Cys Pro Tyr
1               5                   10                  15

Tyr Ser Pro Ser Leu Tyr Ala Arg Cys Ile Asp Gly Phe Cys Thr Leu
            20                  25                  30

Phe Leu Ser
        35

<210> SEQ ID NO 814
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 814

Glu Met Thr Thr Thr Ala Thr Ile Pro Cys Thr Ser Ile Asp Asp Cys
1               5                   10                  15

Pro Lys Met Pro Leu Val Val Lys Cys Ile Asp Asn Phe Cys Asn Tyr
            20                  25                  30

Phe Glu Ile Lys
            35

<210> SEQ ID NO 815
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 815

Gly Lys Thr His Tyr Ser Glu Ile Ile Glu Cys Lys Asn Asp Ala Asp
1               5                   10                  15

Cys Pro Ile Gly Tyr Lys Cys Ile Asp Glu Met Cys Lys Tyr Gly
            20                  25                  30

<210> SEQ ID NO 816
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 816

Ile Tyr Phe Arg Lys Pro Pro Pro Cys Ile Thr Asp Lys Asp Cys Pro
1               5                   10                  15

Gln Met Lys Ile Asn Asn Val Arg Cys Arg Lys Gly Phe Cys Ile Gln
            20                  25                  30

Ile His Lys Phe Thr Pro
            35

<210> SEQ ID NO 817
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 817

Gln Ile Met Phe Ser Asp Cys Lys Thr Asp Lys Asp Cys Pro Gln Phe
1               5                   10                  15

Arg Arg Ala Asn Ile Arg Cys Arg Lys Gly Gln Cys Val Lys Leu
            20                  25                  30

<210> SEQ ID NO 818
<211> LENGTH: 40
<212> TYPE: PRT
<213> ORGANISM: Artificial sequence
<220> FEATURE:
<223> OTHER INFORMATION: Peptide derived from Medicago truncatula

<400> SEQUENCE: 818

Phe Leu Thr Gln Cys Lys Phe Ser Cys Lys Thr Ile Phe Asn Cys Pro
1               5                   10                  15

Ala Leu Val Tyr His Gln His Ala Ser Cys Leu Asp Gly Phe Cys Trp
            20                  25                  30

Tyr Glu Glu Lys Phe Glu Asp Glu
            35                  40

<210> SEQ ID NO 819
<211> LENGTH: 39
<212> TYPE: PRT

-continued

```
<213> ORGANISM: Artificial sequence
<220> FEATURE:
<223> OTHER INFORMATION: Peptide derived from Medicago truncatula

<400> SEQUENCE: 819

Val Tyr Asp Ser Ile Pro Tyr Val Asn Ser Gly Pro Cys Val Thr Asp
1               5                   10                  15

Lys Asp Cys Pro Lys Val Ser Gln Tyr Asn Ile Arg Cys Arg Lys Gly
            20                  25                  30

Gln Cys Ala Arg Ile Arg Val
        35

<210> SEQ ID NO 820
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 820

Thr Asn Phe Lys Arg Lys Gln Ile Pro Phe Tyr Phe Ile Arg Glu
1               5                   10                  15

Phe Tyr Pro Cys Phe Ile Asp Gly Asn Cys Pro Arg Asn Met Cys Lys
            20                  25                  30

Val Tyr Gln Ile Pro Lys Cys Val Gly Gly Leu Cys Arg Cys Ile Pro
        35                  40                  45

Leu Arg Cys Gly Arg Trp Glu Lys
    50                  55

<210> SEQ ID NO 821
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 821

His Ile Glu Cys Lys Asn Asp Phe Asp Cys Pro Lys Asn Met Cys Leu
1               5                   10                  15

Ala Pro Arg Val Ala Trp Cys Val Asn Asn Lys Cys Glu Cys Val Leu
            20                  25                  30

Thr Tyr Gly Pro Lys Tyr Ser Thr Met Lys Glu Lys Leu Leu Gln Lys
        35                  40                  45

Glu Lys Ile
    50

<210> SEQ ID NO 822
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 822

Val Pro His Thr Asp Ile Pro Cys Glu Pro Asp Ala Asp Cys Pro Lys
1               5                   10                  15

Ser Leu His Glu Tyr Phe Glu Met Lys Cys Ile Asp Lys Lys Cys Glu
            20                  25                  30

Trp Ser Arg Lys Thr Ser Leu Ile Pro
        35                  40

<210> SEQ ID NO 823
```

```
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 823

Val Asp Ile Tyr Cys Glu Thr Asp Ala Asp Cys Pro Gln Ile Thr Asp
1               5                   10                  15

Trp Phe Tyr Val Val Lys Cys Val Asp His Lys Cys Glu Leu Thr Lys
            20                  25                  30

Lys Leu Arg Arg Leu Tyr Glu Tyr Gln Thr Gln Lys Ser Ala Glu Thr
        35                  40                  45

Pro Tyr Ile
    50

<210> SEQ ID NO 824
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 824

Glu Gln Cys Val Ser Asp Ala Asp Cys Gln Ile Lys Phe Pro Gly Pro
1               5                   10                  15

Arg Gln His Leu Leu Arg Cys Thr Gln Gly Asn Cys Val Met Leu Val
            20                  25                  30

Gly Gln Gly Lys Asn Tyr Phe Ser Ile Met Ser Lys Thr Leu Phe Ser
        35                  40                  45

Leu Leu Val Ile Ile Phe Leu Leu Leu
    50                  55

<210> SEQ ID NO 825
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 825

Leu His Asp Cys Glu Tyr Asp Asp Cys Pro Lys Ser Thr Ser Lys
1               5                   10                  15

Arg Thr Tyr Arg Cys Ile Asn Lys Lys Cys Arg Ser Tyr Phe Thr Arg
            20                  25                  30

Val Glu Lys
        35

<210> SEQ ID NO 826
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 826

Thr Thr Ser Cys Ile Thr Asp Asp Cys Pro Lys Ala Val Ser Phe
1               5                   10                  15

Leu Val Phe Lys Cys Ile Asp Asn Ile Cys Val Arg Val Glu Ile Leu
            20                  25                  30

<210> SEQ ID NO 827
<211> LENGTH: 34
```

```
<212> TYPE: PRT
<213> ORGANISM: Artificial sequence
<220> FEATURE:
<223> OTHER INFORMATION: Peptide derived from Medicago truncatula

<400> SEQUENCE: 827

Asn Tyr Asn Pro Pro Cys Val Ser Asp Lys Asp Cys Pro Ser Pro Lys
1               5                   10                  15

Ser Pro Lys Ser Asn Ile Arg Cys Arg Gln Gly Tyr Cys Val Asn Leu
            20                  25                  30

Tyr Ser

<210> SEQ ID NO 828
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 828

Val Arg Ile Pro Arg Pro Leu Ile Asp Pro Leu Asn Cys His Ile Asp
1               5                   10                  15

Ile His Cys Ile Tyr Lys Glu Cys Arg Arg Pro Phe Lys Pro Ser Cys
            20                  25                  30

Leu Asn Phe Lys Cys Asp Cys Gly Lys Glu
        35                  40

<210> SEQ ID NO 829
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 829

Gln Ile Ile Phe Arg Gln Cys Lys Thr Asp Lys Asp Cys Pro Lys Leu
1               5                   10                  15

Gly Arg Ala Asn Ile Arg Cys Arg Glu Gly Tyr Cys Val Arg Ile
            20                  25                  30

<210> SEQ ID NO 830
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 830

Thr Pro Ile Pro Cys Asn Thr Pro Ala Asp Cys Pro Lys Arg Val Cys
1               5                   10                  15

Ile Tyr Pro Leu Arg Ala Lys Cys Ile Asn Phe Asn Cys Glu Cys Asp
            20                  25                  30

Tyr Val Lys Lys
        35

<210> SEQ ID NO 831
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 831

Gly Asp Ile Pro Cys Glu Ser Arg Glu Gln Cys Pro Asn Thr Ala Thr
```

```
                1               5                  10                 15
Arg Arg Tyr Ala Cys Leu Asn Lys Leu Cys Tyr Cys Tyr Asp Asn Asn
                20                 25                 30

Tyr Pro Asn Gly Trp Asn Pro Phe Glu Pro
                35                 40

<210> SEQ ID NO 832
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 832

Phe Val Lys Cys Glu Thr Thr Asp Asp Cys Pro Lys Ser Asp Tyr Ile
1               5                  10                 15

Arg Gln Tyr Glu Cys Val Asn Asn Trp Cys Arg Leu Ala Arg Leu His
                20                 25                 30

Glu Phe Gln Pro Lys Lys Ser Thr Leu Thr Ser
                35                 40

<210> SEQ ID NO 833
<211> LENGTH: 82
<212> TYPE: PRT
<213> ORGANISM: Artificial sequence
<220> FEATURE:
<223> OTHER INFORMATION: Peptide derived from Medicago truncatula

<400> SEQUENCE: 833

Phe Thr Phe Ser Ile Leu Cys Gln Val Asn Ser Asp Cys Leu Gly Glu
1               5                  10                 15

Ile Cys Leu Pro Pro Lys Thr His Trp Cys Asn Lys Ile Leu Leu Glu
                20                 25                 30

Ile Tyr Ile Ser Cys His Leu Val Thr Met Leu Glu Pro Asn Asn Leu
                35                 40                     45

Tyr Leu Leu Pro Phe Leu Ile Ser Trp Thr Arg Asn Asn Leu Tyr Ile
            50                 55                 60

Ile Leu Gly Leu Ser Leu Phe Ser Arg Thr Asn Ser Leu Val Leu Ser
65                  70                 75                 80

Trp Arg

<210> SEQ ID NO 834
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 834

Tyr Pro Gly Cys Glu Thr Asp Ala Glu Cys Pro Lys Ile Tyr Glu Leu
1               5                  10                 15

Tyr Pro Leu Ile Tyr Lys Cys Glu Asn Lys Phe Cys Ile Leu Ser Gln
                20                 25                 30

Val Leu Pro Tyr Ile Val
                35

<210> SEQ ID NO 835
<211> LENGTH: 36
<212> TYPE: PRT
<213> ORGANISM: Artificial sequence
<220> FEATURE:
<223> OTHER INFORMATION: Peptide derived from Medicago truncatula
```

```
<400> SEQUENCE: 835

Phe Asn Pro Leu Ile Arg Gln Tyr Cys Val Thr Asp Lys Asp Cys Pro
1               5                   10                  15

Lys Phe Lys Lys Tyr Asn Ile Arg Cys Arg Lys Gly Phe Cys Val Gln
            20                  25                  30

Val Asn Gly Gly
            35

<210> SEQ ID NO 836
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 836

Ala Gln Asn Asp Trp Met Lys Cys Lys Thr Asp Glu Cys Pro Lys
1               5                   10                  15

Val Ser Asn Pro Pro Leu Tyr Phe Lys Cys Ile Asp Arg Gly Cys Arg
            20                  25                  30

Ile Val Ile Lys Met Arg Phe
            35

<210> SEQ ID NO 837
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 837

Tyr Val Glu Cys Glu Thr Asp Ala Asp Cys Gln Pro Asn Met Cys Lys
1               5                   10                  15

Trp Pro Phe Ile Val Gln Cys Tyr Lys Asn Val Cys Ile Cys Val His
            20                  25                  30

His Thr Asn Pro Tyr Leu
            35

<210> SEQ ID NO 838
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 838

Asp Glu Cys Gln Ile Asp Ala Asp Cys Pro Lys Ser Gly Asn Leu Phe
1               5                   10                  15

Tyr Ile Tyr Lys Cys Ile Asn His Lys Cys Glu Leu Val Ala Ala His
            20                  25                  30

Leu Arg Phe Tyr
            35

<210> SEQ ID NO 839
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 839

Ile Leu Glu Cys Ile Phe Asp Ile Asp Cys Pro Thr Lys Lys Cys Ala
```

```
                1               5                  10                  15
Pro Pro Leu Val Ala Lys Cys Asp Met Tyr Glu Cys Tyr Cys Arg Cys
                        20                  25                  30

Pro Pro Asn Asn
            35

<210> SEQ ID NO 840
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 840

Met Val Ser Thr Asn Ala Tyr Ile His Arg Cys Ile His Gln Asp Asp
1               5                  10                  15

Cys Pro Lys Tyr Met Cys Glu Ile Ser Val Leu Pro Glu Cys Ile Asn
                        20                  25                  30

Gly Phe Cys Thr Cys Val
            35

<210> SEQ ID NO 841
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 841

Gln Lys Phe Asn Glu Cys Tyr Glu Asp Thr Asp Cys Pro Ile Gln Met
1               5                  10                  15

Cys Gly Tyr Pro Phe Asn Val Asp Cys Val Gly Asn Lys Cys Thr Cys
                        20                  25                  30

Val Tyr Asn Pro
            35

<210> SEQ ID NO 842
<211> LENGTH: 59
<212> TYPE: PRT
<213> ORGANISM: Artificial Sequence
<220> FEATURE:
<223> OTHER INFORMATION: Peptide derived from Medicago truncatula

<400> SEQUENCE: 842

Ala Tyr Tyr Glu Cys Ser Asn Asp Ser Ala Cys Gln Ala Thr Thr Lys
1               5                  10                  15

Cys Val Leu Pro Arg Val Pro Arg Cys Ile Lys Tyr Lys Cys Leu Cys
                        20                  25                  30

Gly Asn Ser Asn Gly Ser Gly Asn Arg Trp Ser Thr Arg Pro Asn Arg
            35                  40                  45

Ile Gln Lys Gly Ser Thr Glu Ser Asn Tyr Phe
        50                  55

<210> SEQ ID NO 843
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 843

Lys Ser Ile Cys Lys Val Asp Asp Asp Cys Pro Gln Arg Phe Val Met
1               5                  10                  15
```

```
Tyr Pro Leu Met Phe Met Cys Ile Lys Asn Ile Cys Arg Leu Val Asn
            20                  25                  30

Glu

<210> SEQ ID NO 844
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 844

Ala Thr Lys Glu Lys Phe His Ser Cys Val Asn Ala Asn Asp Cys Pro
1               5                   10                  15

Tyr Asp Phe Cys Ser Pro Pro Lys Tyr Ala Lys Cys Val Tyr Asn Ser
            20                  25                  30

Cys Tyr Cys Glu Asp Gln Gly Arg Leu
        35                  40

<210> SEQ ID NO 845
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 845

Met His Ile Glu Thr Val Thr Thr Cys Ile Tyr Asp Ser Asp Cys Pro
1               5                   10                  15

Glu Asp Met Cys Tyr Pro Pro Lys Lys Ser Phe Cys Ser Thr Phe Glu
            20                  25                  30

Ile Leu Ser Ile Glu Arg Lys Val Gly Val Cys Glu Cys Ile
        35                  40                  45

<210> SEQ ID NO 846
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 846

Val Arg Lys Pro Glu Cys Arg Gln Asn Ser Asp Cys Pro Pro Tyr Phe
1               5                   10                  15

Cys Ile Lys Pro Thr Val Pro Lys Cys Ile Lys Phe Lys Cys Leu Cys
            20                  25                  30

Lys

<210> SEQ ID NO 847
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 847

Leu Asn Gly Asn Arg His Gly Lys Asp Arg Cys Phe Lys Asp Ser Asp
1               5                   10                  15

Cys Pro Lys Tyr Met Cys Pro Ser Ser Leu Val Ala Lys Cys Ile Lys
            20                  25                  30

Lys Leu Cys Ser Cys Arg Lys Pro Gly Leu Gln Ile Gln Leu Asn Pro
        35                  40                  45
```

Lys

<210> SEQ ID NO 848
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 848

Lys Asn Ile Asp Glu Lys Cys Phe Arg Asp Asp Cys Ala Lys Asn
1               5                   10                  15

Met Cys Pro Ser Tyr Leu Val Val Lys Cys Val Asn Gly Ile Tyr Lys
            20                  25                  30

Cys Val Arg Pro
        35

<210> SEQ ID NO 849
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 849

Asn Cys Thr Phe Ile Gly Phe Gln Asp Asn Pro Cys Lys Thr Asp Asn
1               5                   10                  15

Asp Cys Arg Lys Val Arg Gly Val Asn Leu Arg Cys Arg Asn Gly His
            20                  25                  30

Cys Val Met Ile Leu Gln
        35

<210> SEQ ID NO 850
<211> LENGTH: 43
<212> TYPE: PRT
<213> ORGANISM: Artificial sequence
<220> FEATURE:
<223> OTHER INFORMATION: Peptide derived from Medicago truncatula

<400> SEQUENCE: 850

Ile Glu Gly Thr Met Ser Cys Phe His Asp Ala Asp Cys Val His Lys
1               5                   10                  15

Arg Cys Gln Leu Pro Gln Ile Pro Lys Cys Val Gly Lys Lys Cys Arg
            20                  25                  30

Cys Arg Gly Gln Tyr Gln Ala Asn Pro Met Gly
        35                  40

<210> SEQ ID NO 851
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 851

Glu Val His Arg Cys Ile Glu Tyr Thr Asp Cys Pro Glu Asp Met Cys
1               5                   10                  15

His Leu Pro Leu Val Val Val Cys His Asp His Ile Cys Lys Cys Leu
            20                  25                  30

Arg Leu Pro
        35

-continued

```
<210> SEQ ID NO 852
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 852

Ser Ala Phe Ser Gly Cys Met Asn Asp Ser Asp Cys Pro Asp Leu Phe
1               5                   10                  15

Cys Leu Pro Pro Leu Asp Met Lys Cys His Glu Leu Val Cys Lys Cys
            20                  25                  30

Arg

<210> SEQ ID NO 853
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 853

His Tyr Arg Glu Leu Ile Cys Lys Thr Asp Asn Cys Pro Arg Arg
1               5                   10                  15

Gly Thr Asn Lys Tyr Phe Ile His Lys Cys Ile Asp Tyr Arg Cys Gln
            20                  25                  30

Trp Ile Pro Arg
        35

<210> SEQ ID NO 854
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 854

Leu Lys Val Ile Ile Pro Ser Ser Thr Cys Asp Ser Asp Tyr Asp Cys
1               5                   10                  15

Leu Arg Tyr Glu Glu Ala Leu Asn Val Ile Thr Cys Cys Asn Asn Gly
            20                  25                  30

Leu Cys Val Met Phe Cys Pro Asp Phe Asp
        35                  40

<210> SEQ ID NO 855
<211> LENGTH: 26
<212> TYPE: PRT
<213> ORGANISM: Artificial sequence
<220> FEATURE:
<223> OTHER INFORMATION: Peptide derived from Medicago truncatula

<400> SEQUENCE: 855

Phe Glu Asp Ser Asp Cys Pro Tyr Asp Met Cys Tyr Ala Gly Phe Gln
1               5                   10                  15

Pro Lys Cys Val Asn Gly Trp Cys Asp Cys
            20                  25

<210> SEQ ID NO 856
<211> LENGTH: 48
<212> TYPE: PRT
<213> ORGANISM: Artificial sequence
<220> FEATURE:
<223> OTHER INFORMATION: Peptide derived from Medicago truncatula

<400> SEQUENCE: 856
```

```
Ile Asp Asp Ser Asp Cys Pro Tyr Asp Met Cys Asp Pro Gly Leu Leu
1               5                   10                  15

Pro Arg Cys Leu Asn Gly Trp Cys Asp Cys Ser Arg Phe Gln Pro Trp
                20                  25                  30

Pro Met Asp Ser Met Ser Ser Asn Leu Arg Glu Phe Thr Leu Pro Asn
            35                  40                  45
```

<210> SEQ ID NO 857
<211> LENGTH: 29
<212> TYPE: PRT
<213> ORGANISM: Artificial sequence
<220> FEATURE:
<223> OTHER INFORMATION: Peptide derived from Medicago truncatula

<400> SEQUENCE: 857

```
Asp Ser Asp Cys Pro Ser Phe Leu Cys Asp His Asp Gly Val Met Lys
1               5                   10                  15

Cys Phe Ser Asn Gly Cys Ser Cys Val Asp Pro Ser Asp
                20                  25
```

<210> SEQ ID NO 858
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 858

```
Ser Asn Pro Cys Val Ser Thr Arg Asp Cys Thr Thr His Thr Cys Asn
1               5                   10                  15

Pro Pro Leu Val Ala Arg Cys Ile Asn Leu Arg Cys Tyr Cys Gly Tyr
                20                  25                  30

Lys
```

<210> SEQ ID NO 859
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 859

```
Leu Leu Pro Cys Gly Thr Asp Asp Cys Ala Asn Asp Pro Cys Ile
1               5                   10                  15

Pro Pro Glu Tyr Pro His Cys His Met Glu Gln Cys His Cys Val
                20                  25                  30
```

<210> SEQ ID NO 860
<211> LENGTH: 85
<212> TYPE: PRT
<213> ORGANISM: Artificial sequence
<220> FEATURE:
<223> OTHER INFORMATION: Peptide derived from Medicago truncatula

<400> SEQUENCE: 860

```
Leu Tyr Val Cys Arg Ser Val Ser Asp Cys Pro Glu Asn Phe Cys Val
1               5                   10                  15

Pro Pro Leu Thr Ile Gln Cys Ile Asn Tyr Thr Cys Ile Cys Asp Asp
                20                  25                  30

Pro Pro Tyr Gly Glu Pro Glu Tyr Asp Asn Asn Asp Asp Phe Val Thr
            35                  40                  45

Leu Asn Arg Glu Lys Ala Lys Ile Lys Asn Glu Glu Met Met Met Arg
```

```
                    50                  55                  60
Glu Arg Asp Met Met Ile Glu Ile Glu Thr Tyr Ser Val Ala Asp Asp
 65                  70                  75                  80

Leu Asp Pro His Leu
                85

<210> SEQ ID NO 861
<211> LENGTH: 30
<212> TYPE: PRT
<213> ORGANISM: Artificial sequence
<220> FEATURE:
<223> OTHER INFORMATION: Peptide derived from Medicago truncatula

<400> SEQUENCE: 861

Leu Ile Phe Cys Phe Glu Asp Ile Asn Cys Pro Phe Asp Lys Cys Phe
 1               5                  10                  15

Pro Gln Leu Pro Lys Cys Ile Asn Ser Phe Cys Glu Cys Val
                20                  25                  30

<210> SEQ ID NO 862
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 862

Leu Ile Asp Cys Lys Thr Val Asp Asp Cys Pro Ser Ser Trp Thr Lys
 1               5                  10                  15

Ile Tyr Lys Cys Ile Asp Asn Lys Cys Arg Tyr Ser Val Val Lys Gly
                20                  25                  30

Leu Ile Ile
        35

<210> SEQ ID NO 863
<211> LENGTH: 30
<212> TYPE: PRT
<213> ORGANISM: Artificial sequence
<220> FEATURE:
<223> OTHER INFORMATION: Peptide derived from Medicago truncatula

<400> SEQUENCE: 863

Lys His Val Arg Asp Cys Pro Lys Gly Ile Trp Arg Ser Cys Arg Tyr
 1               5                  10                  15

Lys Cys Ile Asp Asn Lys Cys Val Phe Thr Tyr Trp Pro His
                20                  25                  30

<210> SEQ ID NO 864
<211> LENGTH: 51
<212> TYPE: PRT
<213> ORGANISM: Artificial sequence
<220> FEATURE:
<223> OTHER INFORMATION: Peptide derived from Medicago truncatula

<400> SEQUENCE: 864

Tyr Ile Leu Cys Lys Thr Val Asn Asp Cys Pro Pro Asn Thr Arg Asn
 1               5                  10                  15

Leu Arg Tyr Arg Cys Ile Asp Gly Lys Cys Lys Ser His Arg Val Leu
                20                  25                  30

Tyr Glu Trp Asp Glu Ser His Thr Gln Asp Ile Thr Ile Thr Pro Cys
            35                  40                  45

Ile Glu Glu
        50
```

-continued

```
<210> SEQ ID NO 865
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 865

Gln Asn Ile Asp Ser Gly Gly Asn Arg Arg Cys Phe Arg Asp Ser Asp
1               5                   10                  15

Cys Pro Lys Asn Met Cys Pro Ser Tyr Leu Val Val Lys Cys Leu Arg
            20                  25                  30

Ser Asn Cys Lys Cys Val Arg Pro Gly Leu Gln Val Arg Leu Asn Pro
        35                  40                  45

Asn

<210> SEQ ID NO 866
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 866

Leu Asn Gly His Gly Arg Asn Arg Cys Phe Arg Asp Ser Asp Cys Pro
1               5                   10                  15

Lys Val Met Cys Pro Ser Tyr Leu Val Thr Lys Cys Phe Lys Lys His
            20                  25                  30

Cys Arg Cys Arg Lys Pro Gly Leu Gln Val Gln Leu Asn Pro Lys
        35                  40                  45

<210> SEQ ID NO 867
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 867

Thr Asn Phe Glu Arg Lys Gln Ile Ser Phe Ser Phe Phe Met Lys Glu
1               5                   10                  15

Tyr Trp Pro Cys Val Thr Asp Asp Cys Pro Ser Asp Leu Cys Lys
            20                  25                  30

Lys Val Asp Gln Ile Pro Lys Cys Val Gly Gly Leu Cys Lys Cys Phe
        35                  40                  45

Pro Ile Arg Phe Gly Gln Trp Glu Arg
    50                  55

<210> SEQ ID NO 868
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 868

Leu Val Gln Asn Glu Cys Val Thr Asp Gly Asp Cys Arg Arg Leu Tyr
1               5                   10                  15

Pro His Leu Ile Pro Arg Tyr Pro Met Cys Asn Glu Gly Thr Cys Val
            20                  25                  30

Cys Ile Phe Glu
```

-continued

<210> SEQ ID NO 869
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 869

Gly Ile Arg Cys His Asp Val Ser Glu Cys Pro Lys Gly Leu Tyr Cys
1               5                   10                  15

Asn Val Gly Ser His Met Glu Cys Val Lys His Gln Cys Lys Cys Ile
            20                  25                  30

Lys Asn Phe Glu Pro Ile Asp Leu Ala
        35                  40

<210> SEQ ID NO 870
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 870

Ile Arg Thr Tyr Arg Glu Cys Glu Asn Ala Ser Asp Cys Tyr Ser Ile
1               5                   10                  15

Tyr Trp Arg Ala Pro Tyr Gly Thr Met Arg Cys Val Lys Gly His Cys
            20                  25                  30

Lys Gln Ile Lys Asp Val Lys Val Met Lys Phe Leu Tyr Cys Val
        35                  40                  45

<210> SEQ ID NO 871
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 871

Ile Ile Leu Cys Lys Asp His Phe Asp Cys Tyr Glu Asn Ile Arg Lys
1               5                   10                  15

Leu Arg Cys Asp Phe Asp Thr Glu Lys Pro Phe Cys Ile Ser Leu Asn
            20                  25                  30

Val Cys Gln Cys Ile Lys Gln
        35

<210> SEQ ID NO 872
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 872

Phe Arg Cys Leu Arg Asn Leu Asp Cys Pro Asp Ser Met Cys Ser Ser
1               5                   10                  15

Ala Tyr Thr Pro Arg Cys Arg His Arg Thr Cys Val Cys Leu Asn Asn
            20                  25                  30

Asp Glu Ile Lys Ile Leu
        35

<210> SEQ ID NO 873

```
<211> LENGTH: 32
<212> TYPE: PRT
<213> ORGANISM: Artificial sequence
<220> FEATURE:
<223> OTHER INFORMATION: Peptide derived from Medicago truncatula

<400> SEQUENCE: 873

Ala Ile Pro Cys Ile Thr Asp Ala Asn Cys Pro Cys Val Phe Pro Leu
1               5                   10                  15

Lys Pro Arg Cys Asn Phe Gly Tyr Cys Ile Cys Glu Glu Met Ile Pro
            20                  25                  30

<210> SEQ ID NO 874
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 874

Arg Gln Gly Cys Lys Ile Asp Tyr Asp Cys Ile Lys Val Val Cys Lys
1               5                   10                  15

Asp Gly His Ala Ala Arg Cys Ile Met Arg Arg Cys Glu Cys Val Glu
            20                  25                  30

Ile Leu Asn Pro Ile Asp Leu Gly Ser Thr
        35                  40

<210> SEQ ID NO 875
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 875

Gly Asn Tyr Lys Cys Gln Thr Asn Tyr Asp Cys Leu Arg Met Trp Cys
1               5                   10                  15

Pro Ile Gly Ile Ser Pro Arg Cys Ile Lys Arg Cys Lys Cys Ile
            20                  25                  30

Glu Thr Leu Val Gln
        35

<210> SEQ ID NO 876
<211> LENGTH: 52
<212> TYPE: PRT
<213> ORGANISM: Artificial sequence
<220> FEATURE:
<223> OTHER INFORMATION: Peptide derived from Medicago truncatula

<400> SEQUENCE: 876

Glu Glu Ile Ile Ile Ile Lys Cys Gln Thr Ala Lys Asp Cys Pro Asp
1               5                   10                  15

Ile Tyr Asn Leu Phe Pro Leu Val Tyr Lys Cys Ile Asp Asn Ile Cys
            20                  25                  30

Val Asp Val Arg Leu Glu Pro Pro Tyr Asp Met Ser Ile Ser Pro Lys
        35                  40                  45

Ser Val His Lys
    50

<210> SEQ ID NO 877
<211> LENGTH: 39
<212> TYPE: PRT
<213> ORGANISM: Artificial sequence
<220> FEATURE:
```

<223> OTHER INFORMATION: Peptide derived from Medicago truncatula

<400> SEQUENCE: 877

Ala Tyr Val Thr Arg Phe Trp Cys Tyr Arg Asp Leu Asp Cys Arg Lys
1               5                   10                  15

Asp Met Cys Lys Pro Pro Phe Asn Pro Arg Cys His Asn His Ile Cys
            20                  25                  30

Ile Cys Arg Leu Trp Gly Leu
        35

<210> SEQ ID NO 878
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 878

Thr Thr Arg Cys Val Arg Asn Ser Asp Cys Arg His His Ile Cys Met
1               5                   10                  15

Tyr Pro Leu Val Pro Arg Cys Lys Tyr Pro Leu Cys Arg Cys Val
            20                  25                  30

<210> SEQ ID NO 879
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 879

His Lys Arg Cys Arg Val Asp Phe Asp Cys Arg Met Arg Met Cys Val
1               5                   10                  15

Tyr Pro Thr Val Ser Val Cys Ile Asp Arg Leu Cys Arg Cys Arg Arg
            20                  25                  30

Pro Pro Asn Met
        35

<210> SEQ ID NO 880
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 880

Gln Lys Arg Cys Lys Glu Asp Phe Asp Cys Arg Ile Arg Ser Cys Ala
1               5                   10                  15

Tyr Pro Leu Ile Pro Val Cys Ile Asp Pro Phe Cys Arg Cys Arg Arg
            20                  25                  30

Ala Ser Ile
        35

<210> SEQ ID NO 881
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 881

Glu Arg Thr Cys Lys Glu Asp Phe Asp Cys Arg Met Arg Tyr Cys Val
1               5                   10                  15

```
Tyr Pro Thr Ile Pro Leu Cys Asp Val Lys His Cys Arg Cys Arg Arg
            20                  25                  30

Pro Pro Asn Leu
        35

<210> SEQ ID NO 882
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 882

Asp Val Ile Asn Cys Thr Gln Asp Ser Asp Cys Gln Ser Ile Gly Cys
1               5                   10                  15

Leu Ser His Leu Lys Pro Lys Cys Thr Met Leu Gly Phe Phe Phe Asn
            20                  25                  30

Ala Phe Val Gly Ile Cys Glu Cys Asp Gln Val Met
        35                  40

<210> SEQ ID NO 883
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 883

Thr Ile Asn Val Met Cys Tyr Tyr Asp His Asp Cys Pro Phe Val Leu
1               5                   10                  15

Asp His Ile Ala Glu Cys Lys Gly Gly Val Cys Glu Tyr Thr Ala Phe
            20                  25                  30

Phe Tyr Glu
        35

<210> SEQ ID NO 884
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 884

Asn Asp Arg Ile Val Tyr His Gly Cys Tyr Ser Asp Asp Gln Cys Pro
1               5                   10                  15

Asn Glu Cys Pro Ala Ile Leu Met Arg Cys Ile His Ser Leu Cys Val
            20                  25                  30

Glu Phe Ile Lys Thr Asp Pro Leu Phe Ile
        35                  40

<210> SEQ ID NO 885
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 885

Asp Lys Pro Arg Tyr Thr Pro Arg Asn Ala Val Lys Ile Ala Glu Cys
1               5                   10                  15

Val Ser Tyr Thr Asp Cys Gln Gly Gly Cys Pro Ala Cys Tyr Met Arg
            20                  25                  30

Cys Ile Asp Gly Gln Cys Glu Pro Phe Ile Ile Lys Phe Ile
```

-continued

```
                35                  40                  45

<210> SEQ ID NO 886
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 886

Tyr Asn Tyr Ile Asp Cys Pro Val Gly Cys Arg Ala Cys Tyr Met Arg
1               5                   10                  15

Cys Ile Asp Gly Gln Cys Ile Pro Phe Ile Lys Lys Leu Ile Leu Phe
            20                  25                  30

His Leu Tyr Val Ile Val Glu
        35

<210> SEQ ID NO 887
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 887

Gly Leu Ile Pro Cys Val Ser Asp Ala Asp Cys Pro Glu Glu Leu Ala
1               5                   10                  15

Leu Val Met Lys Cys Ile Asn Lys Leu Cys Glu Leu Val Met Glu
            20                  25                  30

<210> SEQ ID NO 888
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 888

Ile Asp Asp Ser His Cys Pro His Asp Ile Cys Pro Phe His Leu Lys
1               5                   10                  15

Pro Lys Cys Ile Phe Thr Lys Val Val Gly Gln Lys Phe Phe Ser Phe
            20                  25                  30

Ser Leu Asp Gly Lys Cys Gly Cys Met
        35                  40

<210> SEQ ID NO 889
<211> LENGTH: 42
<212> TYPE: PRT
<213> ORGANISM: Artificial sequence
<220> FEATURE:
<223> OTHER INFORMATION: Peptide derived from Medicago truncatula

<400> SEQUENCE: 889

Asp Lys Phe Val Phe Asp Lys Asn Gly Ala Asp Arg Cys Arg Ser Ile
1               5                   10                  15

Leu Asp Cys Pro Gln Asp Lys Cys Phe Pro Leu Leu Thr Leu Val Cys
            20                  25                  30

Val Asn Phe Ala Cys Asp Cys Leu His Val
        35                  40

<210> SEQ ID NO 890
<211> LENGTH: 35
<212> TYPE: PRT
<213> ORGANISM: Artificial sequence
```

-continued

```
<220> FEATURE:
<223> OTHER INFORMATION: Peptide derived from Medicago truncatula

<400> SEQUENCE: 890

Gln Tyr Asn Ile Gly Cys Lys Thr Asp Asp Cys Gln Lys Tyr Tyr
1               5                   10                  15

Thr Lys Met Phe Gly Met Lys Cys Phe Lys Ser Trp Cys Ile Thr Gly
            20                  25                  30

Ile Leu Asp
        35

<210> SEQ ID NO 891
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 891

Glu Asp Tyr Tyr Tyr Ile Glu Cys Gln Arg Asp Phe Asp Cys Pro Gln
1               5                   10                  15

Leu Asn Ser Glu Ile Phe Ala Phe Lys Cys Ile Glu Lys Leu Cys Lys
            20                  25                  30

Leu Glu Phe Ile Tyr Gln Gln Ala Pro Phe Leu Leu Gly Gln Val
        35                  40                  45

<210> SEQ ID NO 892
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 892

Tyr Lys Cys Asn Ile Asp Val Asp Cys Pro Ile Thr Pro Ser Pro Lys
1               5                   10                  15

Phe Lys Trp Lys Cys Ile Asn Lys Arg Cys Leu Tyr Ile Arg Phe Asp
            20                  25                  30

Glu Ile Trp Thr Ser Asp Pro Arg Glu
        35                  40

<210> SEQ ID NO 893
<211> LENGTH: 33
<212> TYPE: PRT
<213> ORGANISM: Artificial sequence
<220> FEATURE:
<223> OTHER INFORMATION: Peptide derived from Medicago truncatula

<400> SEQUENCE: 893

Leu Thr Lys Cys Glu Thr Asp Ala Asn Cys Pro Glu Ile Ser Ile Phe
1               5                   10                  15

Ser Pro Phe Phe Tyr Lys Cys Ile Asn Asn Gly Cys Val Leu Ile Met
            20                  25                  30

Leu

<210> SEQ ID NO 894
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 894
```

```
Leu Lys Lys Cys Ile Thr Phe Glu Asp Cys Pro Ile Ser Lys Thr Arg
1               5                   10                  15

Val Tyr Lys Cys Leu His Gly Glu Cys Arg Tyr Thr Ile Pro Tyr Ile
            20                  25                  30

Pro Lys Val Pro Lys Val Lys
        35
```

<210> SEQ ID NO 895
<211> LENGTH: 49
<212> TYPE: PRT
<213> ORGANISM: Artificial sequence
<220> FEATURE:
<223> OTHER INFORMATION: Peptide derived from Medicago truncatula

<400> SEQUENCE: 895

```
Glu Val Asp Trp Ile Tyr His Leu Cys Asp Thr Asp Thr Asp Cys Pro
1               5                   10                  15

Glu His Trp Ser Lys Phe Phe Ile Tyr Lys Cys Val Asn His Val Cys
            20                  25                  30

Asp Ser Ile Ser Lys Val Thr Thr Asp Ser Lys Glu Tyr Lys Asn Phe
        35                  40                  45

Pro
```

<210> SEQ ID NO 896
<211> LENGTH: 61
<212> TYPE: PRT
<213> ORGANISM: Artificial sequence
<220> FEATURE:
<223> OTHER INFORMATION: Peptide derived from Medicago truncatula

<400> SEQUENCE: 896

```
Ala His Val Glu Cys His Asn Asp Ser Ala Cys Glu Lys Thr Val Lys
1               5                   10                  15

Cys Met Leu Pro Arg Ile Pro Arg Cys Ile Lys Tyr Gln Cys Leu Cys
            20                  25                  30

Gly Tyr Ser Asp Asp Pro Gly Asn Arg Trp Ser Thr Arg Pro Lys Arg
        35                  40                  45

Ile Gln Lys Gly Ser Thr Glu Arg Lys Gly Phe Leu Tyr
    50                  55                  60
```

<210> SEQ ID NO 897
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 897

```
Val Tyr Ile Lys Cys Lys Thr Asp Ala Asp Cys Pro Lys Ser Glu Ser
1               5                   10                  15

Thr Ile Phe Ala Met Lys Cys Asn Asn Tyr Arg Cys Ile Tyr Asp Tyr
            20                  25                  30

Ile His Lys Arg Asn Ser Tyr Ala Thr
        35                  40
```

<210> SEQ ID NO 898
<211> LENGTH: 46
<212> TYPE: PRT
<213> ORGANISM: Artificial sequence
<220> FEATURE:
<223> OTHER INFORMATION: Peptide derived from Medicago truncatula

<400> SEQUENCE: 898

```
Thr Tyr Asp Ala Tyr Asp Glu Cys Gln Thr Glu Leu Asp Cys Pro Lys
1               5                   10                  15

Asn Ile Asp Cys Val Tyr Pro Lys Ser Met Lys Cys Ile Asp Lys Lys
            20                  25                  30

Cys Ile Cys Val Gly Ala Arg Met Ile Ile Pro Arg Val Leu
        35                  40                  45
```

<210> SEQ ID NO 899
<211> LENGTH: 39
<212> TYPE: PRT
<213> ORGANISM: Artificial sequence
<220> FEATURE:
<223> OTHER INFORMATION: Peptide derived from Medicago truncatula

<400> SEQUENCE: 899

```
Asn Gly Tyr Arg Asn Ile Lys Tyr Cys Phe Ile Asp Thr Asp Cys Pro
1               5                   10                  15

Arg Ser Met Cys His Tyr Pro Glu Ile Val Arg Cys Val Asp Gln Cys
            20                  25                  30

Lys Cys Val Arg Ile Met Pro
        35
```

<210> SEQ ID NO 900
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 900

```
Cys Thr Glu His Arg His Cys Glu Ile Ala Met Cys Lys Phe Pro Phe
1               5                   10                  15

Ile Val Arg Cys Ser Met Asn Glu Cys Asn Cys Glu Arg Val His Tyr
            20                  25                  30

Leu Ile
```

<210> SEQ ID NO 901
<211> LENGTH: 47
<212> TYPE: PRT
<213> ORGANISM: Artificial sequence
<220> FEATURE:
<223> OTHER INFORMATION: Peptide derived from Medicago truncatula

<400> SEQUENCE: 901

```
Lys Asn Glu Pro Glu Pro Lys Phe Ile Glu Cys Val Thr Asp Ala Asp
1               5                   10                  15

Cys Leu Asn Ser Gln Ser Lys Met Tyr Ala Leu Ile Cys Glu Lys Asn
            20                  25                  30

Arg Cys Ile Tyr Glu Phe Leu Lys Ser Met His Tyr Asn Leu Ser
        35                  40                  45
```

<210> SEQ ID NO 902
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 902

```
Glu Cys Ile Asn Asp Ile Asp Cys Pro Gln Thr Gly Asn Leu Phe Tyr
1               5                   10                  15

Val Phe Ile Cys Lys Asn Arg Ile Cys Glu Leu Ile Asn Lys Tyr Pro
```

-continued

```
              20                  25                  30

Gln Asn

<210> SEQ ID NO 903
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 903

Asp Ile Tyr Glu Glu Cys Glu Thr Asp Asp Tyr Cys Pro Lys Tyr Arg
1               5                   10                  15

Asp Leu Leu Tyr Val Phe Lys Cys Ile Asp Lys Arg Cys Glu Leu Val
              20                  25                  30

Glu Ala His Ala
        35

<210> SEQ ID NO 904
<211> LENGTH: 44
<212> TYPE: PRT
<213> ORGANISM: Artificial sequence
<220> FEATURE:
<223> OTHER INFORMATION: Peptide derived from Medicago truncatula

<400> SEQUENCE: 904

Val His Asp Val Ala His Thr Asp Ile Pro Cys Glu Pro Asp Ala Asp
1               5                   10                  15

Cys Pro Lys Ser Leu His Glu Tyr Phe Glu Met Lys Cys Ile Asp Lys
              20                  25                  30

Lys Cys Glu Trp Ser Arg Lys Thr Ser Leu Ile Pro
        35                  40

<210> SEQ ID NO 905
<211> LENGTH: 34
<212> TYPE: PRT
<213> ORGANISM: Artificial sequence
<220> FEATURE:
<223> OTHER INFORMATION: Peptide derived from Medicago truncatula

<400> SEQUENCE: 905

Ser Tyr Tyr Gly Cys Glu Thr Asp Ala Asp Cys Pro Arg Ser Met Asn
1               5                   10                  15

Lys Asp Phe Tyr Leu Lys Cys Val Asp Lys Lys Cys Glu Trp Thr Ala
              20                  25                  30

Lys Ile

<210> SEQ ID NO 906
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 906

Cys Glu Thr Asp Ala Asp Cys Pro Arg Tyr Thr His Asn Asn Phe Ser
1               5                   10                  15

Leu Lys Cys Ile Asn Lys Cys Glu Trp Ser Ala Lys Leu His
              20                  25                  30

<210> SEQ ID NO 907
<211> LENGTH: 49
<212> TYPE: PRT
```

-continued

<213> ORGANISM: Artificial sequence
<220> FEATURE:
<223> OTHER INFORMATION: Peptide derived from Medicago truncatula

<400> SEQUENCE: 907

Glu Asp Ile Gly Gly Asn Cys Glu Cys Ile Arg Asp Glu Asp Cys Phe
1               5                   10                  15

Lys Gln Lys Arg Asp Glu Asp Cys His Lys Glu Tyr Cys Met Ile Phe
            20                  25                  30

Tyr Val His Lys Cys Glu Asn Tyr Lys Cys Val Cys Ala Gly Met Phe
        35                  40                  45

Asn

<210> SEQ ID NO 908
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 908

Gln Glu Val Leu Gln Tyr Glu Leu Phe Asp Cys Asn Glu Asp Arg Asp
1               5                   10                  15

Cys Asp Asn Val Ile Cys Val Ala Gly Gly Ile Pro Lys Cys Ile Thr
            20                  25                  30

Pro Phe Cys Phe Cys Phe
        35

<210> SEQ ID NO 909
<211> LENGTH: 36
<212> TYPE: PRT
<213> ORGANISM: Artificial sequence
<220> FEATURE:
<223> OTHER INFORMATION: Peptide derived from Medicago truncatula

<400> SEQUENCE: 909

Ile Tyr Tyr Pro Ile Ser Arg Pro Cys Lys Thr Asp Lys Asp Cys Pro
1               5                   10                  15

Asn Arg Lys Asn Tyr Lys Gly Lys Cys Arg Lys Gly Phe Cys Met Ser
            20                  25                  30

Ser Arg Leu Arg
        35

<210> SEQ ID NO 910
<211> LENGTH: 57
<212> TYPE: PRT
<213> ORGANISM: Artificial sequence
<220> FEATURE:
<223> OTHER INFORMATION: Peptide derived from Medicago truncatula

<400> SEQUENCE: 910

Ile Ser Ile Tyr Val Arg Cys Ala Ser Thr Asn Glu Cys Tyr Thr Thr
1               5                   10                  15

Phe Lys Phe Ala Pro Leu Gly Ser Met Arg Cys Val Glu Gly Tyr Cys
            20                  25                  30

Lys His Leu Lys Asp Phe Lys Val Lys Thr Pro Leu Gln Ile Lys Glu
        35                  40                  45

Ile Thr Pro Leu Leu Leu His Phe Pro
    50                  55

<210> SEQ ID NO 911
<211> LENGTH: 33

```
<212> TYPE: PRT
<213> ORGANISM: Artificial sequence
<220> FEATURE:
<223> OTHER INFORMATION: Peptide derived from Medicago truncatula

<400> SEQUENCE: 911

Tyr Ile Asn Cys Lys Thr Asp Asp Cys Pro Lys Leu Glu Ser Arg
1               5                   10                  15

Met Val Val Leu Lys Cys Thr Asn Ser Arg Cys Ala Ala Val Ile Leu
                20                  25                  30

His

<210> SEQ ID NO 912
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 912

Asn His Glu Ile Ser Gly Trp Ile Thr Glu Leu Pro Phe Gly Met Cys
1               5                   10                  15

Thr Ser Ile Leu Asp Cys Pro Met Asp Ser Cys Thr His Pro Gln Gln
                20                  25                  30

Pro Trp Cys Glu Leu His Gly Val Pro Ile Leu Tyr His Gly Ser Glu
            35                  40                  45

Ile Gly Leu Cys Ile Cys Ile
        50                  55

<210> SEQ ID NO 913
<211> LENGTH: 55
<212> TYPE: PRT
<213> ORGANISM: Artificial sequence
<220> FEATURE:
<223> OTHER INFORMATION: Peptide derived from Medicago truncatula

<400> SEQUENCE: 913

Asn His Ala Ile Ser Gly Leu Leu Pro Lys Leu Pro Phe Gly Cys Cys
1               5                   10                  15

Thr Ser Asn Leu Asp Cys Pro Arg His Met Cys Thr His Pro Gln Gln
                20                  25                  30

Pro Trp Cys Ile Phe Tyr Gly Asn Arg Ile Met Tyr Arg Gly Ser Arg
            35                  40                  45

Leu Gly Ile Cys Lys Cys Ser
        50                  55

<210> SEQ ID NO 914
<211> LENGTH: 56
<212> TYPE: PRT
<213> ORGANISM: Artificial sequence
<220> FEATURE:
<223> OTHER INFORMATION: Peptide derived from Medicago truncatula

<400> SEQUENCE: 914

Ser Leu His Glu Ile Ser Gly Tyr Val Leu Gly Leu Pro Ala Gly Tyr
1               5                   10                  15

Cys Thr Ser Asn His His Cys Pro Val Tyr Asn Cys Thr His Pro Lys
                20                  25                  30

Gln Pro Trp Cys Lys Leu Val Arg Leu Gln Leu Leu Phe His Gly Ser
            35                  40                  45

Leu Ile Gly Leu Cys Asp Cys Ile
        50                  55
```

<210> SEQ ID NO 915
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 915

Leu Asn Glu Cys Thr Gln Asp Tyr Asp Cys Pro Ile Glu Met Cys Pro
1               5                   10                  15

Phe Pro Phe Gln Pro Lys Cys Ile Met Leu Lys Asn Leu Ser Ile Phe
            20                  25                  30

Ser Asn Ser Gly Ile Cys Ser Cys Thr
        35                  40

<210> SEQ ID NO 916
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 916

Gly Asn Phe Phe Glu Phe Phe His Lys Cys Thr Gln Asp Ser Asp Cys
1               5                   10                  15

Pro Ser Leu Leu Cys Arg Asn Lys Ser Glu Leu Pro Lys Cys Ile Ala
            20                  25                  30

Gly Phe Met Cys Arg Cys Pro Asn Val
        35                  40

<210> SEQ ID NO 917
<211> LENGTH: 37
<212> TYPE: PRT
<213> ORGANISM: Artificial sequence
<220> FEATURE:
<223> OTHER INFORMATION: Peptide derived from Medicago truncatula

<400> SEQUENCE: 917

Glu Pro Asp Asp Asn Gln Lys Asn Cys Val Ser Asp Ser Asp Cys Tyr
1               5                   10                  15

Lys Lys Phe His Leu Pro Arg His Phe Ile Met Lys Cys Ile Lys Asn
            20                  25                  30

Arg Cys Thr Phe Val
        35

<210> SEQ ID NO 918
<211> LENGTH: 28
<212> TYPE: PRT
<213> ORGANISM: Artificial sequence
<220> FEATURE:
<223> OTHER INFORMATION: Peptide derived from Medicago truncatula

<400> SEQUENCE: 918

His Cys Val Ile Asp Ala His Cys Pro Arg Asn Met Cys Gly Phe His
1               5                   10                  15

Phe Pro Pro Arg Cys Val Glu Gly Asp Cys Val Cys
            20                  25

<210> SEQ ID NO 919
<211> LENGTH: 30
<212> TYPE: PRT
<213> ORGANISM: Artificial sequence
<220> FEATURE:

```
<223> OTHER INFORMATION: Peptide derived from Medicago truncatula

<400> SEQUENCE: 919

Gln Val Lys Cys Lys Thr Val Lys Asp Cys Pro Ile Arg Arg Asn Arg
1               5                   10                  15

Lys Tyr Tyr Cys Leu Phe Gly Ile Cys Lys Tyr Asp Val Met
            20                  25                  30

<210> SEQ ID NO 920
<211> LENGTH: 29
<212> TYPE: PRT
<213> ORGANISM: Artificial sequence
<220> FEATURE:
<223> OTHER INFORMATION: Peptide derived from Medicago truncatula

<400> SEQUENCE: 920

Leu Cys Asp Ser Asn Arg Asp Cys Arg Gly Tyr His Cys Asn Trp Pro
1               5                   10                  15

Lys Phe Pro Ile Cys Val Arg Met Ile Cys Glu Cys Ile
            20                  25

<210> SEQ ID NO 921
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 921

Gln Ile Phe Pro Lys Trp Cys Leu Tyr Asp Lys Asp Cys Pro Gln Asn
1               5                   10                  15

Met Cys Arg Pro Gly Arg Ile Pro Lys Cys Ile Phe Gly His Cys Asn
            20                  25                  30

Cys Val Lys Gln Arg Ser
        35

<210> SEQ ID NO 922
<211> LENGTH: 35
<212> TYPE: PRT
<213> ORGANISM: Artificial sequence
<220> FEATURE:
<223> OTHER INFORMATION: Peptide derived from Medicago truncatula

<400> SEQUENCE: 922

Ala Pro Pro Val Tyr Cys Ile Glu Asp Glu Asp Cys Tyr Asp Leu Cys
1               5                   10                  15

Thr Ser Pro Leu Val Glu Ile Cys Thr Asn Tyr Gln Cys Ile Cys Leu
            20                  25                  30

Lys Arg Phe
        35

<210> SEQ ID NO 923
<211> LENGTH: 38
<212> TYPE: PRT
<213> ORGANISM: Artificial sequence
<220> FEATURE:
<223> OTHER INFORMATION: Peptide derived from Medicago truncatula

<400> SEQUENCE: 923

Lys Asn Ser Gln Gly Asn Lys Glu Asn Ile Cys Phe Lys Asp Ala Asp
1               5                   10                  15

Cys Pro Gln Asp Ile Cys Ser Tyr Pro Phe Lys Pro Lys Cys Asn Ile
            20                  25                  30
```

```
Tyr Gly Tyr Cys Ser Cys
        35

<210> SEQ ID NO 924
<211> LENGTH: 31
<212> TYPE: PRT
<213> ORGANISM: Artificial sequence
<220> FEATURE:
<223> OTHER INFORMATION: Peptide derived from Medicago truncatula

<400> SEQUENCE: 924

Phe Leu Pro Cys Val Thr Lys Asp Asp Cys Ala Tyr Asp Glu Cys Ile
1               5                   10                  15

Ser Pro Arg Lys Pro Thr Cys Tyr Leu Glu Thr Cys His Cys Leu
            20                  25                  30

<210> SEQ ID NO 925
<211> LENGTH: 41
<212> TYPE: PRT
<213> ORGANISM: Artificial sequence
<220> FEATURE:
<223> OTHER INFORMATION: Peptide derived from Medicago truncatula

<400> SEQUENCE: 925

Trp Arg Cys Lys Lys Thr Asp Asp Cys Ile Lys Ile Glu Phe Cys Lys
1               5                   10                  15

Phe Pro Lys Ile Ala Arg Cys Thr Lys Pro Lys Phe Leu Phe Leu Glu
            20                  25                  30

Phe Gly Thr Gly Phe Cys Thr Cys Asp
        35                  40
```

NODULE SPECIFIC MEDICAGO PEPTIDES HAVING ANTIMICROBIAL ACTIVITY AND PHARMACEUTICAL COMPOSITIONS CONTAINING THE SAME

FIELD OF THE INVENTION

The invention relates to nodule-specific *Medicago* peptides having antimicrobial activity and pharmaceutical compositions containing the same.

BACKGROUND OF THE INVENTION

Symbiotic nitrogen fixation takes place in particular plant root organs named nodules. Nodule formation on plants of the Leguminosae family is a result of consecutive interactions with bacteria of the Rhizobiaceae family (rhizobia). The interaction is considered mutually beneficial.

The bacteria within the nodule cells gain the ability to fix nitrogen gas by means of their nitrogenase enzyme complex and supply the host plant with the reduced nitrogen for plant growth. The plant provides photosynthates to the bacteria and a microaerobic niche for the oxygen-sensitive nitrogenase. Nodule development is induced by lipochitooligosaccharide signals of rhizobia, called Nod factors.

Nodules are formed on a particular host only in response to compatible rhizobia producing Nod factors with the adequate chemical structure (Dénarié, J., Debellé, F. & Promé, J.-C. (1996) *Annu. Rev. Biochem.* 65, 503-535). This is one of the major causes of the generally pronounced host specificity in *Rhizobium*-legume symbiosis. Nod factors induce cell divisions in the root cortex and successive divisions lead to the formation of the nodule primordium. Simultaneously, the rhizobia enter the host plant via the root hairs through the formation of tubular structures called infection threads which traverse the root epidermis and cortex and then the nodule primordium.

Rhizobia are released from infection threads in the cytoplasm of postmitotic nondividing cells by endocytosis. The term "bacteroid" refers to these intracellular membrane encapsulated bacteria. In legumes of the Papilionoideae subfamily, the nodules can be of either the determinate or the indeterminate type (Franssen, H. J., Vijn, I., Yang, W. C. & Bisseling, T. (1992) *Plant Mol. Biol.* 19, 89-107). In the case of determinate nodules, the initial cell division activity required for nodule primordium formation ceases rapidly and therefore the determinate nodules contain no meristem. Differentiation of infected cells occurs synchronously and the mature nodule contains symbiotic cells with a homogenous population of nitrogen-fixing bacteroids (Franssen, H. J., Vijn, I., Yang, W. C. & Bisseling, T. (1992) *Plant Mol. Biol.* 19, 89-107). Legumes such as bean (*Phaseolus vulgaris*) or *Lotus japonicus* form this type of nodules.

In contrast, cell division activity in the indeterminate nodules is maintained and forms an apical meristem (nodule zone I). Because the size of the meristem is constant, cell division activity and production of new sets of meristematic cells are balanced with the exit of the same number of cells from the mitotic cell cycle. These postmitotic cells are unable to divide and enter the nodule differentiation program. The infection thread penetrates into the submeristematic cells and liberates the rhizobia. In the infected cells, both partners differentiate progressively along the 12-15 cell layers of the infection zone (or zone II), ending in the formation of nitrogen fixing cells that will constitute the constantly growing nodule zone III (2).

Legumes of the galegoid clade (such as *Medicago* spp., *Vicia sativa*, and *Pisum sativum*) are examples of plants forming indeterminate nodules.

In *Medicago truncatula* nodules several hundreds of peptide coding genes are expressed (Kevei et al., 2002, *Mol. Plant-Microbe Interact.*, 15, 922-931; Mergaert et al., 2003, *Plant Physiol.* 132, 161-173; Alunni et al., 2007, *Mol. Plant-Microbe Interact.* 20, 1138-1148). Production of these peptides in the infected plant cells and their targeting to the bacteroids (Van de Velde et al., 2010) correlate with irreversible terminal differentiation of bacteroids involving genome amplification, cell elongation and branching, loss of cell division capacity and increase in membrane permeability (Mergaert et al., 2006, Proc. Natl. Acad. Sci. USA. 103(13):5230-5).

Natural products are the sources of most antibiotics, however the antimicrobial potential of plant peptides has been largely unexplored.

Nowadays, we face the danger of the emergence of antibiotic resistant bacteria as a consequence of misuse of traditional antibiotics that places selection pressure on the bacterium strains. Antimicrobial peptides are rarely used as antibiotics. Moreover, antibiotics such as polymyxins (cyclic peptide with hydrophobic tail) have adverse effects such as nephrotoxic and neurotoxic (Falagas M E, Kasiakou S K; February 2006; "Toxicity of polymyxins: a systematic review of the evidence from old and recent studies". *Crit Care* 10 (1): R27) and, though effective, are therefore used only if less toxic antibiotics are ineffective or are contraindicated. Its typical use cases are infections with strains of *Pseudomonas aeruginosa* or *Enterobacteriaceae* species that are highly resistant to other types of antibiotics such as cephalosporins. Further, polymyxins are not absorbed from the gastrointestinal tract and therefore must be administered intravenously and active only against Gram–bacteria.

SUMMARY OF THE INVENTION

Thus there is a growing need for the discovery of new safe antibiotics with improved efficacy against multiple strains of bacteria, in particular the antibiotic resistant ones, that are administrable by oral route, nasal inspiration or topical (local surface) treatments for example in case of skin infections.

One of the aims of the invention is to provide peptides having broad-spectrum antibiotic activity.

Another aim of the invention is to provide peptides having further fungicidal and antiviral activities.

Still another aim of the invention is to provide pharmaceutical compositions comprising said peptides presenting no adverse side effects.

The present invention relates to the use of at least one peptide originated from *Medicago truncatula* nodules, comprising the SEQ IDs NO: 1-463 or at least one peptide having a sequence derived from said SEQ IDs NO: 1-463 by deletion of about 9 to about 44 contiguous amino acids, from the N-terminal part of the peptide, in particular peptides having the SEQ IDS NO: 464 to 925, for the preparation of a drug intended for the treatment of diseases induced by microorganisms, wherein said peptides have a broad-spectrum and fast antibiotic activity, in particular killing of the bacteria within 1 to 3 hours.

In an advantageous embodiment, the present invention relates to the use of at least one peptide originated from *Medicago truncatula* nodules, comprising the SEQ IDs NO: 1-463 or at least one peptide having a sequence derived from said SEQ IDs NO: 1-463 by deletion of about 9 to about 44 contiguous amino acids, in particular the SEQ IDS NO: 464 to 925, for the preparation of a drug intended for the treatment of human, animal or plant diseases induced by microorganisms, wherein said peptides have a broad-spectrum and fast antibiotic activity, in particular killing of the bacteria within 1 to 3 hours.

By the expression "peptide originated from *Medicago* nodules", it is meant peptides that have been isolated from the nodules of legume of the galegoid clade such as *Medicago truncatula* but it also covers synthetic peptides having the sequence of said isolated peptides.

Isolated peptides from *Medicago* nodules are free of the nodule environment, i.e. of compounds, other than said peptides, that are present in the nodule.

Isolated peptides from Medicago nodules or synthesized peptides have a purity being equal or more than about 90%, in particular more than about 95%.

The sequence of said isolated peptides covers the sequence of amino acids given in the sequence listing as well as the modified peptide after the translation, such as for instance a glycosylated peptide.

Synthetic peptides can be prepared by chemical (peptides synthesis) or biological ways well known from a man skilled in the art (recombinant production).

Peptides from *Medicago truncatula* nodules are cysteine rich peptides (4 or 6 cysteines) and are synthesized in the cell with a signal peptide which is a short (from 9 to 60 amino acids long) peptide chain that directs the transport of the said peptides.

The amino acids comprising the signal peptide are cleaved off the protein (corresponding to the deletion above cited) in the endoplasmic reticulum leading thus to the mature peptide.

By the expression "contiguous amino acids" is meant amino acids touching or connected throughout in an unbroken sequence.

SEQ IDs NO: 1 to 463 corresponds thus to the mature peptides containing the signal peptide and SEQ IDs NO: 464-925 corresponds to the mature peptides after cleavage of said signal peptide being 9-44 contiguous amino acids long.

Table I give the correlation between SEQ IDs NO: 1-463 and SEQ IDs: 464- 925 (for the reader's convenience, the numbering of the present document and of the priority document EP 09 305 547.3 are indicated) and their corresponding NCR (Nodule Cystein Rich) number that is a numbering given by the inventors:

TABLE I

| MATURE PEPTIDE AND SIGNAL PEPTIDE SEQ ID NO: (Present document) | MATURE PEPTIDE AND SIGNAL PEPTIDE SEQ ID NO: (Priority document EP 09 305 547.3) | NCR NUMBER | MATURE PEPTIDE SEQ ID NO: (Priority document EP 09 305 547.3) | MATURE PEPTIDE SEQ ID NO: (Present document) |
|---|---|---|---|---|
| SEQ ID NO: 1 | SEQ ID NO: 1 | NCR001 | SEQ ID NO: 523 | SEQ ID NO: 464 |
| SEQ ID NO: 2 | SEQ ID NO: 2 | NCR002 | — | SEQ ID NO: 465 |
| SEQ ID NO: 3 | SEQ ID NO: 3 | NCR003 | — | SEQ ID NO: 466 |
| SEQ ID NO: 4 | SEQ ID NO: 4 | NCR004 | SEQ ID NO: 516 | SEQ ID NO: 467 |
| SEQ ID NO: 5 | SEQ ID NO: 5 | NCR005 | | SEQ ID NO: 468 |
| SEQ ID NO: 6 | SEQ ID NO: 6 | NCR006 | SEQ ID NO: 355 | SEQ ID NO: 469 |
| SEQ ID NO: 7 | SEQ ID NO: 7 | NCR007 | SEQ ID NO: 539 | SEQ ID NO: 470 |
| SEQ ID NO: 8 | SEQ ID NO: 8 | NCR008 | SEQ ID NO: 524 | SEQ ID NO: 471 |
| SEQ ID NO: 9 | SEQ ID NO: 9 | NCR009 | SEQ ID NO: 395 | SEQ ID NO: 472 |
| SEQ ID NO: 10 | SEQ ID NO: 10 | NCR010 | SEQ ID NO: 495 | SEQ ID NO: 473 |
| SEQ ID NO: 11 | SEQ ID NO: 11 | NCR011 | SEQ ID NO: 356 | SEQ ID NO: 474 |
| SEQ ID NO: 12 | SEQ ID NO: 12 | NCR012 | SEQ ID NO: 414 | SEQ ID NO: 475 |
| SEQ ID NO: 13 | SEQ ID NO: 13 | NCR013 | SEQ ID NO: 455 | SEQ ID NO: 476 |
| SEQ ID NO: 14 | SEQ ID NO: 14 | NCR014 | SEQ ID NO: 525 | SEQ ID NO: 477 |
| SEQ ID NO: 15 | SEQ ID NO: 15 | NCR015 | — | SEQ ID NO: 478 |
| SEQ ID NO: 16 | — | NCR016 | — | SEQ ID NO: 479 |
| SEQ ID NO: 17 | — | NCR017 | — | SEQ ID NO: 480 |
| SEQ ID NO: 18 | SEQ ID NO: 16 | NCR018 | SEQ ID NO: 415 | SEQ ID NO: 481 |
| SEQ ID NO: 19 | SEQ ID NO: 17 | NCR019 | SEQ ID NO: 561 | SEQ ID NO: 482 |
| SEQ ID NO: 20 | SEQ ID NO: 18 | NCR020 | SEQ ID NO: 424 | SEQ ID NO: 483 |
| SEQ ID NO: 21 | SEQ ID NO: 19 | NCR021 | SEQ ID NO: 329 | SEQ ID NO: 484 |
| SEQ ID NO: 22 | SEQ ID NO: 20 | NCR022 | SEQ ID NO: 471 | SEQ ID NO: 485 |
| SEQ ID NO: 23 | SEQ ID NO: 21 | NCR023 | SEQ ID NO: 499 | SEQ ID NO: 486 |
| SEQ ID NO: 24 | SEQ ID NO: 22 | NCR024 | SEQ ID NO: 472 | SEQ ID NO: 487 |
| SEQ ID NO: 25 | SEQ ID NO: 23 | NCR025 | SEQ ID NO: 509 | SEQ ID NO: 488 |
| SEQ ID NO: 26 | SEQ ID NO: 24 | NCR026 | SEQ ID NO: 436 | SEQ ID NO: 489 |
| SEQ ID NO: 27 | SEQ ID NO: 25 | NCR027 | — | SEQ ID NO: 490 |
| SEQ ID NO: 28 | SEQ ID NO: 26 | NCR028 | SEQ ID NO: 548 | SEQ ID NO: 491 |
| SEQ ID NO: 29 | SEQ ID NO: 27 | NCR029 | SEQ ID NO: 357 | SEQ ID NO: 492 |
| SEQ ID NO: 30 | SEQ ID NO: 28 | NCR030 | SEQ ID NO: 396 | SEQ ID NO: 493 |
| SEQ ID NO: 31 | SEQ ID NO: 29 | NCR031 | SEQ ID NO: 337 | SEQ ID NO: 494 |
| SEQ ID NO: 32 | SEQ ID NO: 30 | NCR032 | — | SEQ ID NO: 495 |
| SEQ ID NO: 33 | SEQ ID NO: 31 | NCR033 | — | SEQ ID NO: 496 |
| SEQ ID NO: 34 | SEQ ID NO: 32 | NCR034 | SEQ ID NO: 485 | SEQ ID NO: 497 |
| SEQ ID NO: 35 | SEQ ID NO: 33 | NCR035 | SEQ ID NO: 385 | SEQ ID NO: 498 |
| SEQ ID NO: 36 | SEQ ID NO: 34 | NCR036 | SEQ ID NO: 397 | SEQ ID NO: 499 |
| SEQ ID NO: 37 | SEQ ID NO: 35 | NCR037 | SEQ ID NO: 358 | SEQ ID NO: 500 |
| SEQ ID NO: 38 | SEQ ID NO: 36 | NCR038 | — | SEQ ID NO: 501 |
| SEQ ID NO: 39 | SEQ ID NO: 37 | NCR039 | — | SEQ ID NO: 502 |
| SEQ ID NO: 40 | SEQ ID NO: 38 | NCR040 | — | SEQ ID NO: 503 |
| SEQ ID NO: 41 | SEQ ID NO: 39 | NCR041 | — | SEQ ID NO: 504 |
| SEQ ID NO: 42 | — | NCR042 | — | SEQ ID NO: 505 |

TABLE I-continued

| MATURE PEPTIDE AND SIGNAL PEPTIDE SEQ ID NO: (Present document) | MATURE PEPTIDE AND SIGNAL PEPTIDE SEQ ID NO: (Priority document EP 09 305 547.3) | NCR NUMBER | MATURE PEPTIDE SEQ ID NO: (Priority document EP 09 305 547.3) | MATURE PEPTIDE SEQ ID NO: (Present document) |
|---|---|---|---|---|
| SEQ ID NO: 43 | SEQ ID NO: 40 | NCR043 | SEQ ID NO: 398 | SEQ ID NO: 506 |
| SEQ ID NO: 44 | SEQ ID NO: 41 | NCR044 | SEQ ID NO: 399 | SEQ ID NO: 507 |
| SEQ ID NO: 45 | SEQ ID NO: 42 | NCR045 | SEQ ID NO: 386 | SEQ ID NO: 508 |
| SEQ ID NO: 46 | SEQ ID NO: 43 | NCR046 | — | SEQ ID NO: 509 |
| SEQ ID NO: 47 | SEQ ID NO: 44 | NCR047 | SEQ ID NO: 400 | SEQ ID NO: 510 |
| SEQ ID NO: 48 | SEQ ID NO: 45 | NCR048 | — | SEQ ID NO: 511 |
| SEQ ID NO: 49 | SEQ ID NO: 46 | NCR049 | — | SEQ ID NO: 512 |
| SEQ ID NO: 50 | SEQ ID NO: 47 | NCR050 | — | SEQ ID NO: 513 |
| SEQ ID NO: 51 | SEQ ID NO: 48 | NCR051 | SEQ ID NO: 473 | SEQ ID NO: 514 |
| SEQ ID NO: 52 | SEQ ID NO: 49 | NCR052 | SEQ ID NO: 345 | SEQ ID NO: 515 |
| SEQ ID NO: 53 | SEQ ID NO: 50 | NCR053 | SEQ ID NO: 437 | SEQ ID NO: 516 |
| SEQ ID NO: 54 | SEQ ID NO: 51 | NCR054 | SEQ ID NO: 425 | SEQ ID NO: 517 |
| SEQ ID NO: 55 | SEQ ID NO: 52 | NCR055 | SEQ ID NO: 438 | SEQ ID NO: 518 |
| SEQ ID NO: 56 | SEQ ID NO: 53 | NCR056 | — | SEQ ID NO: 519 |
| SEQ ID NO: 57 | SEQ ID NO: 54 | NCR057 | SEQ ID NO: 486 | SEQ ID NO: 520 |
| SEQ ID NO: 58 | SEQ ID NO: 55 | NCR058 | SEQ ID NO: 359 | SEQ ID NO: 521 |
| SEQ ID NO: 59 | SEQ ID NO: 56 | NCR059 | SEQ ID NO: 387 | SEQ ID NO: 522 |
| SEQ ID NO: 60 | SEQ ID NO: 57 | NCR060 | SEQ ID NO: 360 | SEQ ID NO: 523 |
| SEQ ID NO: 61 | SEQ ID NO: 58 | NCR061 | — | SEQ ID NO: 524 |
| SEQ ID NO: 62 | SEQ ID NO: 59 | NCR062 | SEQ ID NO: 338 | SEQ ID NO: 525 |
| SEQ ID NO: 63 | SEQ ID NO: 60 | NCR063 | SEQ ID NO: 324 | SEQ ID NO: 526 |
| SEQ ID NO: 64 | — | NCR064 | | SEQ ID NO: 527 |
| SEQ ID NO: 65 | SEQ ID NO: 61 | NCR065 | SEQ ID NO: 339 | SEQ ID NO: 528 |
| SEQ ID NO: 66 | SEQ ID NO: 62 | NCR066 | — | SEQ ID NO: 529 |
| SEQ ID NO: 67 | SEQ ID NO: 63 | NCR067 | SEQ ID NO: 426 | SEQ ID NO: 530 |
| SEQ ID NO: 68 | SEQ ID NO: 64 | NCR068 | SEQ ID NO: 427 | SEQ ID NO: 531 |
| SEQ ID NO: 69 | SEQ ID NO: 65 | NCR069 | SEQ ID NO: 456 | SEQ ID NO: 532 |
| SEQ ID NO: 70 | SEQ ID NO: 66 | NCR070 | — | SEQ ID NO: 533 |
| SEQ ID NO: 71 | SEQ ID NO: 67 | NCR071 | — | SEQ ID NO: 534 |
| SEQ ID NO: 72 | SEQ ID NO: 68 | NCR072 | SEQ ID NO: 346 | SEQ ID NO: 535 |
| SEQ ID NO: 73 | SEQ ID NO: 69 | NCR073 | SEQ ID NO: 439 | SEQ ID NO: 536 |
| SEQ ID NO: 74 | SEQ ID NO: 70 | NCR074 | SEQ ID NO: 347 | SEQ ID NO: 537 |
| SEQ ID NO: 75 | SEQ ID NO: 71 | NCR075 | — | SEQ ID NO: 538 |
| SEQ ID NO: 76 | SEQ ID NO: 72 | NCR076 | SEQ ID NO: 487 | SEQ ID NO: 539 |
| SEQ ID NO: 77 | SEQ ID NO: 73 | NCR077 | SEQ ID NO: 540 | SEQ ID NO: 540 |
| SEQ ID NO: 78 | SEQ ID NO: 74 | NCR078 | SEQ ID NO: 416 | SEQ ID NO: 541 |
| SEQ ID NO: 79 | SEQ ID NO: 75 | NCR079 | SEQ ID NO: 348 | SEQ ID NO: 542 |
| SEQ ID NO: 80 | SEQ ID NO: 76 | NCR080 | SEQ ID NO: 361 | SEQ ID NO: 543 |
| SEQ ID NO: 81 | SEQ ID NO: 77 | NCR081 | SEQ ID NO: 362 | SEQ ID NO: 544 |
| SEQ ID NO: 82 | SEQ ID NO: 78 | NCR082 | SEQ ID NO: 349 | SEQ ID NO: 545 |
| SEQ ID NO: 83 | SEQ ID NO: 79 | NCR083 | SEQ ID NO: 363 | SEQ ID NO: 546 |
| SEQ ID NO: 84 | SEQ ID NO: 80 | NCR084 | SEQ ID NO: 488 | SEQ ID NO: 547 |
| SEQ ID NO: 85 | SEQ ID NO: 81 | NCR085 | SEQ ID NO: 417 | SEQ ID NO: 548 |
| SEQ ID NO: 86 | SEQ ID NO: 82 | NCR086 | SEQ ID NO: 364 | SEQ ID NO: 549 |
| SEQ ID NO: 87 | SEQ ID NO: 83 | NCR087 | — | SEQ ID NO: 550 |
| SEQ ID NO: 88 | SEQ ID NO: 84 | NCR088 | SEQ ID NO: 440 | SEQ ID NO: 551 |
| SEQ ID NO: 89 | SEQ ID NO: 85 | NCR089 | SEQ ID NO: 536 | SEQ ID NO: 552 |
| SEQ ID NO: 90 | SEQ ID NO: 86 | NCR090 | SEQ ID NO: 418 | SEQ ID NO: 553 |
| SEQ ID NO: 91 | SEQ ID NO: 87 | NCR091 | — | SEQ ID NO: 554 |
| SEQ ID NO: 92 | — | NCR092 | — | SEQ ID NO: 555 |
| SEQ ID NO: 93 | SEQ ID NO: 88 | NCR093 | SEQ ID NO: 500 | SEQ ID NO: 556 |
| SEQ ID NO: 94 | SEQ ID NO: 89 | NCR094 | SEQ ID NO: 441 | SEQ ID NO: 557 |
| SEQ ID NO: 95 | SEQ ID NO: 90 | NCR095 | SEQ ID NO: 350 | SEQ ID NO: 558 |
| SEQ ID NO: 96 | SEQ ID NO: 91 | NCR096 | SEQ ID NO: 442 | SEQ ID NO: 559 |
| SEQ ID NO: 97 | SEQ ID NO: 92 | NCR097 | SEQ ID NO: 322 | SEQ ID NO: 560 |
| SEQ ID NO: 98 | SEQ ID NO: 93 | NCR098 | SEQ ID NO: 517 | SEQ ID NO: 561 |
| SEQ ID NO: 99 | SEQ ID NO: 94 | NCR099 | SEQ ID NO: 474 | SEQ ID NO: 562 |
| SEQ ID NO: 100 | SEQ ID NO: 95 | NCR100 | SEQ ID NO: 532 | SEQ ID NO: 563 |
| SEQ ID NO: 101 | SEQ ID NO: 96 | NCR101 | SEQ ID NO: 419 | SEQ ID NO: 564 |
| SEQ ID NO: 102 | SEQ ID NO: 97 | NCR102 | SEQ ID NO: 489 | SEQ ID NO: 565 |
| SEQ ID NO: 103 | SEQ ID NO: 98 | NCR103 | SEQ ID NO: 475 | SEQ ID NO: 566 |
| SEQ ID NO: 104 | SEQ ID NO: 99 | NCR104 | SEQ ID NO: 518 | SEQ ID NO: 567 |
| SEQ ID NO: 105 | SEQ ID NO: 100 | NCR105 | SEQ ID NO: 551 | SEQ ID NO: 568 |
| SEQ ID NO: 106 | SEQ ID NO: 101 | NCR106 | SEQ ID NO: 510 | SEQ ID NO: 569 |
| SEQ ID NO: 107 | SEQ ID NO: 102 | NCR107 | SEQ ID NO: 351 | SEQ ID NO: 570 |
| SEQ ID NO: 108 | SEQ ID NO: 103 | NCR108 | SEQ ID NO: 542 | SEQ ID NO: 571 |
| SEQ ID NO: 109 | SEQ ID NO: 104 | NCR109 | SEQ ID NO: 325 | SEQ ID NO: 572 |
| SEQ ID NO: 110 | SEQ ID NO: 105 | NCR110 | — | SEQ ID NO: 573 |
| SEQ ID NO: 111 | SEQ ID NO: 106 | NCR111 | SEQ ID NO: 559 | SEQ ID NO: 574 |
| SEQ ID NO: 112 | SEQ ID NO: 107 | NCR112 | — | SEQ ID NO: 575 |
| SEQ ID NO: 113 | SEQ ID NO: 108 | NCR113 | SEQ ID NO: 501 | SEQ ID NO: 576 |

TABLE I-continued

| MATURE PEPTIDE AND SIGNAL PEPTIDE SEQ ID NO: (Present document) | MATURE PEPTIDE AND SIGNAL PEPTIDE SEQ ID NO: (Priority document EP 09 305 547.3) | NCR NUMBER | MATURE PEPTIDE SEQ ID NO: (Priority document EP 09 305 547.3) | MATURE PEPTIDE SEQ ID NO: (Present document) |
|---|---|---|---|---|
| SEQ ID NO: 114 | SEQ ID NO: 109 | NCR114 | SEQ ID NO: 526 | SEQ ID NO: 577 |
| SEQ ID NO: 115 | SEQ ID NO: 110 | NCR115 | SEQ ID NO: 330 | SEQ ID NO: 578 |
| SEQ ID NO: 116 | SEQ ID NO: 111 | NCR116 | SEQ ID NO: 511 | SEQ ID NO: 579 |
| SEQ ID NO: 117 | SEQ ID NO: 112 | NCR117 | SEQ ID NO: 443 | SEQ ID NO: 580 |
| SEQ ID NO: 118 | SEQ ID NO: 113 | NCR118 | SEQ ID NO: 537 | SEQ ID NO: 581 |
| SEQ ID NO: 119 | SEQ ID NO: 114 | NCR119 | SEQ ID NO: 365 | SEQ ID NO: 582 |
| SEQ ID NO: 120 | SEQ ID NO: 115 | NCR120 |  | SEQ ID NO: 583 |
| SEQ ID NO: 121 | SEQ ID NO: 116 | NCR121 | SEQ ID NO: 401 | SEQ ID NO: 584 |
| SEQ ID NO: 122 | SEQ ID NO: 117 | NCR122 | SEQ ID NO: 402 | SEQ ID NO: 585 |
| SEQ ID NO: 123 | — | NCR123 | — | SEQ ID NO: 586 |
| SEQ ID NO: 124 | SEQ ID NO: 118 | NCR124 | SEQ ID NO: 327 | SEQ ID NO: 587 |
| SEQ ID NO: 125 | SEQ ID NO: 119 | NCR125 |  | SEQ ID NO: 588 |
| SEQ ID NO: 126 | SEQ ID NO: 120 | NCR126 |  | SEQ ID NO: 589 |
| SEQ ID NO: 127 | SEQ ID NO: 121 | NCR127 | SEQ ID NO: 519 | SEQ ID NO: 590 |
| SEQ ID NO: 128 | SEQ ID NO: 122 | NCR128 | SEQ ID NO: 366 | SEQ ID NO: 591 |
| SEQ ID NO: 129 | SEQ ID NO: 123 | NCR129 | SEQ ID NO: 388 | SEQ ID NO: 592 |
| SEQ ID NO: 130 | SEQ ID NO: 124 | NCR130 | SEQ ID NO: 403 | SEQ ID NO: 593 |
| SEQ ID NO: 131 | SEQ ID NO: 125 | NCR131 | SEQ ID NO: 476 | SEQ ID NO: 594 |
| SEQ ID NO: 132 | SEQ ID NO: 126 | NCR132 | — | SEQ ID NO: 595 |
| SEQ ID NO: 133 | SEQ ID NO: 127 | NCR133 | SEQ ID NO: 490 | SEQ ID NO: 596 |
| SEQ ID NO: 134 | SEQ ID NO: 128 | NCR134 | SEQ ID NO: 547 | SEQ ID NO: 597 |
| SEQ ID NO: 135 | SEQ ID NO: 129 | NCR135 | SEQ ID NO: 477 | SEQ ID NO: 598 |
| SEQ ID NO: 136 | SEQ ID NO: 130 | NCR136 | SEQ ID NO: 367 | SEQ ID NO: 599 |
| SEQ ID NO: 137 | SEQ ID NO: 131 | NCR137 | SEQ ID NO: 389 | SEQ ID NO: 600 |
| SEQ ID NO: 138 | SEQ ID NO: 132 | NCR138 | SEQ ID NO: 390 | SEQ ID NO: 601 |
| SEQ ID NO: 139 | SEQ ID NO: 133 | NCR139 | SEQ ID NO: 502 | SEQ ID NO: 602 |
| SEQ ID NO: 140 | SEQ ID NO: 134 | NCR140 | SEQ ID NO: 563 | SEQ ID NO: 603 |
| SEQ ID NO: 141 | SEQ ID NO: 135 | NCR141 | SEQ ID NO: 562 | SEQ ID NO: 604 |
| SEQ ID NO: 142 | SEQ ID NO: 136 | NCR142 | — | SEQ ID NO: 605 |
| SEQ ID NO: 143 | SEQ ID NO: 137 | NCR143 | SEQ ID NO: 404 | SEQ ID NO: 606 |
| SEQ ID NO: 144 | SEQ ID NO: 138 | NCR144 | SEQ ID NO: 405 | SEQ ID NO: 607 |
| SEQ ID NO: 145 | SEQ ID NO: 139 | NCR145 | SEQ ID NO: 352 | SEQ ID NO: 608 |
| SEQ ID NO: 146 | SEQ ID NO: 140 | NCR146 | SEQ ID NO: 457 | SEQ ID NO: 609 |
| SEQ ID NO: 147 | SEQ ID NO: 141 | NCR147 | SEQ ID NO: 406 | SEQ ID NO: 610 |
| SEQ ID NO: 148 | SEQ ID NO: 142 | NCR148 | — | SEQ ID NO: 611 |
| SEQ ID NO: 149 | SEQ ID NO: 143 | NCR149 | — | SEQ ID NO: 612 |
| SEQ ID NO: 150 | SEQ ID NO: 144 | NCR150 | SEQ ID NO: 328 | SEQ ID NO: 613 |
| SEQ ID NO: 151 | SEQ ID NO: 145 | NCR151 | — | SEQ ID NO: 614 |
| SEQ ID NO: 152 | SEQ ID NO: 146 | NCR152 | SEQ ID NO: 407 | SEQ ID NO: 615 |
| SEQ ID NO: 153 | SEQ ID NO: 147 | NCR153 | — | SEQ ID NO: 616 |
| SEQ ID NO: 154 | SEQ ID NO: 148 | NCR154 | SEQ ID NO: 331 | SEQ ID NO: 617 |
| SEQ ID NO: 155 | SEQ ID NO: 149 | NCR155 | — | SEQ ID NO: 618 |
| SEQ ID NO: 156 | SEQ ID NO: 150 | NCR156 | SEQ ID NO: 428 | SEQ ID NO: 619 |
| SEQ ID NO: 157 | SEQ ID NO: 151 | NCR157 | SEQ ID NO: 368 | SEQ ID NO: 620 |
| SEQ ID NO: 158 | SEQ ID NO: 152 | NCR158 | SEQ ID NO: 527 | SEQ ID NO: 621 |
| SEQ ID NO: 159 | SEQ ID NO: 153 | NCR159 | SEQ ID NO: 478 | SEQ ID NO: 622 |
| SEQ ID NO: 160 | SEQ ID NO: 154 | NCR160 | SEQ ID NO: 408 | SEQ ID NO: 623 |
| SEQ ID NO: 161 | SEQ ID NO: 155 | NCR161 | SEQ ID NO: 340 | SEQ ID NO: 624 |
| SEQ ID NO: 162 | SEQ ID NO: 156 | NCR162 | SEQ ID NO: 429 | SEQ ID NO: 625 |
| SEQ ID NO: 163 | SEQ ID NO: 157 | NCR163 | SEQ ID NO: 503 | SEQ ID NO: 626 |
| SEQ ID NO: 164 | SEQ ID NO: 158 | NCR164 | SEQ ID NO: 444 | SEQ ID NO: 627 |
| SEQ ID NO: 165 | SEQ ID NO: 159 | NCR165 | SEQ ID NO: 458 | SEQ ID NO: 628 |
| SEQ ID NO: 166 | SEQ ID NO: 160 | NCR166 | SEQ ID NO: 496 | SEQ ID NO: 629 |
| SEQ ID NO: 167 | SEQ ID NO: 161 | NCR167 | SEQ ID NO: 459 | SEQ ID NO: 630 |
| SEQ ID NO: 168 | SEQ ID NO: 162 | NCR168 | SEQ ID NO: 479 | SEQ ID NO: 631 |
| SEQ ID NO: 169 | SEQ ID NO: 163 | NCR169 | SEQ ID NO: 430 | SEQ ID NO: 632 |
| SEQ ID NO: 170 | SEQ ID NO: 164 | NCR170 | SEQ ID NO: 369 | SEQ ID NO: 633 |
| SEQ ID NO: 171 | SEQ ID NO: 165 | NCR171 | SEQ ID NO: 445 | SEQ ID NO: 634 |
| SEQ ID NO: 172 | SEQ ID NO: 166 | NCR172 | SEQ ID NO: 420 | SEQ ID NO: 635 |
| SEQ ID NO: 173 | SEQ ID NO: 167 | NCR173 | SEQ ID NO: 520 | SEQ ID NO: 636 |
| SEQ ID NO: 174 | SEQ ID NO: 168 | NCR174 | SEQ ID NO: 491 | SEQ ID NO: 637 |
| SEQ ID NO: 175 | SEQ ID NO: 169 | NCR175 | SEQ ID NO: 543 | SEQ ID NO: 638 |
| SEQ ID NO: 176 | SEQ ID NO: 170 | NCR176 | SEQ ID NO: 341 | SEQ ID NO: 639 |
| SEQ ID NO: 177 | SEQ ID NO: 171 | NCR177 | SEQ ID NO: 326 | SEQ ID NO: 640 |
| SEQ ID NO: 178 | SEQ ID NO: 172 | NCR178 | SEQ ID NO: 370 | SEQ ID NO: 641 |
| SEQ ID NO: 179 | SEQ ID NO: 173 | NCR179 | — | SEQ ID NO: 642 |
| SEQ ID NO: 180 | SEQ ID NO: 174 | NCR180 | — | SEQ ID NO: 643 |
| SEQ ID NO: 181 | SEQ ID NO: 175 | NCR181 | SEQ ID NO: 541 | SEQ ID NO: 644 |
| SEQ ID NO: 182 | SEQ ID NO: 176 | NCR182 | — | SEQ ID NO: 645 |
| SEQ ID NO: 183 | SEQ ID NO: 177 | NCR183 | SEQ ID NO: 492 | SEQ ID NO: 646 |
| SEQ ID NO: 184 | SEQ ID NO: 178 | NCR184 | — | SEQ ID NO: 647 |

TABLE I-continued

| MATURE PEPTIDE AND SIGNAL PEPTIDE SEQ ID NO: (Present document) | MATURE PEPTIDE AND SIGNAL PEPTIDE SEQ ID NO: (Priority document EP 09 305 547.3) | NCR NUMBER | MATURE PEPTIDE SEQ ID NO: (Priority document EP 09 305 547.3) | MATURE PEPTIDE SEQ ID NO: (Present document) |
|---|---|---|---|---|
| SEQ ID NO: 185 | SEQ ID NO: 179 | NCR185 | SEQ ID NO: 431 | SEQ ID NO: 648 |
| SEQ ID NO: 186 | SEQ ID NO: 180 | NCR186 | — | SEQ ID NO: 649 |
| SEQ ID NO: 187 | SEQ ID NO: 181 | NCR187 | SEQ ID NO: 497 | SEQ ID NO: 650 |
| SEQ ID NO: 188 | — | NCR188 | — | SEQ ID NO: 651 |
| SEQ ID NO: 189 | SEQ ID NO: 182 | NCR189 | SEQ ID NO: 521 | SEQ ID NO: 652 |
| SEQ ID NO: 190 | SEQ ID NO: 183 | NCR190 | SEQ ID NO: 512 | SEQ ID NO: 653 |
| SEQ ID NO: 191 | — | NCR191 | — | SEQ ID NO: 654 |
| SEQ ID NO: 192 | SEQ ID NO: 184 | NCR192 | SEQ ID NO: 332 | SEQ ID NO: 655 |
| SEQ ID NO: 193 | SEQ ID NO: 185 | NCR193 | SEQ ID NO: 480 | SEQ ID NO: 656 |
| SEQ ID NO: 194 | SEQ ID NO: 186 | NCR194 | SEQ ID NO: 391 | SEQ ID NO: 657 |
| SEQ ID NO: 195 | SEQ ID NO: 187 | NCR195 | SEQ ID NO: 522 | SEQ ID NO: 658 |
| SEQ ID NO: 196 | SEQ ID NO: 188 | NCR196 | SEQ ID NO: 493 | SEQ ID NO: 659 |
| SEQ ID NO: 197 | SEQ ID NO: 189 | NCR197 | SEQ ID NO: 460 | SEQ ID NO: 660 |
| SEQ ID NO: 198 | SEQ ID NO: 190 | NCR198 | — | SEQ ID NO: 661 |
| SEQ ID NO: 199 | SEQ ID NO: 191 | NCR199 | — | SEQ ID NO: 662 |
| SEQ ID NO: 200 | SEQ ID NO: 192 | NCR200 | SEQ ID NO: 432 | SEQ ID NO: 663 |
| SEQ ID NO: 201 | SEQ ID NO: 193 | NCR201 | SEQ ID NO: 446 | SEQ ID NO: 664 |
| SEQ ID NO: 202 | — | NCR202 | — | SEQ ID NO: 665 |
| SEQ ID NO: 203 | SEQ ID NO: 194 | NCR203 | SEQ ID NO: 433 | SEQ ID NO: 666 |
| SEQ ID NO: 204 | SEQ ID NO: 195 | NCR204 | SEQ ID NO: 333 | SEQ ID NO: 667 |
| SEQ ID NO: 205 | SEQ ID NO: 196 | NCR205 | — | SEQ ID NO: 668 |
| SEQ ID NO: 206 | SEQ ID NO: 197 | NCR206 | SEQ ID NO: 447 | SEQ ID NO: 669 |
| SEQ ID NO: 207 | SEQ ID NO: 198 | NCR207 | SEQ ID NO: 392 | SEQ ID NO: 670 |
| SEQ ID NO: 208 | SEQ ID NO: 199 | NCR208 | SEQ ID NO: 353 | SEQ ID NO: 671 |
| SEQ ID NO: 209 | SEQ ID NO: 200 | NCR209 | SEQ ID NO: 371 | SEQ ID NO: 672 |
| SEQ ID NO: 210 | SEQ ID NO: 201 | NCR210 | SEQ ID NO: 481 | SEQ ID NO: 673 |
| SEQ ID NO: 211 | SEQ ID NO: 202 | NCR211 | — | SEQ ID NO: 674 |
| SEQ ID NO: 212 | SEQ ID NO: 203 | NCR212 | SEQ ID NO: 482 | SEQ ID NO: 675 |
| SEQ ID NO: 213 | SEQ ID NO: 204 | NCR213 | SEQ ID NO: 461 | SEQ ID NO: 676 |
| SEQ ID NO: 214 | SEQ ID NO: 205 | NCR214 | SEQ ID NO: 498 | SEQ ID NO: 677 |
| SEQ ID NO: 215 | SEQ ID NO: 206 | NCR215 | SEQ ID NO: 372 | SEQ ID NO: 678 |
| SEQ ID NO: 216 | SEQ ID NO: 207 | NCR216 | SEQ ID NO: 462 | SEQ ID NO: 679 |
| SEQ ID NO: 217 | SEQ ID NO: 208 | NCR217 | SEQ ID NO: 409 | SEQ ID NO: 680 |
| — | SEQ ID NO: 209 | NCR218 | SEQ ID NO: 323 | — |
| SEQ ID NO: 218 | SEQ ID NO: 210 | NCR219 | — | SEQ ID NO: 681 |
| SEQ ID NO: 219 | SEQ ID NO: 211 | NCR220 | SEQ ID NO: 373 | SEQ ID NO: 682 |
| SEQ ID NO: 220 | SEQ ID NO: 212 | NCR221 | SEQ ID NO: 334 | SEQ ID NO: 683 |
| SEQ ID NO: 221 | SEQ ID NO: 213 | NCR222 | SEQ ID NO: 374 | SEQ ID NO: 684 |
| SEQ ID NO: 222 | SEQ ID NO: 214 | NCR223 | SEQ ID NO: 393 | SEQ ID NO: 685 |
| SEQ ID NO: 223 | SEQ ID NO: 215 | NCR224 | SEQ ID NO: 375 | SEQ ID NO: 686 |
| SEQ ID NO: 224 | SEQ ID NO: 216 | NCR225 | SEQ ID NO: 448 | SEQ ID NO: 687 |
| SEQ ID NO: 225 | — | NCR226 | — | SEQ ID NO: 688 |
| SEQ ID NO: 226 | SEQ ID NO: 217 | NCR227 | SEQ ID NO: 513 | SEQ ID NO: 689 |
| SEQ ID NO: 227 | SEQ ID NO: 218 | NCR228 | SEQ ID NO: 421 | SEQ ID NO: 690 |
| SEQ ID NO: 228 | SEQ ID NO: 219 | NCR229 | SEQ ID NO: 544 | SEQ ID NO: 691 |
| SEQ ID NO: 229 | SEQ ID NO: 220 | NCR230 | SEQ ID NO: 546 | SEQ ID NO: 692 |
| SEQ ID NO: 230 | SEQ ID NO: 221 | NCR231 | SEQ ID NO: 504 | SEQ ID NO: 693 |
| SEQ ID NO: 231 | SEQ ID NO: 222 | NCR232 | SEQ ID NO: 463 | SEQ ID NO: 694 |
| SEQ ID NO: 232 | SEQ ID NO: 223 | NCR233 | SEQ ID NO: 505 | SEQ ID NO: 695 |
| SEQ ID NO: 233 | SEQ ID NO: 224 | NCR234 | — | SEQ ID NO: 696 |
| SEQ ID NO: 234 | SEQ ID NO: 225 | NCR235 | SEQ ID NO: 434 | SEQ ID NO: 697 |
| SEQ ID NO: 235 | SEQ ID NO: 226 | NCR236 | SEQ ID NO: 555 | SEQ ID NO: 698 |
| SEQ ID NO: 236 | SEQ ID NO: 227 | NCR237 | SEQ ID NO: 464 | SEQ ID NO: 699 |
| SEQ ID NO: 237 | SEQ ID NO: 228 | NCR238 | SEQ ID NO: 552 | SEQ ID NO: 700 |
| SEQ ID NO: 238 | SEQ ID NO: 229 | NCR239 | SEQ ID NO: 494 | SEQ ID NO: 701 |
| SEQ ID NO: 239 | SEQ ID NO: 230 | NCR242 | SEQ ID NO: 528 | SEQ ID NO: 702 |
| SEQ ID NO: 240 | SEQ ID NO: 231 | NCR243 | SEQ ID NO: 506 | SEQ ID NO: 703 |
| — | SEQ ID NO: 232 | NCR244 | SEQ ID NO: 342 | — |
| SEQ ID NO: 241 | SEQ ID NO: 233 | NCR245 | SEQ ID NO: 449 | SEQ ID NO: 704 |
| SEQ ID NO: 242 | SEQ ID NO: 234 | NCR246 | SEQ ID NO: 450 | SEQ ID NO: 705 |
| SEQ ID NO: 243 | SEQ ID NO: 235 | NCR247 | SEQ ID NO: 321 | SEQ ID NO: 706 |
| SEQ ID NO: 244 | SEQ ID NO: 236 | NCR248 | — | SEQ ID NO: 707 |
| SEQ ID NO: 245 | SEQ ID NO: 237 | NCR249 | — | SEQ ID NO: 708 |
| SEQ ID NO: 246 | — | NCR250 | — | SEQ ID NO: 709 |
| SEQ ID NO: 247 | SEQ ID NO: 238 | NCR251 | SEQ ID NO: 376 | SEQ ID NO: 710 |
| SEQ ID NO: 248 | SEQ ID NO: 239 | NCR252 | — | SEQ ID NO: 711 |
| SEQ ID NO: 249 | SEQ ID NO: 240 | NCR253 | — | SEQ ID NO: 712 |
| SEQ ID NO: 250 | SEQ ID NO: 241 | NCR254 | — | SEQ ID NO: 713 |
| SEQ ID NO: 251 | — | NCR255 | — | SEQ ID NO: 714 |
| SEQ ID NO: 252 | SEQ ID NO: 242 | NCR256 | SEQ ID NO: 553 | SEQ ID NO: 715 |
| SEQ ID NO: 253 | SEQ ID NO: 243 | NCR257 | SEQ ID NO: 549 | — |

TABLE I-continued

| MATURE PEPTIDE AND SIGNAL PEPTIDE SEQ ID NO: (Present document) | MATURE PEPTIDE AND SIGNAL PEPTIDE SEQ ID NO: (Priority document EP 09 305 547.3) | NCR NUMBER | MATURE PEPTIDE SEQ ID NO: (Priority document EP 09 305 547.3) | MATURE PEPTIDE SEQ ID NO: (Present document) |
|---|---|---|---|---|
| SEQ ID NO: 254 | SEQ ID NO: 244 | NCR258 | — | SEQ ID NO: 716 |
| SEQ ID NO: 255 | SEQ ID NO: 245 | NCR259 | — | SEQ ID NO: 717 |
| SEQ ID NO: 256 | SEQ ID NO: 246 | NCR260 | SEQ ID NO: 465 | SEQ ID NO: 718 |
| SEQ ID NO: 257 | SEQ ID NO: 247 | NCR261 | — | SEQ ID NO: 719 |
| SEQ ID NO: 258 | SEQ ID NO: 248 | NCR262 | — | SEQ ID NO: 720 |
| SEQ ID NO: 259 | SEQ ID NO: 249 | NCR263 | SEQ ID NO: 354 | SEQ ID NO: 721 |
| SEQ ID NO: 260 | SEQ ID NO: 250 | NCR264 | — | SEQ ID NO: 722 |
| SEQ ID NO: 261 | SEQ ID NO: 251 | NCR265 | SEQ ID NO: 377 | SEQ ID NO: 723 |
| SEQ ID NO: 262 | SEQ ID NO: 252 | NCR266 | SEQ ID NO: 451 | SEQ ID NO: 724 |
| SEQ ID NO: 263 | SEQ ID NO: 253 | NCR267 | — | SEQ ID NO: 725 |
| SEQ ID NO: 264 | SEQ ID NO: 254 | NCR268 | — | SEQ ID NO: 726 |
| SEQ ID NO: 265 | SEQ ID NO: 255 | NCR269 | SEQ ID NO: 529 | SEQ ID NO: 727 |
| SEQ ID NO: 266 | SEQ ID NO: 256 | NCR270 | SEQ ID NO: 410 | SEQ ID NO: 728 |
| SEQ ID NO: 267 | SEQ ID NO: 257 | NCR271 | — | SEQ ID NO: 729 |
| SEQ ID NO: 268 | SEQ ID NO: 258 | NCR272 | — | SEQ ID NO: 730 |
| SEQ ID NO: 269 | SEQ ID NO: 259 | NCR273 | SEQ ID NO: 507 | SEQ ID NO: 731 |
| SEQ ID NO: 270 | SEQ ID NO: 260 | NCR274 | SEQ ID NO: 508 | SEQ ID NO: 732 |
| SEQ ID NO: 271 | SEQ ID NO: 261 | NCR275 | — | SEQ ID NO: 733 |
| SEQ ID NO: 272 | — | NCR276 | — | SEQ ID NO: 734 |
| SEQ ID NO: 273 | — | NCR277 | — | SEQ ID NO: 735 |
| SEQ ID NO: 274 | SEQ ID NO: 262 | NCR278 | SEQ ID NO: 378 | SEQ ID NO: 736 |
| SEQ ID NO: 275 | SEQ ID NO: 263 | NCR279 | SEQ ID NO: 435 | SEQ ID NO: 737 |
| SEQ ID NO: 276 | SEQ ID NO: 264 | NCR280 | SEQ ID NO: 320 | SEQ ID NO: 738 |
| SEQ ID NO: 277 | — | NCR281 | — | SEQ ID NO: 739 |
| SEQ ID NO: 278 | SEQ ID NO: 265 | NCR282 | SEQ ID NO: 335 | SEQ ID NO: 740 |
| SEQ ID NO: 279 | SEQ ID NO: 266 | NCR283 | — | SEQ ID NO: 741 |
| SEQ ID NO: 280 | SEQ ID NO: 267 | NCR284 | SEQ ID NO: 343 | SEQ ID NO: 742 |
| SEQ ID NO: 281 | SEQ ID NO: 268 | NCR285 | — | SEQ ID NO: 743 |
| SEQ ID NO: 282 | SEQ ID NO: 269 | NCR286 | SEQ ID NO: 483 | SEQ ID NO: 744 |
| SEQ ID NO: 283 | SEQ ID NO: 270 | NCR287 | — | SEQ ID NO: 745 |
| SEQ ID NO: 284 | SEQ ID NO: 271 | NCR288 | — | SEQ ID NO: 746 |
| SEQ ID NO: 285 | SEQ ID NO: 272 | NCR289 | SEQ ID NO: 452 | SEQ ID NO: 747 |
| SEQ ID NO: 286 | SEQ ID NO: 273 | NCR290 | SEQ ID NO: 411 | SEQ ID NO: 748 |
| SEQ ID NO: 287 | — | NCR291 | — | SEQ ID NO: 749 |
| SEQ ID NO: 288 | — | NCR292 | — | SEQ ID NO: 750 |
| SEQ ID NO: 289 | SEQ ID NO: 274 | NCR293 | SEQ ID NO: 554 | SEQ ID NO: 751 |
| SEQ ID NO: 290 | SEQ ID NO: 275 | NCR294 | — | SEQ ID NO: 752 |
| SEQ ID NO: 291 | SEQ ID NO: 276 | NCR295 | — | SEQ ID NO: 753 |
| SEQ ID NO: 292 | SEQ ID NO: 277 | NCR296 | — | SEQ ID NO: 754 |
| SEQ ID NO: 293 | SEQ ID NO: 278 | NCR297 | — | SEQ ID NO: 755 |
| SEQ ID NO: 294 | SEQ ID NO: 279 | NCR298 | — | SEQ ID NO: 756 |
| SEQ ID NO: 295 | SEQ ID NO: 280 | NCR299 | — | SEQ ID NO: 757 |
| SEQ ID NO: 296 | SEQ ID NO: 281 | NCR300 | SEQ ID NO: 422 | SEQ ID NO: 758 |
| SEQ ID NO: 297 | SEQ ID NO: 282 | NCR301 | SEQ ID NO: 453 | SEQ ID NO: 759 |
| SEQ ID NO: 298 | SEQ ID NO: 283 | NCR302 | — | SEQ ID NO: 760 |
| SEQ ID NO: 299 | SEQ ID NO: 284 | NCR303 | SEQ ID NO: 514 | SEQ ID NO: 761 |
| SEQ ID NO: 300 | SEQ ID NO: 285 | NCR304 | SEQ ID NO: 556 | SEQ ID NO: 762 |
| SEQ ID NO: 301 | SEQ ID NO: 286 | NCR305 | — | SEQ ID NO: 763 |
| SEQ ID NO: 302 | SEQ ID NO: 287 | NCR306 | — | SEQ ID NO: 764 |
| SEQ ID NO: 303 | — | NCR307 | — | SEQ ID NO: 765 |
| SEQ ID NO: 304 | — | NCR308 | — | SEQ ID NO: 766 |
| SEQ ID NO: 305 | SEQ ID NO: 288 | NCR309 | SEQ ID NO: 515 | SEQ ID NO: 767 |
| SEQ ID NO: 306 | SEQ ID NO: 289 | NCR310 | SEQ ID NO: 466 | SEQ ID NO: 768 |
| SEQ ID NO: 307 | SEQ ID NO: 290 | NCR311 | — | SEQ ID NO: 769 |
| SEQ ID NO: 308 | SEQ ID NO: 291 | NCR312 | SEQ ID NO: 412 | SEQ ID NO: 770 |
| SEQ ID NO: 309 | SEQ ID NO: 292 | NCR313 | SEQ ID NO: 336 | SEQ ID NO: 771 |
| SEQ ID NO: 310 | SEQ ID NO: 293 | NCR314 | SEQ ID NO: 379 | SEQ ID NO: 772 |
| SEQ ID NO: 311 | SEQ ID NO: 294 | NCR315 | SEQ ID NO: 423 | SEQ ID NO: 773 |
| SEQ ID NO: 312 | SEQ ID NO: 295 | NCR316 | SEQ ID NO: 394 | SEQ ID NO: 774 |
| SEQ ID NO: 313 | SEQ ID NO: 296 | NCR317 | SEQ ID NO: 467 | SEQ ID NO: 775 |
| SEQ ID NO: 314 | SEQ ID NO: 297 | NCR318 | SEQ ID NO: 538 | SEQ ID NO: 776 |
| SEQ ID NO: 315 | SEQ ID NO: 298 | NCR319 | SEQ ID NO: 533 | SEQ ID NO: 777 |
| SEQ ID NO: 316 | SEQ ID NO: 299 | NCR320 | SEQ ID NO: 380 | SEQ ID NO: 778 |
| SEQ ID NO: 317 | SEQ ID NO: 300 | NCR321 | SEQ ID NO: 468 | SEQ ID NO: 779 |
| SEQ ID NO: 318 | SEQ ID NO: 301 | NCR322 | SEQ ID NO: 413 | SEQ ID NO: 780 |
| SEQ ID NO: 319 | SEQ ID NO: 302 | NCR323 | SEQ ID NO: 381 | SEQ ID NO: 781 |
| SEQ ID NO: 320 | SEQ ID NO: 303 | NCR324 | SEQ ID NO: 382 | SEQ ID NO: 782 |
| SEQ ID NO: 321 | SEQ ID NO: 304 | NCR325 | SEQ ID NO: 383 | SEQ ID NO: 783 |
| SEQ ID NO: 322 | SEQ ID NO: 305 | NCR326 | SEQ ID NO: 384 | SEQ ID NO: 784 |
| SEQ ID NO: 323 | SEQ ID NO: 306 | NCR327 | SEQ ID NO: 530 | SEQ ID NO: 785 |
| SEQ ID NO: 324 | SEQ ID NO: 307 | NCR328 | SEQ ID NO: 534 | SEQ ID NO: 786 |

TABLE I-continued

| MATURE PEPTIDE AND SIGNAL PEPTIDE SEQ ID NO: (Present document) | MATURE PEPTIDE AND SIGNAL PEPTIDE SEQ ID NO: (Priority document EP 09 305 547.3) | NCR NUMBER | MATURE PEPTIDE SEQ ID NO: (Priority document EP 09 305 547.3) | MATURE PEPTIDE SEQ ID NO: (Present document) |
|---|---|---|---|---|
| SEQ ID NO: 325 | SEQ ID NO: 308 | NCR329 | SEQ ID NO: 454 | SEQ ID NO: 787 |
| SEQ ID NO: 326 | SEQ ID NO: 309 | NCR330 | SEQ ID NO: 545 | SEQ ID NO: 788 |
| SEQ ID NO: 327 | SEQ ID NO: 310 | NCR331 | SEQ ID NO: 560 | SEQ ID NO: 789 |
| SEQ ID NO: 328 | SEQ ID NO: 311 | NCR332 | SEQ ID NO: 558 | SEQ ID NO: 790 |
| SEQ ID NO: 329 | SEQ ID NO: 312 | NCR333 | SEQ ID NO: 550 | SEQ ID NO: 791 |
| SEQ ID NO: 330 | SEQ ID NO: 313 | NCR334 | SEQ ID NO: 535 | SEQ ID NO: 792 |
| SEQ ID NO: 331 | SEQ ID NO: 314 | NCR335 | SEQ ID NO: 557 | SEQ ID NO: 793 |
| SEQ ID NO: 332 | SEQ ID NO: 315 | NCR336 | SEQ ID NO: 469 | SEQ ID NO: 794 |
| SEQ ID NO: 333 | SEQ ID NO: 316 | NCR337 | SEQ ID NO: 470 | SEQ ID NO: 795 |
| SEQ ID NO: 334 | SEQ ID NO: 317 | NCR338 | SEQ ID NO: 344 | SEQ ID NO: 796 |
| SEQ ID NO: 335 | SEQ ID NO: 318 | NCR339 | SEQ ID NO: 531 | SEQ ID NO: 797 |
| SEQ ID NO: 336 | SEQ ID NO: 319 | NCR340 | SEQ ID NO: 484 | SEQ ID NO: 798 |
| SEQ ID NO: 337 | — | NCR341 | — | SEQ ID NO: 799 |
| SEQ ID NO: 338 | — | NCR342 | — | SEQ ID NO: 800 |
| SEQ ID NO: 339 | — | NCR343 | — | SEQ ID NO: 801 |
| SEQ ID NO: 340 | — | NCR344 | — | SEQ ID NO: 802 |
| SEQ ID NO: 341 | — | NCR345 | — | SEQ ID NO: 803 |
| SEQ ID NO: 342 | — | NCR346 | — | SEQ ID NO: 804 |
| SEQ ID NO: 343 | — | NCR347 | — | SEQ ID NO: 805 |
| SEQ ID NO: 344 | — | NCR348 | — | SEQ ID NO: 806 |
| SEQ ID NO: 345 | — | NCR349 | — | SEQ ID NO: 807 |
| SEQ ID NO: 346 | — | NCR350 | — | SEQ ID NO: 808 |
| SEQ ID NO: 347 | — | NCR351 | — | SEQ ID NO: 809 |
| SEQ ID NO: 348 | — | NCR352 | — | SEQ ID NO: 810 |
| SEQ ID NO: 349 | — | NCR353 | — | SEQ ID NO: 811 |
| SEQ ID NO: 350 | — | NCR354 | — | SEQ ID NO: 812 |
| SEQ ID NO: 351 | — | NCR355 | — | SEQ ID NO: 813 |
| SEQ ID NO: 352 | — | NCR356 | — | SEQ ID NO: 814 |
| SEQ ID NO: 353 | — | NCR357 | — | SEQ ID NO: 815 |
| SEQ ID NO: 354 | — | NCR358 | — | SEQ ID NO: 816 |
| SEQ ID NO: 355 | — | NCR359 | — | SEQ ID NO: 817 |
| SEQ ID NO: 356 | — | NCR360 | — | SEQ ID NO: 818 |
| SEQ ID NO: 357 | — | NCR361 | — | SEQ ID NO: 819 |
| SEQ ID NO: 358 | — | NCR362 | — | SEQ ID NO: 820 |
| SEQ ID NO: 359 | — | NCR363 | — | SEQ ID NO: 821 |
| SEQ ID NO: 360 | — | NCR364 | — | SEQ ID NO: 822 |
| SEQ ID NO: 361 | — | NCR365 | — | SEQ ID NO: 823 |
| SEQ ID NO: 362 | — | NCR366 | — | SEQ ID NO: 824 |
| SEQ ID NO: 363 | — | NCR367 | — | SEQ ID NO: 825 |
| SEQ ID NO: 364 | — | NCR368 | — | SEQ ID NO: 826 |
| SEQ ID NO: 365 | — | NCR369 | — | SEQ ID NO: 827 |
| SEQ ID NO: 366 | — | NCR370 | — | SEQ ID NO: 828 |
| SEQ ID NO: 367 | — | NCR371 | — | SEQ ID NO: 829 |
| SEQ ID NO: 368 | — | NCR372 | — | SEQ ID NO: 830 |
| SEQ ID NO: 369 | — | NCR373 | — | SEQ ID NO: 831 |
| SEQ ID NO: 370 | — | NCR374 | — | SEQ ID NO: 832 |
| SEQ ID NO: 371 | — | NCR375 | — | SEQ ID NO: 833 |
| SEQ ID NO: 372 | — | NCR376 | — | SEQ ID NO: 834 |
| SEQ ID NO: 373 | — | NCR377 | — | SEQ ID NO: 835 |
| SEQ ID NO: 374 | — | NCR378 | — | SEQ ID NO: 836 |
| SEQ ID NO: 375 | — | NCR379 | — | SEQ ID NO: 837 |
| SEQ ID NO: 376 | — | NCR380 | — | SEQ ID NO: 838 |
| SEQ ID NO: 377 | — | NCR381 | — | SEQ ID NO: 839 |
| SEQ ID NO: 378 | — | NCR382 | — | SEQ ID NO: 840 |
| SEQ ID NO: 379 | — | NCR383 | — | SEQ ID NO: 841 |
| SEQ ID NO: 380 | — | NCR384 | — | SEQ ID NO: 842 |
| SEQ ID NO: 381 | — | NCR385 | — | SEQ ID NO: 843 |
| SEQ ID NO: 382 | — | NCR386 | — | SEQ ID NO: 844 |
| SEQ ID NO: 383 | — | NCR387 | — | SEQ ID NO: 845 |
| SEQ ID NO: 384 | — | NCR388 | — | SEQ ID NO: 846 |
| SEQ ID NO: 385 | — | NCR389 | — | SEQ ID NO: 847 |
| SEQ ID NO: 386 | — | NCR390 | — | SEQ ID NO: 848 |
| SEQ ID NO: 387 | — | NCR391 | — | SEQ ID NO: 849 |
| SEQ ID NO: 388 | — | NCR392 | — | SEQ ID NO: 850 |
| SEQ ID NO: 389 | — | NCR393 | — | SEQ ID NO: 851 |
| SEQ ID NO: 390 | — | NCR394 | — | SEQ ID NO: 852 |
| SEQ ID NO: 391 | — | NCR395 | — | SEQ ID NO: 853 |
| SEQ ID NO: 392 | — | NCR396 | — | SEQ ID NO: 854 |
| SEQ ID NO: 393 | — | NCR397 | — | SEQ ID NO: 855 |
| SEQ ID NO: 394 | — | NCR398 | — | SEQ ID NO: 856 |
| SEQ ID NO: 395 | — | NCR399 | — | SEQ ID NO: 857 |

TABLE I-continued

| MATURE PEPTIDE AND SIGNAL PEPTIDE SEQ ID NO: (Present document) | MATURE PEPTIDE AND SIGNAL PEPTIDE SEQ ID NO: (Priority document EP 09 305 547.3) | NCR NUMBER | MATURE PEPTIDE SEQ ID NO: (Priority document EP 09 305 547.3) | MATURE PEPTIDE SEQ ID NO: (Present document) |
|---|---|---|---|---|
| SEQ ID NO: 396 | — | NCR400 | — | SEQ ID NO: 858 |
| SEQ ID NO: 397 | — | NCR401 | — | SEQ ID NO: 859 |
| SEQ ID NO: 398 | — | NCR402 | — | SEQ ID NO: 860 |
| SEQ ID NO: 399 | — | NCR403 | — | SEQ ID NO: 861 |
| SEQ ID NO: 400 | — | NCR404 | — | SEQ ID NO: 862 |
| SEQ ID NO: 401 | — | NCR405 | — | SEQ ID NO: 863 |
| SEQ ID NO: 402 | — | NCR406 | — | SEQ ID NO: 864 |
| SEQ ID NO: 403 | — | NCR407 | — | SEQ ID NO: 865 |
| SEQ ID NO: 404 | — | NCR408 | — | SEQ ID NO: 866 |
| SEQ ID NO: 405 | — | NCR409 | — | SEQ ID NO: 867 |
| SEQ ID NO: 406 | — | NCR410 | — | SEQ ID NO: 868 |
| SEQ ID NO: 407 | — | NCR411 | — | SEQ ID NO: 869 |
| SEQ ID NO: 408 | — | NCR412 | — | SEQ ID NO: 870 |
| SEQ ID NO: 409 | — | NCR413 | — | SEQ ID NO: 871 |
| SEQ ID NO: 410 | — | NCR414 | — | SEQ ID NO: 872 |
| SEQ ID NO: 411 | — | NCR415 | — | SEQ ID NO: 873 |
| SEQ ID NO: 412 | — | NCR416 | — | SEQ ID NO: 874 |
| SEQ ID NO: 413 | — | NCR417 | — | SEQ ID NO: 875 |
| SEQ ID NO: 414 | — | NCR418 | — | SEQ ID NO: 876 |
| SEQ ID NO: 415 | — | NCR419 | — | SEQ ID NO: 877 |
| SEQ ID NO: 416 | — | NCR420 | — | SEQ ID NO: 878 |
| SEQ ID NO: 417 | — | NCR421 | — | SEQ ID NO: 879 |
| SEQ ID NO: 418 | — | NCR422 | — | SEQ ID NO: 880 |
| SEQ ID NO: 419 | — | NCR423 | — | SEQ ID NO: 881 |
| SEQ ID NO: 420 | — | NCR424 | — | SEQ ID NO: 882 |
| SEQ ID NO: 421 | — | NCR425 | — | SEQ ID NO: 883 |
| SEQ ID NO: 422 | — | NCR426 | — | SEQ ID NO: 884 |
| SEQ ID NO: 423 | — | NCR427 | — | SEQ ID NO: 885 |
| SEQ ID NO: 424 | — | NCR428 | — | SEQ ID NO: 886 |
| SEQ ID NO: 425 | — | NCR429 | — | SEQ ID NO: 887 |
| SEQ ID NO: 426 | — | NCR430 | — | SEQ ID NO: 888 |
| SEQ ID NO: 427 | — | NCR431 | — | SEQ ID NO: 889 |
| SEQ ID NO: 428 | — | NCR432 | — | SEQ ID NO: 890 |
| SEQ ID NO: 429 | — | NCR433 | — | SEQ ID NO: 891 |
| SEQ ID NO: 430 | — | NCR434 | — | SEQ ID NO: 892 |
| SEQ ID NO: 431 | — | NCR435 | — | SEQ ID NO: 893 |
| SEQ ID NO: 432 | — | NCR436 | — | SEQ ID NO: 894 |
| SEQ ID NO: 433 | — | NCR437 | — | SEQ ID NO: 895 |
| SEQ ID NO: 434 | — | NCR438 | — | SEQ ID NO: 896 |
| SEQ ID NO: 435 | — | NCR439 | — | SEQ ID NO: 897 |
| SEQ ID NO: 436 | — | NCR440 | — | SEQ ID NO: 898 |
| SEQ ID NO: 437 | — | NCR441 | — | SEQ ID NO: 899 |
| SEQ ID NO: 438 | — | NCR442 | — | SEQ ID NO: 900 |
| SEQ ID NO: 439 | — | NCR443 | — | SEQ ID NO: 901 |
| SEQ ID NO: 440 | — | NCR444 | — | SEQ ID NO: 902 |
| SEQ ID NO: 441 | — | NCR445 | — | SEQ ID NO: 903 |
| SEQ ID NO: 442 | — | NCR446 | — | SEQ ID NO: 904 |
| SEQ ID NO: 443 | — | NCR447 | — | SEQ ID NO: 905 |
| SEQ ID NO: 444 | — | NCR448 | — | SEQ ID NO: 906 |
| SEQ ID NO: 445 | — | NCR449 | — | SEQ ID NO: 907 |
| SEQ ID NO: 446 | — | NCR450 | — | SEQ ID NO: 908 |
| SEQ ID NO: 447 | — | NCR451 | — | SEQ ID NO: 909 |
| SEQ ID NO: 448 | — | NCR452 | — | SEQ ID NO: 910 |
| SEQ ID NO: 449 | — | NCR453 | — | SEQ ID NO: 911 |
| SEQ ID NO: 450 | — | NCR454 | — | SEQ ID NO: 912 |
| SEQ ID NO: 451 | — | NCR455 | — | SEQ ID NO: 913 |
| SEQ ID NO: 452 | — | NCR456 | — | SEQ ID NO: 914 |
| SEQ ID NO: 453 | — | NCR457 | — | SEQ ID NO: 915 |
| SEQ ID NO: 454 | — | NCR458 | — | SEQ ID NO: 916 |
| SEQ ID NO: 455 | — | NCR459 | — | SEQ ID NO: 917 |
| SEQ ID NO: 456 | — | NCR460 | — | SEQ ID NO: 918 |
| SEQ ID NO: 457 | — | NCR461 | — | SEQ ID NO: 919 |
| SEQ ID NO: 458 | — | NCR462 | — | SEQ ID NO: 920 |
| SEQ ID NO: 459 | — | NCR463 | — | SEQ ID NO: 921 |
| SEQ ID NO: 460 | — | NCR464 | — | SEQ ID NO: 922 |
| SEQ ID NO: 461 | — | NCR465 | — | SEQ ID NO: 923 |
| SEQ ID NO: 462 | — | NCR466 | — | SEQ ID NO: 924 |
| SEQ ID NO: 463 | — | NCR467 | — | SEQ ID NO: 925 |

By the word "microorganisms" is meant organisms that are microscopic such as bacteria, fungi, archaea, protists or viruses.

By the term "bacteria", it must be understood:
Gram+bacteria such as Actinobacteria, Firmicutes or Tenericutes,
Gram−bacteria such as Aquificae, Bacteroidetes/Chlorobi, Chlamydiae/Verrucomicrobia, Deinococcus-Thermus, Fusobacteria, Gemmatimonadetes, Nitrospirae, Proteobacteria, Spirochaetes, Synergistetes, and
Others such as Acidobacteria, Chloroflexi, Chrysiogenetes, Cyanobacteria, Deferribacteres, Dictyoglomi, Fibrobacteres, Planctomycetes, Thermodesulfobacteria, Thermotogae.

By the expression "broad-spectrum" it must be understood that peptides of the invention are able to act as an antibiotic effective against a wide range of infectious microorganisms, in particular with activity against a wide range of disease-causing bacteria (e.g. Gram−*Pseudomonas aeruginosa* and Gram+*Staphylococcus aureus*).

This is in contrast to a narrow-spectrum antibiotic which is effective against only specific families of bacteria.

By the expression "fast antibiotic activity" is meant that peptides of the invention decreased the bacterial count by 3 to 5 orders of magnitude (from $10^6$-$10^9$ to $10^1$-$10^6$) after the peptide was added to the bacterium culture for less than three hours at 10 μM. See Tables V., VI. and IX. and example 6.

The broad spectrum activity and the fast antibiotic activity can be easily determined by a propidium iodide staining test (PI staining) or a colony forming unit (CFU) determination (see example 1 and example 2, respectively).

Antibiotics have the capacity to kill (biocidal activity) or inhibit the growth (biostatic activity) of microorganisms.

Depending on the dose, peptides of the invention are able first to inhibit the growth of the bacteria or to directly kill the bacteria, i.e. lead to the eradication of the bacteria.

The time necessary to achieve this eradication is comprised from about 5 minutes to about 3 hours, preferably from about 10 minutes to about 1 hour, preferably from 15 minutes to about 1 hours, more preferably from about 20 minutes to 1 hour, more preferably from about 30 minutes to 1 hour, more preferably from about 40 minutes to 1 hour, more preferably from about 50 minutes to 1 hour, more preferably from about 55 minutes to 1 hour, more preferably from about 1 hour to about 3 hours, more preferably from about 1 hour to about 2 hours, in particular 1 hour.

Surprisingly, peptides of the invention exhibit no bactericidal activity, i.e. no activity of killing the bacterium, when they are locked in nodules and have surprisingly demonstrated their bactericidal activity once there have been isolated from nodules.

Therefore, one of the advantages of the invention is to provide peptides having a bactericidal activity on a large panel of bacteria (see example 5) and a fast action.

Another advantage of the invention is to provide peptides which are active not only in human but also in animals or plants.

DETAILED DESCRIPTION OF THE INVENTION

In an advantageous embodiment, the present invention relates to the use of at least one peptide originated from *Medicago truncatula* nodules, comprising the SEQ IDs NO: 1-463 or at least one peptide having a sequence derived from said SEQ IDs NO: 1-463 by deletion of about 9 to about 44 contiguous amino acids, from the N-terminal part of the peptide, in particular peptides having the SEQ IDS NO: 464 to 925, for the preparation of a drug intended for the treatment of human or animal diseases induced by microorganisms, wherein said peptides have a broad-spectrum and fast antibiotic activity, in particular killing of the bacteria within 1 to 3 hours.

In an advantageous embodiment, the present invention relates to the use of at least one peptide originated from *Medicago truncatula* nodules, comprising the SEQ IDs NO: 1-463 or at least one peptide having a sequence derived from said SEQ IDs NO: 1-463 by deletion of about 9 to about 44 contiguous amino acids, from the N-terminal part of the peptide, in particular peptides having the SEQ IDS NO: 464 to 925, for the preparation of a drug intended for the treatment of plant diseases induced by microorganisms, wherein said peptides have a broad-spectrum and fast antibiotic activity, in particular killing of the bacteria within 1 to 3 hours.

In an advantageous embodiment, said peptides are administered on the plant surface for the prevention and/or the control of micro organisms inducing plant diseases.

Indeed, said peptides have stimulation properties of plant natural defences and/or fungicide properties.

Said peptides can thus be applied by different ways on the surface of the plants, in particular by spraying on the leaves or the and/or the stem.

In an advantageous embodiment, the present invention relates to the use of the peptides above defined, wherein said peptides derive from the peptides of SEQ ID NO: 1 to 925 above defined:
by substitution, and/or suppression, and/or addition of one or several amino acids, of the above-mentioned peptides, and/or
by modification of at least one —CO—NH— peptide linkage of the peptide chain of the above-mentioned peptides, particularly by introduction of a retro or retro-inverso type linkage, and/or
by substitution of at least one amino acid of the peptide chain of the sequence or of the above-mentioned peptide, with a non-proteinogenic amino acid,
or are fragments of peptides of SEQ ID NO: 1 to 925, provided that the fast antibiotic activity is maintained,
or peptides having more than 80%, preferably more than 85%, preferably more than 90% and more preferably more than 95% of homology with peptides of SEQ ID NO: 1 to 925, provided that the fast antibiotic activity is maintained.

Thus, peptides having the SEQ ID NO:1 to 463 or SEQ ID NO: 464 to 925 can have an amino acid sequence wherein one or more amino acids are substituted or suppressed everywhere inside said sequence or wherein one or more proteinogenic amino acids, i.e. natural amino acids, are added to said sequence, provided that, in each of above cases the fast antibiotic activity of the peptides would be conserved.

Peptides having the SEQ ID NO:1 to 463 or SEQ ID NO: 464 to 925 can also have an amide linkage (—CO—NH— peptide linkage) modified by introduction of a retro amide linkage (—NH—CO— peptide linkage) or a retro inverso amide linkage (—NH—CO— peptide linkage and an inverse absolute configuration of the amino acid) provided that, in each of above cases the antibiotic activity of the peptides would be conserved.

By the expression "non-proteinogenic amino acids", it must be understood either amino acids not found in proteins (like carnitine, GABA, or L-DOPA), or not coded for in the standard genetic code (like hydroxyproline and selenomethionine) provided that, in each of above cases the fast antibiotic activity of the peptides is conserved.

In an advantageous embodiment, the present invention relates to the use of peptides above defined, wherein said microorganisms are bacteria of Gram− or Gram+bacteria.

A list of Gram− or Gram+bacteria can be found in DSMZ catalogue: (http://www.dsmz.de/microorganisms/bacteria catalogue.php)

Examples of Gram−bacteria without being limited to them are the following: *Sinorhizobium meliloti, Pseudomonas aeruginosa, Pseudomonas syringae, Xanthomonas* . . .

Examples of Gram+bacteria without being limited to them are the following: *Clavibacter michigense, Curtobacterium, flaccumfaciens, Bacillus substilis, Staphylococcus aureus* . . .

In an advantageous embodiment, the present invention relates to the use of peptides above defined, wherein said peptides further have an anti-viral and/or fungicidal activity.

Another advantage of the invention is to provide peptides having not only an antibacterial activity but also an antiviral activity or a fungicidal activity, for example on *Kluyveromyces lactis* or *Pichia patoris*.

In a more advantageous embodiment, the present invention relates to the use of peptides above defined, wherein said peptides are cationic peptides (pI>8) in association with one or more anionic peptides (pI<6) and/or one or more neutral peptides (6≤pI≤8).

The isoelectric point (pI), is the pH at which a peptide carries no net electrical charge.

pI can be determined with techniques well known by a man skilled in the art (www.expasy.ch/tools/pi_tool.html)

Peptides are constituted with hydrophobic amino acids, hydrophilic amino acids, positively or negatively charged amino acids.

Peptides having a pI higher than 8 are cationic peptides.
Peptides having a pI lower than 6 are anionic peptides.
Peptides having a pI comprised between 6 and 8 are neutral peptides.

Therefore, according to the invention:
cationic peptides can be associated with anionic peptides, or
cationic peptides can be associated with neutral peptides, or
cationic peptides can be associated with anionic and neutral peptides, Surprisingly, it has been found by the invention that peptides having the better antibiotic activity are cationic peptides and that anionic or neutral peptides can stabilize cationic peptides when associated with them, leading thus to an improved and fast antibiotic activity.

In a more advantageous embodiment, the present invention relates to the use of peptides above defined, wherein said cationic peptides are selected from the list consisting of SEQ ID NO:469; SEQ ID NO:474; SEQ ID NO:480; SEQ ID NO:483; SEQ ID NO:484; SEQ ID NO:485; SEQ ID NO:486; SEQ ID NO:489; SEQ ID NO:490; SEQ ID NO:492; SEQ ID NO:493; SEQ ID NO:494; SEQ ID NO:495; SEQ ID NO:496; SEQ ID NO:497; SEQ ID NO:498; SEQ ID NO:499; SEQ ID NO:500; SEQ ID NO:501; SEQ ID NO:502; SEQ ID NO:503; SEQ ID NO:504; SEQ ID NO:505; SEQ ID NO:506; SEQ ID NO:507; SEQ ID NO:508; SEQ ID NO:509; SEQ ID NO:510; SEQ ID NO:511; SEQ ID NO:512; SEQ ID NO:513; SEQ ID NO:515; SEQ ID NO:516; SEQ ID NO:518; SEQ ID NO:520; SEQ ID NO:523; SEQ ID NO:524; SEQ ID NO:530; SEQ ID NO:531; SEQ ID NO:532; SEQ ID NO:533; SEQ ID NO:534; SEQ ID NO:536; SEQ ID NO:538; SEQ ID NO:541; SEQ ID NO:543; SEQ ID NO:544; SEQ ID NO:546; SEQ ID NO:549; SEQ ID NO:554; SEQ ID NO:555; SEQ ID NO:556; SEQ ID NO:561; SEQ ID NO:563; SEQ ID NO:564; SEQ ID NO:565; SEQ ID NO:566; SEQ ID NO:567; SEQ ID NO:569; SEQ ID NO:573; SEQ ID NO:582; SEQ ID NO:583; SEQ ID NO:593; SEQ ID NO:596; SEQ ID NO:597; SEQ ID NO:598; SEQ ID NO:599; SEQ ID NO:600; SEQ ID NO:606; SEQ ID NO:610; SEQ ID NO:611; SEQ ID NO:613; SEQ ID NO:618; SEQ ID NO:620; SEQ ID NO:622; SEQ ID NO:623; SEQ ID NO:632; SEQ ID NO:633; SEQ ID NO:634; SEQ ID NO:635; SEQ ID NO:636; SEQ ID NO:639; SEQ ID NO:642; SEQ ID NO:644; SEQ ID NO:646; SEQ ID NO:647; SEQ ID NO:651; SEQ ID NO:652; SEQ ID NO:655; SEQ ID NO:658; SEQ ID NO:659; SEQ ID NO:662; SEQ ID NO:663; SEQ ID NO:670; SEQ ID NO:675; SEQ ID NO:681; SEQ ID NO:683; SEQ ID NO:684; SEQ ID NO:685; SEQ ID NO:690; SEQ ID NO:694; SEQ ID NO:700; SEQ ID NO:705; SEQ ID NO:706; SEQ ID NO:709; SEQ ID NO:713; SEQ ID NO:715; SEQ ID NO:720; SEQ ID NO:721; SEQ ID NO:725; SEQ ID NO:731; SEQ ID NO:737; SEQ ID NO:738; SEQ ID NO:739; SEQ ID NO:742; SEQ ID NO:743; SEQ ID NO:744; SEQ ID NO:746; SEQ ID NO:750; SEQ ID NO:753; SEQ ID NO:757; SEQ ID NO:758; SEQ ID NO:761; SEQ ID NO:766; SEQ ID NO:769; SEQ ID NO:772; SEQ ID NO:774; SEQ ID NO:775; SEQ ID NO:780; SEQ ID NO:781; SEQ ID NO:782; SEQ ID NO:783; SEQ ID NO:784; SEQ ID NO:787; SEQ ID NO:793; SEQ ID NO:794; SEQ ID NO:799; SEQ ID NO:800; SEQ ID NO:807; SEQ ID NO:812; SEQ ID NO:816; SEQ ID NO:817; SEQ ID NO:819; SEQ ID NO:820; SEQ ID NO:821; SEQ ID NO:824; SEQ ID NO:825; SEQ ID NO:827; SEQ ID NO:828; SEQ ID NO:829; SEQ ID NO:830; SEQ ID NO:835; SEQ ID NO:836; SEQ ID NO:842; SEQ ID NO:846; SEQ ID NO:847; SEQ ID NO:848; SEQ ID NO:849; SEQ ID NO:850; SEQ ID NO:853; SEQ ID NO:858; SEQ ID NO:862; SEQ ID NO:863; SEQ ID NO:865; SEQ ID NO:866; SEQ ID NO:870; SEQ ID NO:872; SEQ ID NO:875; SEQ ID NO:877; SEQ ID NO:878; SEQ ID NO:879; SEQ ID NO:880; SEQ ID NO:881; SEQ ID NO:892; SEQ ID NO:894; SEQ ID NO:896; SEQ ID NO:897; SEQ ID NO:899; SEQ ID NO:909; SEQ ID NO:910; SEQ ID NO:913; SEQ ID NO:917; SEQ ID NO:919; SEQ ID NO:921 and SEQ ID NO:925.

Table II give the NCR correlation and the pI>8 of the cationic peptides above defined:

TABLE II

| SEQ ID NO: | PEPTIDE | pI |
|---|---|---|
| SEQ ID NO: 469 | NCR006 | 8.50 |
| SEQ ID NO: 474 | NCR011 | 8.85 |
| SEQ ID NO: 480 | NCR017 | 8.20 |
| SEQ ID NO: 483 | NCR020 | 9.56 |
| SEQ ID NO: 484 | NCR021 | 9.30 |
| SEQ ID NO: 485 | NCR022 | 9.27 |
| SEQ ID NO: 486 | NCR023 | 8.33 |
| SEQ ID NO: 489 | NCR026 | 8.46 |
| SEQ ID NO: 490 | NCR027 | 8.75 |
| SEQ ID NO: 492 | NCR029 | 8.44 |
| SEQ ID NO: 493 | NCR030 | 10.37 |
| SEQ ID NO: 494 | NCR031 | 8.34 |
| SEQ ID NO: 495 | NCR032 | 9.62 |
| SEQ ID NO: 496 | NCR033 | 8.92 |
| SEQ ID NO: 497 | NCR034 | 8.92 |
| SEQ ID NO: 498 | NCR035 | 9.42 |
| SEQ ID NO: 499 | NCR036 | 9.13 |
| SEQ ID NO: 500 | NCR037 | 9.25 |

TABLE II-continued

| SEQ ID NO: | PEPTIDE | pI |
|---|---|---|
| SEQ ID NO: 501 | NCR038 | 8.87 |
| SEQ ID NO: 502 | NCR039 | 9.22 |
| SEQ ID NO: 503 | NCR040 | 8.54 |
| SEQ ID NO: 504 | NCR041 | 9.22 |
| SEQ ID NO: 505 | NCR042 | 9.45 |
| SEQ ID NO: 506 | NCR043 | 9.20 |
| SEQ ID NO: 507 | NCR044 | 10.32 |
| SEQ ID NO: 508 | NCR045 | 9.39 |
| SEQ ID NO: 509 | NCR046 | 9.21 |
| SEQ ID NO: 510 | NCR047 | 9.50 |
| SEQ ID NO: 511 | NCR048 | 8.53 |
| SEQ ID NO: 512 | NCR049 | 8.51 |
| SEQ ID NO: 513 | NCR050 | 9.13 |
| SEQ ID NO: 515 | NCR052 | 9.13 |
| SEQ ID NO: 516 | NCR053 | 8.67 |
| SEQ ID NO: 518 | NCR055 | 9.21 |
| SEQ ID NO: 520 | NCR057 | 8.43 |
| SEQ ID NO: 523 | NCR060 | 8.66 |
| SEQ ID NO: 524 | NCR061 | 8.20 |
| SEQ ID NO: 530 | NCR067 | 9.10 |
| SEQ ID NO: 531 | NCR068 | 8.49 |
| SEQ ID NO: 532 | NCR069 | 9.10 |
| SEQ ID NO: 533 | NCR070 | 8.18 |
| SEQ ID NO: 534 | NCR071 | 8.29 |
| SEQ ID NO: 536 | NCR073 | 8.85 |
| SEQ ID NO: 538 | NCR075 | 8.34 |
| SEQ ID NO: 541 | NCR078 | 8.40 |
| SEQ ID NO: 543 | NCR080 | 9.10 |
| SEQ ID NO: 544 | NCR081 | 8.51 |
| SEQ ID NO: 546 | NCR083 | 8.49 |
| SEQ ID NO: 549 | NCR086 | 8.87 |
| SEQ ID NO: 554 | NCR091 | 9.15 |
| SEQ ID NO: 555 | NCR092 | 8.18 |
| SEQ ID NO: 556 | NCR093 | 9.33 |
| SEQ ID NO: 561 | NCR098 | 9.24 |
| SEQ ID NO: 563 | NCR100 | 8.56 |
| SEQ ID NO: 564 | NCR101 | 9.46 |
| SEQ ID NO: 565 | NCR102 | 9.10 |
| SEQ ID NO: 566 | NCR103 | 8.30 |
| SEQ ID NO: 567 | NCR104 | 8.95 |
| SEQ ID NO: 569 | NCR106 | 9.00 |
| SEQ ID NO: 573 | NCR110 | 8.53 |
| SEQ ID NO: 582 | NCR119 | 9.30 |
| SEQ ID NO: 583 | NCR120 | 8.40 |
| SEQ ID NO: 593 | NCR130 | 9.62 |
| SEQ ID NO: 596 | NCR133 | 9.13 |
| SEQ ID NO: 597 | NCR134 | 8.36 |
| SEQ ID NO: 598 | NCR135 | 8.88 |
| SEQ ID NO: 599 | NCR136 | 8.85 |
| SEQ ID NO: 600 | NCR137 | 9.70 |
| SEQ ID NO: 606 | NCR143 | 9.38 |
| SEQ ID NO: 610 | NCR147 | 9.76 |
| SEQ ID NO: 611 | NCR148 | 9.14 |
| SEQ ID NO: 613 | NCR150 | 8.34 |
| SEQ ID NO: 618 | NCR155 | 9.44 |
| SEQ ID NO: 620 | NCR157 | 8.27 |
| SEQ ID NO: 622 | NCR159 | 8.66 |
| SEQ ID NO: 623 | NCR160 | 8.65 |
| SEQ ID NO: 632 | NCR169 | 8.45 |
| SEQ ID NO: 633 | NCR170 | 9.18 |
| SEQ ID NO: 634 | NCR171 | 8.62 |
| SEQ ID NO: 635 | NCR172 | 8.65 |
| SEQ ID NO: 636 | NCR173 | 8.88 |
| SEQ ID NO: 639 | NCR176 | 8.65 |
| SEQ ID NO: 642 | NCR179 | 9.79 |
| SEQ ID NO: 644 | NCR181 | 9.51 |
| SEQ ID NO: 646 | NCR183 | 10.10 |
| SEQ ID NO: 647 | NCR184 | 9.56 |
| SEQ ID NO: 651 | NCR188 | 8.52 |
| SEQ ID NO: 652 | NCR189 | 9.15 |
| SEQ ID NO: 655 | NCR192 | 9.70 |
| SEQ ID NO: 658 | NCR195 | 8.61 |
| SEQ ID NO: 659 | NCR196 | 8.63 |
| SEQ ID NO: 662 | NCR199 | 8.20 |
| SEQ ID NO: 663 | NCR200 | 8.31 |
| SEQ ID NO: 670 | NCR207 | 9.70 |
| SEQ ID NO: 675 | NCR212 | 9.04 |
| SEQ ID NO: 681 | NCR219 | 8.28 |
| SEQ ID NO: 683 | NCR221 | 8.32 |
| SEQ ID NO: 684 | NCR222 | 8.37 |
| SEQ ID NO: 685 | NCR223 | 8.32 |
| SEQ ID NO: 690 | NCR228 | 8.66 |
| SEQ ID NO: 694 | NCR232 | 8.92 |
| SEQ ID NO: 700 | NCR238 | 9.24 |
| SEQ ID NO: 705 | NCR246 | 9.07 |
| SEQ ID NO: 706 | NCR247 | 10.15 |
| SEQ ID NO: 709 | NCR250 | 9.22 |
| SEQ ID NO: 713 | NCR254 | 8.28 |
| SEQ ID NO: 715 | NCR256 | 8.69 |
| SEQ ID NO: 720 | NCR262 | 8.58 |
| SEQ ID NO: 721 | NCR263 | 8.37 |
| SEQ ID NO: 725 | NCR267 | 8.26 |
| SEQ ID NO: 731 | NCR273 | 9.34 |
| SEQ ID NO: 737 | NCR279 | 8.51 |
| SEQ ID NO: 738 | NCR280 | 9.80 |
| SEQ ID NO: 739 | NCR281 | 8.53 |
| SEQ ID NO: 742 | NCR284 | 8.92 |
| SEQ ID NO: 743 | NCR285 | 8.27 |
| SEQ ID NO: 744 | NCR286 | 8.66 |
| SEQ ID NO: 746 | NCR288 | 8.29 |
| SEQ ID NO: 750 | NCR292 | 9.03 |
| SEQ ID NO: 753 | NCR295 | 8.40 |
| SEQ ID NO: 757 | NCR299 | 8.57 |
| SEQ ID NO: 758 | NCR300 | 9.56 |
| SEQ ID NO: 761 | NCR303 | 9.34 |
| SEQ ID NO: 766 | NCR308 | 8.77 |
| SEQ ID NO: 769 | NCR311 | 8.51 |
| SEQ ID NO: 772 | NCR314 | 8.87 |
| SEQ ID NO: 774 | NCR316 | 8.76 |
| SEQ ID NO: 775 | NCR317 | 9.13 |
| SEQ ID NO: 780 | NCR322 | 8.58 |
| SEQ ID NO: 781 | NCR323 | 8.94 |
| SEQ ID NO: 782 | NCR324 | 9.50 |
| SEQ ID NO: 783 | NCR325 | 8.64 |
| SEQ ID NO: 784 | NCR326 | 8.64 |
| SEQ ID NO: 787 | NCR329 | 8.89 |
| SEQ ID NO: 793 | NCR335 | 11.22 |
| SEQ ID NO: 794 | NCR336 | 8.92 |
| SEQ ID NO: 799 | NCR341 | 8.52 |
| SEQ ID NO: 800 | NCR342 | 9.39 |
| SEQ ID NO: 807 | NCR349 | 8.96 |
| SEQ ID NO: 812 | NCR354 | 8.52 |
| SEQ ID NO: 816 | NCR358 | 9.50 |
| SEQ ID NO: 817 | NCR359 | 9.27 |
| SEQ ID NO: 819 | NCR361 | 8.85 |
| SEQ ID NO: 820 | NCR362 | 9.24 |
| SEQ ID NO: 821 | NCR363 | 8.26 |
| SEQ ID NO: 824 | NCR366 | 8.20 |
| SEQ ID NO: 825 | NCR367 | 8.51 |
| SEQ ID NO: 827 | NCR369 | 8.52 |
| SEQ ID NO: 828 | NCR370 | 8.29 |
| SEQ ID NO: 829 | NCR371 | 9.28 |
| SEQ ID NO: 830 | NCR372 | 8.28 |
| SEQ ID NO: 835 | NCR377 | 9.44 |
| SEQ ID NO: 836 | NCR378 | 8.52 |
| SEQ ID NO: 842 | NCR384 | 8.97 |
| SEQ ID NO: 846 | NCR388 | 8.98 |
| SEQ ID NO: 847 | NCR389 | 9.39 |
| SEQ ID NO: 848 | NCR390 | 8.08 |
| SEQ ID NO: 849 | NCR391 | 8.41 |
| SEQ ID NO: 850 | NCR392 | 8.53 |
| SEQ ID NO: 853 | NCR395 | 8.85 |
| SEQ ID NO: 858 | NCR400 | 8.29 |
| SEQ ID NO: 862 | NCR404 | 8.18 |
| SEQ ID NO: 863 | NCR405 | 9.18 |
| SEQ ID NO: 865 | NCR407 | 9.05 |
| SEQ ID NO: 866 | NCR408 | 9.72 |
| SEQ ID NO: 870 | NCR412 | 8.87 |
| SEQ ID NO: 872 | NCR414 | 8.02 |
| SEQ ID NO: 875 | NCR417 | 8.77 |
| SEQ ID NO: 877 | NCR419 | 8.53 |
| SEQ ID NO: 878 | NCR420 | 8.80 |
| SEQ ID NO: 879 | NCR421 | 9.13 |
| SEQ ID NO: 880 | NCR422 | 8.54 |
| SEQ ID NO: 881 | NCR423 | 8.29 |
| SEQ ID NO: 892 | NCR434 | 8.18 |

TABLE II-continued

| SEQ ID NO: | PEPTIDE | pI |
|---|---|---|
| SEQ ID NO: 894 | NCR436 | 9.31 |
| SEQ ID NO: 896 | NCR438 | 8.95 |
| SEQ ID NO: 897 | NCR439 | 8.49 |
| SEQ ID NO: 899 | NCR441 | 8.01 |
| SEQ ID NO: 909 | NCR451 | 9.96 |
| SEQ ID NO: 910 | NCR452 | 8.79 |
| SEQ ID NO: 913 | NCR455 | 8.64 |
| SEQ ID NO: 917 | NCR459 | 8.20 |
| SEQ ID NO: 919 | NCR461 | 9.39 |
| SEQ ID NO: 921 | NCR463 | 8.76 |
| SEQ ID NO: 925 | NCR467 | 8.27 |

In a more advantageous embodiment, said cationic peptides above defined are selected from the list consisting of: SEQ ID NO:706 (NCR 247), SEQ ID NO:498 (NCR 035), SEQ ID NO:518 (NCR 055), SEQ ID NO:520 (NCR 57).

Examples 3-5 show that cationic peptides are potent antibiotic peptides and FIG. 1 shows that they have a fast antibiotic activity.

Indeed, at a concentration of 10 µM in 3 hours, peptides of the invention can eradicate bacteria such as *Sinorhizobium meliloti* while tetracyclin and kanamycin which are well known antibiotics, cannot eradicate the sensitive bacteria in 3 hours at doses equal to or tenfold higher than the invention peptide doses.

In a more advantageous embodiment, said anionic peptides are selected from the list consisting of SEQ ID NO:464; SEQ ID NO:465; SEQ ID NO:467; SEQ ID NO:468; SEQ ID NO:470; SEQ ID NO:471; SEQ ID NO:472; SEQ ID NO:476; SEQ ID NO:477; SEQ ID NO:478; SEQ ID NO:479; SEQ ID NO:481; SEQ ID NO:482; SEQ ID NO:487; SEQ ID NO:488; SEQ ID NO:514; SEQ ID NO:521; SEQ ID NO:522; SEQ ID NO:526; SEQ ID NO:528; SEQ ID NO:529; SEQ ID NO:537; SEQ ID NO:539; SEQ ID NO:545; SEQ ID NO:550; SEQ ID NO:551; SEQ ID NO:552; SEQ ID NO:558; SEQ ID NO:562; SEQ ID NO:568; SEQ ID NO:571; SEQ ID NO:574; SEQ ID NO:575; SEQ ID NO:576; SEQ ID NO:577; SEQ ID NO:580; SEQ ID NO:586; SEQ ID NO:588; SEQ ID NO:590; SEQ ID NO:592; SEQ ID NO:595; SEQ ID NO:602; SEQ ID NO:603; SEQ ID NO:604; SEQ ID NO:605; SEQ ID NO:608; SEQ ID NO:614; SEQ ID NO:615; SEQ ID NO:616; SEQ ID NO:617; SEQ ID NO:619; SEQ ID NO:621; SEQ ID NO:625; SEQ ID NO:626; SEQ ID NO:627; SEQ ID NO:629; SEQ ID NO:630; SEQ ID NO:631; SEQ ID NO:640; SEQ ID NO:641; SEQ ID NO:643; SEQ ID NO:648; SEQ ID NO:650; SEQ ID NO:654; SEQ ID NO:656; SEQ ID NO:657; SEQ ID NO:666; SEQ ID NO:667; SEQ ID NO:672; SEQ ID NO:673; SEQ ID NO:674; SEQ ID NO:677; SEQ ID NO:678; SEQ ID NO:679; SEQ ID NO:680; SEQ ID NO:682; SEQ ID NO:686; SEQ ID NO:687; SEQ ID NO:688; SEQ ID NO:693; SEQ ID NO:696; SEQ ID NO:697; SEQ ID NO:702; SEQ ID NO:704; SEQ ID NO:711; SEQ ID NO:719; SEQ ID NO:722; SEQ ID NO:728; SEQ ID NO:729; SEQ ID NO:732; SEQ ID NO:733; SEQ ID NO:735; SEQ ID NO:736; SEQ ID NO:741; SEQ ID NO:745; SEQ ID NO:747; SEQ ID NO:748; SEQ ID NO:749; SEQ ID NO:752; SEQ ID NO:754; SEQ ID NO:759; SEQ ID NO:760; SEQ ID NO:762; SEQ ID NO:763; SEQ ID NO:767; SEQ ID NO:768; SEQ ID NO:770; SEQ ID NO:771; SEQ ID NO:773; SEQ ID NO:777; SEQ ID NO:778; SEQ ID NO:786; SEQ ID NO:792; SEQ ID NO:795; SEQ ID NO:796; SEQ ID NO:797; SEQ ID NO:803; SEQ ID NO:805; SEQ ID NO:808; SEQ ID NO:810; SEQ ID NO:811; SEQ ID NO:813; SEQ ID NO:814; SEQ ID NO:815; SEQ ID NO:818; SEQ ID NO:822; SEQ ID NO:823; SEQ ID NO:826; SEQ ID NO:831; SEQ ID NO:834; SEQ ID NO:837; SEQ ID NO:839; SEQ ID NO:840; SEQ ID NO:841; SEQ ID NO:845; SEQ ID NO:851; SEQ ID NO:852; SEQ ID NO:854; SEQ ID NO:855; SEQ ID NO:856; SEQ ID NO:857; SEQ ID NO:859; SEQ ID NO:860; SEQ ID NO:861; SEQ ID NO:868; SEQ ID NO:873; SEQ ID NO:876; SEQ ID NO:882; SEQ ID NO:883; SEQ ID NO:884; SEQ ID NO:887; SEQ ID NO:889; SEQ ID NO:891; SEQ ID NO:893; SEQ ID NO:895; SEQ ID NO:901; SEQ ID NO:902; SEQ ID NO:903; SEQ ID NO:904; SEQ ID NO:907; SEQ ID NO:908; SEQ ID NO:912; SEQ ID NO:915; SEQ ID NO:922 and SEQ ID NO:924;

Table III give the NCR correlation and the pI<6 of the anionic peptides above defined:

TABLE III

| SEQ ID NO: | PEPTIDE | pI |
|---|---|---|
| SEQ ID NO: 464 | NCR001 | 5.01 |
| SEQ ID NO: 465 | NCR002 | 4.29 |
| SEQ ID NO:467 | NCR004 | 5.66 |
| SEQ ID NO: 468 | NCR005 | 5.38 |
| SEQ ID NO: 470 | NCR007 | 4.97 |
| SEQ ID NO: 471 | NCR008 | 5.15 |
| SEQ ID NO: 472 | NCR009 | 4.36 |
| SEQ ID NO: 476 | NCR013 | 5.61 |
| SEQ ID NO: 477 | NCR014 | 4.78 |
| SEQ ID NO: 478 | NCR015 | 5.39 |
| SEQ ID NO: 479 | NCR016 | 4.71 |
| SEQ ID NO: 481 | NCR018 | 4.68 |
| SEQ ID NO: 482 | NCR019 | 4.45 |
| SEQ ID NO: 487 | NCR024 | 4.03 |
| SEQ ID NO: 488 | NCR025 | 4.59 |
| SEQ ID NO: 514 | NCR051 | 4.14 |
| SEQ ID NO: 521 | NCR058 | 4.53 |
| SEQ ID NO: 522 | NCR059 | 4.52 |
| SEQ ID NO: 526 | NCR063 | 4.52 |
| SEQ ID NO: 528 | NCR065 | 5.43 |
| SEQ ID NO: 529 | NCR066 | 3.21 |
| SEQ ID NO: 537 | NCR074 | 4.51 |
| SEQ ID NO: 539 | NCR076 | 4.86 |
| SEQ ID NO: 545 | NCR082 | 4.63 |
| SEQ ID NO: 550 | NCR087 | 4.13 |
| SEQ ID NO: 551 | NCR088 | 4.23 |
| SEQ ID NO: 552 | NCR089 | 5.68 |
| SEQ ID NO: 558 | NCR095 | 3.62 |
| SEQ ID NO: 562 | NCR099 | 5.84 |
| SEQ ID NO: 568 | NCR105 | 5.39 |
| SEQ ID NO: 571 | NCR108 | 4.70 |
| SEQ ID NO: 574 | NCR111 | 5.40 |
| SEQ ID NO: 575 | NCR112 | 4.71 |
| SEQ ID NO: 576 | NCR113 | 5.00 |
| SEQ ID NO: 577 | NCR114 | 4.40 |
| SEQ ID NO: 580 | NCR117 | 4.52 |
| SEQ ID NO: 586 | NCR123 | 3.87 |
| SEQ ID NO: 588 | NCR125 | 5.29 |
| SEQ ID NO: 590 | NCR127 | 4.45 |
| SEQ ID NO: 592 | NCR129 | 4.44 |
| SEQ ID NO: 595 | NCR132 | 4.55 |
| SEQ ID NO: 602 | NCR139 | 4.38 |
| SEQ ID NO: 603 | NCR140 | 4.39 |
| SEQ ID NO: 604 | NCR141 | 4.36 |
| SEQ ID NO: 605 | NCR142 | 3.82 |
| SEQ ID NO: 608 | NCR145 | 4.89 |
| SEQ ID NO: 614 | NCR151 | 3.21 |
| SEQ ID NO: 615 | NCR152 | 5.00 |
| SEQ ID NO: 616 | NCR153 | 3.96 |
| SEQ ID NO: 617 | NCR154 | 4.39 |
| SEQ ID NO: 619 | NCR156 | 4.23 |
| SEQ ID NO: 621 | NCR158 | 3.50 |
| SEQ ID NO: 625 | NCR162 | 3.71 |

TABLE III-continued

| SEQ ID NO: | PEPTIDE | pI |
|---|---|---|
| SEQ ID NO: 626 | NCR163 | 4.70 |
| SEQ ID NO: 627 | NCR164 | 3.90 |
| SEQ ID NO: 629 | NCR166 | 4.94 |
| SEQ ID NO: 630 | NCR167 | 3.71 |
| SEQ ID NO: 631 | NCR168 | 3.61 |
| SEQ ID NO: 640 | NCR177 | 4.56 |
| SEQ ID NO: 641 | NCR178 | 5.38 |
| SEQ ID NO: 643 | NCR180 | 4.63 |
| SEQ ID NO: 648 | NCR185 | 4.90 |
| SEQ ID NO: 650 | NCR187 | 4.07 |
| SEQ ID NO: 654 | NCR191 | 3.84 |
| SEQ ID NO: 656 | NCR193 | 4.78 |
| SEQ ID NO: 657 | NCR194 | 5.79 |
| SEQ ID NO: 666 | NCR203 | 4.64 |
| SEQ ID NO: 667 | NCR204 | 4.66 |
| SEQ ID NO: 672 | NCR209 | 4.50 |
| SEQ ID NO: 673 | NCR210 | 4.44 |
| SEQ ID NO: 674 | NCR211 | 5.45 |
| SEQ ID NO: 677 | NCR214 | 3.81 |
| SEQ ID NO: 678 | NCR215 | 3.97 |
| SEQ ID NO: 679 | NCR216 | 4.03 |
| SEQ ID NO: 680 | NCR217 | 5.48 |
| SEQ ID NO: 682 | NCR220 | 5.30 |
| SEQ ID NO: 686 | NCR224 | 4.65 |
| SEQ ID NO: 687 | NCR225 | 4.86 |
| SEQ ID NO: 688 | NCR226 | 3.51 |
| SEQ ID NO: 693 | NCR231 | 5.00 |
| SEQ ID NO: 696 | NCR234 | 4.26 |
| SEQ ID NO: 697 | NCR235 | 4.53 |
| SEQ ID NO: 702 | NCR242 | 4.51 |
| SEQ ID NO: 704 | NCR245 | 4.66 |
| SEQ ID NO: 711 | NCR252 | 4.45 |
| SEQ ID NO: 719 | NCR261 | 5.54 |
| SEQ ID NO: 722 | NCR264 | 5.65 |
| SEQ ID NO: 728 | NCR270 | 5.36 |
| SEQ ID NO: 729 | NCR271 | 5.13 |
| SEQ ID NO: 732 | NCR274 | 4.14 |
| SEQ ID NO: 733 | NCR275 | 4.60 |
| SEQ ID NO: 735 | NCR277 | 4.13 |
| SEQ ID NO: 736 | NCR278 | 3.96 |
| SEQ ID NO: 741 | NCR283 | 4.94 |
| SEQ ID NO: 745 | NCR287 | 3.41 |
| SEQ ID NO: 747 | NCR289 | 4.30 |
| SEQ ID NO: 748 | NCR290 | 4.78 |
| SEQ ID NO: 749 | NCR291 | 4.50 |
| SEQ ID NO: 752 | NCR294 | 4.72 |
| SEQ ID NO: 754 | NCR296 | 4.13 |
| SEQ ID NO: 759 | NCR301 | 4.36 |
| SEQ ID NO: 760 | NCR302 | 4.34 |
| SEQ ID NO: 762 | NCR304 | 5.66 |
| SEQ ID NO: 763 | NCR305 | 4.88 |
| SEQ ID NO: 767 | NCR309 | 5.37 |
| SEQ ID NO: 768 | NCR310 | 4.35 |
| SEQ ID NO: 770 | NCR312 | 4.84 |
| SEQ ID NO: 771 | NCR313 | 4.95 |
| SEQ ID NO: 773 | NCR315 | 3.98 |
| SEQ ID NO: 777 | NCR319 | 4.96 |
| SEQ ID NO: 778 | NCR320 | 4.80 |
| SEQ ID NO: 786 | NCR328 | 5.62 |
| SEQ ID NO: 792 | NCR334 | 5.62 |
| SEQ ID NO: 795 | NCR337 | 5.02 |
| SEQ ID NO: 796 | NCR338 | 4.52 |
| SEQ ID NO: 797 | NCR339 | 4.65 |
| SEQ ID NO: 803 | NCR345 | 4.57 |
| SEQ ID NO: 805 | NCR347 | 3.65 |
| SEQ ID NO: 808 | NCR350 | 4.72 |
| SEQ ID NO: 810 | NCR352 | 4.63 |
| SEQ ID NO: 811 | NCR353 | 3.73 |
| SEQ ID NO: 813 | NCR355 | 3.57 |
| SEQ ID NO: 814 | NCR356 | 4.26 |
| SEQ ID NO: 815 | NCR357 | 4.86 |
| SEQ ID NO: 818 | NCR360 | 4.92 |
| SEQ ID NO: 822 | NCR364 | 5.57 |
| SEQ ID NO: 823 | NCR365 | 5.03 |
| SEQ ID NO: 826 | NCR368 | 4.13 |
| SEQ ID NO: 831 | NCR373 | 4.83 |
| SEQ ID NO: 834 | NCR376 | 4.49 |
| SEQ ID NO: 837 | NCR379 | 5.41 |
| SEQ ID NO: 839 | NCR381 | 4.72 |
| SEQ ID NO: 840 | NCR382 | 5.41 |
| SEQ ID NO: 841 | NCR383 | 3.89 |
| SEQ ID NO: 845 | NCR387 | 4.43 |
| SEQ ID NO: 851 | NCR393 | 5.88 |
| SEQ ID NO: 852 | NCR394 | 4.57 |
| SEQ ID NO: 854 | NCR396 | 3.61 |
| SEQ ID NO: 855 | NCR397 | 3.44 |
| SEQ ID NO: 856 | NCR398 | 3.69 |
| SEQ ID NO: 857 | NCR399 | 3.58 |
| SEQ ID NO: 859 | NCR401 | 4.02 |
| SEQ ID NO: 860 | NCR402 | 3.94 |
| SEQ ID NO: 861 | NCR403 | 4.14 |
| SEQ ID NO: 868 | NCR410 | 4.81 |
| SEQ ID NO: 873 | NCR415 | 4.56 |
| SEQ ID NO: 876 | NCR418 | 4.93 |
| SEQ ID NO: 882 | NCR424 | 4.13 |
| SEQ ID NO: 883 | NCR425 | 4.12 |
| SEQ ID NO: 884 | NCR426 | 4.74 |
| SEQ ID NO: 887 | NCR429 | 3.92 |
| SEQ ID NO: 889 | NCR431 | 5.46 |
| SEQ ID NO: 891 | NCR433 | 4.20 |
| SEQ ID NO: 893 | NCR435 | 4.56 |
| SEQ ID NO: 895 | NCR437 | 4.93 |
| SEQ ID NO: 901 | NCR443 | 5.76 |
| SEQ ID NO: 902 | NCR444 | 4.65 |
| SEQ ID NO: 903 | NCR445 | 4.31 |
| SEQ ID NO: 904 | NCR446 | 5.49 |
| SEQ ID NO: 907 | NCR449 | 4.83 |
| SEQ ID NO: 908 | NCR450 | 3.68 |
| SEQ ID NO: 912 | NCR454 | 4.53 |
| SEQ ID NO: 915 | NCR457 | 4.14 |
| SEQ ID NO: 922 | NCR464 | 3.82 |
| SEQ ID NO: 924 | NCR466 | 4.70 |

In a more advantageous embodiment, said anionic peptides above defined are selected from the list consisting of: SEQ ID NO:686 (NCR 224), SEQ ID NO:697 (NCR 235), SEQ ID NO:514 (NCR 051), SEQ ID NO:464 (NCR 001).

Examples 3 and 4 show that anionic peptides are potential antibiotic peptides.

In a more advantageous embodiment, said neutral peptides are selected from the list consisting of:

SEQ ID NO:466; SEQ ID NO:473; SEQ ID NO:475; SEQ ID NO:491; SEQ ID NO:517; SEQ ID NO:519; SEQ ID NO:525; SEQ ID NO:527; SEQ ID NO:535; SEQ ID NO:540; SEQ ID NO:542; SEQ ID NO:547; SEQ ID NO:548; SEQ ID NO:553; SEQ ID NO:557; SEQ ID NO:559; SEQ ID NO:560; SEQ ID NO:570; SEQ ID NO:572; SEQ ID NO:578; SEQ ID NO:579; SEQ ID NO:581; SEQ ID NO:584; SEQ ID NO:585; SEQ ID NO:587; SEQ ID NO:589; SEQ ID NO:591; SEQ ID NO:594; SEQ ID NO:601; SEQ ID NO:607; SEQ ID NO:609; SEQ ID NO:612; SEQ ID NO:624; SEQ ID NO:628; SEQ ID NO:637; SEQ ID NO:638; SEQ ID NO:645; SEQ ID NO:649; SEQ ID NO:653; SEQ ID NO:660; SEQ ID NO:661; SEQ ID NO:664; SEQ ID NO:665; SEQ ID NO:668; SEQ ID NO:669; SEQ ID NO:671; SEQ ID NO:676; SEQ ID NO:689; SEQ ID NO:691; SEQ ID NO:692; SEQ ID NO:695; SEQ ID NO:698; SEQ ID NO:699; SEQ ID NO:701; SEQ ID NO:703; SEQ ID NO:707; SEQ ID NO:708; SEQ ID NO:710; SEQ ID NO:712; SEQ ID NO:714; SEQ ID NO:716; SEQ ID NO:717; SEQ ID NO:718; SEQ ID NO:723; SEQ ID NO:724; SEQ ID NO:726; SEQ ID NO:727; SEQ ID NO:730; SEQ ID NO:734; SEQ ID NO:740; SEQ ID NO:751; SEQ ID NO:755; SEQ ID NO:756; SEQ ID NO:764; SEQ ID NO:765; SEQ ID NO:776; SEQ ID NO:779; SEQ ID NO:785; SEQ ID

NO:788; SEQ ID NO:789; SEQ ID NO:790; SEQ ID NO:791; SEQ ID NO:798; SEQ ID NO:801; SEQ ID NO:802; SEQ ID NO:804; SEQ ID NO:806; SEQ ID NO:809; SEQ ID NO:832; SEQ ID NO:833; SEQ ID NO:838; SEQ ID NO:843; SEQ ID NO:844; SEQ ID NO:864; SEQ ID NO:867; SEQ ID NO:869; SEQ ID NO:871; SEQ ID NO:874; SEQ ID NO:885; SEQ ID NO:886; SEQ ID NO:888; SEQ ID NO:890; SEQ ID NO:898; SEQ ID NO:900; SEQ ID NO:905; SEQ ID NO:906; SEQ ID NO:911; SEQ ID NO:914; SEQ ID NO:916; SEQ ID NO:918; SEQ ID NO:920 and SEQ ID NO:923.

Table IV give the NCR correlation and the 6≤pI≤8 of the neutral peptides above defined:

TABLE IV

| SEQ ID NO: | PEPTIDE | pI |
|---|---|---|
| SEQ ID NO: 466 | NCR003 | 7.21 |
| SEQ ID NO: 473 | NCR010 | 6.25 |
| SEQ ID NO: 475 | NCR012 | 6.25 |
| SEQ ID NO: 491 | NCR028 | 6.01 |
| SEQ ID NO: 517 | NCR054 | 6.50 |
| SEQ ID NO: 519 | NCR056 | 7.17 |
| SEQ ID NO: 525 | NCR062 | 7.78 |
| SEQ ID NO: 527 | NCR064 | 6.95 |
| SEQ ID NO: 535 | NCR072 | 6.10 |
| SEQ ID NO: 540 | NCR077 | 7.79 |
| SEQ ID NO: 542 | NCR079 | 6.77 |
| SEQ ID NO: 547 | NCR084 | 6.71 |
| SEQ ID NO: 548 | NCR085 | 6.03 |
| SEQ ID NO: 553 | NCR090 | 6.66 |
| SEQ ID NO: 557 | NCR094 | 6.21 |
| SEQ ID NO: 559 | NCR096 | 6.01 |
| SEQ ID NO: 560 | NCR097 | 7.86 |
| SEQ ID NO: 570 | NCR107 | 6.34 |
| SEQ ID NO: 572 | NCR109 | 7.88 |
| SEQ ID NO: 578 | NCR115 | 7.53 |
| SEQ ID NO: 579 | NCR116 | 6.05 |
| SEQ ID NO: 581 | NCR118 | 7.89 |
| SEQ ID NO: 584 | NCR121 | 6.71 |
| SEQ ID NO: 585 | NCR122 | 6.42 |
| SEQ ID NO: 587 | NCR124 | 6.92 |
| SEQ ID NO: 589 | NCR126 | 6.56 |
| SEQ ID NO: 591 | NCR128 | 7.01 |
| SEQ ID NO: 594 | NCR131 | 6.97 |
| SEQ ID NO: 601 | NCR138 | 6.13 |
| SEQ ID NO: 607 | NCR144 | 6.92 |
| SEQ ID NO: 609 | NCR146 | 7.86 |
| SEQ ID NO: 612 | NCR149 | 7.80 |
| SEQ ID NO: 624 | NCR161 | 7.96 |
| SEQ ID NO: 628 | NCR165 | 7.85 |
| SEQ ID NO: 637 | NCR174 | 6.02 |
| SEQ ID NO: 638 | NCR175 | 6.97 |
| SEQ ID NO: 645 | NCR182 | 6.11 |
| SEQ ID NO: 649 | NCR186 | 6.23 |
| SEQ ID NO: 653 | NCR190 | 6.87 |
| SEQ ID NO: 660 | NCR197 | 7.73 |
| SEQ ID NO: 661 | NCR198 | 6.13 |
| SEQ ID NO: 664 | NCR201 | 6.74 |
| SEQ ID NO: 665 | NCR202 | 7.11 |
| SEQ ID NO: 668 | NCR205 | 7.63 |
| SEQ ID NO: 669 | NCR206 | 6.25 |
| SEQ ID NO: 671 | NCR208 | 7.76 |
| SEQ ID NO: 676 | NCR213 | 6.25 |
| SEQ ID NO: 689 | NCR227 | 6.36 |
| SEQ ID NO: 691 | NCR229 | 6.55 |
| SEQ ID NO: 692 | NCR230 | 6.11 |
| SEQ ID NO: 695 | NCR233 | 7.96 |
| SEQ ID NO: 698 | NCR236 | 7.72 |
| SEQ ID NO: 699 | NCR237 | 6.71 |
| SEQ ID NO: 701 | NCR239 | 6.94 |
| SEQ ID NO: 703 | NCR243 | 6.88 |
| SEQ ID NO: 707 | NCR248 | 7.62 |
| SEQ ID NO: 708 | NCR249 | 6.03 |
| SEQ ID NO: 710 | NCR251 | 6.27 |
| SEQ ID NO: 712 | NCR253 | 6.88 |

TABLE IV-continued

| SEQ ID NO: | PEPTIDE | pI |
|---|---|---|
| SEQ ID NO: 714 | NCR255 | 7.20 |
| SEQ ID NO: 716 | NCR258 | 6.15 |
| SEQ ID NO: 717 | NCR259 | 7.65 |
| SEQ ID NO: 718 | NCR260 | 6.89 |
| SEQ ID NO: 723 | NCR265 | 6.71 |
| SEQ ID NO: 724 | NCR266 | 7.79 |
| SEQ ID NO: 726 | NCR268 | 7.10 |
| SEQ ID NO: 727 | NCR269 | 6.71 |
| SEQ ID NO: 730 | NCR272 | 6.12 |
| SEQ ID NO: 734 | NCR276 | 7.05 |
| SEQ ID NO: 740 | NCR282 | 7.77 |
| SEQ ID NO: 751 | NCR293 | 6.87 |
| SEQ ID NO: 755 | NCR297 | 7.77 |
| SEQ ID NO: 756 | NCR298 | 7.75 |
| SEQ ID NO: 764 | NCR306 | 6.04 |
| SEQ ID NO: 765 | NCR307 | 6.26 |
| SEQ ID NO: 776 | NCR318 | 7.89 |
| SEQ ID NO: 779 | NCR321 | 7.86 |
| SEQ ID NO: 785 | NCR327 | 6.88 |
| SEQ ID NO: 788 | NCR330 | 6.09 |
| SEQ ID NO: 789 | NCR331 | 7.96 |
| SEQ ID NO: 790 | NCR332 | 7.86 |
| SEQ ID NO: 791 | NCR333 | 6.40 |
| SEQ ID NO: 798 | NCR340 | 7.88 |
| SEQ ID NO: 801 | NCR343 | 6.35 |
| SEQ ID NO: 802 | NCR344 | 7.79 |
| SEQ ID NO: 804 | NCR346 | 7.75 |
| SEQ ID NO: 806 | NCR348 | 7.75 |
| SEQ ID NO: 809 | NCR351 | 7.76 |
| SEQ ID NO: 832 | NCR374 | 7.77 |
| SEQ ID NO: 833 | NCR375 | 7.72 |
| SEQ ID NO: 838 | NCR380 | 6.29 |
| SEQ ID NO: 843 | NCR385 | 7.76 |
| SEQ ID NO: 844 | NCR386 | 6.88 |
| SEQ ID NO: 864 | NCR406 | 6.31 |
| SEQ ID NO: 867 | NCR409 | 7.61 |
| SEQ ID NO: 869 | NCR411 | 7.14 |
| SEQ ID NO: 871 | NCR413 | 6.88 |
| SEQ ID NO: 874 | NCR416 | 7.64 |
| SEQ ID NO: 885 | NCR427 | 7.61 |
| SEQ ID NO: 886 | NCR428 | 7.70 |
| SEQ ID NO: 888 | NCR430 | 7.73 |
| SEQ ID NO: 890 | NCR432 | 7.75 |
| SEQ ID NO: 898 | NCR440 | 6.23 |
| SEQ ID NO: 900 | NCR442 | 7.15 |
| SEQ ID NO: 905 | NCR447 | 6.26 |
| SEQ ID NO: 906 | NCR448 | 7.79 |
| SEQ ID NO: 911 | NCR453 | 7.78 |
| SEQ ID NO: 914 | NCR456 | 7.71 |
| SEQ ID NO: 916 | NCR458 | 7.64 |
| SEQ ID NO: 918 | NCR460 | 6.54 |
| SEQ ID NO: 920 | NCR462 | 7.64 |
| SEQ ID NO: 923 | NCR465 | 7.61 |

In a more advantageous embodiment, said neutral peptides above defined are selected from the list consisting of: SEQ ID NO:547 (NCR 084), SEQ ID NO:691 (NCR 229).

In a more advantageous embodiment, the present invention relates to the use of peptides as defined above, wherein said peptides are active against both Gram− and Gram+bacteria.

Antibiotic such as polymyxin B are active against Gram− bacteria limiting thus their use.

Peptides of the invention are active against Gram− and Gram+ as demonstrated by example 5 (in the rest of the specification, polymyxin or polymyxin B represent the same compound).

Further, as can be seen from example 7 and example 8, peptides of the invention have no adverse effects on mammalian cells and on plants, respectively.

In a more advantageous embodiment, said peptides above defined are active at a concentration range from about 1 to about 100 µg/ml, preferably from about 1 to 50 µg/ml, in particular from about 10 to about 50 µg/ml.

Below 1 µg/ml, the concentration is too low to produce an effect.

Above 100 µg/ml, the concentration is too high and can lead to adverse effects.

As can be shown by example 3, peptides of the invention are active at low doses such as 50 µg/ml and example 4B shows that peptides of the invention present a higher activity than the one of polymyxin.

In a more advantageous embodiment, peptides of the invention are active at doses of 10, 20, 30, 40, 50, 60, 70, 80, 90, 100 µg/ml In a preferred embodiment, peptides of the invention are active at doses of 1, 2, 3, 4, 5, 6, 7, 8, 9, 10 µg/ml.

In a more advantageous embodiment, peptides of the invention are insensitive or weakly sensitive to physiological salt (2 mM) of divalent cations such as $Mg^{++}$ or $Ca^{++}$. The sensitivity towards $Mg^{++}$ or $Ca^{++}$ could be compensated by addition of EDTA at equimolar concentration.

In a more advantageous embodiment, the present invention relates to the use of peptides above defined, wherein the number of colony forming units of bacteria dropped 3 to 9 orders of magnitude, in particular 5 to 7 orders, in 3 hours of contact with said peptides.

Example 5 shows that peptides of the invention are able to diminish the content of the bacteria, starting from an initial concentration of bacteria comprised from $10^6$ to $10^9$, by a factor 1000 to one billion to reach a final concentration in bacteria comprised from 0 to $10^6$.

In another aspect, the present invention relates to the use of at least one gene coding for a peptide originated from *Medicago truncatula* nodules, comprising the SEQ IDs NO: 1-463 or at least one gene coding for a peptide having a sequence derived from said SEQ IDs NO: 1-463 by deletion of about 9 to about 44 contiguous amino acids, from the N-terminal part of the peptide, in particular a gene coding for a peptide having the SEQ IDS NO: 464 to 925, for the preparation of transgenic plants that do not express said peptide in their genome or in a part of the said plant such as leaves or stem.

In another aspect, the invention relates to a pharmaceutical composition comprising at least two peptides of SEQ IDs NO: 1-463, as above defined, or peptides of SEQ ID 464 to 925, as above defined, in association with a pharmaceutical acceptable vehicle, provided that said peptides have a purity being equal or more than about 90%, in particular more than about 95%.

Peptides of the pharmaceutical composition can be isolated from *Medicago truncatula* nodules or synthesized by chemical or biological way with a purity higher or equal to about 90%, in particular more than about 95%.

Thus when the peptides of the invention are isolated from *Medicago truncatula* nodules, they have not the same environment as in the nodules, and therefore have different functions from that of the peptides contained in the nodules.

In an advantageous embodiment, the above defined pharmaceutical composition, comprises one or more cationic peptides (pI>8) in association with one or more anionic peptides (pI<6) and/or one or more neutral peptides (6≤pI≤8).

In an advantageous embodiment, said cationic peptides comprised in the pharmaceutical composition above defined, are selected from the list consisting of: SEQ ID NO:469; SEQ ID NO:474; SEQ ID NO:480; SEQ ID NO:483; SEQ ID NO:484; SEQ ID NO:485; SEQ ID NO:486; SEQ ID NO:489; SEQ ID NO:490; SEQ ID NO:492; SEQ ID NO:493; SEQ ID NO:494; SEQ ID NO:495; SEQ ID NO:496; SEQ ID NO:497; SEQ ID NO:498; SEQ ID NO:499; SEQ ID NO:500; SEQ ID NO:501; SEQ ID NO:502; SEQ ID NO:503; SEQ ID NO:504; SEQ ID NO:505; SEQ ID NO:506; SEQ ID NO:507; SEQ ID NO:508; SEQ ID NO:509; SEQ ID NO:510; SEQ ID NO:511; SEQ ID NO:512; SEQ ID NO:513; SEQ ID NO:515; SEQ ID NO:516; SEQ ID NO:518; SEQ ID NO:520; SEQ ID NO:523; SEQ ID NO:524; SEQ ID NO:530; SEQ ID NO:531; SEQ ID NO:532; SEQ ID NO:533; SEQ ID NO:534; SEQ ID NO:536; SEQ ID NO:538; SEQ ID NO:541; SEQ ID NO:543; SEQ ID NO:544; SEQ ID NO:546; SEQ ID NO:549; SEQ ID NO:554; SEQ ID NO:555; SEQ ID NO:556; SEQ ID NO:561; SEQ ID NO:563; SEQ ID NO:564; SEQ ID NO:565; SEQ ID NO:566; SEQ ID NO:567; SEQ ID NO:569; SEQ ID NO:573; SEQ ID NO:582; SEQ ID NO:583; SEQ ID NO:593; SEQ ID NO:596; SEQ ID NO:597; SEQ ID NO:598; SEQ ID NO:599; SEQ ID NO:600; SEQ ID NO:606; SEQ ID NO:610; SEQ ID NO:611; SEQ ID NO:613; SEQ ID NO:618; SEQ ID NO:620; SEQ ID NO:622; SEQ ID NO:623; SEQ ID NO:632; SEQ ID NO:633; SEQ ID NO:634; SEQ ID NO:635; SEQ ID NO:636; SEQ ID NO:639; SEQ ID NO:642; SEQ ID NO:644; SEQ ID NO:646; SEQ ID NO:647; SEQ ID NO:651; SEQ ID NO:652; SEQ ID NO:655; SEQ ID NO:658; SEQ ID NO:659; SEQ ID NO:662; SEQ ID NO:663; SEQ ID NO:670; SEQ ID NO:675; SEQ ID NO:681; SEQ ID NO:683; SEQ ID NO:684; SEQ ID NO:685; SEQ ID NO:690; SEQ ID NO:694; SEQ ID NO:700; SEQ ID NO:705; SEQ ID NO:706; SEQ ID NO:709; SEQ ID NO:713; SEQ ID NO:715; SEQ ID NO:720; SEQ ID NO:721; SEQ ID NO:725; SEQ ID NO:731; SEQ ID NO:737; SEQ ID NO:738; SEQ ID NO:739; SEQ ID NO:742; SEQ ID NO:743; SEQ ID NO:744; SEQ ID NO:746; SEQ ID NO:750; SEQ ID NO:753; SEQ ID NO:757; SEQ ID NO:758; SEQ ID NO:761; SEQ ID NO:766; SEQ ID NO:769; SEQ ID NO:772; SEQ ID NO:774; SEQ ID NO:775; SEQ ID NO:780; SEQ ID NO:781; SEQ ID NO:782; SEQ ID NO:783; SEQ ID NO:784; SEQ ID NO:787; SEQ ID NO:793; SEQ ID NO:794; SEQ ID NO:799; SEQ ID NO:800; SEQ ID NO:807; SEQ ID NO:812; SEQ ID NO:816; SEQ ID NO:817; SEQ ID NO:819; SEQ ID NO:820; SEQ ID NO:821; SEQ ID NO:824; SEQ ID NO:825; SEQ ID NO:827; SEQ ID NO:828; SEQ ID NO:829; SEQ ID NO:830; SEQ ID NO:835; SEQ ID NO:836; SEQ ID NO:842; SEQ ID NO:846; SEQ ID NO:847; SEQ ID NO:848; SEQ ID NO:849; SEQ ID NO:850; SEQ ID NO:853; SEQ ID NO:858; SEQ ID NO:862; SEQ ID NO:863; SEQ ID NO:865; SEQ ID NO:866; SEQ ID NO:870; SEQ ID NO:872; SEQ ID NO:875; SEQ ID NO:877; SEQ ID NO:878; SEQ ID NO:879; SEQ ID NO:880; SEQ ID NO:881; SEQ ID NO:892; SEQ ID NO:894; SEQ ID NO:896; SEQ ID NO:897; SEQ ID NO:899; SEQ ID NO:909; SEQ ID NO:910; SEQ ID NO:913; SEQ ID NO:917; SEQ ID NO:919; SEQ ID NO:921 and SEQ ID NO:925.

For the correlation with NCR peptides, see table II above.

In an advantageous embodiment, said cationic peptides comprised in the pharmaceutical composition above defined, are selected from the list consisting of: SEQ ID NO:706 (NCR 247), SEQ ID NO:498 (NCR 035), SEQ ID NO:518 (NCR 055), SEQ ID NO:520 (NCR 57).

In an advantageous embodiment, said anionic peptides comprised in the pharmaceutical composition above defined, are selected from the list consisting of:

SEQ ID NO:464; SEQ ID NO:465; SEQ ID NO:467; SEQ ID NO:468; SEQ ID NO:470; SEQ ID NO:471; SEQ ID NO:472; SEQ ID NO:476; SEQ ID NO:477; SEQ ID

NO:478; SEQ ID NO:479; SEQ ID NO:481; SEQ ID
NO:482; SEQ ID NO:487; SEQ ID NO:488; SEQ ID
NO:514; SEQ ID NO:521; SEQ ID NO:522; SEQ ID
NO:526; SEQ ID NO:528; SEQ ID NO:529; SEQ ID
NO:537; SEQ ID NO:539; SEQ ID NO:545; SEQ ID
NO:550; SEQ ID NO:551; SEQ ID NO:552; SEQ ID
NO:558; SEQ ID NO:562; SEQ ID NO:568; SEQ ID
NO:571; SEQ ID NO:574; SEQ ID NO:575; SEQ ID
NO:576; SEQ ID NO:577; SEQ ID NO:580; SEQ ID
NO:586; SEQ ID NO:588; SEQ ID NO:590; SEQ ID
NO:592; SEQ ID NO:595; SEQ ID NO:602; SEQ ID
NO:603; SEQ ID NO:604; SEQ ID NO:605; SEQ ID
NO:608; SEQ ID NO:614; SEQ ID NO:615; SEQ ID
NO:616; SEQ ID NO:617; SEQ ID NO:619; SEQ ID
NO:621; SEQ ID NO:625; SEQ ID NO:626; SEQ ID
NO:627; SEQ ID NO:629; SEQ ID NO:630; SEQ ID
NO:631; SEQ ID NO:640; SEQ ID NO:641; SEQ ID
NO:643; SEQ ID NO:648; SEQ ID NO:650; SEQ ID
NO:654; SEQ ID NO:656; SEQ ID NO:657; SEQ ID
NO:666; SEQ ID NO:667; SEQ ID NO:672; SEQ ID
NO:673; SEQ ID NO:674; SEQ ID NO:677; SEQ ID
NO:678; SEQ ID NO:679; SEQ ID NO:680; SEQ ID
NO:682; SEQ ID NO:686; SEQ ID NO:687; SEQ ID
NO:688; SEQ ID NO:693; SEQ ID NO:696; SEQ ID
NO:697; SEQ ID NO:702; SEQ ID NO:704; SEQ ID
NO:711; SEQ ID NO:719; SEQ ID NO:722; SEQ ID
NO:728; SEQ ID NO:729; SEQ ID NO:732; SEQ ID
NO:733; SEQ ID NO:735; SEQ ID NO:736; SEQ ID
NO:741; SEQ ID NO:745; SEQ ID NO:747; SEQ ID
NO:748; SEQ ID NO:749; SEQ ID NO:752; SEQ ID
NO:754; SEQ ID NO:759; SEQ ID NO:760; SEQ ID
NO:762; SEQ ID NO:763; SEQ ID NO:767; SEQ ID
NO:768; SEQ ID NO:770; SEQ ID NO:771; SEQ ID
NO:773; SEQ ID NO:777; SEQ ID NO:778; SEQ ID
NO:786; SEQ ID NO:792; SEQ ID NO:795; SEQ ID
NO:796; SEQ ID NO:797; SEQ ID NO:803; SEQ ID
NO:805; SEQ ID NO:808; SEQ ID NO:810; SEQ ID
NO:811; SEQ ID NO:813; SEQ ID NO:814; SEQ ID
NO:815; SEQ ID NO:818; SEQ ID NO:822; SEQ ID
NO:823; SEQ ID NO:826; SEQ ID NO:831; SEQ ID
NO:834; SEQ ID NO:837; SEQ ID NO:839; SEQ ID
NO:840; SEQ ID NO:841; SEQ ID NO:845; SEQ ID
NO:851; SEQ ID NO:852; SEQ ID NO:854; SEQ ID
NO:855; SEQ ID NO:856; SEQ ID NO:857; SEQ ID
NO:859; SEQ ID NO:860; SEQ ID NO:861; SEQ ID
NO:868; SEQ ID NO:873; SEQ ID NO:876; SEQ ID
NO:882; SEQ ID NO:883; SEQ ID NO:884; SEQ ID
NO:887; SEQ ID NO:889; SEQ ID NO:891; SEQ ID
NO:893; SEQ ID NO:895; SEQ ID NO:901; SEQ ID
NO:902; SEQ ID NO:903; SEQ ID NO:904; SEQ ID
NO:907; SEQ ID NO:908; SEQ ID NO:912; SEQ ID
NO:915; SEQ ID NO:922 and SEQ ID NO:924;

For the correlation with NCR peptides, see table III above.

In an advantageous embodiment, said anionic peptides comprised in the pharmaceutical composition above defined, are selected from the list consisting of: SEQ ID NO:686 (NCR 224), SEQ ID NO:697 (NCR 235), SEQ ID NO:514 (NCR 051), SEQ ID NO:464 (NCR 001).

In an advantageous embodiment, said neutral peptides comprised in the pharmaceutical composition above defined, are selected from the list consisting of:

SEQ ID NO:466; SEQ ID NO:473; SEQ ID NO:475; SEQ ID NO:491; SEQ ID NO:517; SEQ ID NO:519; SEQ ID NO:525; SEQ ID NO:527; SEQ ID NO:535; SEQ ID NO:540; SEQ ID NO:542; SEQ ID NO:547; SEQ ID NO:548; SEQ ID NO:553; SEQ ID NO:557; SEQ ID NO:559; SEQ ID NO:560; SEQ ID NO:570; SEQ ID NO:572; SEQ ID NO:578; SEQ ID NO:579; SEQ ID NO:581; SEQ ID NO:584; SEQ ID NO:585; SEQ ID NO:587; SEQ ID NO:589; SEQ ID NO:591; SEQ ID NO:594; SEQ ID NO:601; SEQ ID NO:607; SEQ ID NO:609; SEQ ID NO:612; SEQ ID NO:624; SEQ ID NO:628; SEQ ID NO:637; SEQ ID NO:638; SEQ ID NO:645; SEQ ID NO:649; SEQ ID NO:653; SEQ ID NO:660; SEQ ID NO:661; SEQ ID NO:664; SEQ ID NO:665; SEQ ID NO:668; SEQ ID NO:669; SEQ ID NO:671; SEQ ID NO:676; SEQ ID NO:689; SEQ ID NO:691; SEQ ID NO:692; SEQ ID NO:695; SEQ ID NO:698; SEQ ID NO:699; SEQ ID NO:701; SEQ ID NO:703; SEQ ID NO:707; SEQ ID NO:708; SEQ ID NO:710; SEQ ID NO:712; SEQ ID NO:714; SEQ ID NO:716; SEQ ID NO:717; SEQ ID NO:718; SEQ ID NO:723; SEQ ID NO:724; SEQ ID NO:726; SEQ ID NO:727; SEQ ID NO:730; SEQ ID NO:734; SEQ ID NO:740; SEQ ID NO:751; SEQ ID NO:755; SEQ ID NO:756; SEQ ID NO:764; SEQ ID NO:765; SEQ ID NO:776; SEQ ID NO:779; SEQ ID NO:785; SEQ ID NO:788; SEQ ID NO:789; SEQ ID NO:790; SEQ ID NO:791; SEQ ID NO:798; SEQ ID NO:801; SEQ ID NO:802; SEQ ID NO:804; SEQ ID NO:806; SEQ ID NO:809; SEQ ID NO:832; SEQ ID NO:833; SEQ ID NO:838; SEQ ID NO:843; SEQ ID NO:844; SEQ ID NO:864; SEQ ID NO:867; SEQ ID NO:869; SEQ ID NO:871; SEQ ID NO:874; SEQ ID NO:885; SEQ ID NO:886; SEQ ID NO:888; SEQ ID NO:890; SEQ ID NO:898; SEQ ID NO:900; SEQ ID NO:905; SEQ ID NO:906; SEQ ID NO:911; SEQ ID NO:914; SEQ ID NO:916; SEQ ID NO:918; SEQ ID NO:920 and SEQ ID NO:923.

For the correlation with NCR peptides, see table IV above.

In an advantageous embodiment, said neutral peptides comprised in the pharmaceutical composition above defined, are selected from the list consisting of: SEQ ID NO:547 (NCR 084), SEQ ID NO:691 (NCR 229).

DESCRIPTION OF THE FIGURES

FIG. 2A: PI staining:
x-axis from left to right: buffer (control), polymyxin B (50 μg/ml, positive control), bacteria heat killed (control), NCR035, NCR051, NCR055, NCR057, NCR084, NCR0224, NCR229, NCR235, NCR247.
y-axis: percentage of PI staining.

FIG. 2B: CFU determination:
x-axis: from left to right: buffer (control), polymyxin B (50 μg/ml, positive control), bacteria heat killed (control), NCR035, NCR051, NCR055, NCR057, NCR084, NCR0224, NCR229, NCR235, NCR247.
y-axis: percentage of relative CFU obtained.

FIG. 3A: PI staining for NCR035:
x-axis: from left to right: buffer (control), polymyxin B (50 µg/ml, positive control), bacteria heat killed (control), NCR035 (1 µg/ml), NCR035 (2 µg/ml), NCR035 (5 µg/ml), NCR035 (10 µg/ml), NCR035 (20 µg/ml), NCR035 (50 µg/ml).
y-axis: percentage of maximum PI staining obtained with heat killed bacteria.

FIG. 3B: PI staining for NCR055:
x-axis: from left to right: buffer (control), polymyxin B (50 µg/ml, positive control), bacteria heat killed (control), NCR055 (1 µg/ml), NCR055 (2 µg/ml), NCR055 (5 µg/ml), NCR055 (10 µg/ml), NCR055 (20 µg/ml), NCR055 (50 µg/ml).
y-axis: percentage of maximum PI staining obtained with heat killed bacteria.

FIG. 3C: PI staining for NCR057:
x-axis: from left to right: buffer (control), polymyxin B (50 µg/ml, positive control), bacteria heat killed (control), NCR057 (1 µg/ml), NCR057 (2 µg/ml), NCR057 (5 µg/ml), NCR057 (10 µg/ml), NCR057 (20 µg/ml), NCR057 (50 µg/ml).
y-axis: percentage of maximum PI staining obtained with heat killed bacteria.

FIG. 3D: PI staining for NCR0247:
x-axis: from left to right: buffer (control), polymyxin B (50 µg/ml, positive control), bacteria heat killed (control), NCR0247 (1 µg/ml), NCR0247 (2 µg/ml), NCR0247 (5 µg/ml), NCR0247 (10 µg/ml), NCR0247 (20 µg/ml), NCR0247 (50 µg/ml).
y-axis: percentage of maximum PI staining obtained with heat killed bacteria.

FIG. 3E: PI staining for NCR224:
x-axis: from left to right: buffer (control), polymyxin B (50 µg/ml, positive control), bacteria heat killed (control), NCR224 (1 µg/ml), NCR224 (2 g/ml), NCR224 (5 µg/ml), NCR224 (10 µg/ml), NCR224 (20 µg/ml), NCR224 (50 µg/ml).
y-axis: percentage of maximum PI staining obtained with heat killed bacteria.

FIG. 4A:
x-axis: from left to right: buffer (control), polymyxin B (50 µg/ml, positive control), bacteria heat killed (control), NCR035 (20 µg/ml), NCR035 (50 µg/ml).
y-axis: percentage of relative CFU.

FIG. 4B:
x-axis: from left to right: buffer (control), polymyxin B (50 µg/ml, positive control), bacteria heat killed (control), NCR055 (20 µg/ml), NCR055 (50 µg/ml).
y-axis: percentage of relative CFU.

FIG. 4C:
x-axis: from left to right: buffer (control), polymyxin B (50 µg/ml, positive control), bacteria heat killed (control), NCR057 (20 µg/ml), NCR057 (50 µg/ml).
y-axis: percentage of relative CFU.

FIG. 4D:
x-axis: from left to right: buffer (control), polymyxin B (50 µg/ml, positive control), bacteria heat killed (control), NCR224 (20 µg/ml), NCR224 (50 µg/ml).
y-axis: percentage of relative CFU.

FIG. 4E:
x-axis: from left to right: buffer (control), polymyxin B (50 µg/ml, positive control), bacteria heat killed (control), NCR247 (20 µg/ml), NCR247 (50 µg/ml).
y-axis: percentage of relative CFU.

FIG. 6: Ca cation
x-axis: from left to right: untreated cells, heat killed, NCR247S+0.1 mM $CaCl_2$, NCR247S+0.5 mM $CaCl_2$, NCR247S+1 mM $CaCl_2$, NCR247S+2 mM $CaCl_2$, NCR247S+5 mM $CaCl_2$,
y-axis: percentage of maximum PI staining obtained with heat killed bacteria.
NCRxxxS correspond to NCRxxx
FIG. 7: Mg cation
x-axis: from left to right: untreated cells, heat killed, NCR247S+0.1 mM $MgCl_2$, NCR247S+0.5 mM $MgCl_2$, NCR247S+1 mM $MgCl_2$, NCR247S+2 mM $MgCl_2$, NCR247S+5 mM $MgCl_2$,
y-axis: percentage of maximum PI staining obtained with heat killed bacteria.
NCRxxxS correspond to NCRxxx

FIG. 9A: treatment with NCR 057 or NCR 087 or NCR 224 peptides.
FIG. 9B: treatment with NCR 035 or NCR 051 or NCR 055 peptides.
FIG. 9C: treatment with NCR 229 or NCR 235 or NCR 247 peptides.
FIG. 9D: treatment with water or polymyxin B (50 µg/ml=42 µM).

FIGS. 11A to 11F present the antifungal effect of NCR 247 peptide on Fusarium graminearum (causing fusariose in plants) after 24 h or 48 h of incubation.
FIGS. 11D to 11F show the hyphae development of *Fusarium graminearum.
*
FIGS. 11A and 11D: control
FIGS. 11B and 11E: Medicago sativa defensin (MsDef)

FIGS. 11C and 11F: NCR 247 showing that NCR 247 inhibits the spores and hyphae development at 50 μg/ml.

Results are the same at 24 h and 48 h.

FIG. 12A to 12E present the antifungal effect of NCR 247 on *Aspergillus flavus* at various concentration after 24 h of incubation.

FIG. 12A: Control showing the growth of the fungi.
FIG. 12B: Effect of Amphotericin B (AMB antifungal agent) at 125 μg/ml.
FIG. 12C: Effect of NCR 247 at 25 μg/ml
FIG. 12D: Effect of NRC 247 at 50 μg/ml
FIG. 12E: Effect of NCR 247 at 100 μg/ml.

FIG. 13A to 13D present the antifungal effect of NCR 247 on *Aspergillus flavus* at various concentration after 48 h of incubation.

Figure 13:
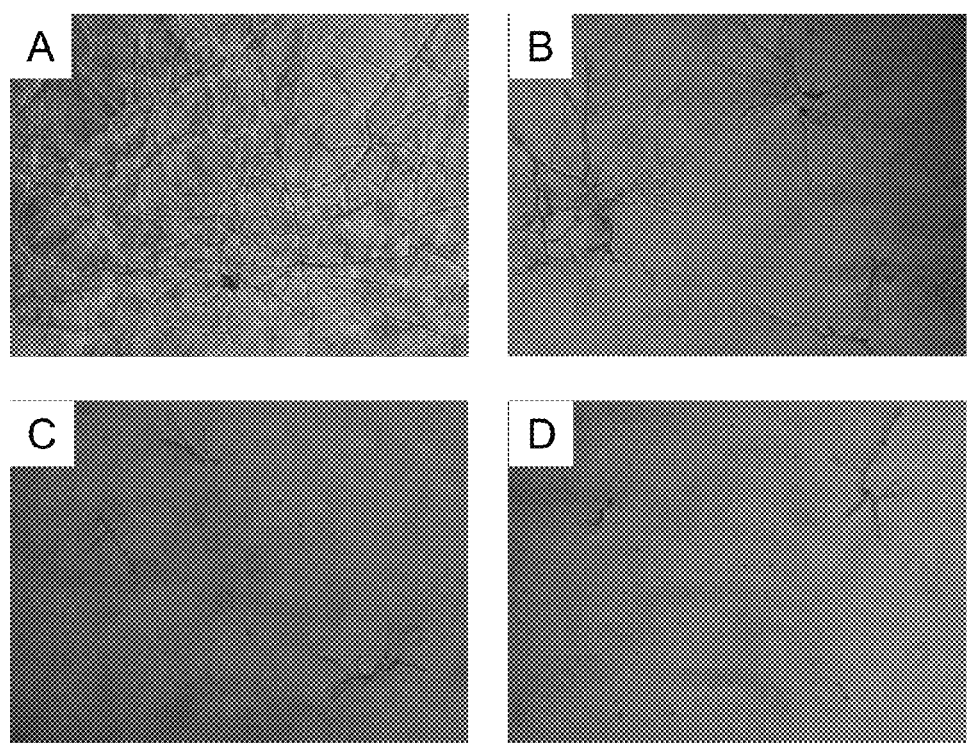

FIG. 13A: Control showing the growth of the fungi.
FIG. 13B: Effect of NCR 247 at 25 μg/ml
FIG. 13C: Effect of NRC 247 at 50 μg/ml
FIG. 13D: Effect of NCR 247 at 100 μg/ml.

Figure 14:
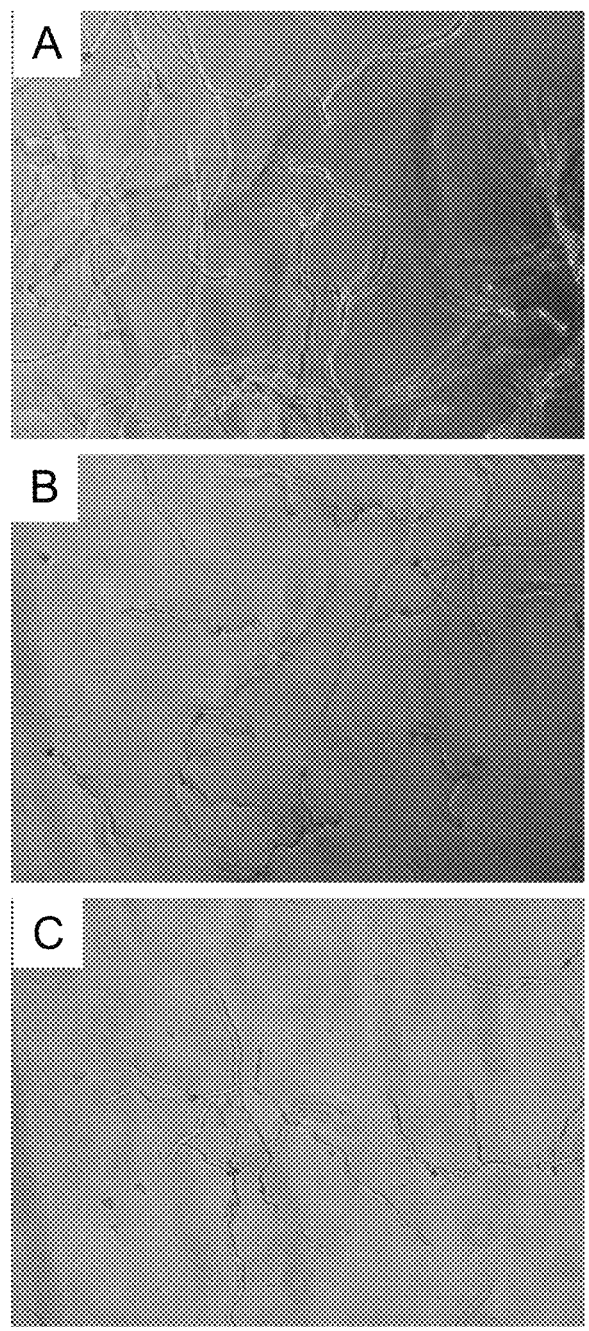

FIG. 14A to 14C present the antifungal effect of NCR 035 on *Aspergillus flavus* at various concentration after 24 h of incubation.

Control showing the growth of the fungi (see FIG. 12A)
FIG. 14A: Effect of NCR 035 at 25 μg/ml
FIG. 14B: Effect of NRC 035 at 50 μg/ml
FIG. 14C: Effect of NCR 035 at 100 μg/ml.

Figure 15:
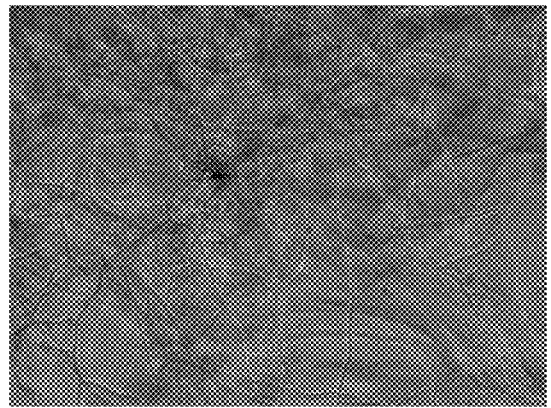

FIG. 15 presents the antifungal effect of NCR 035 on *Aspergillus flavus* at 100 μg/ml after 48 h of incubation.

Control showing the growth of the fungi (see FIG. 12A)
FIG. 15: Effect of NCR 035.

Results are the same with 25 μg/ml and 50 μg/ml for 48 h of incubation for this peptide.

Figure 16:
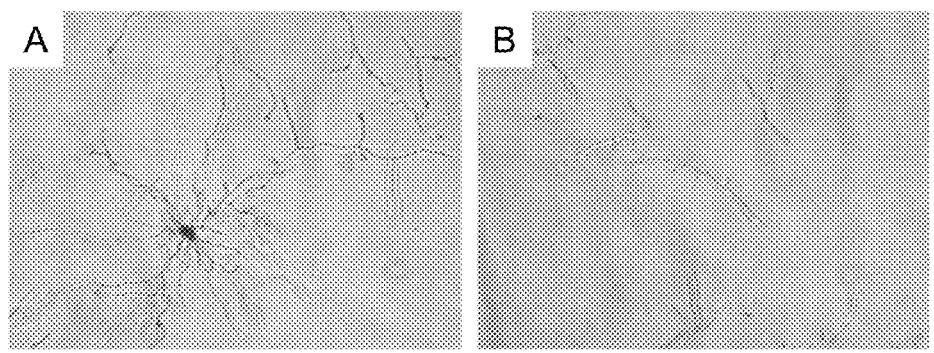

FIG. 16A to 16B present the antifungal effect of NCR 055 on *Aspergillus flavus* at various concentration after 24 h of incubation.

Control showing the growth of the fungi (see FIG. 12A)
FIG. 16A: Effect of NCR 055 at 50 μg/ml
FIG. 16B: Effect of NRC 055 at 100 μg/ml FIG. 17A to 17B present the antifungal effect of NCR 055 on *Aspergillus flavus* at various concentration after 48 h of incubation.

Figure 17:
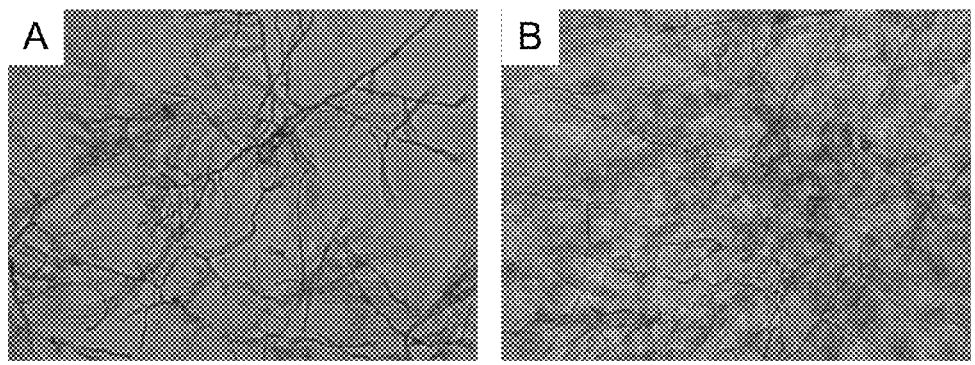

Control showing the growth of the fungi (see FIG. 12A)
FIG. 17A: Effect of NCR 055 at 50 μg/ml
FIG. 17B: Effect of NRC 055 at 100 μg/ml FIG. 18A to 18C present the antifungal effect of NCR 247 on *Aspergillus niger* at various concentration after 24 h of incubation.

Figure 18:
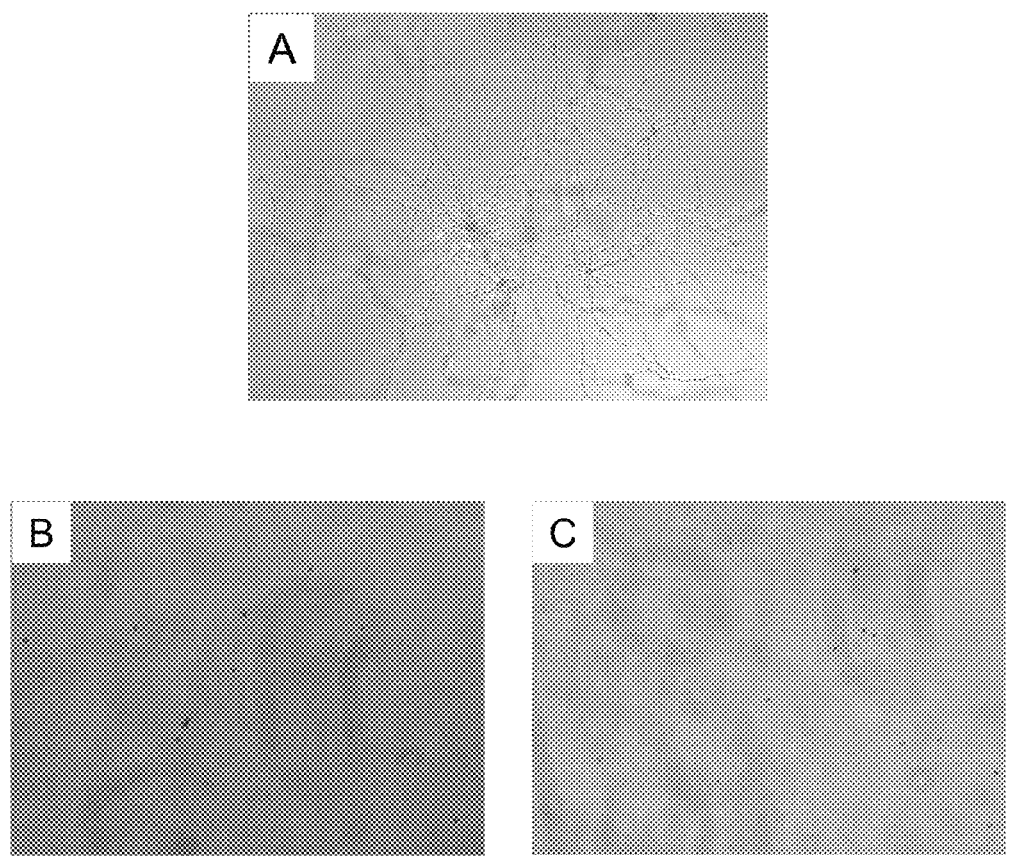

FIG. 18A: Control showing the growth of the fungi at 24 h
FIG. 18B: Effect of NCR 247 at 50μg/ml
FIG. 18C: Effect of NRC 247 at 100 μg/ml FIG. 19A to 19D present the antifungal effect of NCR 035 on *Aspergillus niger* at various concentration after 24 h or 48 h of incubation.

Figure 19:
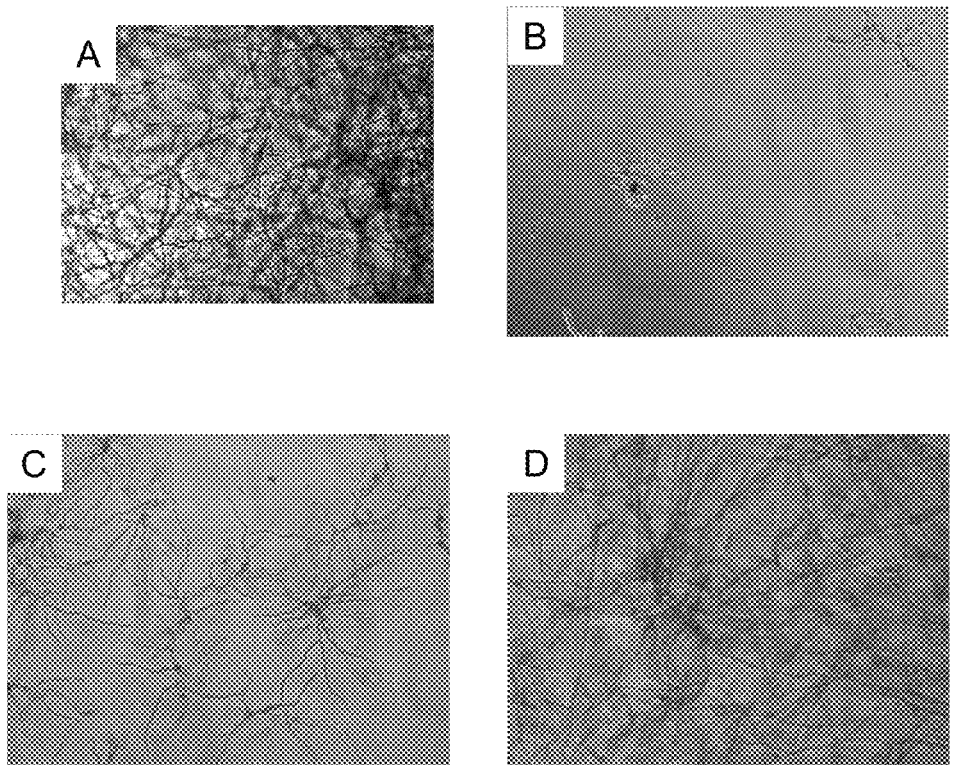

Control showing the growth of the fungi at 24 h (see FIG. 18A)
FIG. 19A: Control showing the growth of the fungi at 48 h
FIG. 19B: Effect of NCR 035 at 50 μg/ml at 24 h
FIG. 19C: Effect of NRC 035 at 100 μg/ml at 24 h
FIG. 19D: Effect of NRC 035 at 100 μg/ml at 48 h FIG. 20A to 20C present the antifungal effect of NCR 055 on *Aspergillus niger* at various concentration after 24 h or 48 h of incubation.

Figure 20:
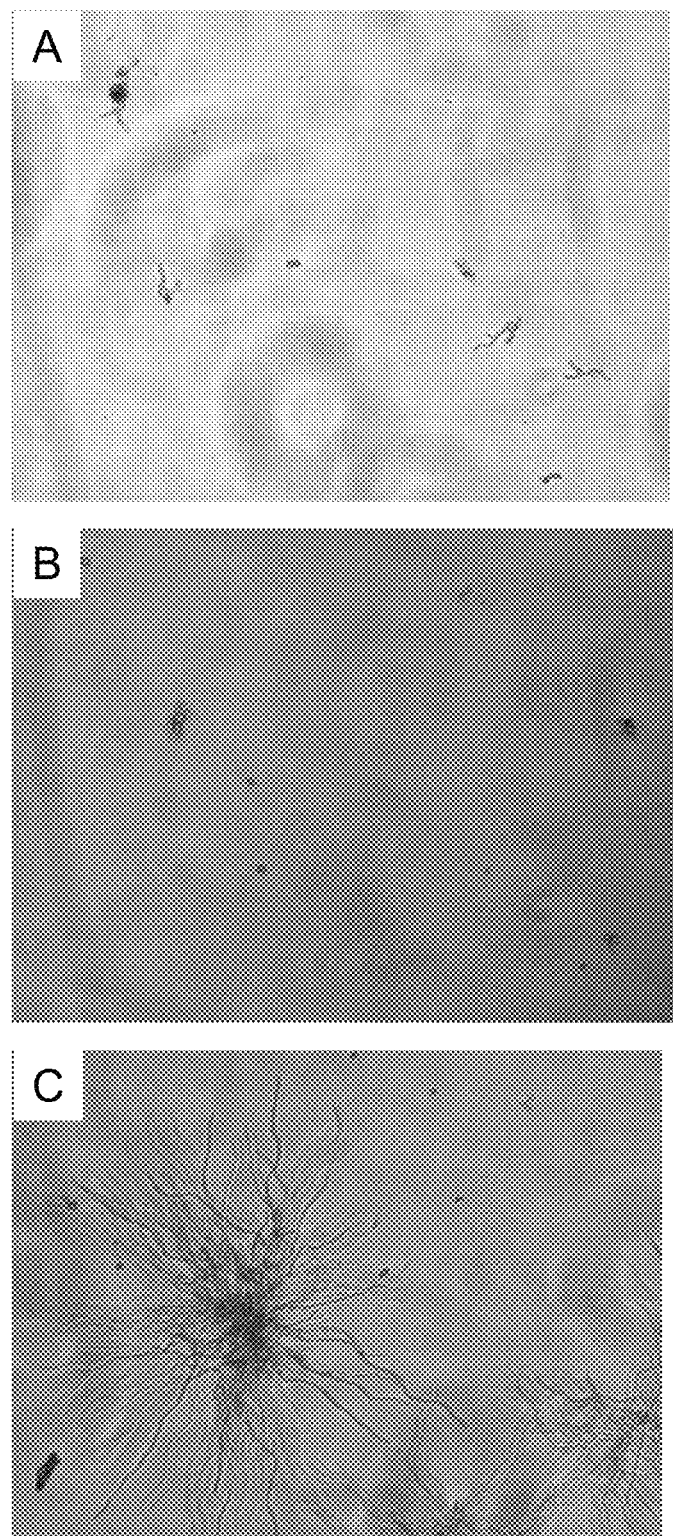

Control showing the growth of the fungi at 24 and 48 h(see FIGS. 18A and 19A)
FIG. 20A: Effect of NCR 055 at 50 μg/ml at 24 h
FIG. 20B: Effect of NRC 055 at 100 μg/ml at 24 h
FIG. 20C: Effect of NRC 055 at 100 μg/ml at 48 h The result is the same for NCR 055 at 50 μg/ml at 48 h as at 24 h FIG. 21A to 21C present the antifungal effect of NCR 247 on *Candida albicans* at various concentration after 24 h of incubation.

Figure 21:
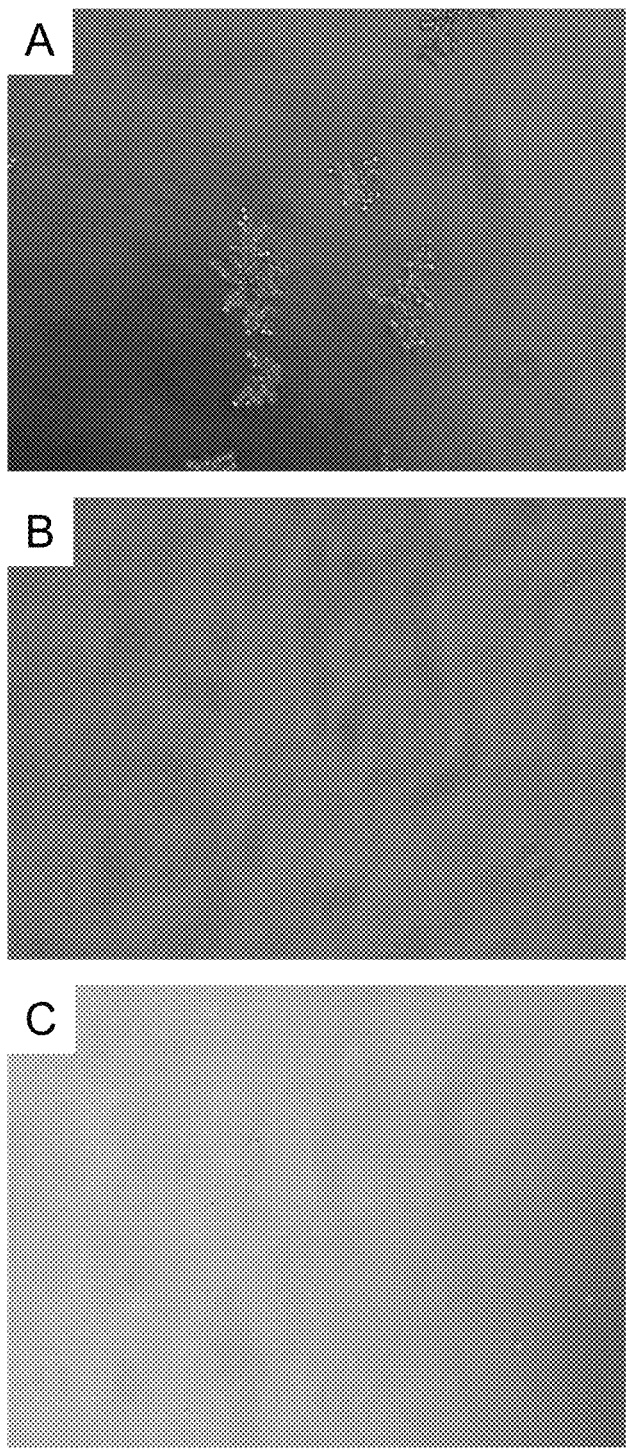

FIG. 21A: Control showing the growth of the fungi.
FIG. 21B: Effect of Amphotericin B (AMB antifungal agent) at 125 μg/ml.
FIG. 21C: Effect of NCR 247 at 100 μg/ml FIG. 22A to 22C present the antifungal effect of NCR 035 on *Candida albicans* at various concentration after 24 h of incubation.

Figure 22:
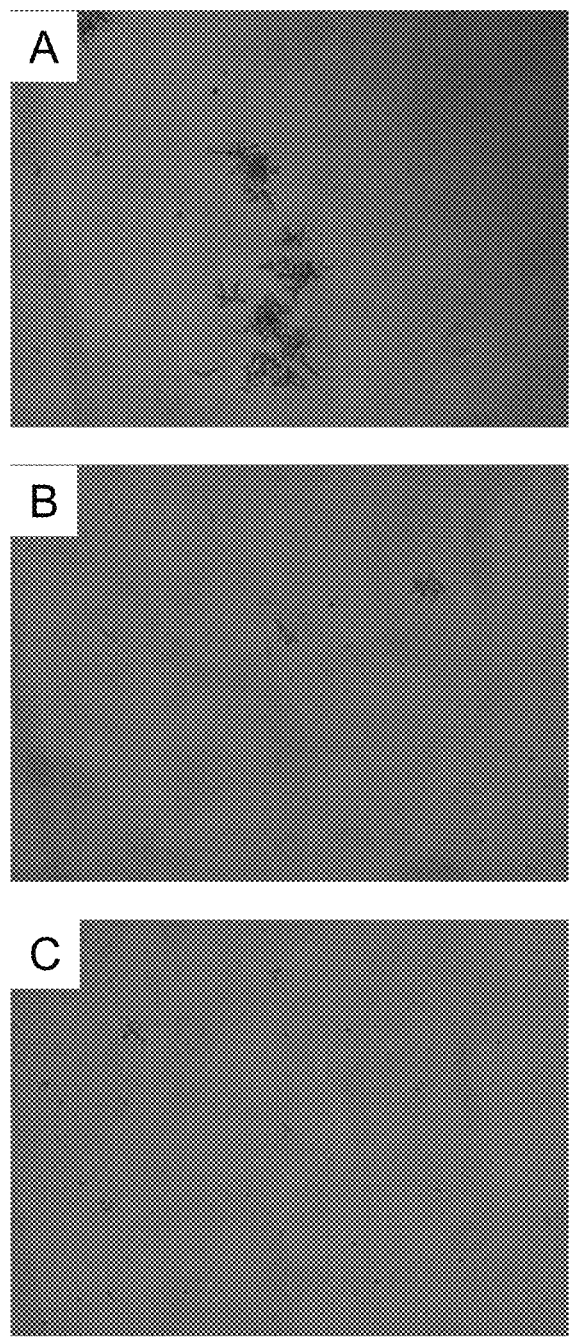

Control showing the growth of the fungi (see FIG. 21A)
FIG. 22A: Effect of NCR 035 at 25 μg/ml
FIG. 22B: Effect of NRC 035 at 50 μg/ml
FIG. 22C: Effect of NCR 035 at 100 μg/ml.

Figure 23:
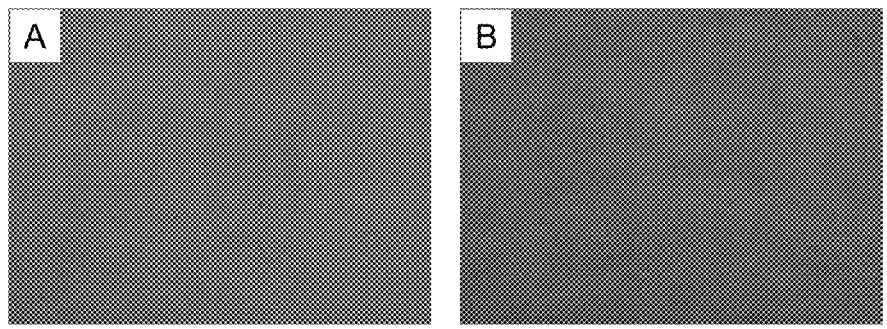

FIG. 23A to 23B present the antifungal effect of NCR 055 on *Candida albicans* at various concentration after 24 h of incubation.

Control showing the growth of the fungi (see FIG. 21A)
FIG. 23A: Effect of NRC 055 at 50 μg/ml
FIG. 23B: Effect of NCR 055 at 100 μg/ml.

Figure 24:
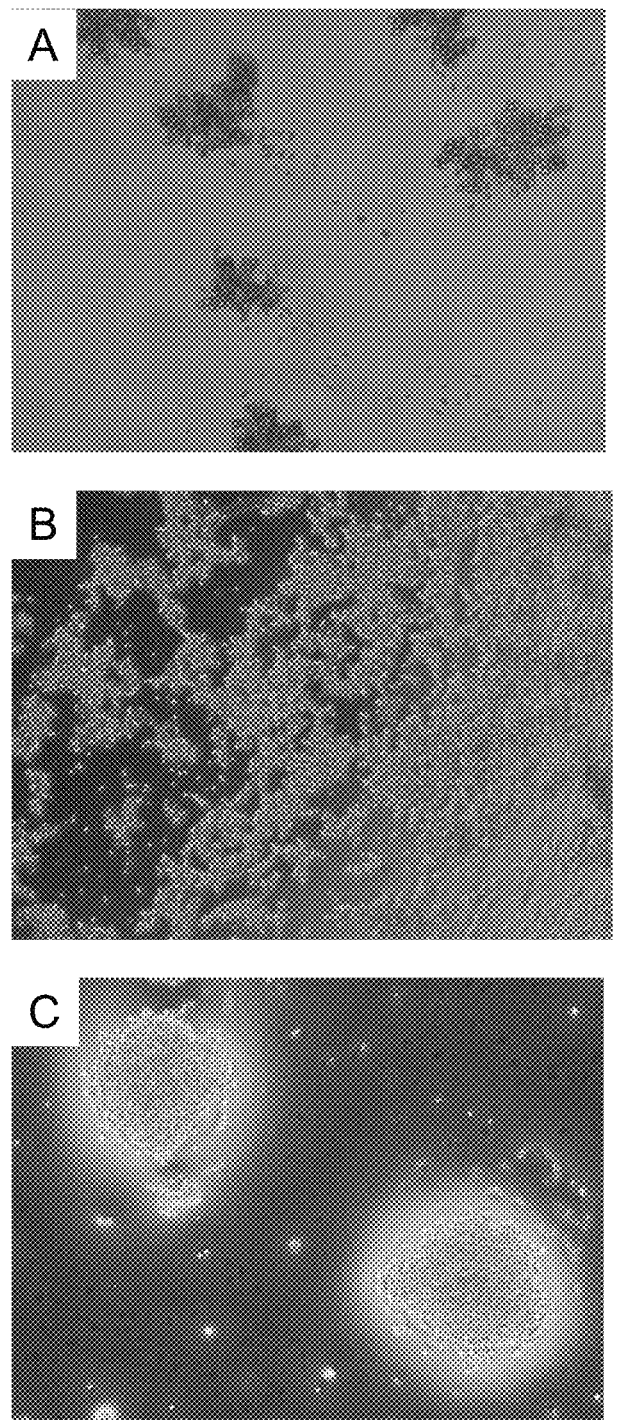

FIG. 24A to 24C present the antifungal effect of NCR 035 on *Candida albicans* at various concentration after 48 h of incubation.

FIG. 24A: Control showing the growth of the fungi.
FIG. 24B: Effect of NRC 035 at 25 μg/ml
FIG. 24C: Effect of NCR 035 at 100 μg/ml.

FIG. 25A to 25E present the antifungal effect of NCR 247 on *Candida crusei* at various concentration after 24 h of incubation.

Figure 25:
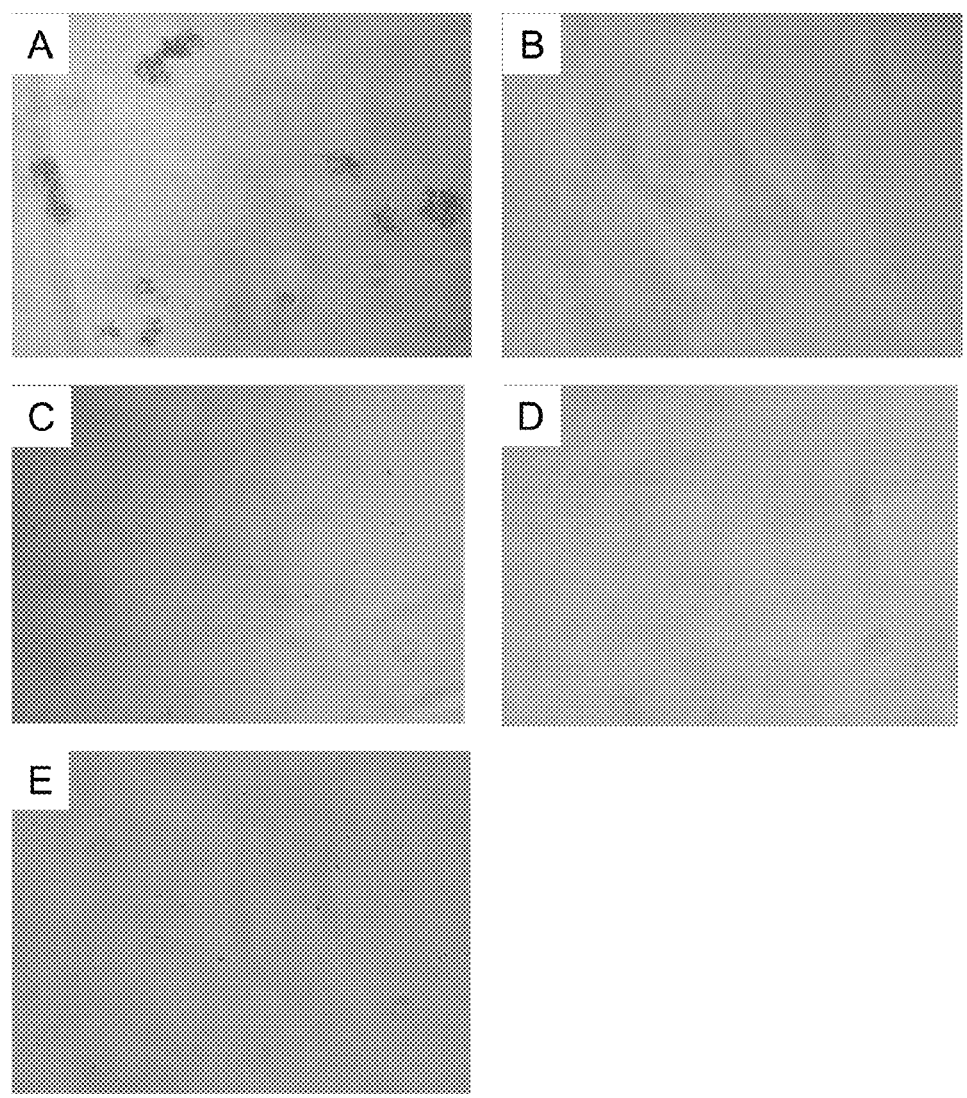

FIG. 25A: Control showing the growth of the fungi.
FIG. 25B: Effect of Amphotericin B (AMB antifungal agent) at 125 μg/ml.
FIG. 25C: Effect of NCR 247 at 25 μg/ml
FIG. 25D: Effect of NCR 247 at 50 μg/ml
FIG. 25E: Effect of NCR 247 at 100 μg/ml FIG. 26A to 26C present the antifungal effect of NCR 035 on *Candida crusei* at various concentration after 24 h of incubation.

Figure 26:
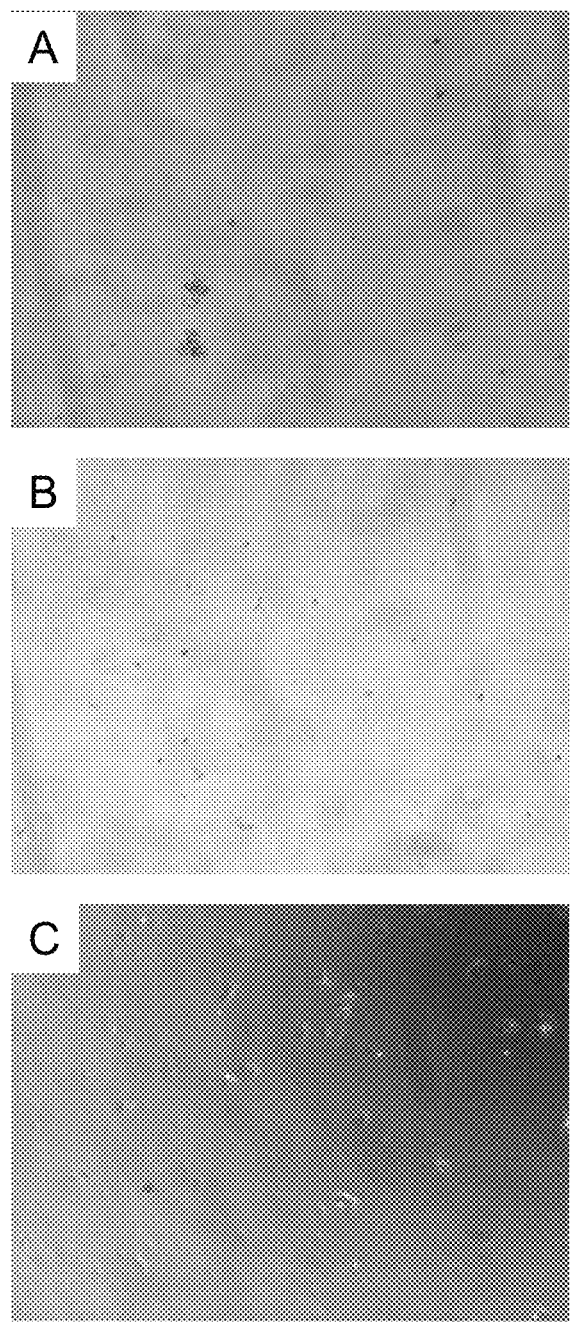

Control showing the growth of the fungi (see FIG. 25A)
FIG. 26A: Effect of NCR 035 at 25 μg/ml
FIG. 26B: Effect of NCR 035 at 50 μg/ml
FIG. 26C: Effect of NCR 035 at 100 μg/ml FIG. 27A to 27B present the antifungal effect of NCR 055 on *Candida crusei* at various concentration after 24 h of incubation.

Figure 27:
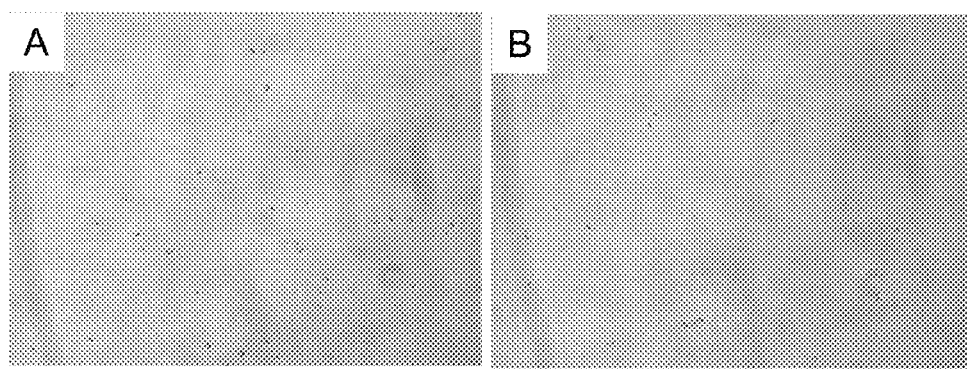

Control showing the growth of the fungi (see FIG. 25A)
FIG. 27A: Effect of NCR 055 at 50 μg/ml
FIG. 27B: Effect of NCR 055 at 100 μg/ml FIG. 28A to 28B present the antifungal effect of NCR 035 on *Candida crusei* at various concentration after 48 h of incubation.

Figure 28:
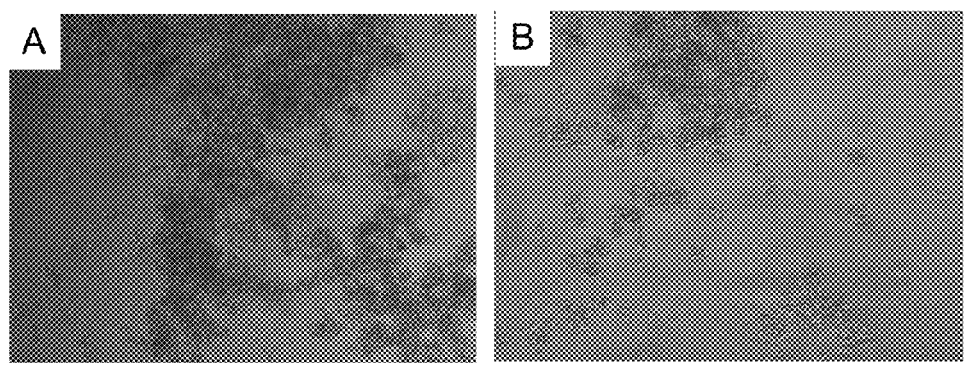

FIG. 28A: Control showing the growth of the fungi
FIG. 28B: Effect of NCR 035 at 25 μg/ml FIG. 29A to 29E present the antifungal effect of NCR 247 on *Candida parapsilosis* at various concentration after 24 h of incubation.

Figure 29:
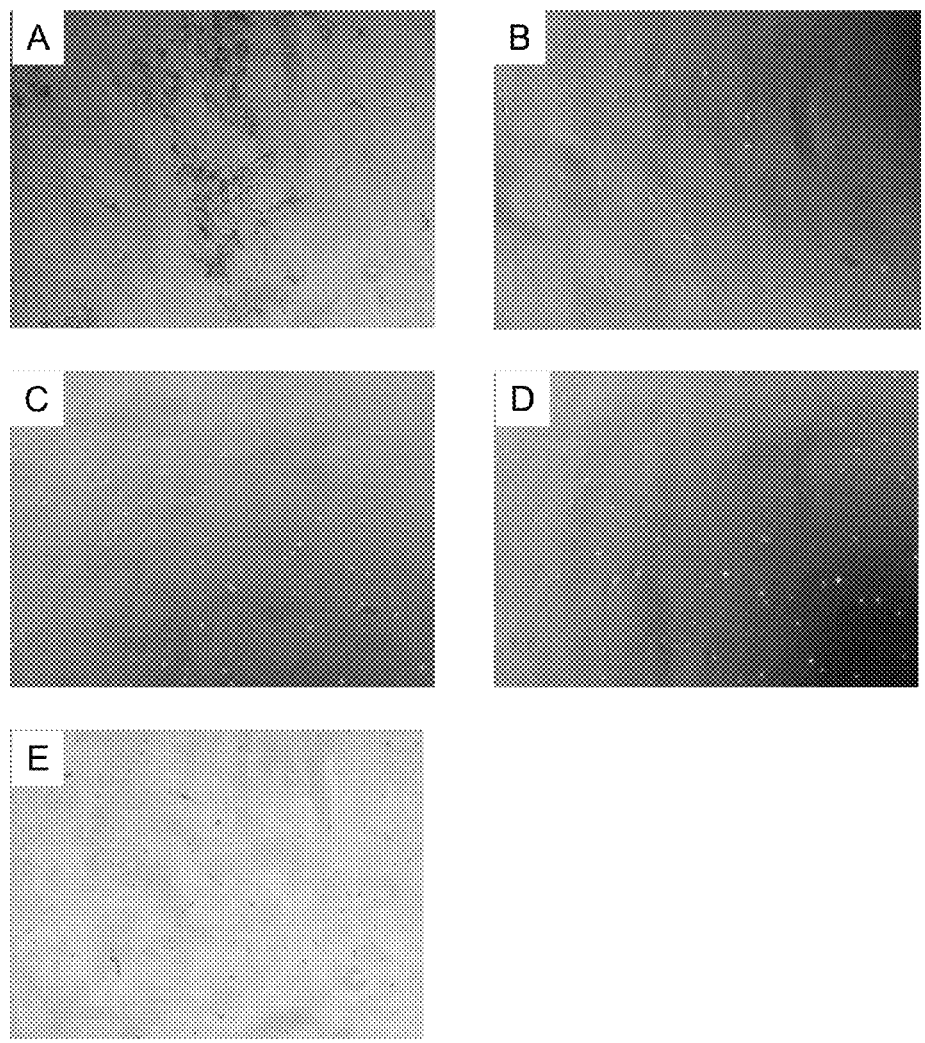

FIG. 29A: Control showing the growth of the fungi.
FIG. 29B: Effect of Amphotericin B (AMB antifungal agent) at 125 μg/ml.
FIG. 29C: Effect of NCR 247 at 25 μg/ml
FIG. 29D: Effect of NCR 247 at 50 μg/ml
FIG. 29E: Effect of NCR 247 at 100 μg/ml FIG. 30A to 30C present the antifungal effect of NCR 035 on *Candida parapsilosis* at various concentration after 24 h of incubation.

Figure 30:
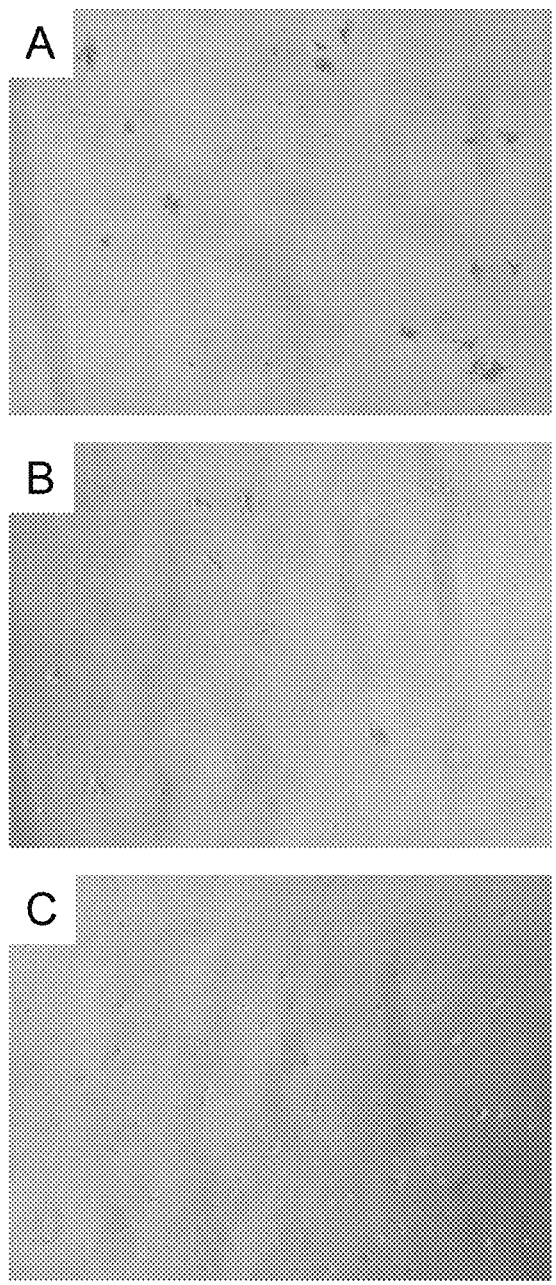
Figure 31:
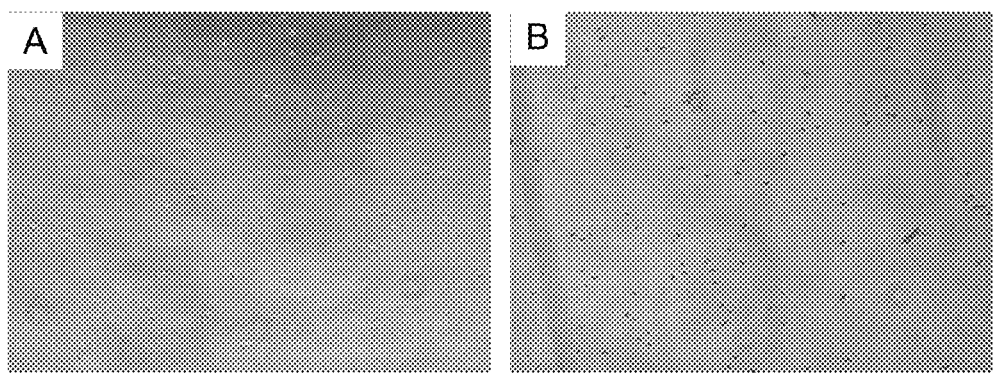
Figure 32:
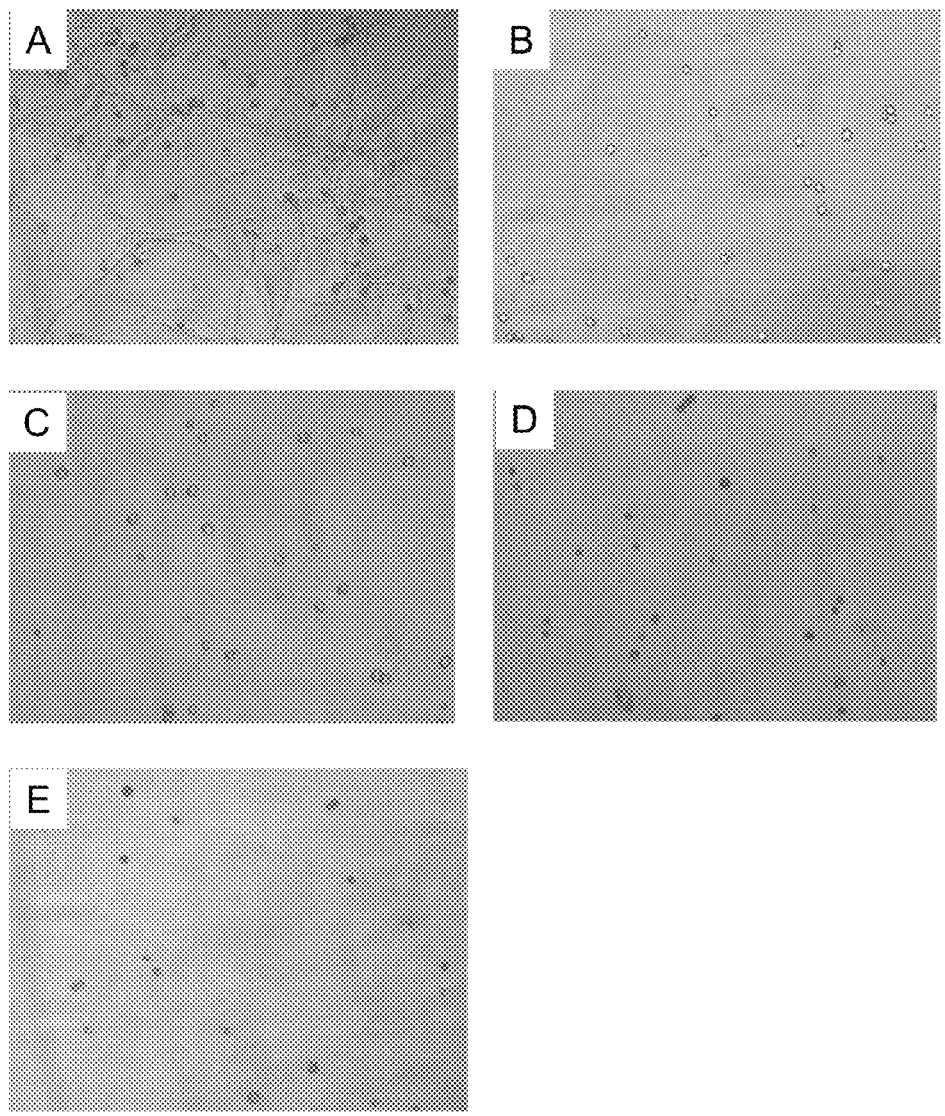
Figure 33:
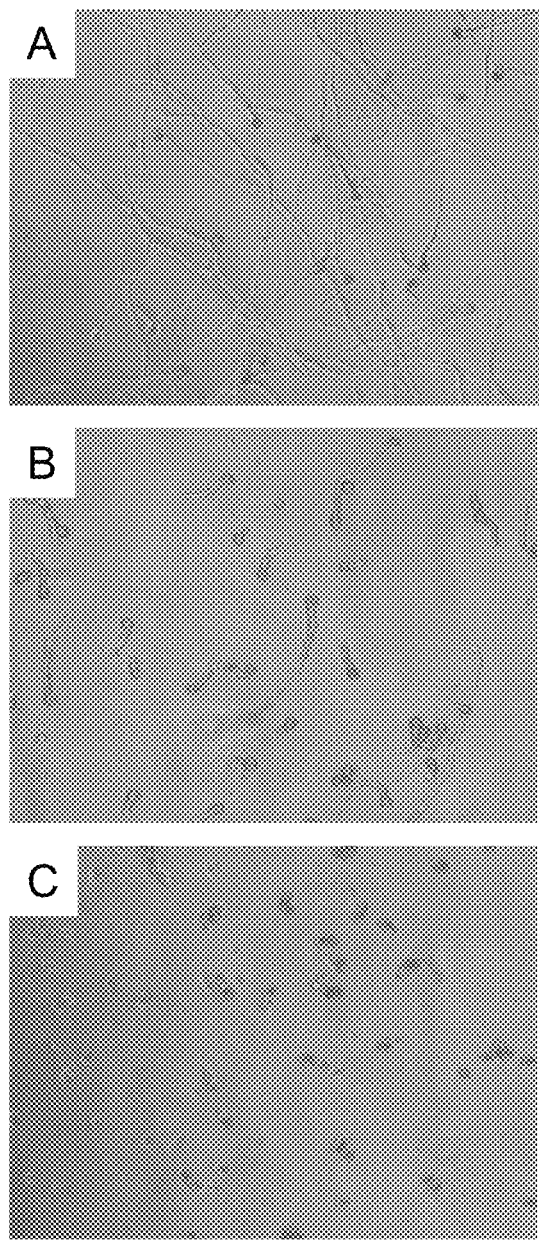
Figure 34:
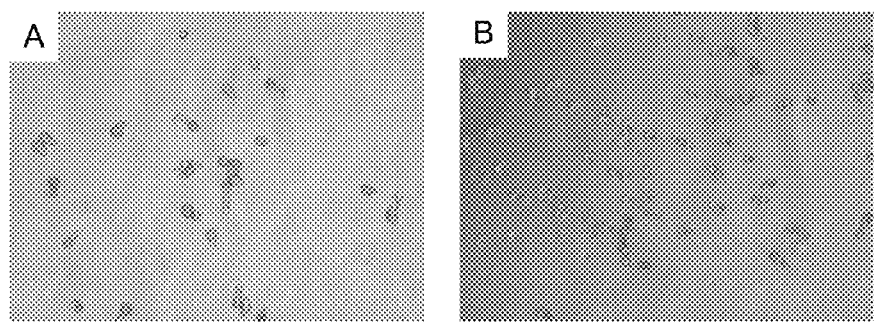
Figure 35:
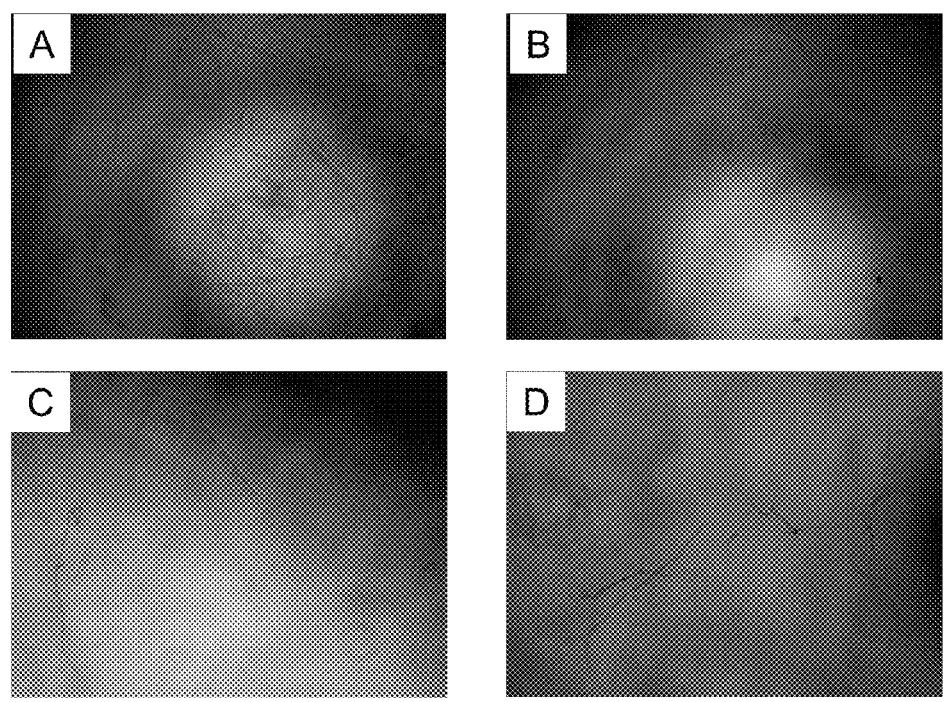
Figure 36:
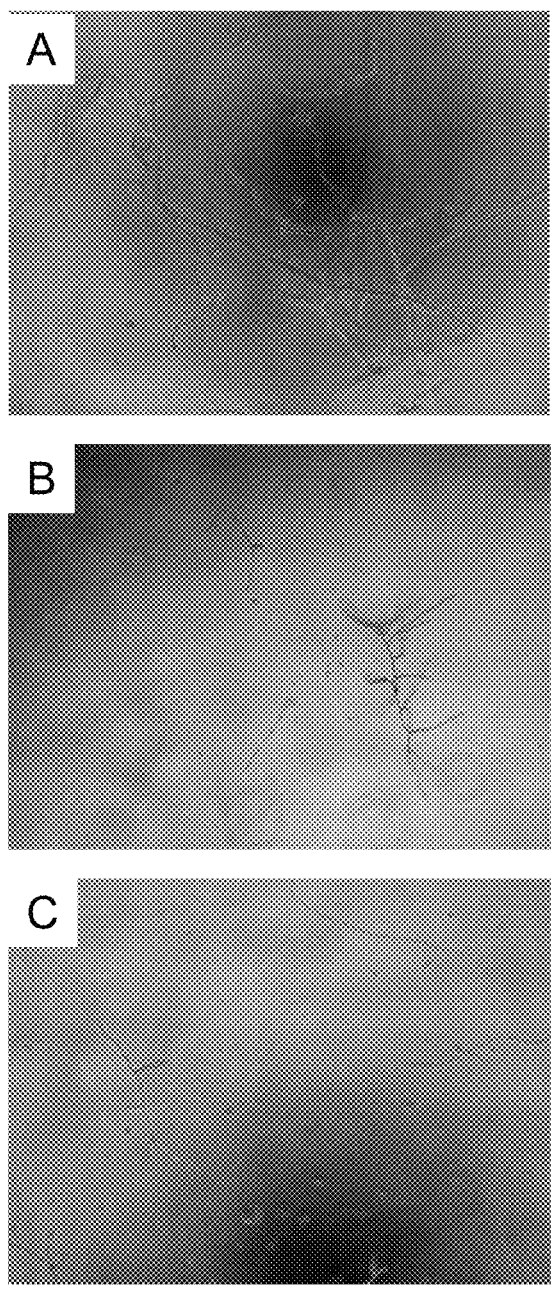
Figure 37:
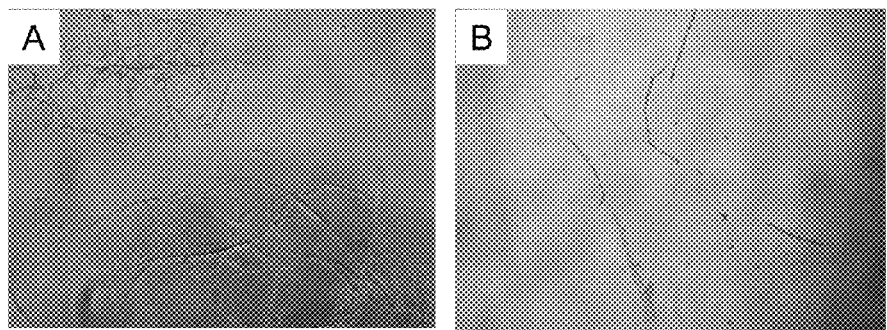
Figure 38:
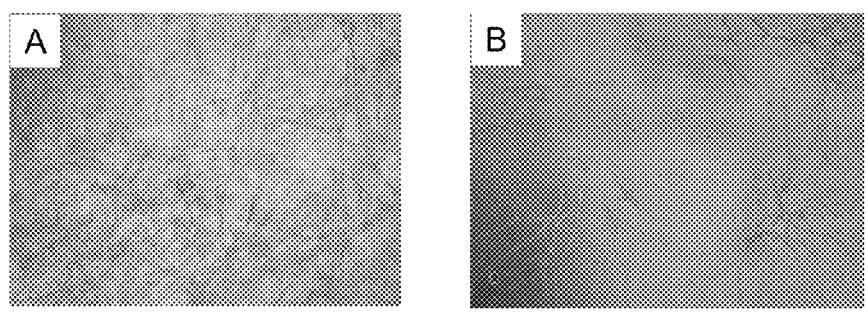

Control showing the growth of the fungi (see FIG. 29A)
FIG. 30A: Effect of NCR 035 at 25 µg/ml
FIG. 30B: Effect of NCR 035 at 50 µg/ml
FIG. 30C: Effect of NCR 035 at 100 µg/ml
FIG. 31A to 31B present the antifungal effect of NCR 055 on *Candida parapsilosis* at various concentration after 24 h of incubation.
Control showing the growth of the fungi (see FIG. 29A)
FIG. 31A: Effect of NCR 055 at 50 µg/ml
FIG. 31B: Effect of NCR 055 at 100 µg/ml
FIG. 32A to 32E present the antifungal effect of NCR 247 on *Rhizopus stolonifer* var. *stolonifer* at various concentration after 24 h of incubation.
FIG. 32A: Control showing the growth of the fungi.
FIG. 32B: Effect of Amphotericin B (AMB antifungal agent) at 125 µg/ml.
FIG. 32C: Effect of NCR 247 at 25 µg/ml
FIG. 32D: Effect of NCR 247 at 50 µg/ml
FIG. 32E: Effect of NCR 247 at 100 µg/ml
FIG. 33A to 33C present the antifungal effect of NCR 035 on *Rhizopus stolonifer* var. *stolonifer* at various concentration after 24 h of incubation.
Control showing the growth of the fungi (see FIG. 32A)
FIG. 33A: Effect of NCR 035 at 25 µg/ml
FIG. 33B: Effect of NCR 035 at 50 µg/ml
FIG. 33C: Effect of NCR 035 at 100 µg/ml
FIG. 34A to 34B present the antifungal effect of NCR 055 on *Rhizopus stolonifer* var. *stolonifer* at various concentration after 24 h of incubation.
Control showing the growth of the fungi (see FIG. 32A)
FIG. 34A: Effect of NCR 055 at 50 µg/ml
FIG. 34B: Effect of NCR 055 at 100 µg/ml
FIG. 35A to 35D present the antifungal effect of NCR 247 on *Fusarium graminearum* at various concentration after 24 h of incubation.
FIG. 35A: Control showing the growth of the fungi.
FIG. 35B: Effect of Amphotericin B (AMB antifungal agent) at 125 µg/ml.
FIG. 35C: Effect of NCR 247 at 25 µg/ml
FIG. 35D: Effect of NCR 247 at 100 µg/ml
FIG. 36A to 36C present the antifungal effect of NCR 035 on *Fusarium graminearum* at various concentration after 24 h of incubation.
Control showing the growth of the fungi (see FIG. 35A)
FIG. 36A: Effect of NCR 035 at 25 µg/ml
FIG. 36B: Effect of NCR 035 at 50 µg/ml
FIG. 36C: Effect of NCR 035 at 100 µg/ml
FIG. 37A to 37B present the antifungal effect of NCR 055 on *Fusarium graminearum* at various concentration after 24 h of incubation.
Control showing the growth of the fungi (see FIG. 35A)
FIG. 37A: Effect of NCR 055 at 50 µg/ml
FIG. 37B: Effect of NCR 055 at 100 µg/ml
FIG. 38A to 38B present the antifungal effect of NCR 035 on *Fusarium graminearum* at various concentration after 48 h of incubation.
Control showing the growth of the fungi (see FIG. 35A)
FIG. 38A: Control showing the growth of the fungi.
FIG. 38B: Effect of NCR 035 at 100 µg/ml

EXAMPLES

Example 1

PI Staining

Propidum Iodide (PI) is able to intercalate into the DNA structure and emits fluorescence only in DNA bound form. PI is able to enter only into cells that lost the membrane integrity therefore it is commonly used for identifying dead cells by detecting fluorescence emission intensity. Intact membranes are impervious for PI, therefore PI is excluded from alive cells, and no fluorescence is observed.

PI staining was measured in a BMG Labtech Fluostar Optima fluorimeter (excitation: 520 nm, emission: 610 nm). Reactions were initiated by addition of NCR peptides to the bacteria. Kinetic measurements were performed, in most cases a plateau of fluorescence intensity was reached within minutes.

Control reactions:
Buffer only: to measure background fluorescence and to determine the PI staining of the untreated cells (negative control).
Polymyxin B (positive control, 50 µg/ml final concentration): a cyclic peptide antibiotic with attached fatty acid was used as positive control for PI uptake. This is a bacteriostatic and bactericidal antibiotic mainly effective against Gram-negative bacteria (e.g. *Pseudomonas aeruginosa*).
Heat treatment (positive control): boiling the bacteria for 10 minutes resulted in maximal PI fluorescence.

Example 2

CFU (Colony Forming Unit) Determination

To determine the bactericidal effect, peptide-treated bacteria were plated at different dilutions and CFUs were counted, inhibitory concentration was determined.
Control reactions:
Buffer only: to determine the CFUs of the untreated cells (negative control).
Polymyxin B (positive control, 50 µg/ml final concentration) was used as positive control for cell killing.
Heat treatment (positive control): boiling the bacteria for 10 mins killed the bacteria.

Example 3

Figure 1D:
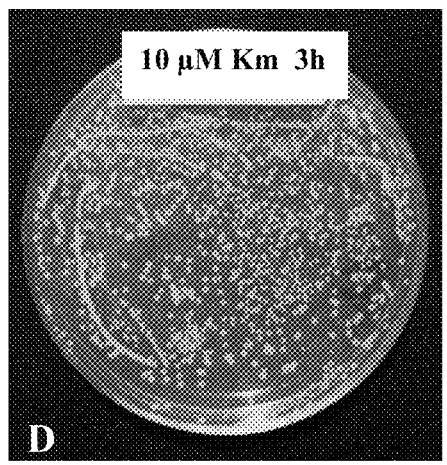
FIG. 1 presents the CFU obtained after treatment during 3 hours of bacterium *Sinorhizobium meliloti* (starting CFU was : $10^7$ colony/ml) with:
A: control without NCR peptides or antibiotics
B: tetracyclin (Tc) at 10 μM,
C: tetracyclin at 100 μM,
D: kanamycin (Km) at 10 μM,
E: kanamycin at 100 μM,
F: NCR 055 at 10 μM,
F: NCR 035 at 10 μM,
F: NCR 247 at 10 μM,
G: polymyxin-B at 10 μM.
Figure 1E:
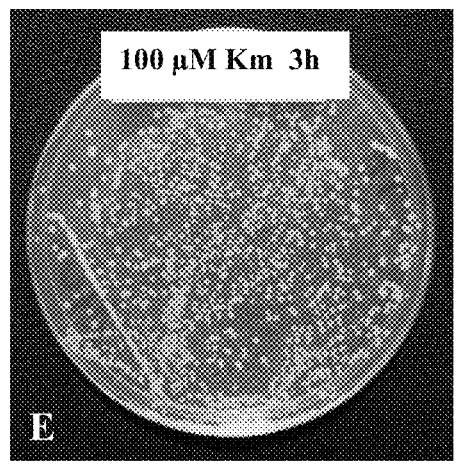
Figure 1F:
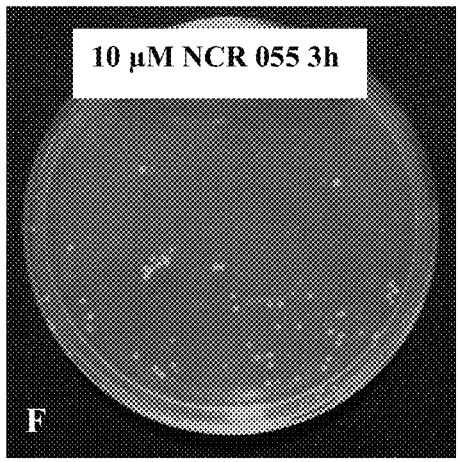
Figure 1G:
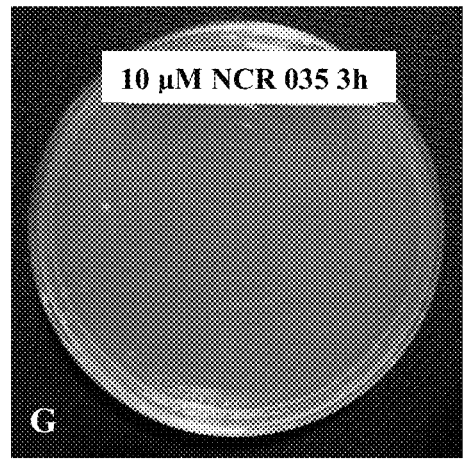
Figure 1H:
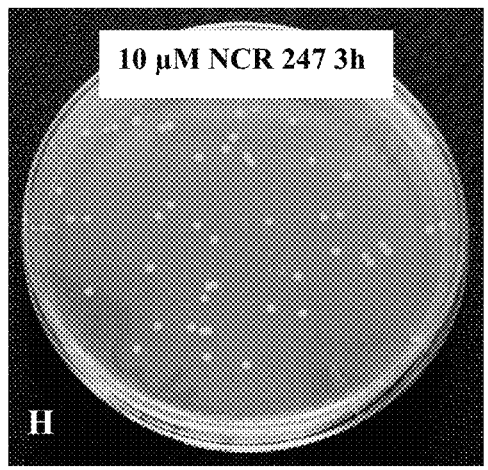
Figure 1I:
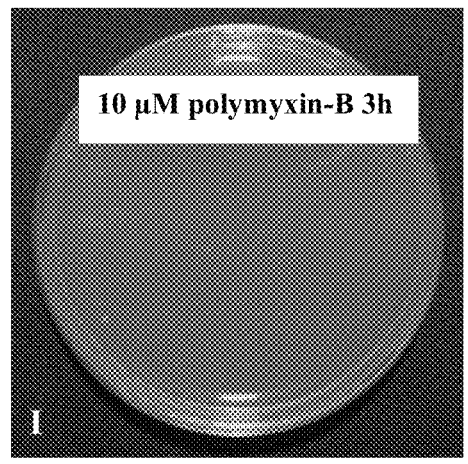
Figure 2A:
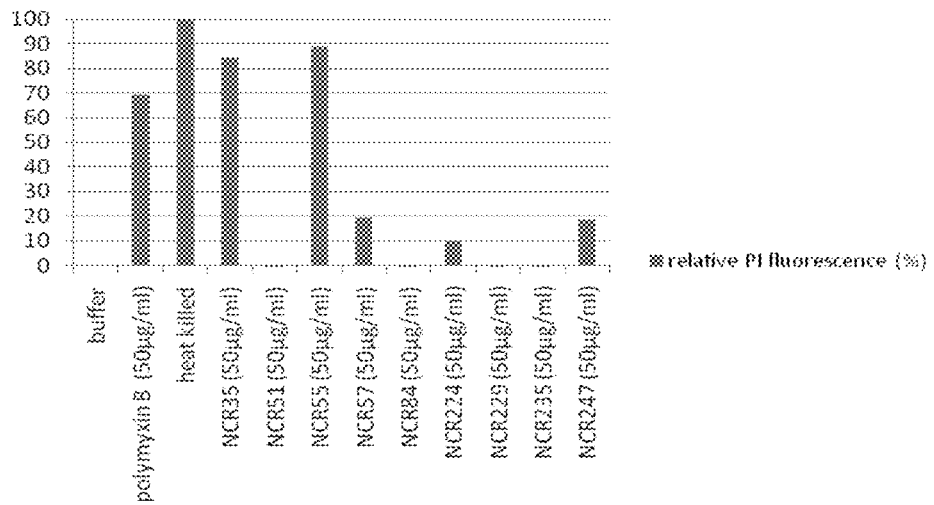
FIGS. 2A and 2B presents the results obtained after treatment of *Sinorhizobium meliloti* AK631 bacteria with 50 μg/ml of various NCRs in microtiter plates.

Treatment of *Sinorhizobium meliloti* or Other Bacteria with 50 µg/ml NCRs in Microtiter Plates for 3 Hours Growth of bacteria:
From a fresh plate, a single colony was inoculated in 2 ml liquid medium and grown overnight at 30° C. with shaking. Next morning a 100-fold dilution in liquid medium was carried out and the culture was grown up to $OD_{600}$=0.25 and diluted again to $OD_{600}$=0.05 and then grown until $OD_{600}$=0.2.
Bacteria were harvested by centrifugation at 13000 rpm for 1 min and resuspended in 10 mM K-P buffer, pH7 at $OD_{600}$=0.1.
Treatment setup:
80 µl log phase bacteria (OD=0.1, approximately 2-3×10$^6$ cells) in 10 mM K phosphate buffer (pH=7.0) was mixed with 10 µl peptide in buffer (50 µg/ml final concentration) and 10 µl PI in buffer (5 µg/ml final concentration).
Total volume: 100 µl.
Results:
FIG. 2A presents the results for PI staining:
NCR35, NCR55 and to a lesser extent NCR57 and NCR247 provoked PI uptake.
The effects of NCR35 and NCR55 were comparable to heat killed bacteria or bacteria treated with polymyxin B.

Figure 2B:
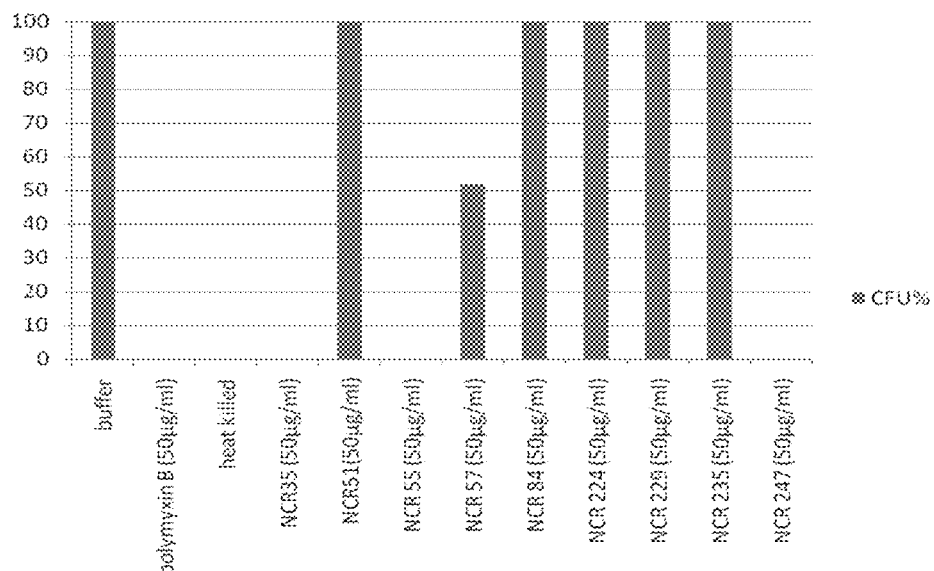
Figure 3A:
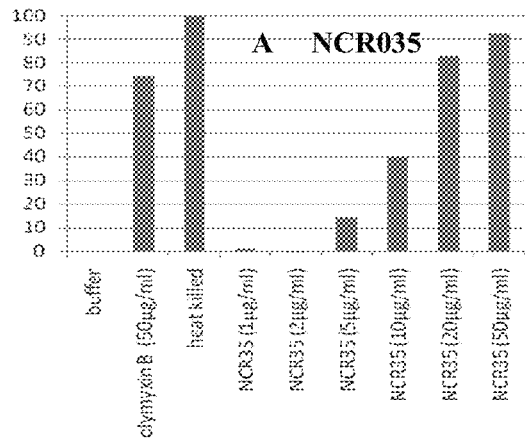
FIGS. 3A to 3E present the results obtained for the relative PI fluorescence of NCR treated *S. meliloti* cells with various concentrations of NCR in comparison to polymyxin B and heat treatments.
Figure 3B:
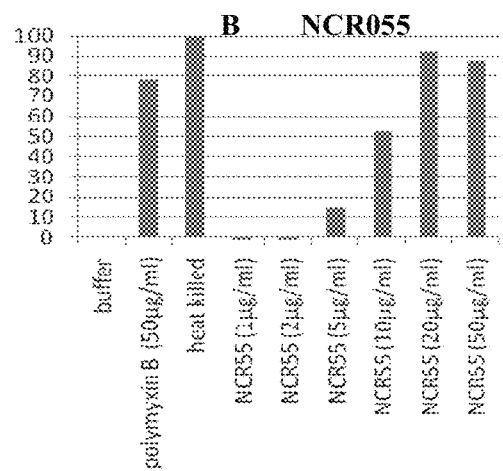
Figure 3C:
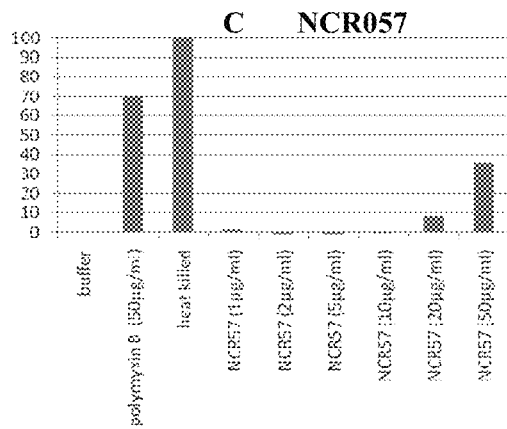
Figure 3D:
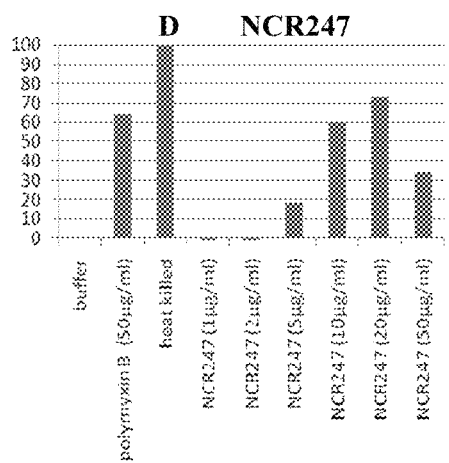
Figure 3E:
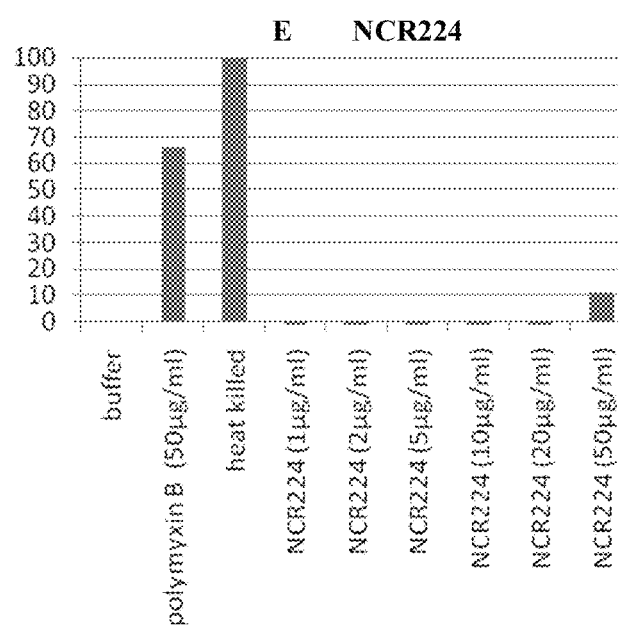
Figure 4A:
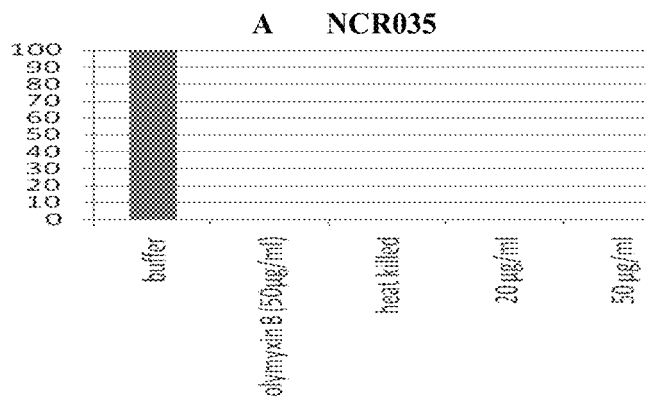
FIGS. 4A to 4E presents the CFUs of *S. meliloti* after treatment with various NCRs at 20 and 50 µg/ml concentrations for 1 hr.
Figure 4B:
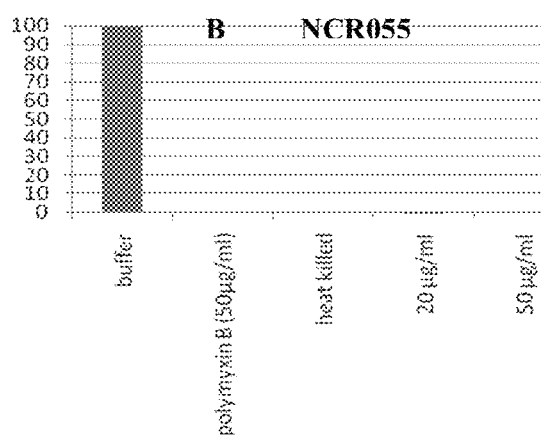
Figure 4C:
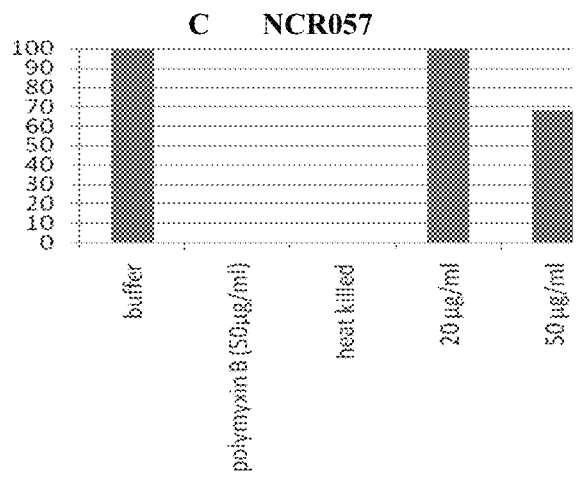
Figure 4D:
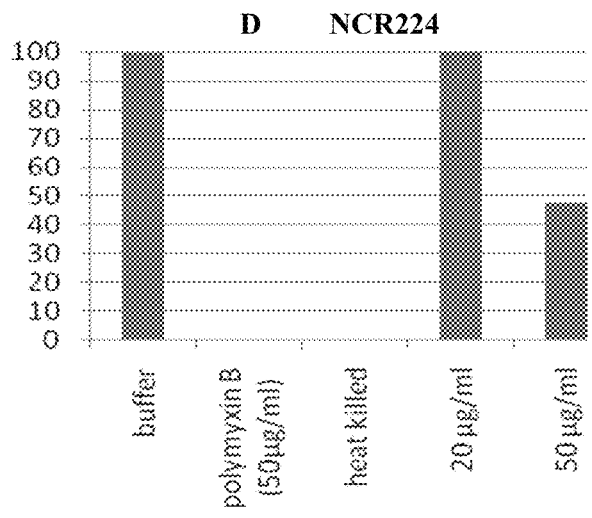
Figure 4E:
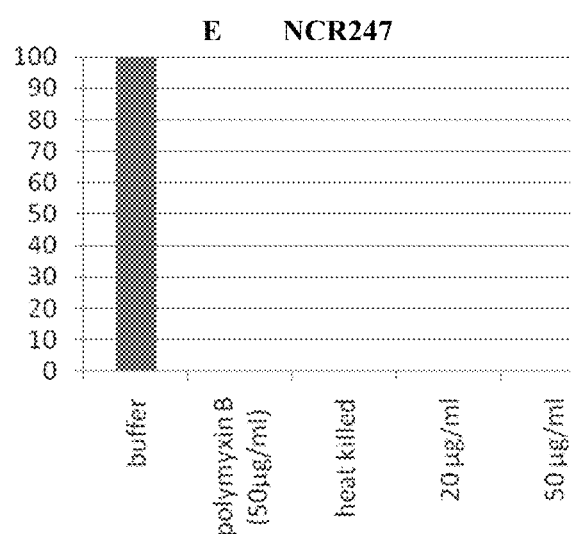

FIG. 2B presents the results obtained for CFU determination:

Out of the 2-3×10⁶ bacteria, none formed colony after treatment with 50 μg of NCR35, NCR55 and NCR247 peptides as in the case of heat killed or polymyxin B treated bacteria.

NCR57 and NCR224 resulted in reduced growth capacity.

Example 4

Treatment of *Sinorhizobium meliloti* with Different Concentrations of Peptides

PI Staining:
Peptides (NCRs) were added at 1, 2, 5, 10, 20 and 50 μg/ml concentrations to log phase bacteria.
Polymyxin B was added at 50 μg/ml.
NCR35, NCR55 and NCR247 resulted in significant PI fluorescence at 10 or 20 μg/ml while NCR 57 was more active at higher concentrations (20 and 50 μg/ml).
Results:
FIGS. 3A to 3E present the results obtained for the relative PI fluorescence of NCR treated *S. meliloti* cells with various concentrations of NCR in comparison to polymyxin B and heat treatments.
NCR 035 shows a high activity from 2 μg/ml in contrast to polymyxin.
CFU Determination:
A) Table V to IX and FIGS. 4A to 4E present the CFUs of *S. meliloti*, after treatment with NCRs at 20 and 50 μg/ml concentrations for 1 hr.
Results with NCR 035:

TABLE V

|  | CFU % | CFU (colony/ml) |
|---|---|---|
| buffer | 100 | 9900000 |
| polymyxin B (50 μg/ml) | 0 | 0 |
| heat killed | 0 | 0 |
| 20 μg/ml NCR 035 | 0 | 21000 |
| 50 μg/ml NCR 035 | 0 | 0 |

Results with NCR 055:

TABLE VI

|  | CFU % | CFU (colony/ml) |
|---|---|---|
| buffer | 100 | 4100000 |
| polymyxin B (50 μg/ml) | 0 | 0 |
| heat killed | 0 | 0 |
| 20 μg/ml NCR055 | 0 | 1800 |
| 50 μg/ml NCR055 | 0 | 0 |

Results with NCR 057:

TABLE VII

|  | CFU % | CFU (colony/ml) |
|---|---|---|
| buffer | 100 | 6600000 |
| polymyxin B (50 μg/ml) | 0 | 0 |
| heat killed | 0 | 0 |
| 20 μg/ml NCR057 | 148 | 9800000 |
| 50 μg/ml NCR057 | 68 | 4500000 |

Results with NCR 224:

TABLE VIII

|  | CFU % | CFU (colony/ml) |
|---|---|---|
| buffer | 100 | 40800000 |
| polymyxin B (50 μg/ml) | 0 | 0 |
| heat killed | 0 | 0 |
| 20 μg/ml NCR224 | 130 | 52900000 |
| 50 μg/ml NCR224 | 48 | 19600000 |

Results with NCR 247:

TABLE IX

|  | CFU % | CFU (colony/ml) |
|---|---|---|
| buffer | 100 | 3100000 |
| polymyxin B (50 μg/ml) | 0 | 0 |
| heat killed | 0 | 0 |
| 20 μg/ml NCR247 | 0 | 0 |
| 50 μg/ml NCR247 | 0 | 0 |

NCR35, 55, 57 and 247 are able to eradicate the bacteria in less than an hour from the low dose of 20 μg/ml.

Figure 5:
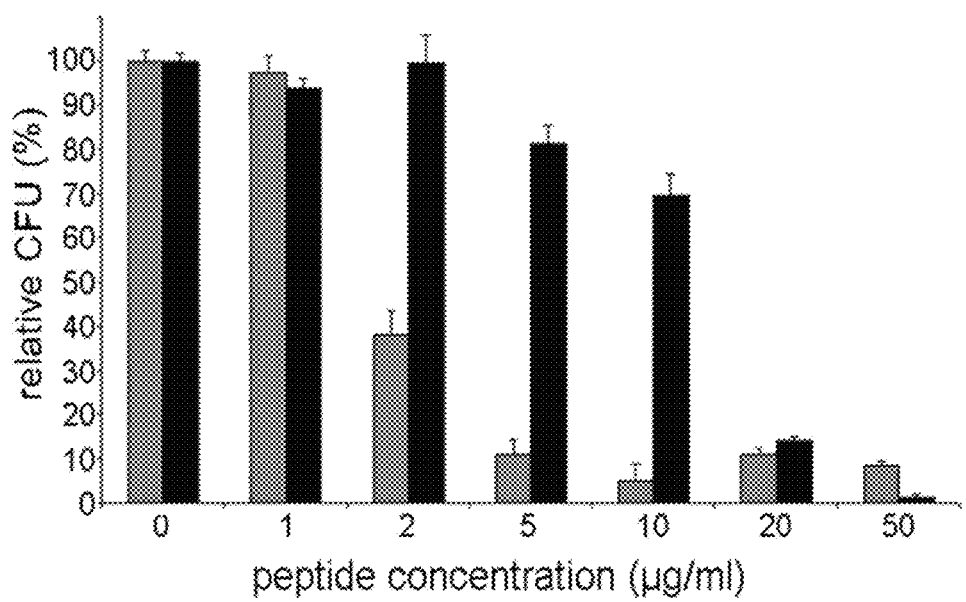
FIG. 5 presents the comparison between Polymyxin B and NCR 035 at different doses.
x-axis: from left to right: NCR035 peptide (black histograms) or polymyxin (dark grey histograms) concentrations: 0, 1, 2, 5, 10, 20, 50 µg/ml
y-axis: percentage of relative CFU.

B) Comparison between peptides (NCR035) or polymyxin B
Peptides (NCR035) or polymyxin B were added at 1, 2, 5, 10, 20 and 50 μg/ml concentrations to log phase bacteria.
FIG. 5 present the results comparison between Polymyxin B and NCR 035 at different doses.

Example 5

Broad Spectrum Activity Treatment of *Sinorhizobium meliloti* and Other Bacteria with 50 μg/ml NCRs in Microtiter Plates Method as in example 3

TABLE X

| BACTERIA | NONE | Polymyxin B | NCR 035 | NCR 055 | NCR 057 | NCR 247 |
|---|---|---|---|---|---|---|
| Gram negatives | | | | | | |
| *Sinorhizobium meliloti* (AK631) | PI CFU: 10⁷ | PI: 70 CFU: 10⁵ | PI: 90 CFU: 0 | PI: 80 CFU: 0 | PI: 35 CFU: 10⁶ | PI: 70 CFU: 0 |
| *Pseudomonas aeruginosa* | PI CFU: 10⁷ | PI: 50 CFU: 0 | — — | PI: 10 CFU: 10⁵ | — — | PI: 15 CFU: 0 |
| *Pseudomonas* | PI | PI: 95 | PI: 100 | PI: 85 | PI: 50 | PI: 60 |

TABLE X-continued

| BACTERIA | NONE | Polymyxin B | NCR 035 | NCR 055 | NCR 057 | NCR 247 |
|---|---|---|---|---|---|---|
| syringae pv tomato DC3000 | CFU: $10^7$ | CFU: 0 | CFU: $10^7$ | CFU: 0 | CFU: $10^6$ | CFU: 0 |
| Xanthomonas 2880 | PI CFU: $10^7$ | PI: 100 CFU: 0 | PI: 100 CFU: $10^2$ | PI: 100 CFU: $10^4$ | PI: 65 CFU: $10^6$ | PI: 48 CFU: 0 |
| Gram positives | | | | | | |
| Clavibacter michigense | PI CFU: $10^9$ | PI: 60 CFU: 0 | PI: 110 CFU: $10^4$ | PI: 100 CFU: 0 | PI: 70 CFU: $10^6$ | PI: 50 CFU: 0 |
| Curtobacterium, flaccumfaciens | PI CFU: $10^9$ | PI: 60 CFU: 0 | PI: 78 CFU: $10^5$ | PI: 80 CFU: 0 | PI: 60 CFU: 0 | PI: 27 CFU: 0 |
| Bacillus subtilis | PI CFU: $10^6$ | PI: 60 CFU: $10^6$ | PI: 100 CFU: $10^3$ | PI: 100 CFU: 0 | PI: — CFU: $10^6$ | PI: 18 CFU: $10^6$ |
| Staphylococcus aureus | PI CFU: $10^6$ | PI: 75 CFU: $10^6$ | PI: 100 CFU: $10^6$ | PI: 100 CFU: $10^4$ | PI: 47 CFU: $10^6$ | PI: 30 CFU: $10^5$ |

PI does not need to be equal to 100% to lead to an eradication of bacteria (CFU=0). NCR 035, 055 and 247 are the most active and possess the broader spectrum of activity.

Interestingly, NCR 055 presents a better killing activity than polymyxin B on bacteria such as resistant bacteria, for example Staphylococcus aureus.

Figure 10:
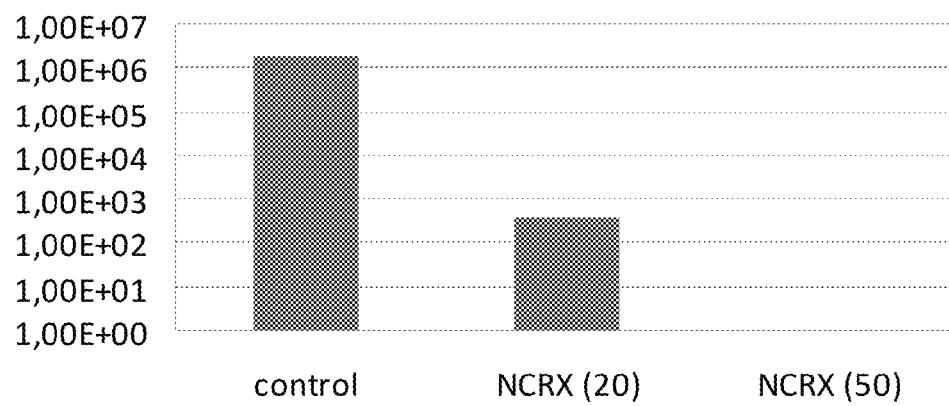
FIG. 10 presents the effect of NCR 247 peptide on a bacterial strain (*Pseudomonas aeruginosa*) resistant to conventional antibiotics at 20 and 50 pg/ml. At 50 µg/ml, the *Pseudomonas aeruginosa* is completely eradicated by NCR 247.
x-axis: from left to right: control, NCR 247 at 20 µg/ml and NCR at 50 µg/ml.
y-axis: CFU

Also, NCR 247 present a potent killing activity on antibiotic resistant bacteria such as Pseudomonas aeruginosa as also shown in FIG. 10.

Example 6

Fast Antibiotic Activity

NCR peptides (10 µM) and $10^7$ bacteria (*Sinorhizobium meliloti*) were incubated in microtiter plates and after 3 hours the number of surviving bacteria was counted in a dilution series on the basis of the colony forming units.
Similarly, tetracycline or kanamycin (both at 10 or 100 µM) or Polymyxin B at 10 µM have also been tested and a negative control containing no peptides or antibiotics has been carried out.

Tetracycline or kanamycin at concentrations tenfold higher than NCR 035, 055 or 247 was unable to kill bacteria during 3 hours showing thus the fast antibiotic activity of peptides of the invention.
Results are presented in FIG. 1.

Example 7

Toxicity of NCR Peptides in Mammalian Cell Culture

Testing the cytotoxicity of the peptides for eukaryotic cells
The effects of the peptides on human cell cultures were studied by several approaches.
1. Cell viability was evaluated by measuring respiratory activity using colorimetric assays (MTT or XTT metabolism assay) on MRC5 normal fibroblast, HT1080 fibrosarcoma, U2OS osteosarcoma and MCF7 breast carcinoma cells. The cell viability of the peptide treated and untreated control cultures were comparable or identical.
2. The effect of the peptides on eukaryotic cell membrane was studied using PI staining and FACS on CaSki cervical carcinoma cells. No membrane permeability change was detected with any of the tested peptides.

Figure 8:
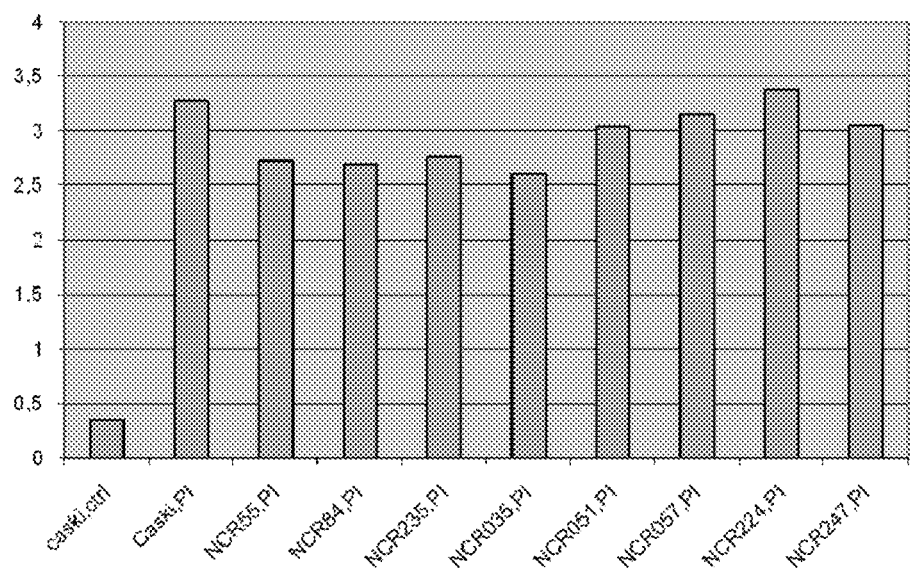
FIG. 8 presents the effects of the peptides on human cell cultures (Caski cells).
This figure shows the PI staining after one hour of incubation with the peptides.
x-axis: PI staining positive cells (%)
y-axis: from left to right histogram: Caski (control), Caski (PI), NCR055 (PI), NCR084 (PI), NCR235 (PI), NCR035 (PI), NCR051 (PI), NCR057 (PI), NCR224 (PI), NCR247 (PI).

These results suggest that the tested plant peptides have no cytotoxicity on human cell cultures.
Results are presented in FIG. 8.
MTT: Methylthiazolyldiphenyl-tetrazolium bromide
XTT: 2,3-Bis(2-methoxy-4-nitro-5-sulfophenyl)-2H-tetrazolium-5 -carboxanilide inner salt
PI: propidium iodide
FACS: fluorescence activated cell sorting

Example 8

Effect of NCR Peptides on Plants Growth

Protocol: Effect of the peptides on Arabidopsis germination and seedling growth (A. Allen et al, Planta (2008) 227: 331-339).

The synthesized peptides were diluted to 100 µM concentration in 10 mM Tris-HCl pH 7.4 and filter sterilized. This dilution was mixed with equal volume of 2×root assay media (per liter: 2.15 g Murashige and Skoog basal salts, 1 g MES, 2% sucrose, 2×Gamborg's vitamins) (final peptide conc. 50 µM) in a 96-well assay plate. A single, sterilized *Arabidopsis* (ecotype:
wassilewskiya) seed was placed in each well and grown with gentle shaking (100 rpm) at 22° C. under a 16 h photoperiod for 7 days. The germinated seedlings were transferred on 1×root assay medium containing 1% agar and photographed after 4 days of incubation. Polymyxin B (50 µg/ml=42 µM) was used as an AMP (antimicrobial peptide) control in the assay.

Figure 9:
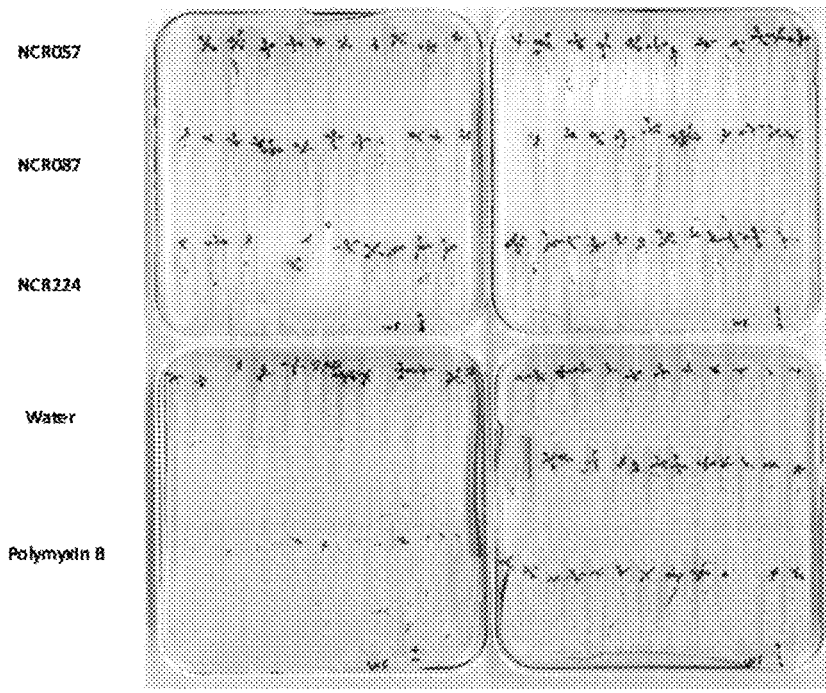
FIG. 9A to 9D presents the effect of NCR peptides (final peptide concentration: 50 µM) on *Arabidopsis* germination and seedling growth.

Results: Polymyxin B affects the plant growth, in particular it inhibits growth whereas NCR 035, 051, 055, 057, 087, 224, 229, 235, 247 peptides have no effect on the growth.
Results are presented in FIG. 9.

Example 9

Effect of Salts of Divalent Cations ($Mg^{++}$ and $Ca^{++}$) on the Activity of NCR Peptides

TABLE XI

| Plate | A1 Negative control. | A2 Positive control. | A3 NCR247 | A4 NCR247 | A5 NCR247 | A6 NCR247 | A7 NCR247 | A8 NCR247 |
|---|---|---|---|---|---|---|---|---|
| Bacteria *S. meliloti* (AK631) | 70 µl | 70 µl | 70 µl | 70 µl | 70 µl | 70 µl | 70 µl | 70 µl |

TABLE XI-continued

| | | | | | | | | |
|---|---|---|---|---|---|---|---|---|
| Buffer 10 mM K-P pH: 7 | 20 μl | 20 μl | 10 μl | ∅ | ∅ | ∅ | ∅ | ∅ |
| Peptide (500 μg/ml) | ∅ | ∅ | 10 μl | 10 μl | 10 μl | 10 μl | 10 μl | 10 μl |
| CaCl₂ | ∅ | ∅ | ∅ | 10 μl 1 mM | 10 μl 5 mM | 10 μl 10 mM | 10 μl 20 mM | 10 μl 50 mM |
| PI 10X | 10 μl | 10 μl | 10 μl | 10 μl | 10 μl | 10 μl | 10 μl | 10 μl |
| Plate | B1 Negative control | B2 Positive control | B3 NCR247 | B4 NCR247 | B5 NCR247 | B6 NCR247 | B7 NCR247 | B8 NCR247 |
| Bacteria S. meliloti (AK631) | 70 μl | 70 μl | 70 μl | 70 μl | 70 μl | 70 μl | 70 μl | 70 μl |
| Buffer 10 mM K-P pH.: 7 | 20 μl | 20 μl | 10 μl | ∅ | ∅ | ∅ | ∅ | ∅ |
| Peptide (500 μg/ml) | ∅ | ∅ | 10 μl | 10 μl | 10 μl | 10 μl | 10 μl | 10 μl |
| MgCl₂ | ∅ | ∅ | ∅ | 10 μl 1 mM | 10 μl 5 mM | 10 μl 10 mM | 10 μl 20 mM | 10 μl 50 mM |
| PI 10X | 10 μl | 10 μl | 10 μl | 10 μl | 10 μl | 10 μl | 10 μl | 10 μl |

$Mg^{++}$ or $Ca^{++}$ was added at final concentrations from 0.1 mM to 5 mM to bacteria (*S. meliloti* (AK631), in a buffer (10 mM K-P pH:7), containing or not NCR 247 peptide (NCR247) and the PI staining was determined Heat killed cells: 95° C.—10 minutes (in buffer)

Figure 6:
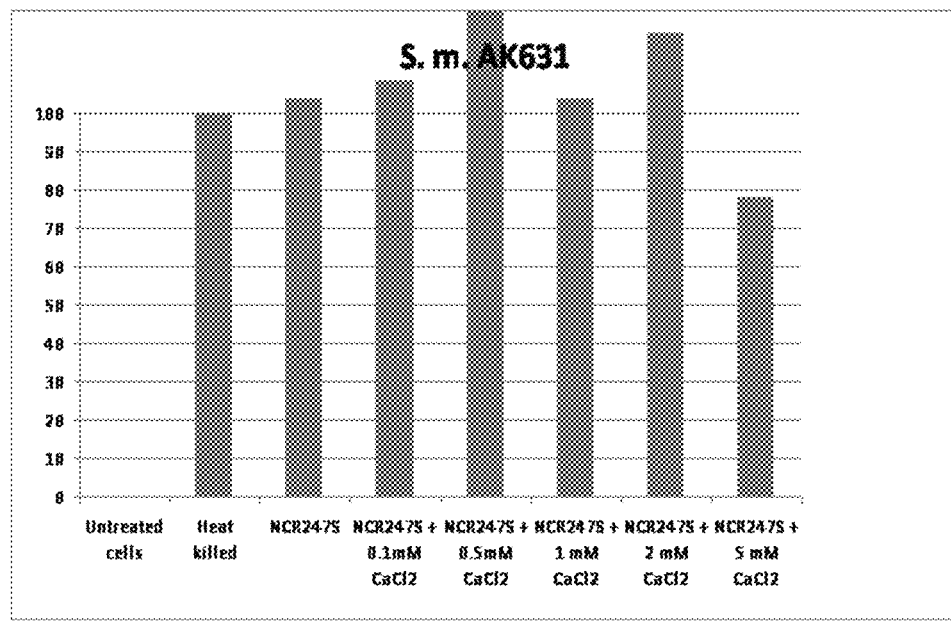
FIGS. 6 and 7 presents the effect of salts of divalent cations ($Mg^{++}$ and $Ca^{++}$) on the activity of NCR peptides.
Figure 7:
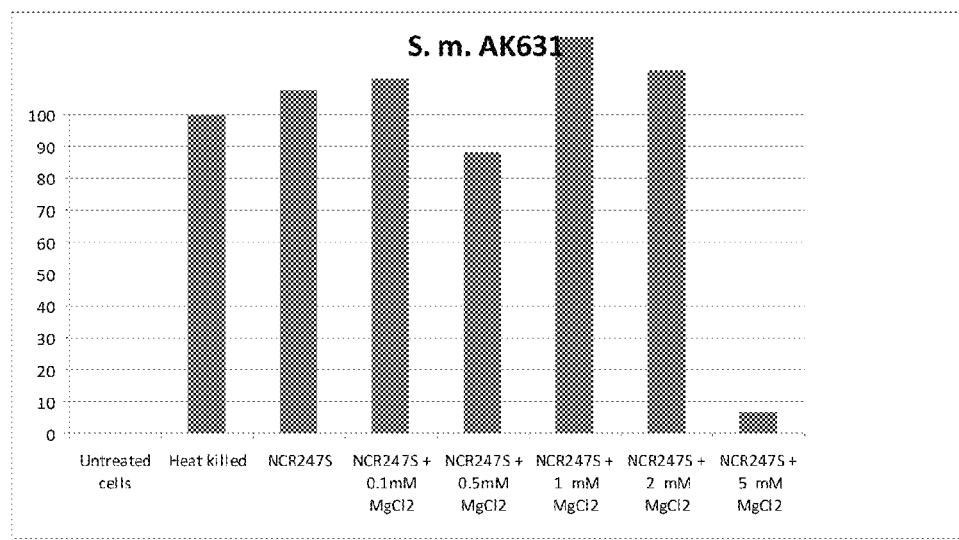

The results are presented in FIGS. 6 and 7.

At a final concentration comprised between 0.1 mM and 2 mM, $Mg^{++}$ or $Ca^{++}$ do not change the activity of NCR peptides.

At a final concentration of 5 mM, Mg and Ca to a lesser extent, exert negative effects on activity of NCR peptides that can be compensated by the addition of EDTA 5 mM (or by increasing the concentration of peptides).

Example 10

Anti-Fungal Activity of NCR Peptides

Protocol:

The fungal strains were maintained on malt extract medium (0.5% malt extract, 0.5% yeast extract, 0.5% glucose, 1.0% $KH_2PO_4$ and 1.5% agar).

The antifungal activity of NCR peptides was measured in an in vitro assay using 96-well microtiter plates. Fifty microliters of each protein dilution were added to each well of the microtiter plate containing 50 μl of spore suspension prepared in low-salt fungal medium at a concentration of $10^4$ spores/ml. The photographs were taken after incubation for 24 and 48 h at 25° C. and the optical density of the cultures were measured at 590nm in the same time.

The germination-inhibitory effect of NCRs was also examined on solid minimal medium in the case of *Fusarium graminerum*. 50 μl of spore suspension prepared in low-salt medium was incubated with 50 μl NCR247 at the indicated concentrations for 20 h at 25° C. than it was plated onto solid minimal medium.

The low-salt medium contained: $K_2HPO_4$ (5 mM), $MgSO_4$ (100 μM), $FeSO_4$ (10 μM), $CoCl_2$ (0.2 μM), $CuSO_4$ (0.2 μM), $Na_2MoO_4$ (4 μM), $H_3BO_3$ (1 μM), KI (0.2 μM), $ZnSO_4$ (1 μM), $MnSO_4$ (0.2 μM), glucose (20 g/l), asparagine (2 g/l), methionine (40 mg/l), myo-inositol (4 mg/l), biotin (0.4 mg/l), thiamine-HCl (2 mg/l), and pyridoxine-HCl (0.4 mg/l).

The minimal medium contained: 1% glucose, 0.5% $(NH_4)_2SO_4$, 0.1% $KH_2PO_4$, 0.05% $MgSO_4$ and was solidified with 1.5% agar.

Figure 11:
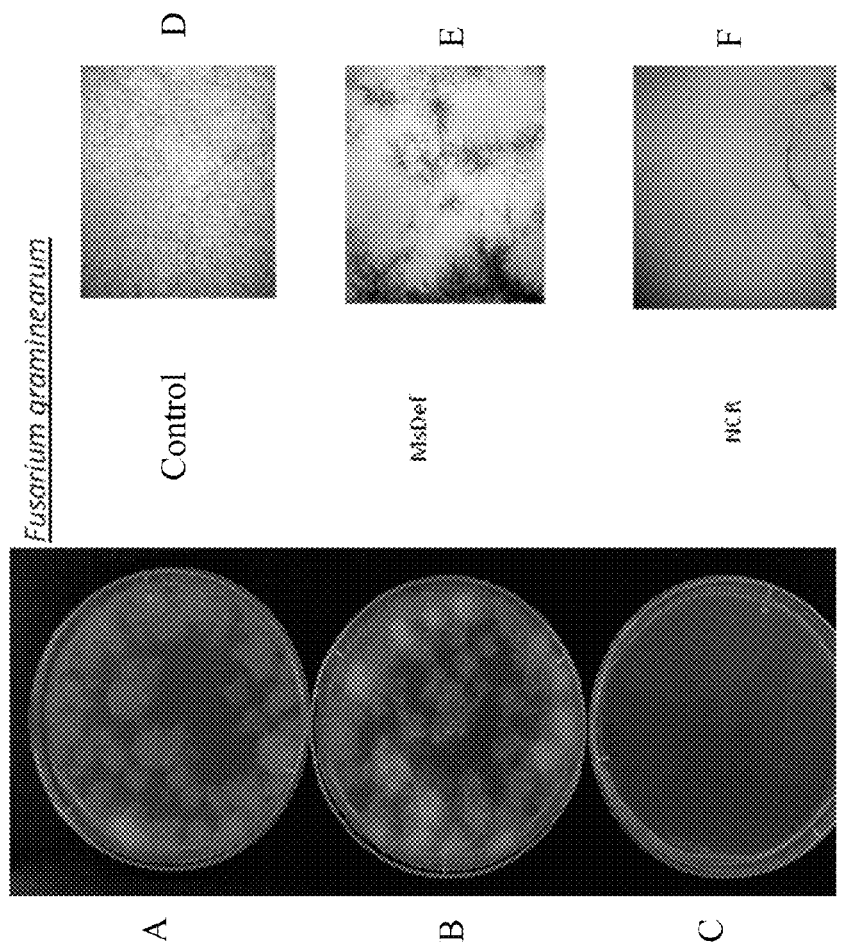
FIGS. 11 A to 11C show the development of spores onto solid minimal medium (example 9).
Figure 12:
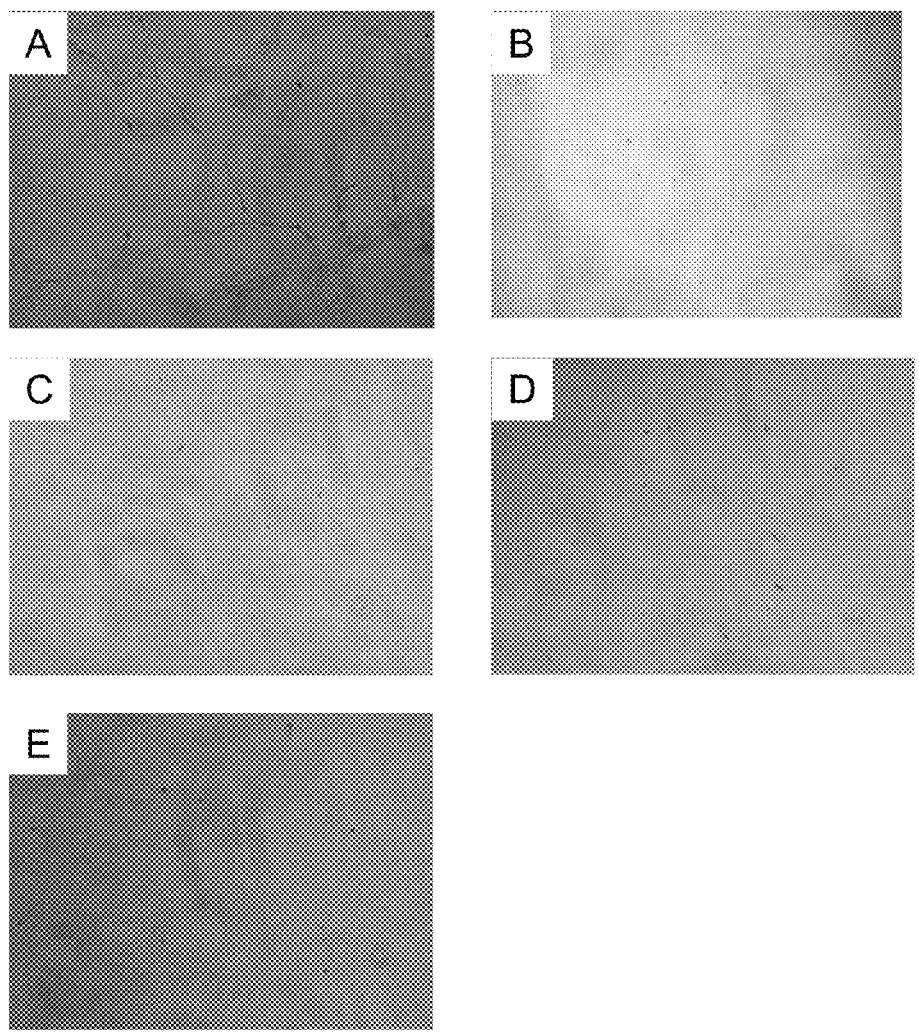

Results:

The results are presented in the table below (table XII and XIII) and on FIGS. 10 to 12:

TABLE XII

| | NCR247 | | | NCR035 | | | NCR055 | | AMB |
|---|---|---|---|---|---|---|---|---|---|
| 24 h | 100 μg/ml | 50 μg/ml | 25 μg/ml | 100 μg/ml | 50 μg/ml | 25 μg/ml | 100 μg/ml | 50 μg/ml | 125 μg/ml |
| *Aspergillus flavus* | +++ | +++ | +++ | ++ | + | − | ++ | + | +++ |
| *Aspergillus niger* | +++ | +++ | +++ | + | − | − | ++ | ++ | +++ |
| *Candida albicans* | +++ | +++ | +++ | ++ | ++ | + | +++ | +++ | +++ |
| *Candida crusei* | +++ | +++ | +++ | ++ | ++ | + | +++ | +++ | +++ |
| *Candida parapsilosis* | +++ | +++ | +++ | ++ | ++ | + | +++ | +++ | +++ |
| *Rhizopus stolonifer* var. *stolonifer* | +++ | +++ | +++ | ++ | + | − | +++ | ++ | +++ |

TABLE XII-continued

|  | NCR247 | | | NCR035 | | | NCR055 | | AMB |
|---|---|---|---|---|---|---|---|---|---|
| 24 h | 100 µg/ml | 50 µg/ml | 25 µg/ml | 100 µg/ml | 50 µg/ml | 25 µg/ml | 100 µg/ml | 50 µg/ml | 125 µg/ml |
| *Fusarium graminearum* | ++ | ++ | ++ | ++ | + | − | ++ | − | ++ |

Fungal (hyphal) growth after 48 hours of incubation
AMB: Amfotericin B (antifungal agent).
+++: high sensitivity, no hyphal growth
++: medium sensitivity
+: low sensitivity
−: no effect

TABLE XIII

|  | NCR247 | | | NCR035 | | | NCR055 | | AMB |
|---|---|---|---|---|---|---|---|---|---|
| 48 h | 100 µg/ml | 50 µg/ml | 25 µg/ml | 100 µg/ml | 50 µg/ml | 25 µg/ml | 100 µg/ml | 50 µg/ml | 125 µg/ml |
| *Aspergillus flavus* | ++ | ++ | + | | | | + | | +++ |
| *Aspergillus niger* | +++ | +++ | +++ | | − | − | ++ | | +++ |
| *Candida albicans* | +++ | +++ | +++ | | | | +++ | +++ | +++ |
| *Candida crusei* | +++ | +++ | +++ | | | | +++ | +++ | +++ |
| *Candida parapsilosis* | +++ | +++ | +++ | | ++ | + | +++ | +++ | +++ |
| *Rhizopus stolonifer* var. *stolonifer* | +++ | +++ | +++ | ++ | + | − | +++ | | +++ |
| *Fusarium graminearum* | ++ | ++ | ++ | | + | − | ++ | − | ++ |

Fungal (hyphal) growth after 48 hours of incubation
AMB: Amfotericin B.
+++: high sensitivity, no hyphal growth
++: medium sensitivity
+: low sensitivity
—: no effect
Results in light grey boxes: increased inhibition versus 24 h of incubation (table XII)
Results in dark grey boxes: decreased inhibition versus 24 h of incubation (table XII).

---

The invention claimed is:

1. A method for treating a disease induced by microorganisms, comprising administering an effective amount of at least one isolated peptide originated from *Medicago truncatula* nodules, the at least one peptide comprising the amino acid sequence selected from the group consisting of SEQ ID NOs: 464-925, to a patient in need thereof,
wherein the microorganism is selected from the group consisting of fungus, Gram negative bacteria and Gram positive bacteria.

2. The method according to claim 1, wherein said at least one isolated peptide is a cationic peptide having a pI>8, in association with one or more anionic peptides having a pI<6 and/or one or more neutral peptides having a 6≤pI≤8.

3. The method according to claim 2, wherein said cationic peptide is selected from the group consisting of: SEQ ID NO:469; SEQ ID NO:474; SEQ ID NO:480; SEQ ID NO:483; SEQ ID NO:484; SEQ ID NO:485; SEQ ID NO:486; SEQ ID NO:489; SEQ ID NO:490; SEQ ID NO:492; SEQ ID NO:493; SEQ ID NO:494; SEQ ID NO:495; SEQ ID NO:496; SEQ ID NO:497; SEQ ID NO:498; SEQ ID NO:499; SEQ ID NO:500; SEQ ID NO:501; SEQ ID NO:502; SEQ ID NO:503; SEQ ID NO:504; SEQ ID NO:505; SEQ ID NO:506; SEQ ID NO:507; SEQ ID NO:508; SEQ ID NO:509; SEQ ID NO:510; SEQ ID NO:511; SEQ ID NO:512; SEQ ID NO:513; SEQ ID NO:515; SEQ ID NO:516; SEQ ID NO:518; SEQ ID NO:520; SEQ ID NO:523; SEQ ID NO:524; SEQ ID NO:530; SEQ ID NO:531; SEQ ID NO:532; SEQ ID NO:533; SEQ ID NO:534; SEQ ID NO:536; SEQ ID NO:538; SEQ ID NO:541; SEQ ID NO:543; SEQ ID NO:544; SEQ ID NO:546; SEQ ID NO:549; SEQ ID NO:554; SEQ ID NO:555; SEQ ID NO:556; SEQ ID NO:561; SEQ ID NO:563; SEQ ID NO:564; SEQ ID NO:565; SEQ ID NO:566; SEQ ID NO:567; SEQ ID NO:569; SEQ ID NO:573; SEQ ID NO:582; SEQ ID NO:583; SEQ ID NO:593; SEQ ID NO:596; SEQ ID NO:597; SEQ ID NO:598; SEQ ID NO:599; SEQ ID NO:600; SEQ ID NO:606; SEQ ID NO:610; SEQ ID NO:611; SEQ ID NO:613; SEQ ID NO:618; SEQ ID NO:620; SEQ ID NO:622; SEQ ID NO:623; SEQ ID NO:632; SEQ ID NO:633; SEQ ID NO:634; SEQ ID NO:635; SEQ ID NO:636; SEQ ID NO:639; SEQ ID NO:642; SEQ ID NO:644; SEQ ID NO:646; SEQ ID NO:647; SEQ ID NO:651; SEQ ID NO:652; SEQ ID NO:655; SEQ ID NO:658; SEQ ID NO:659; SEQ ID NO:662; SEQ ID NO:663; SEQ ID NO:670; SEQ ID NO:675; SEQ ID NO:681; SEQ ID NO:683; SEQ ID NO:684; SEQ ID NO:685; SEQ ID NO:690; SEQ ID NO:694; SEQ ID NO:700; SEQ ID NO:705; SEQ ID NO:706; SEQ ID NO:709; SEQ ID NO:713; SEQ ID NO:715; SEQ ID NO:720; SEQ ID NO:721; SEQ ID NO:725; SEQ ID NO:731; SEQ ID NO:737; SEQ ID NO:738; SEQ ID NO:739; SEQ ID NO:742; SEQ ID NO:743; SEQ ID NO:744; SEQ ID NO:746; SEQ ID NO:750; SEQ ID NO:753; SEQ ID NO:757; SEQ ID NO:758; SEQ ID NO:761; SEQ ID NO:766; SEQ ID NO:769; SEQ ID NO:772; SEQ ID NO:774; SEQ ID NO:775; SEQ ID NO:780; SEQ ID NO:781; SEQ ID NO:782; SEQ ID NO:783; SEQ ID NO:784; SEQ ID NO:787; SEQ ID NO:793; SEQ ID NO:794; SEQ ID NO:799; SEQ ID NO:800; SEQ ID NO:807; SEQ ID NO:812; SEQ ID NO:816; SEQ ID NO:817; SEQ ID NO:819; SEQ ID NO:820; SEQ ID NO:821; SEQ ID NO:824; SEQ ID NO:825; SEQ ID NO:827; SEQ ID NO:828; SEQ ID NO:829; SEQ ID NO:830; SEQ ID NO:835; SEQ ID NO:836; SEQ ID NO:842; SEQ ID NO:846; SEQ ID NO:847; SEQ ID NO:848; SEQ ID NO:849; SEQ ID NO:850; SEQ ID NO:853; SEQ ID NO:858; SEQ ID NO:862; SEQ ID NO:863; SEQ ID NO:865; SEQ ID NO:866; SEQ ID NO:870; SEQ ID NO:872; SEQ ID NO:875; SEQ ID NO:877; SEQ ID NO:878; SEQ ID NO:879; SEQ ID NO:880; SEQ ID NO:881; SEQ ID NO:892; SEQ ID NO:894; SEQ ID NO:896; SEQ ID NO:897; SEQ ID NO:899; SEQ ID NO:909; SEQ ID NO:910; SEQ ID NO:913; SEQ ID NO:917; SEQ ID NO:919; SEQ ID NO:921 and SEQ ID NO:925.

4. The method according to claim 2, wherein said cationic peptide is selected from the group consisting of: SEQ ID NO:706 (NCR 247), SEQ ID NO:498 (NCR 035), SEQ ID NO:518 (NCR 055) and SEQ ID NO:520 (NCR 57).

5. The method according to claim 3, wherein
said one or more anionic peptides are selected from the group consisting of: SEQ ID NO:464; SEQ ID NO:465; SEQ ID NO:467; SEQ ID NO:468; SEQ ID NO:470; SEQ ID NO:471; SEQ ID NO:472; SEQ ID NO:476; SEQ ID NO:477; SEQ ID NO:478; SEQ ID NO:479; SEQ ID NO:481; SEQ ID NO:482; SEQ ID NO:487; SEQ ID NO:488; SEQ ID NO:514; SEQ ID NO:521; SEQ ID NO:522; SEQ ID NO:526; SEQ ID NO:528; SEQ ID NO:529; SEQ ID NO:537; SEQ ID NO:539; SEQ ID NO:545; SEQ ID NO:550; SEQ ID NO:551; SEQ ID NO:552; SEQ ID NO:558; SEQ ID NO:562; SEQ ID NO:568; SEQ ID NO:571; SEQ ID NO:574; SEQ ID NO:575; SEQ ID NO:576; SEQ ID NO:577; SEQ ID NO:580; SEQ ID NO:586; SEQ ID NO:588; SEQ ID NO:590; SEQ ID NO:592; SEQ ID NO:595; SEQ ID NO:602; SEQ ID NO:603; SEQ ID NO:604; SEQ ID NO:605; SEQ ID NO:608; SEQ ID NO:614; SEQ ID NO:615; SEQ ID NO:616; SEQ ID NO:617; SEQ ID NO:619; SEQ ID NO:621; SEQ ID NO:625; SEQ ID NO:626; SEQ ID NO:627; SEQ ID NO:629; SEQ ID NO:630; SEQ ID NO:631; SEQ ID NO:640; SEQ ID NO:641; SEQ ID NO:643; SEQ ID NO:648; SEQ ID NO:650; SEQ ID NO:654; SEQ ID NO:656; SEQ ID NO:657; SEQ ID NO:666; SEQ ID NO:667; SEQ ID NO:672; SEQ ID NO:673; SEQ ID NO:674; SEQ ID NO:677; SEQ ID NO:678; SEQ ID NO:679; SEQ ID NO:680; SEQ ID NO:682; SEQ ID NO:686; SEQ ID NO:687; SEQ ID NO:688; SEQ ID NO:693; SEQ ID NO:696; SEQ ID NO:697; SEQ ID NO:702; SEQ ID NO:704; SEQ ID NO:711; SEQ ID NO:719; SEQ ID NO:722; SEQ ID NO:728; SEQ ID NO:729; SEQ ID NO:732; SEQ ID NO:733; SEQ ID NO:735; SEQ ID NO:736; SEQ ID NO:741; SEQ ID NO:745; SEQ ID NO:747; SEQ ID NO:748; SEQ ID NO:749; SEQ ID NO:752; SEQ ID NO:754; SEQ ID NO:759; SEQ ID NO:760; SEQ ID NO:762; SEQ ID NO:763; SEQ ID NO:767; SEQ ID NO:768; SEQ ID NO:770; SEQ ID NO:771; SEQ ID NO:773; SEQ ID NO:777; SEQ ID NO:778; SEQ ID NO:786; SEQ ID NO:792; SEQ ID NO:795; SEQ ID NO:796; SEQ ID NO:797; SEQ ID NO:803; SEQ ID NO:805; SEQ ID NO:808; SEQ ID NO:810; SEQ ID NO:811; SEQ ID NO:813; SEQ ID NO:814; SEQ ID NO:815; SEQ ID NO:818; SEQ ID NO:822; SEQ ID NO:823; SEQ ID NO:826; SEQ ID NO:831; SEQ ID NO:834; SEQ ID NO:837; SEQ ID NO:839; SEQ ID NO:840; SEQ ID NO:841; SEQ ID NO:845; SEQ ID NO:851; SEQ ID NO:852; SEQ ID NO:854; SEQ ID NO:855; SEQ ID NO:856; SEQ ID NO:857; SEQ ID NO:859; SEQ ID NO:860; SEQ ID NO:861; SEQ ID NO:868; SEQ ID NO:873; SEQ ID NO:876; SEQ ID NO:882; SEQ ID NO:883; SEQ ID NO:884; SEQ ID NO:887; SEQ ID NO:889; SEQ ID NO:891; SEQ ID NO:893; SEQ ID NO:895; SEQ ID NO:901; SEQ ID NO:902; SEQ ID NO:903; SEQ ID NO:904; SEQ ID NO:907; SEQ ID NO:908; SEQ ID NO:912; SEQ ID NO:915; SEQ ID NO:922 and SEQ ID NO:924.

6. The method according to claim 3, wherein
said one or more anionic peptides are selected from the group consisting of: SEQ ID NO:686 (NCR 224), SEQ ID NO:697 (NCR 235), SEQ ID NO:514 (NCR 051) and SEQ ID NO:464 (NCR 001).

7. The method according to claim 5, wherein
said one or more neutral peptides are selected from the group consisting of: SEQ ID NO:466; SEQ ID NO:473; SEQ ID NO:475; SEQ ID NO:491; SEQ ID NO:517; SEQ ID NO:519; SEQ ID NO:525; SEQ ID NO:527; SEQ ID NO:535; SEQ ID NO:540; SEQ ID NO:542; SEQ ID NO:547; SEQ ID NO:548; SEQ ID NO:553; SEQ ID NO:557; SEQ ID NO:559; SEQ ID NO:560; SEQ ID NO:570; SEQ ID NO:572; SEQ ID NO:578; SEQ ID NO:579; SEQ ID NO:581; SEQ ID NO:584; SEQ ID NO:585; SEQ ID NO:587; SEQ ID NO:589; SEQ ID NO:591; SEQ ID NO:594; SEQ ID NO:601; SEQ ID NO:607; SEQ ID NO:609; SEQ ID NO:612; SEQ ID NO:624; SEQ ID NO:628; SEQ ID NO:637; SEQ ID NO:638; SEQ ID NO:645; SEQ ID NO:649; SEQ ID NO:653; SEQ ID NO:660; SEQ ID NO:661; SEQ ID NO:664; SEQ ID NO:665; SEQ ID NO:668; SEQ ID NO:669; SEQ ID NO:671; SEQ ID NO:676; SEQ ID NO:689; SEQ ID NO:691; SEQ ID NO:692; SEQ ID NO:695; SEQ ID NO:698; SEQ ID NO:699; SEQ ID NO:701; SEQ ID NO:703; SEQ ID NO:707; SEQ ID NO:708; SEQ ID NO:710; SEQ ID NO:712; SEQ ID NO:714; SEQ ID NO:716; SEQ ID NO:717; SEQ ID NO:718; SEQ ID NO:723; SEQ ID NO:724; SEQ ID NO:726; SEQ ID NO:727; SEQ ID NO:730; SEQ ID NO:734; SEQ ID NO:740; SEQ ID NO:751; SEQ ID NO:755; SEQ ID NO:756; SEQ ID NO:764; SEQ ID NO:765; SEQ ID NO:776; SEQ ID NO:779; SEQ ID NO:785; SEQ ID NO:788; SEQ ID NO:789; SEQ ID NO:790; SEQ ID NO:791; SEQ ID NO:798; SEQ ID NO:801; SEQ ID NO:802; SEQ ID NO:804; SEQ ID NO:806; SEQ ID NO:809; SEQ ID NO:832; SEQ ID NO:833; SEQ ID NO:838; SEQ ID NO:843; SEQ ID NO:844; SEQ ID NO:864; SEQ ID NO:867; SEQ ID NO:869; SEQ ID NO:871; SEQ ID NO:874; SEQ ID NO:885; SEQ ID NO:886; SEQ ID NO:888; SEQ ID NO:890; SEQ ID NO:898; SEQ ID NO:900; SEQ ID NO:905; SEQ ID NO:906; SEQ ID NO:911; SEQ ID NO:914; SEQ ID NO:916; SEQ ID NO:918; SEQ ID NO:920 and SEQ ID NO:923.

8. The method according to claim 2, wherein
said neutral peptides are selected from the group consisting of: SEQ ID NO:547 (NCR 084) and SEQ ID NO:691 (NCR 229).

9. The method according to claim 1, wherein said peptides are active against both Gram negative bacteria and Gram positive bacteria.

10. The method according to claim 1, wherein said peptides are administered at a concentration in a range of from about 1 to about 100 µg/ml.

11. The method according to claim 10, wherein the number of colony forming units of bacteria dropped in a range of 3 to 9 orders of magnitude, in 3 hours after administering said peptides.

12. The method according to claim 1, wherein the at least one peptide comprises the amino acid sequence selected from the group consisting of SEQ ID NOs: 1-463.9.

* * * * *